US010337022B2

(12) United States Patent
Roberts et al.

(10) Patent No.: US 10,337,022 B2

(45) **Date of Patent: *Jul. 2, 2019**

(54) METHODS OF INCREASING ROOT BIOMASS IN PLANTS

(71) Applicant: Agresearch Limited, Hamilton (NZ)

(72) Inventors: Nicholas John Roberts, Feilding (NZ); Kim Archer Richardson, Palmerston North (NZ); Derek William Richard White, Palmerston North (NZ)

(73) Assignee: AgResearch Limited, Hamilton (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 15/523,848

(22) PCT Filed: Nov. 3, 2015

(86) PCT No.: PCT/IB2015/058479

§ 371 (c)(1),
(2) Date: May 2, 2017

(87) PCT Pub. No.: WO2016/071830

PCT Pub. Date: May 12, 2016

(65) Prior Publication Data

US 2018/0094275 A1 Apr. 5, 2018

(30) Foreign Application Priority Data

Nov. 4, 2014 (NZ) ........................................ 701643

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01); *C12N 15/8227* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 4,795,855 | A | 1/1989 | Fillatti et al. |
| 5,004,863 | A | 4/1991 | Umbeck |
| 5,159,135 | A | 10/1992 | Umbeck |
| 5,177,010 | A | 1/1993 | Goldman et al. |
| 5,187,073 | A | 2/1993 | Goldman et al. |
| 5,188,958 | A | 2/1993 | Moloney et al. |
| 5,416,011 | A | 5/1995 | Hinchee et al. |
| 5,463,174 | A | 10/1995 | Moloney et al. |
| 5,563,055 | A | 10/1996 | Townsend et al. |
| 5,569,834 | A | 10/1996 | Hinchee et al. |
| 5,591,616 | A | 1/1997 | Hiei et al. |
| 5,639,952 | A | 6/1997 | Quail et al. |
| 5,656,496 | A | 8/1997 | Quail et al. |
| 5,750,871 | A | 5/1998 | Moloney et al. |
| 5,792,935 | A | 8/1998 | Arntzen et al. |
| 5,824,877 | A | 10/1998 | Hinchee et al. |
| 5,837,848 | A | 11/1998 | Ely et al. |
| 5,846,797 | A | 12/1998 | Strickland |
| 5,952,543 | A | 9/1999 | Firoozabady et al. |
| 5,968,830 | A | 10/1999 | Dan et al. |
| 5,981,840 | A | 11/1999 | Zhao et al. |
| 6,020,539 | A | 2/2000 | Goldman et al. |
| 6,037,522 | A | 3/2000 | Dong et al. |
| 6,074,877 | A | 6/2000 | D'Halluin et al. |
| 6,921,848 | B2 | 7/2005 | Chory et al. |
| 2001/0047525 | A1 | 11/2001 | Bruce et al. |
| 2004/0067506 | A1 | 4/2004 | Scheres et al. |
| 2007/0039067 | A1 | 2/2007 | Feldmann et al. |
| 2017/0314036 | A1* | 11/2017 | Roberts .............. C12N 15/8261 |

FOREIGN PATENT DOCUMENTS

| | | | |
|---|---|---|---|
| CN | 102260679 | A | 11/2011 |
| WO | WO 2002/000894 | A2 | 1/2002 |
| WO | WO 2007/105967 | A1 | 9/2007 |
| WO | WO 2007/124312 | A2 | 11/2007 |
| WO | WO 2007/105967 | A8 | 7/2009 |

OTHER PUBLICATIONS

White, Proc. Natl. Acad. Sci. USA, 2006, vol. 103, pp. 13238-13242 (Year: 2006).*

Abbott et al. (2002) "Simultaneous Suppression of Multiple Genes by Single Transgenes. Down-Regulation of Three Unrelated Lignin Biosynthetic Genes in Tobacco," Plant Physiol. 128(3):844-853.

Achard et al. (2009) "Releasing the brakes of plant growth: how Gas shutdown DELLA proteins," J. Exp. Bot. 60:1085-1092.

Alam et al. (1999) "Transgenic insect-resistant maintainer line (IR68899B) for improvement of hybrid rice," Plant Cell Rep. 18:572-575.

Altpeter et al. (2000) "Generation of large Numbers of independently transformed fertile perennial ryegrass (*Lolium perenne* L.) plants of forage- and turf-type cultivars," Molecular Breeding. 6:519-528.

Altschul et al. (1990) "Basic local alignment search tool," J. Mol. Biol. 215:403-410.

Altschul et al. (1997) "Gapped BLAST and PSI-BLAST: a new generation of protein database search programs," Nucleic Acids Res. 25:3389-3402.

Anjum et al. (2011) "Brassinolide application improves the drought tolerance in maize through modulation of enzymatic antioxidants and leaf gas exchange," J. Agronomy and Crop Sci. 197:177-185.

(Continued)

*Primary Examiner* — Eileen B O Hara

(74) *Attorney, Agent, or Firm* — Leydig, Voit & Mayer, Ltd.

(57) ABSTRACT

The invention provides methods and materials for increasing root biomass in a plant, by increasing the expression of at least one PEAPOD protein, or fragment thereof, in the plant. The invention also provides methods and materials for producing a plant increased root biomass, the method comprising the step of increasing the expression of at least one PEAPOD protein, or fragment thereof, in the plant.

26 Claims, 13 Drawing Sheets

Specification includes a Sequence Listing.

(56) References Cited

OTHER PUBLICATIONS

Bairoch et al. (1994) "PROSITE: recent developments," Nucleic Acids Res. 22:3583-3589.
Baxevanis (2001) "The Molecular Biology Database Collection: an updated compilation of biological database resources," Nucleic Acids Res. 29:1-10.
Bilang et al. (1991) "The 3'-terminal region of the hygromycin-B-resistance gene is important for its activity in *Escherichia coli* and Nicotiana tabacum," Gene. 100:247-250.
Bingham (1991) "Registration of Alfalfa Hybrid Regen-Sy Germplasm for Tissue Culture and Transformation Research," Crop Sci. 31:1098.
Birch (1997) "Plant Transformations: Problems and Strategies for Practical Applications," Ann. Rev. Plant Phys. Plant Mol. Biol. 48:297-326.
Bolton et al. (1962) "A General Method for the Isolation of RNA Complementary to DNA," Proc. Natl. Acad. Sci. USA. 48:1390-1397.
Bowie et al. (1990) "Deciphering the message in protein sequences: tolerance to amino acid substitutions," Science. 247:1306-1310.
Clough et al. (1998) "Floral dip: a simplified method for Agrobacterium-mediated transformation of *Arabidopsis thaliana*," Plant J. 16(6):735-743.
Clouse (2011) "Brassinosteroid signal transduction: from receptor kinase activation to transcriptional networks regulating plant development," Plant Cell. 23:1219-1230.
Clouse et al. (1998) "Brassinosteroids: Essential regulators of plant growth and development," Annu. Rev. Plant Physiol. Plant Mol. Biol. 16:427-451.
Dan et al. (2006) "MicroTom—a high-throughput model transformation system for functional genomics," Plant Cell Reports. 25:432-441.
De Carvalho Niebelet al. (1995) "Post-transcriptional cosuppression of beta-1,3-glucanase genes does not affect accumulation of transgene nuclear mRNA," Plant Cell. 7:347-358.
Doyle et al. (1990) "Isolation of Plant DNA from Fresh Tissue," Focus. 12:13-15.
Falquet et al. (2002) "The PROSITE database, its status in 2002," Nucleic Acids Res. 30:235-238.
Feng et al. (1987) "Progressive sequence alignment as a prerequisite to correct phylogenetic trees," J. Mol. Evol. 25:351-360.
Folta et al. (2006) "Characterization of LF9, an octoploid strawberry genotype selected for rapid regeneration and transformation," Planta. 224(5):1058-1067.
Frohman (1993) "Rapid amplification of complementary DNA ends for generation of full-length complementary DNAs: thermal RACE," Methods Enzymol. 218:340-356.
Gallego-Bartolome et al. (2012) "Molecular mechanism for the interaction between gibberellin and brassionosteroid signalling pathways in *Arabidopsis*," Proc. Natl. Acad. Sci. 109:13446-13451.
Garcia et al. (2008) "A small plant-specific protein family of ABI five binding proteins (AFPs) regulates stress response in germinating *Arabidopsis* seeds and seedlings," Plant Mol. Biol. 67:643-658.
Genbank Database [Online] (Mar. 20, 2017) "*Arabidopsis thaliana* TIFY domain/Divergent CCT motif family protein (PPD1), mRNA," Accession No. NM_202819. National Center for Biotechnology Information. Accessible on the Internet at URL: https://www.ncbi.nlm.nih.gov/nuccore/NM_202819, [Last Accessed Dec. 12, 2017].
Giesen et al. (1998) "A formula for thermal stability (Tm) prediction of PNA/DNA duplexes," Nucleic Acids Res. 26(21):5004-5006.
Gleave (1992) "A versatile binary vector system with a T-DNA organisational structure conducive to efficient integration of cloned DNA into the plant genome," Plant Mol. Biol. 20:1203-1207.
Gonzalez Padilla et al. (2003) "Early antibiotic selection and efficient rooting and acclimatization improve the production of transgenic plum plants (*Prunus domestica* L.)," Plant Cell Rep. 22(1):38-45.
Graham et al. (1995) "Agrobacterium-mediated transformation of soft fruit Rubus, Ribes, and Fragaria," Methods Mol. Biol. 44:129-133.
Guo et al. (Aug. 27, 2013) "Mechanisms and networkes for brassinosteroid regulated gene expression," Current Opinion in Plant Biology. 16:545-553.
He et al. (2005) "BZR1 is a transcriptional repressor with dual roles in brassinosteroid homeostasis and growth responses," Science. 307:1634-1638.
Hellens et al. (2000) "pGreen: a versatile and flexible binary Ti vector for Agrobacterium-mediated plant transformation," Plant Mol. Biol. 42:819-832.
Hellens et al. (2005) "Transient expression vectors for functional genomics, quantification of promoter activity and RNA silencing in plants," Plant Methods. 1:13 pp. 1-14.
Henikoff et al. (1992) "Amino acid substitution matrices from protein blocks," Proc. Natl. Acad. Sci. USA. 89:10915-10919.
Herrera-Estrella et al. (1993) "Expression of chimaeric genes transferred into plant cells using a Ti-plasmid-derived vector," Nature. 303:209-213.
Hofmann et al. (1999) "The PROSITE database, its status in 1999," Nucleic Acids Res. 27:215-219.
Horsch et al. (1985) "A simple and general method for transferring genes into plants," Science. 227:1229-1231.
Hothorn et al. (2011) "Structural basis of steroid hormone perception by the receptor kinase BRI1," Nature. 474:467-471.
Hou et al. (2010) "DELLAs modulate jasmonate signalling via competitive binding to JAZs," Devel. Cell. 19:884-894.
Huang (1994) "On Global Sequence Alignment," Computer Applications in the Biosciences. 10:227-235.
Jeanmougin et al. (1998) "Multiple sequence alignment with Clustal X," Trends Biochem. Sci. 23:403-405.
Jiang et al. (Dec. 19, 2013) "DWARF 53 acts as a repressor of strigolactone signalling in rice," Nature. 504:401-405.
Jiang et al. (Oct. 2013) "Brassinosteroid functions in *Arabidopsis* seed development," Plant Signaling & Behavior. 8(10):e25928.
Jobling et al. (2003) "Immunomodulation of enzyme function in plants by single-domain antibody fragments," Nat. Biotechnol. 21(1):77-80.
Jones et al. (1998) "The effect of chimeric transgene architecture on co-ordinated gene silencing," Planta. 204:499-505.
Joshi (1987) "An inspection of the domain between putative TATA box and translation start site in 79 plant genes," Nucleic Acid Research. 15:6643-6653.
Jouvenot et al. (2003) "Targeted regulation of imprinted genes by synthetic zinc-finger transcription factors," Gene Therapy. 10:513-522.
Karimi et al. (2002) "Gateway vectors for Agrobacterium-mediated plant transformation," Trends Plant Sci. 7:193-195.
Keinonen-Mettala et al. (1998) "Comparisons of the efficiency of some promoters in silver birch (*Betula pendula*)," Plant Cell Rep. 17:356-361.
Khripach et al. (2000) "Twenty years of brassinosteroids: Steroidal plant hormones warrant better crops for the XXI century," Ann. Bot. 86:441-447.
Kinoshita et al. (2005) "Binding of brassinosteroids to the extracellular domain of plant receptor kinase BRI1," Nature. 433:167-171.
Krens et al. (1997) "Transgenic caraway, *Carum carvi* L.: a model species for metabolic engineering," Plant Cell Rep. 17:39-43.
Kumar et al. (1996) "Potato plants expressing antisense and sense S-adenosylmethionine decarboxylase (SAMDC) transgenes show altered levels of polyamines and ethylene: antisense plants display abnormal phenotypes," Plant J. 9(2):147-158.
Lawit et al. (2010) "Maize DELLA Proteins dwarf plant8 and dwarf plant9 as Modulators of Plant Development," Plant Cell Physiol. 51:1854-1868.
Li et al. (1996) "Genetic transformation of cassava (*Manihot esculenta* Crantz)," Nat. Biotechnol. 14:736-740.
Li et al. (2001) "A fast neutron deletion mutagenesis-based reverse genetics system for plants," Plant Journal. 27(3):235-242.
Li et al. (2003) "Transgenic rose lines harboring an antimicrobial protein gene, Ace-AMP1 , demonstrate enhanced resistance to powdery mildew (*Sphaerotheca pannosa*)," Planta, 218:226-232.
Li et al. (Jul. 2013) "Mechanisms of signalling crosstalk between brassinosteroids and gibberellins," Plant Signaling & Behavior. 8(7):e24686.

(56) References Cited

OTHER PUBLICATIONS

Llave et al. (2002) "Cleavage of Scarecrow-like mRNA targets directed by a class of *Arabidopsis* miRNA," Science. 297:2053-2056.
Mathew et al. (2009) "Pasture response to gibberellins: A review and recommendations," NZ. J. Agric. Res. 52:213-225.
Matsuda et al. (2005) "Development of an Agrobacterium-mediated transformation method for pear (*Pyrus communis* L.) with leaf-section and axillary shoot-meristem explants," Plant Cell Rep. 24(1):45-51.
Mcintyre (1996) "Strategies for the suppression of peroxidase gene expression in tobacco. I. Designing efficient ribozymes," Transgenic Res. 5:257-262.
Michelmore et al. (1987) "Transformation of lettuce (*Lactuca sativa*) mediated by Agrobacterium tumefaciens," Plant Cell Rep. 6:439-442.
Murashige et al. (1962) "A Revised Medium for Rapid Growth and Bio Assays with Tobacco Tissue Cultures," Physiol Plant. 15:473-497.
Napoli et al. (1990) "Introduction of a Chimeric Chalcone Synthase Gene into Petunia Results in Reversible Co-Suppression of Homologous Genes in trans," Plant Cell. 2:279-289.
Needleman et al. (1970) "A general method applicable to the search for similarities in the amino acid sequence of two proteins," J. Mol. Biol. 48:443-453.
Nielsen et al. (1991) "Sequence-selective recognition of DNA by strand displacement with a thymine-substituted polyamide," Science. 254(5037):1497-1500.
Nilsson et al. (1992) "Spatial pattern of cauliflower mosaic virus 35S promoter-luciferase expression in transgenic hybrid aspen trees monitored by enzymatic assay and non-destructive imaging," Transgenic Research. 1:209-220.
Niu et al. (1998) "Transgenic peppermint (*Mentha x piperita* L.) plants obtained by cocultivation with Agrobacterium tumefaciens," Plant Cell Rep. 17:165-171.
Notredame et al. (2000) "A novel method for fast and accurate multiple sequence alignment," J. Mol. Biol. 302:205-217.
Oosumi et al. (2006) "High-efficiency transformation of the diploid strawberry (*Fragaria vesca*) for functional genomics," Planta. 223(6):1219-1230.
Ortiz et al. (1996) "Hygromycin resistance as an efficient selectable marker for wheat stable transformation," Plant Cell Rep. 15:877-881.
Pauwels et al. (2010) "NINJA connects the co-repressor TOPLESS to jasmonate signaling," Nature. 464:788-791.
Pena et al. (1995) "High efficiency Agrobacterium-mediated transformation and regeneration of citrus," Plant Sci.104:183-191.
Perez et al. (Jan. 8, 2014) "The non-JAZ TIFY protein TIFY8 from *Arabidopsis thaliana* is a transcriptional repressor," PLoS One. 9(1):e84891.
Prusakova et al. (1999) "The use of emistim, epibrassinolide and uniconazole to overcome quality difference of buckwheat grains," Agrarian Russia. 1999:41-44.
Ramesh et al. (2006) "Improved methods in Agrobacterium-mediated transformation of almond using positive (mannose/pmi) or negative (kanamycin resistance) selection-based protocols," Plant Cell Rep. 25(8):821-828.
Rice et al. (2000) "EMBOSS: The European Molecular Biology Open Software Suite," Trends in Genetics. 16(6):276-277.
Robatzek et al. (2001) "A new member of the Arabidopsis WRKY transcription factor family, AtWRKY6, is associated with both senescence- and defence-related processes," The Plant Journal, 28:123-133.
Samac et al. (2000) "Alfalfa (*Medicago sativa* L.)," Methods Mol. Biol. 343:301-11.
Sanford et al. (1993) "Optimizing the biolistic process for different biological applications," Meth. Enzymol. 217:483-509.
Schrott (1995) "Selectable Marker and Reporter Genes," Ch. 31 In; Potrykus et al.: Eds. Gene Transfer to Plants. Springer-Verlag. Berlin, Germany. pp. 325-336.
She et al. (2011) "Structural insight into brassinosteroid perception by BRI1," Nature. 474:472-476.
Song et al. (2005) "Transformation of Montmorency sour cherry (*Prunus cerasus* L.) and Gisela 6 (P. cerasus x P. canescens) cherry rootstock mediated by Agrobacterium tumefaciens," Plant Cell Rep. 25(2):117-123.
Sun (2011) "The molecular mechanism and evolution of the GA-GID1-DELLA signalling module in plants," Reviews in Current Biology. 21:R338-R345.
Szemenyei et al. (2008) "TOPLESS mediates auxin-dependent transcriptional repression during *Arabidopsis* embryogenesis," Science. 319:1384-1386.
Tatusova et al. (1999) "Blast 2 sequences—a new tool for comparing protein and nucleotide sequences," FEMS Microbiol. Lett. 174:247-250.
Tatusova et al. (1999) "Erratum: Blast 2 sequences—a new tool for comparing protein and nucleotide sequences [FEMS Microbiol. 174 (1999) 247-250]," FEMS Microbiol. Lett. 177:187-188.
Thompson et al. (1994) "CLUSTAL W: improving the sensitivity of progressive multiple sequence alignment through sequence weighting, position-specific gap penalties and weight matrix choice," Nucleic Acids Res. 22:4673-4680.
Thummel et al. (2002) "Steroid signalling in plants and insects-common themes, different pathways," Genes Dev. 16:3113-3129.
Till et al. (2003) "High-throughput TILLING for functional genomics," Methods Mol. Biol. 236:205-220.
Towbin et al. (1994) "Immunoblotting and dot immunobinding—current status and outlook," J. Immunol. Methods. 72:313-340.
Triglia et al. (1988) "A procedure for in vitro amplification of DNA segments that lie outside the boundaries of known sequences," Nucleic Acids Res. 16:8186.
Tuberosa et al. (2006) "Genomics-based approaches to improve drought tolerance of crops," Trends in Plant Science. 11:405-412.
Vanhaeren et al. (Apr. 29, 2014) "Combining growth-promoting genes leads to positive epistasis in *Arabidopsis thaliana*," eLife. 3:e02252. pp. 1-19.
Vanholme et al. (2007) "The tify family previously known as ZIM," Trends in Plant Science. 12:239-244.
Vardhini (2012) "Application of brassinolide mitigates saline stress of certain metabolites of sorghum grown in Karaikal," J. Phytology. 4:1-3.
Wang et al. (2002) "Nuclear-localised BZR1 mediates brassinosteroid-induced growth and feedback suppression of brassinosteroid biosynthesis," Developmental Cell. 2:505-513.
Wang et al. (2006) "Transformation of Actinidia eriantha: a potential species for functional genomics studies in Actinidia," Plant Cell Rep. 25(5):425-431.
Wang et al. (Sep. 9, 2013) "Identification of BZR1-interacting proteins as potential components of the brassinosteroid signalling pathway in *Arabidopsis* through tandem affinity purification," Mol. Cell. Proteomics. 12:3653-3665.
Werner et al. (2010) "Root-specific reduction of cytokinin causes enhanced root growth, drought tolerance, and leaf mineral enrichment in *Arabidopsis* and tobacco," Plant Cell. 22:3905-3920.
Wheeler et al. (2001) "Database resources of the National Center for Biotechnology Information," Nucleic Acids Res. 29:11-16.
White (2006) "PEAPOD regulates lamina size and curvature in *Arabidopsis*," Proc. Natl. Acad. Sci. USA. 103(35):13238-43.
White et al. (2009) "PEAPOD limits and coordinates vascular procambium activity and stomatal density in *Arabidopsis*," In; The Abstracts of Plant Biology 2009. Abstract No. P67003. p. 409.
Winichayakul et al. (2009) "Head-to-tail fusions of camelid antibodies can be expressed in planta and bind in rumen fluid," Biotechnol. Appl. Biochem. 53:111-122.
Yamamoto et al. (1991) "Characterization of cis-acting sequences regulating root-specific gene expression in tobacco," Plant Cell. 3:371-382.
Yao et al. (1995) "Regeneration of transgenic plants from the commercial apple cultivar Royal Gala," Plant Cell Reports. 14:407-412.
Yu et al. (2008) "Activated expression of an Arabidopsis HD-START protein confers drought tolerance with improved root system and reduced stomatal density," Plant Cell. 20:1134-1151.

(56) References Cited

OTHER PUBLICATIONS

Zhu et al. (Apr. 2013) "Brassinosteroid signaling," Development. 140:1615-1620.
International Search Report with Written Opinion corresponding to International Patent Application No. PCT/IB2015/058479, dated Dec. 21, 2015.
European Search Report, dated Apr. 23, 2018, corresponding to International Application No. PCT/IB2015/058479 (filed Nov. 3, 2015), parent of the present application, 12 pp.
Rojas, et al. (2010) "Genetically modified crops for biomass increase. Genes and strategies," GM Crops 1:3, 137-142.

* cited by examiner

| | | |
|---|---|---|
| Amborella trichopoda | LEELTEEDISQLTREDCRRYLKEKGMRRPSWNKYQAIQQVLSLKGL | (SEQ ID NO: 147) |
| Picea abies | ledlshedimqltredcrryliekgmrrpswnksqaiqqvlslkkl | (SEQ ID NO: 148) |
| Picea sitchensis | LEELTEEDIFQLTREDCRRYLKEKGMRRPSWNKSQAIQQVLSLKSL | (SEQ ID NO: 149) |
| Spirodela polyrhiza | LSELTEEDIAQVTREDCRRFLKEKGMRRPSWNKSQAVQQVISLKAL | (SEQ ID NO: 150) |
| Selaginella moellendorffii PPD1 | LEELTELDIRQLTREDCRRYLKERGMRRPSWNKAQAIQQVLSLRSL | (SEQ ID NO: 151) |
| Selaginella moellendorffii PPD2 | LEELTDEDVMQLTREDCRRYLKEKGMRRPSWNKAQAVQQLLSLKSL | (SEQ ID NO: 152) |
| Musa species | LAELTEEDIAQLTREDCRRFLKAKGMRRPSWNKSQAIQQVISLKAL | (SEQ ID NO: 153) |
| Phoenix dactylifera | LSLLTEEDIAQLTREDCRRFLKEKGMRRPSWNKSQAIQQVISLKAL | (SEQ ID NO: 154) |
| Phalaenopsis aphrodite | LNLLTEDDIAQITREECRRFLKDRGMRRPSWNKSQAIQQVISLKAL | (SEQ ID NO: 155) |
| Nicotiana tabacum | LHLLTDDDISQLTREDCRRYLKEKGMRRPSWNKSQAIQQVISLKAL | (SEQ ID NO: 156) |
| Solanum lycopersicum | LYLLTDDDISQLTREDCRRFLKAKGMRKPSWNKSQAIQQVISLKAL | (SEQ ID NO: 157) |
| Solanum tuberosum | LNQLTDDDISQLTREDCRRYLKQKGMRKPSWNKSQAIQQVISLKAL | (SEQ ID NO: 158) |
| Aquilegia coerulea | LFQLTDEDISQLTREDCRKFLRDKGMRRPSWNKSQAIEQVISLKTL | (SEQ ID NO: 159) |
| Populus trichocarpa | LHQLTEDDISQVTREDCRRYLKEKGMRRPSWNKSQAIQQVISLKTL | (SEQ ID NO: 160) |
| Glycine max | LNQLTEDDISQLTREDCRRFLKEKGMRRPSWNKSQAIQQVISLKAL | (SEQ ID NO: 161) |
| Medicago truncatula | LWQLTEDDISQLTREDCRRFLKDKGMRRPSWNKSQAIQQVISLKAL | (SEQ ID NO: 162) |
| Trifolium repens | LNQLTEDDISQLTREDCRRFLKDKGMRRPSWNKSQAIQQVISLKAL | (SEQ ID NO: 163) |
| Arabidopsis thaliana PPD1 | LKLLTEEDISQLTREDCRKFLKDKGMRRPSWNKSQAIQQVLSLKAL | (SEQ ID NO: 164) |
| Arabidopsis thaliana PPD2 | LKLLTEEDISQLTREDCRKFLKEKGMRRPSWNKSQAIQQVLSLKAL | (SEQ ID NO: 165) |
| Gossypium raimondii | LSQLTEEDISQLTREDCRKFLKEKGMRRPSWNKSQAIQQVISFKAL | (SEQ ID NO: 166) |
| Theobroma cacao | LSQLTEEDISQLTREDCRKFLKEKGMRRPSWNKSQAIQQVISLKAL | (SEQ ID NO: 167) |
| Citrus clementine | LSQLTEEDITQLTREDCRKFLKEKGMRRPSWNKSQAIQQVISLKAL | (SEQ ID NO: 168) |
| Morus notabilis | LNQLTEDDISQLTREDCRKYLKEKGMRRPSWNKSQAIQQVISLKAL | (SEQ ID NO: 169) |
| Ricinus communis | LTQLTEEDISQLTREDCRKYLKEKGMRRPSWNKSQAIQQVISLKAL | (SEQ ID NO: 170) |
| Vitis vinifera | LHELTEEDISQLTREDCRKYLKEKGMRRPSWNKSQAIQQVISLKSL | (SEQ ID NO: 171) |
| **Identical amino acids** | *  *  *  * *** **  *   *** ***** **  *  *   * | |

Fig. 1

| | | |
|---|---|---|
| Amborella trichopoda | TREDCRRYLKEKGMRRPSWNKYQAIQQ | (SEQ ID NO: 172) |
| Picea abies | TREDCRRYLKEKGMRRPSWNKSQAIQQ | (SEQ ID NO: 173) |
| Picea sitchensis | TREDCRRYLKEKGMRRPSWNKSQAIQQ | (SEQ ID NO: 174) |
| Spirodela polyrhiza | TREDCRRFLKEKGMRRPSWNKSQAVQQ | (SEQ ID NO: 175) |
| Selaginella moellendorffii PPD1 | TREDCRRYLKERGMRRPSWNKAQAIQQ | (SEQ ID NO: 176) |
| Selaginella moellendorffii PPD2 | TREDCRRYLKEKGMRRPSWNKAQAVQQ | (SEQ ID NO: 177) |
| Musa species | TREDCRRFLKAKGMRRPSWNKSQAIQQ | (SEQ ID NO: 178) |
| Phoenix dactylifera | TREDCRRFLKEKGMRRPSWNKSQAIQQ | (SEQ ID NO: 179) |
| Phalaenopsis aphrodite | TREECRRFLKDRGMRRPSWNKSQAIQQ | (SEQ ID NO: 180) |
| Nicotiana tabacum | TREDCRRYLKEKGMRRPSWNKSQAIQQ | (SEQ ID NO: 181) |
| Solanum lycopersicum | TREDCRRFLKAKGMRKPSWNKSQAIQQ | (SEQ ID NO: 182) |
| Solanum tuberosum | TREDCRRYLKQKGMRKPSWNKSQAIQQ | (SEQ ID NO: 183) |
| Aquilegia coerulea | TREDCRKFLRDKGMRRPSWNKSQAIEQ | (SEQ ID NO: 184) |
| Populus trichocarpa | TREDCRRYLKEKGMRRPSWNKSQAIQQ | (SEQ ID NO: 185) |
| Glycine max | TREDCRRFLKEKGMRRPSWNKSQAIQQ | (SEQ ID NO: 186) |
| Medicago truncatula | TREDCRRFLKDKGMRRPSWNKSQAIQQ | (SEQ ID NO: 187) |
| Trifolium repens | TREDCRRFLKDKGMRRPSWNKSQAIQQ | (SEQ ID NO: 188) |
| Arabidopsis thaliana PPD1 | TREDCRKFLKDKGMRRPSWNKSQAIQQ | (SEQ ID NO: 189) |
| Arabidopsis thaliana PPD2 | TREDCRKFLKEKGMRRPSWNKSQAIQQ | (SEQ ID NO: 190) |
| Gossypium raimondii | TREDCRKFLKEKGMRRPSWNKSQAIQQ | (SEQ ID NO: 191) |
| Theobroma cacao | TREDCRKFLKEKGMRRPSWNKSQAIQQ | (SEQ ID NO: 192) |
| Citrus clementine | TREDCRKFLKEKGMRRPSWNKSQAIQQ | (SEQ ID NO: 193) |
| Morus notabilis | TREDCRKYLKEKGMRRPSWNKSQAIQQ | (SEQ ID NO: 194) |
| Ricinus communis | TREDCRKYLKEKGMRRPSWNKSQAIQQ | (SEQ ID NO: 195) |
| Vitis vinifera | TREDCRKYLKEKGMRRPSWNKSQAIQQ | (SEQ ID NO: 196) |
| **Identical amino acids** | *** ** * *** ***** ** * | |

Fig. 2

| | | |
|---|---|---|
| Amborella trichopoda | TIFYAG | (SEQ ID NO: 197) |
| Picea sitchensis | TIFYAG | (SEQ ID NO: 198) |
| Picea abies | TIFYSG | (SEQ ID NO: 199) |
| Spirodela polyrhiza | TIFYDG | (SEQ ID NO: 200) |
| Selaginella moellendorffii PPD1 | TIFYSG | (SEQ ID NO: 201) |
| Selaginella moellendorffii PPD2 | TMFYDG | (SEQ ID NO: 202) |
| Musa species | TIFYDG | (SEQ ID NO: 203) |
| Elaeis guineensis | TIFYDG | (SEQ ID NO: 204) |
| Phalaenopsis aphrodite | TIFYGG | (SEQ ID NO: 205) |
| Nicotiana tabacum | TIFYCG | (SEQ ID NO: 206) |
| Solanum lycopersicum | TIFYCG | (SEQ ID NO: 207) |
| Solanum tuberosum | TIFYRG | (SEQ ID NO: 208) |
| Aquilegia coerulea | TIFYCG | (SEQ ID NO: 209) |
| Populus trichocarpa | TIFYCG | (SEQ ID NO: 210) |
| Glycine max | TIFYCG | (SEQ ID NO: 211) |
| Medicago truncatula | TIFYCG | (SEQ ID NO: 212) |
| Trifolium repens | TIFYCG | (SEQ ID NO: 213) |
| Arabidopsis thaliana PPD1 | TIFYSG | (SEQ ID NO: 214) |
| Arabidopsis thaliana PPD2 | TIFYSG | (SEQ ID NO: 215) |
| Gossypium raimondii | TIFYCG | (SEQ ID NO: 216) |
| Theobroma cacao | TIFYCG | (SEQ ID NO: 217) |
| Citrus clementine | TIFYCG | (SEQ ID NO: 218) |
| Morus notabilis | TIFYCG | (SEQ ID NO: 219) |
| Ricinus communis | TIFYCG | (SEQ ID NO: 220) |
| Vitis vinifera | TIFYCG | (SEQ ID NO: 221) |
| Identical amino acids | * ** * | |

Fig. 3

Non transformed ryegrass control

Ryegrass vector only control

Constitutive:: PPD *A. trichopoda*

Constitutive:: PPD *A. thaliana* pTobRB7Δ0.6:: PPD *A. thaliana* pTobRB7Δ1.3:: PPD *A. thaliana*

SEQUENCE LISTING

```
<160> NUMBER OF SEQ ID NOS: 224

<210> SEQ ID NO 1
<211> LENGTH: 313
<212> TYPE: PRT
<213> ORGANISM: Arabidopsis thaliana

<400> SEQUENCE: 1

Met Asp Val Gly Val Ser Pro Ala Lys Ser Ile Leu Ala Lys Pro Leu
1               5                   10                  15

Lys Leu Leu Thr Glu Glu Asp Ile Ser Gln Leu Thr Arg Glu Asp Cys
            20                  25                  30

Arg Lys Phe Leu Lys Asp Lys Gly Met Arg Arg Pro Ser Trp Asn Lys
```

```
        35                  40                  45

Ser Gln Ala Ile Gln Gln Val Leu Ser Leu Lys Ala Leu Tyr Glu Pro
    50                  55                  60

Gly Asp Asp Ser Gly Ala Gly Ile Phe Arg Lys Ile Leu Val Ser Gln
65                  70                  75                  80

Pro Val Asn Pro Pro Arg Val Thr Thr Thr Leu Ile Glu Pro Ser Asn
                85                  90                  95

Glu Leu Glu Ala Cys Gly Arg Val Ser Tyr Pro Glu Asp Asn Gly Ala
            100                 105                 110

Cys His Arg Met Asp Ser Pro Arg Ser Ala Glu Phe Ser Gly Gly Ser
        115                 120                 125

Gly His Phe Val Ser Glu Lys Asp Gly His Lys Thr Thr Ile Ser Pro
    130                 135                 140

Arg Ser Pro Ala Glu Thr Ser Glu Leu Val Gly Gln Met Thr Ile Phe
145                 150                 155                 160

Tyr Ser Gly Lys Val Asn Val Tyr Asp Gly Ile Pro Pro Glu Lys Ala
                165                 170                 175

Arg Ser Ile Met His Phe Ala Ala Asn Pro Ile Asp Leu Pro Glu Asn
            180                 185                 190

Gly Ile Phe Ala Ser Ser Arg Met Ile Ser Lys Leu Ile Ser Lys Glu
        195                 200                 205

Lys Met Met Glu Leu Pro Gln Lys Gly Leu Glu Lys Ala Asn Ser Ser
    210                 215                 220

Arg Asp Ser Gly Met Glu Gly Gln Ala Asn Arg Lys Val Ser Leu Gln
225                 230                 235                 240

Arg Tyr Arg Glu Lys Arg Lys Asp Arg Lys Phe Ser Lys Ala Lys Lys
                245                 250                 255

Cys Pro Gly Val Ala Ser Ser Ser Leu Glu Met Phe Leu Asn Cys Gln
            260                 265                 270

Pro Arg Met Lys Ala Ala Tyr Ser Gln Asn Leu Gly Cys Thr Gly Ser
        275                 280                 285

Pro Leu His Ser Gln Ser Pro Glu Ser Gln Thr Lys Ser Pro Asn Leu
    290                 295                 300

Ser Val Asp Leu Asn Ser Glu Gly Ile
305                 310


<210> SEQ ID NO 2
<211> LENGTH: 315
<212> TYPE: PRT
<213> ORGANISM: Arabidopsis thaliana

<400> SEQUENCE: 2

Met Asp Val Gly Val Thr Thr Ala Lys Ser Ile Leu Glu Lys Pro Leu
1               5                   10                  15

Lys Leu Leu Thr Glu Glu Asp Ile Ser Gln Leu Thr Arg Glu Asp Cys
            20                  25                  30

Arg Lys Phe Leu Lys Glu Lys Gly Met Arg Arg Pro Ser Trp Asn Lys
        35                  40                  45

Ser Gln Ala Ile Gln Gln Val Leu Ser Leu Lys Ala Leu Tyr Glu Pro
    50                  55                  60

Gly Asp Asp Ser Gly Ala Gly Ile Leu Arg Lys Ile Leu Val Ser Gln
65                  70                  75                  80

Pro Pro Asn Pro Pro Arg Val Thr Thr Thr Leu Ile Glu Pro Arg Asn
                85                  90                  95
```

-continued

Glu Leu Glu Ala Cys Gly Arg Ile Pro Leu Gln Glu Asp Asp Gly Ala
100 105 110

Cys His Arg Arg Asp Ser Pro Arg Ser Ala Glu Phe Ser Gly Ser Ser
115 120 125

Gly Gln Phe Val Ala Asp Lys Asp Ser His Lys Thr Val Ser Val Ser
130 135 140

Pro Arg Ser Pro Ala Glu Thr Asn Ala Val Val Gly Gln Met Thr Ile
145 150 155 160

Phe Tyr Ser Gly Lys Val Asn Val Tyr Asp Gly Val Pro Pro Glu Lys
165 170 175

Ala Arg Ser Ile Met His Phe Ala Ala Asn Pro Ile Asp Leu Pro Glu
180 185 190

Asn Gly Ile Phe Ala Ser Ser Arg Met Ile Ser Lys Pro Met Ser Lys
195 200 205

Glu Lys Met Val Glu Leu Pro Gln Tyr Gly Leu Glu Lys Ala Pro Ala
210 215 220

Ser Arg Asp Ser Asp Val Glu Gly Gln Ala Asn Arg Lys Val Ser Leu
225 230 235 240

Gln Arg Tyr Leu Glu Lys Arg Lys Asp Arg Arg Phe Ser Lys Thr Lys
245 250 255

Lys Ala Pro Gly Val Ala Ser Ser Ser Leu Glu Met Phe Leu Asn Arg
260 265 270

Gln Pro Arg Met Asn Ala Ala Tyr Ser Gln Asn Leu Ser Gly Thr Gly
275 280 285

His Cys Glu Ser Pro Glu Asn Gln Thr Lys Ser Pro Asn Ile Ser Val
290 295 300

Asp Leu Asn Ser Asp Leu Asn Ser Glu Asp Asn
305 310 315

<210> SEQ ID NO 3
<211> LENGTH: 375
<212> TYPE: PRT
<213> ORGANISM: Populus trichocarpa

<400> SEQUENCE: 3

Met Gln Pro Gly Glu Thr Val Phe Arg Ser Ala Leu Asp Lys Pro Leu
1 5 10 15

His Gln Leu Thr Glu Asp Asp Ile Ser Gln Val Thr Arg Glu Asp Cys
20 25 30

Arg Arg Tyr Leu Lys Glu Lys Gly Met Arg Arg Pro Ser Trp Asn Lys
35 40 45

Ser Gln Ala Ile Gln Gln Val Ile Ser Leu Lys Thr Leu Leu Glu Ala
50 55 60

Thr Pro Glu Thr Glu Ser Pro Arg Arg Arg Leu Tyr Ile Pro Arg Pro
65 70 75 80

Pro Pro His Pro Pro Asp Asn Thr Pro Arg Val Arg Phe Ser Ala Val
85 90 95

Pro Pro Asn Ser Ser Val Ser Glu Arg Gly Ala Ser Ala Glu Thr Pro
100 105 110

Ile Ser Val Pro Ala Glu Glu Pro Val Pro Cys Arg Gln His Asp Pro
115 120 125

Pro Asn Pro Asp Asp Pro Ala Asp Pro Leu Pro Pro Val His Ala Ala
130 135 140

Val Thr Glu Asn Ala Ser Val Ser Pro Arg Thr Thr Gly Met Ala Glu
145 150 155 160

```
Glu Ser Ala Gly Gln Met Thr Ile Phe Tyr Cys Gly Lys Val Asn Val
                165                 170                 175

Tyr Asp Asp Val Pro Gly Asp Lys Ala Gln Ala Ile Met His Leu Ala
            180                 185                 190

Ala Ser Pro Phe Ala Pro Pro Gln Asp Ala Ser Ser Asp Val Ile Pro
        195                 200                 205

Thr Leu Arg Pro Leu Gln Cys Gln Leu Asp Thr Pro Gly Val Lys Ala
    210                 215                 220

Ala Pro Asn Ser Ile Val Ala Asn Phe Pro Thr Leu Pro Thr Val Lys
225                 230                 235                 240

Gly Ala Asp Ser Gly Gln Leu Leu Trp Glu Glu Ser Asn Ile Ala Arg
                245                 250                 255

Glu Asp Asn Leu Glu Gly Ser Thr Ser Arg Lys Ala Ser Leu Gln Arg
            260                 265                 270

Tyr Phe Glu Lys Lys Lys Asp Arg Phe Lys Asn Lys Arg Lys Val Ala
        275                 280                 285

Val Pro Ser Ala Ser Leu Asp Val Phe Leu Ser His Leu Val Gly Asp
    290                 295                 300

Gln Ile Ser Asn Asp His Trp Asn Leu Asn Asp Ala Cys Ser Pro Ser
305                 310                 315                 320

Gln Pro Arg Pro Pro Gln Thr Pro Asn Arg Cys Asn Ser Val Asp Asn
                325                 330                 335

Val Ala Lys Asn Gly Ile Leu Lys Ala Asp Leu Asn Asn Lys Gly Asp
            340                 345                 350

Ala Asp Leu Ser Cys Cys Leu Asp Phe Ser Ser Lys Gln Ile Asn Ala
        355                 360                 365

Trp Cys Leu Cys Leu Gly Cys
    370                 375


<210> SEQ ID NO 4
<211> LENGTH: 346
<212> TYPE: PRT
<213> ORGANISM: Picea abies

<400> SEQUENCE: 4

Met Arg Gly Gly Gly Gly Ala Asp Arg Leu Pro Ala Arg Ala Asn Leu
1               5                   10                  15

Glu Lys Pro Leu Glu Asp Leu Ser His Glu Asp Ile Met Gln Leu Thr
            20                  25                  30

Arg Glu Asp Cys Arg Arg Tyr Leu Ile Glu Lys Gly Met Arg Arg Pro
        35                  40                  45

Ser Trp Asn Lys Ser Gln Ala Ile Gln Gln Val Leu Ser Leu Lys Lys
    50                  55                  60

Leu Phe Glu Ser Gly Pro Asn Asp Glu Lys Arg Ser Ala Ala Thr Asn
65                  70                  75                  80

Arg Pro Asn Pro Asp Glu Asn Leu Lys Glu Ala Ala Ser Val Ser Leu
                85                  90                  95

Leu Tyr Gly Ser Gln Pro Glu Ser Pro Ser Val Val Phe Ala Ser Lys
            100                 105                 110

Asp Ser Asp Thr Phe Asn Leu Glu Trp Leu Ala Lys Thr Glu Leu Pro
        115                 120                 125

Val Leu Ala Ser Gln Pro Arg His Ile Ala Gln Gln Asn Val Phe Leu
    130                 135                 140

Ser Ser Leu Ser Ala Gln Gln Ser Gly Ala Gln Leu Thr Ile Phe Tyr
```

-continued

```
145                 150                 155                 160

Ser Gly Asn Val Asn Val Tyr Asp Asp Val Pro Ala Glu Lys Ala Gln
                165                 170                 175

Glu Ile Met Leu Leu Ala Gly Ser Gly Asn Tyr Pro Pro Ser Ser Thr
            180                 185                 190

Cys Gln Ser Thr Arg Asn Thr Gln Gln Asn Ala Val Arg Ala Ala Tyr
        195                 200                 205

Pro Ser Asn Pro Thr Asn Thr Pro Phe Ile His Gly Val Gly Pro Pro
    210                 215                 220

Leu Ala Thr Val Ala Ser Ser Ser Val Met Ser Ser Pro Ile His Lys
225                 230                 235                 240

Glu Ser Pro Ile Thr Arg Lys Ala Ser Leu Gln Arg Phe Leu Glu Lys
                245                 250                 255

Arg Lys Asp Arg Ser Arg Gly Lys Leu Gly Ala Pro Thr Ile Ser Lys
            260                 265                 270

Lys Pro Leu Leu Met Gly Met Phe Met His Pro Ser Ile Val His Arg
        275                 280                 285

Gln Tyr Trp Thr Asp Thr Ala Lys Arg Lys Ser Gly Lys Pro Asp Ile
    290                 295                 300

Pro Ala Ser Ile Ser Pro Thr Arg Pro Pro His Thr Pro Arg Arg Thr
305                 310                 315                 320

Ser Ser Asp Glu Gln Leu Ser Ala Arg His Ala Arg Gly Asp Ile Ser
                325                 330                 335

Ala Gln Gly Gly Ser Leu His Asn Ser Asn
            340                 345


<210> SEQ ID NO 5
<211> LENGTH: 222
<212> TYPE: PRT
<213> ORGANISM: Picea sitchensis

<400> SEQUENCE: 5

Met Arg Gly Gly Glu Arg Ala Pro Gly Ser Arg Pro Ser Leu Asp Lys
1               5                   10                  15

Pro Leu Glu Glu Leu Thr Glu Glu Asp Ile Phe Gln Leu Thr Arg Glu
            20                  25                  30

Asp Cys Arg Arg Tyr Leu Lys Glu Lys Gly Met Arg Arg Pro Ser Trp
        35                  40                  45

Asn Lys Ser Gln Ala Ile Gln Gln Val Leu Ser Leu Lys Ser Leu Phe
    50                  55                  60

Glu Ser Lys Pro Asn Gln Gln Ser Lys Lys Pro Ser Lys His Lys Pro
65                  70                  75                  80

Ala Thr Leu Gln Phe Glu Thr Ala Arg Asp Ser Thr Phe Ala Gln Ser
                85                  90                  95

Ser Val Ser Gln Glu Gln Ser Leu Gly Phe Ser Trp Ser Lys Glu Val
            100                 105                 110

Leu Asp Lys Gly Thr Ala Glu Arg Gln Arg Leu Cys Ser Asp Ser Gln
        115                 120                 125

Glu Ala His Glu Ile Pro Arg Leu Gly Ser Lys Pro Pro Gln Ser Asn
    130                 135                 140

Thr Glu Gly Lys Arg Cys Ala His Asp Gly His Gly Arg Lys Ser Ala
145                 150                 155                 160

Gln Pro Leu Val Arg Leu Pro Ala Asn Phe Lys Asn Asp Cys Ser Asn
                165                 170                 175
```

-continued

```
Arg Gln Ser Ser His Thr Ser Glu Ser Gln Pro Asp Thr Leu Leu Arg
            180                 185                 190

Ser Asp Ser Phe Gln Gln Pro Thr Ala Gln Leu Thr Ile Phe Tyr Ala
        195                 200                 205

Gly Met Val Asn Val Tyr Asp Asp Val Pro Leu Asp Lys Ala
    210                 215                 220


<210> SEQ ID NO 6
<211> LENGTH: 365
<212> TYPE: PRT
<213> ORGANISM: Gossypium raimondii

<400> SEQUENCE: 6

Met Glu Ala Gly Val Thr Thr Thr Ala Thr Thr Thr Ala Ser Phe Ser
1               5                   10                  15

Ser Ile Leu Asp Lys Pro Leu Ser Gln Leu Thr Glu Glu Asp Ile Ser
            20                  25                  30

Gln Leu Thr Arg Glu Asp Cys Arg Lys Phe Leu Lys Glu Lys Gly Met
        35                  40                  45

Arg Arg Pro Ser Trp Asn Lys Ser Gln Ala Ile Gln Gln Val Ile Ser
    50                  55                  60

Phe Lys Ala Leu Leu Glu Ser Asn Glu Asp Ser Gly Ala Gly Ala Arg
65                  70                  75                  80

Arg Lys Ile Leu Val Cys Pro Pro Pro Ser His Phe Pro Pro Gln Asn
                85                  90                  95

Ala Val Ala Ser Asn Ser Gly Glu Ser Val Lys Glu Ala Val Phe Gly
            100                 105                 110

Glu Glu Glu Ser Leu Tyr Gly Gln Lys Asp Leu Ser Leu Lys Ala Ala
        115                 120                 125

Pro Val Val Gln Met Asn Cys Gln Gly Gly Asp Thr Asp Asp Lys Thr
    130                 135                 140

Leu Ser Pro Ser Leu Gly Ser Pro Arg Glu Tyr Ser Lys Leu Pro Gly
145                 150                 155                 160

Arg Ser Gln Cys Glu Thr Asn Glu Leu Gly Gly Gln Met Thr Ile Phe
                165                 170                 175

Tyr Cys Gly Lys Ile Asn Val Tyr Asp Gly Val Pro Leu Ala Lys Ala
            180                 185                 190

Arg Ala Ile Met His Leu Ala Ala Ser Pro Ile Asp Phe Pro Gln Gly
        195                 200                 205

Asn Leu Cys Asn Gln Asn Gly Ala Phe Arg Ser Phe Leu Gly His Val
    210                 215                 220

Gln Glu Ala Glu Asp Lys Asn Asp Leu Thr Ser Ser Ile Ala Leu Asn
225                 230                 235                 240

Leu Asn Ser His Thr Met His Thr Glu Lys Met Thr Glu Tyr Gln Gln
                245                 250                 255

Gln Phe Arg Gly Lys Ala Asn Ile Ser Arg Asp Ser Asp Val Asp Gly
            260                 265                 270

Gln Val Ser Arg Lys Glu Ser Leu Gln Arg Tyr Leu Glu Lys Arg Lys
        275                 280                 285

Asp Arg Gly Arg Phe Phe Lys Gly Arg Lys Asn Ala Gly Gln Ala Leu
    290                 295                 300

Ser Ser Ser Glu Met Tyr Leu Asn His Gln Ile Arg Ala His Tyr Leu
305                 310                 315                 320

Asn Gly Gln Thr Asn Gln Ser Arg Thr Ser Ser Pro Pro Gln Ser Gly
                325                 330                 335
```

```
Val Pro His Ala Phe Tyr Ser Ser Ala Asp Asn Gln Glu Leu Val Asn
            340                 345                 350

Phe Ser Val Asp Leu Asn Asp Glu Gly Gly Gln Glu His
        355                 360                 365


<210> SEQ ID NO 7
<211> LENGTH: 357
<212> TYPE: PRT
<213> ORGANISM: Aquilegia coerulea

<400> SEQUENCE: 7

Met Lys Pro Asp Glu Thr Val Ser Arg Ser Pro Leu Asp Lys Pro Leu
1               5                   10                  15

Phe Gln Leu Thr Asp Glu Asp Ile Ser Gln Leu Thr Arg Glu Asp Cys
            20                  25                  30

Arg Lys Phe Leu Arg Asp Lys Gly Met Arg Arg Pro Ser Trp Asn Lys
        35                  40                  45

Ser Gln Ala Ile Glu Gln Val Ile Ser Leu Lys Thr Leu Leu Glu Pro
    50                  55                  60

Arg Thr Glu Ser Asp Thr Asn Ala Thr Gly Ile Arg Gln Lys Leu Leu
65                  70                  75                  80

Val Ser Arg Leu Glu Asn Ser Thr Gln Val Pro Leu Asn Asp Lys Thr
                85                  90                  95

Asn Ala Ser Asn Leu Lys Thr Ser Val Gln Ala Ile Asn Ser Gly Lys
            100                 105                 110

Ala Asp Ile His Gly Asp Arg Pro Cys Arg Val Pro Val Pro Val Pro
        115                 120                 125

Asp Asp Asn Thr Ile Thr Val Pro Val Pro Asp Asn Asn Thr Ile Thr
    130                 135                 140

Val Pro Val Pro Asp Asn Asn Ile Thr Ser Ser Arg Asn Leu Asn Ser
145                 150                 155                 160

Thr Asn Gly Leu Val Gly Gln Met Thr Ile Phe Tyr Cys Gly Lys Val
                165                 170                 175

Ile Val Tyr Asp Asp Met Pro Ala Glu Lys Ala His Ala Ile Met Lys
            180                 185                 190

Phe Ala Gly Ser His Ile Asn Val Pro Glu Asp Ser Ser Pro Ala Gly
        195                 200                 205

Ala Ala Val Ile Gln Ser Phe Ala Cys Gln Leu Gln Ala Ala Ser Ile
    210                 215                 220

Arg His Gly Leu Ala Phe Pro Ser Ala Val Ser Pro Pro Leu His Asn
225                 230                 235                 240

Val Val Ala Asp Thr Ser Gln His Cys Arg Glu Glu Val Thr Val Ser
                245                 250                 255

Arg Glu Val Glu Pro Glu Gly Pro Val Ser Arg Lys Ala Ser Val Gln
            260                 265                 270

Arg Tyr Leu Glu Lys Arg Lys Asp Arg Gly Arg Phe Lys Asn Lys Arg
        275                 280                 285

Lys Ile Glu Ser Ser Ser Ser Leu Glu Ile Tyr Leu Asn His Gln Leu
    290                 295                 300

Gly Asp Gln Tyr Leu Asn Glu Lys Ser Ser Gln Ser Arg Ala Cys Ser
305                 310                 315                 320

Pro Pro Gln Pro Arg Ala Pro His Thr Pro Thr Arg Cys Ser Ser Val
                325                 330                 335

Glu Asn Gln Val Thr Asn Val Val Phe Ser Ile Asp Leu Asn Asp Asn
```

340 345 350

Asp Val Arg Glu Gly
355

<210> SEQ ID NO 8
<211> LENGTH: 347
<212> TYPE: PRT
<213> ORGANISM: Aquilegia coerulea

<400> SEQUENCE: 8

Met Lys Pro Asp Glu Thr Val Ser Arg Ser Pro Leu Asp Lys Pro Leu
1 5 10 15

Phe Gln Leu Thr Asp Glu Asp Ile Ser Gln Leu Thr Arg Glu Asp Cys
20 25 30

Arg Lys Phe Leu Arg Asp Lys Gly Met Arg Arg Pro Ser Trp Asn Lys
35 40 45

Ser Gln Ala Ile Glu Gln Val Ile Ser Leu Lys Thr Leu Leu Glu Pro
50 55 60

Arg Thr Glu Ser Asp Thr Asn Ala Thr Gly Ile Arg Gln Lys Leu Leu
65 70 75 80

Val Ser Arg Leu Glu Asn Ser Thr Gln Val Pro Leu Asn Asp Lys Thr
85 90 95

Asn Ala Ser Asn Leu Lys Thr Ser Val Gln Ala Ile Asn Ser Gly Glu
100 105 110

Ala Asp Ile His Gly Asp Arg Pro Cys Arg Val Pro Val Pro Val Pro
115 120 125

Asp Asp Asn Thr Ile Thr Val Pro Val Pro Asp Asn Asn Ile Thr Ser
130 135 140

Ser Arg Asn Leu Asn Ser Thr Asn Gly Leu Val Gly Gln Met Thr Ile
145 150 155 160

Phe Tyr Cys Gly Lys Val Ile Val Tyr Asp Gly Met Pro Ala Glu Lys
165 170 175

Ala His Ala Ile Met Lys Phe Ala Gly Ser His Ile Asn Val Pro Glu
180 185 190

Asp Ser Ser Pro Ala Gly Ala Ala Val Ile Gln Ser Phe Ala Cys Gln
195 200 205

Leu Gln Ala Ala Ser Ile Arg His Gly Leu Ala Phe Pro Ser Ala Val
210 215 220

Ser Pro Pro Leu His Asn Val Val Ala Asp Thr Ser Gln His Cys Arg
225 230 235 240

Glu Glu Val Thr Val Ser Arg Glu Val Glu Pro Glu Gly Pro Val Ser
245 250 255

Arg Lys Ala Ser Val Gln Arg Tyr Leu Glu Lys Arg Lys Asp Arg Gly
260 265 270

Arg Phe Lys Asn Lys Arg Lys Ile Glu Ser Ser Ser Ser Leu Glu Ile
275 280 285

Tyr Leu Asn His Gln Leu Gly Asp Gln Tyr Leu Asn Glu Lys Ser Ser
290 295 300

Gln Ser Arg Ala Cys Ser Pro Pro Gln Pro Arg Ala Pro His Thr Pro
305 310 315 320

Thr Arg Cys Ser Ser Val Glu Asn Gln Val Thr Asn Val Val Phe Ser
325 330 335

Ile Asp Leu Asn Asp Asn Asp Val Arg Glu Gly
340 345

<210> SEQ ID NO 9
<211> LENGTH: 328
<212> TYPE: PRT
<213> ORGANISM: Medicago truncatula

<400> SEQUENCE: 9

```
Met Asn Gly Gly Ser Thr Val Ser Phe Arg Ser Ile Leu Asp Arg Pro
1               5                   10                  15

Leu Asn Gln Leu Thr Glu Asp Asp Ile Ser Gln Leu Thr Arg Glu Asp
            20                  25                  30

Cys Arg Arg Phe Leu Lys Asp Lys Gly Met Arg Arg Pro Ser Trp Asn
        35                  40                  45

Lys Ser Gln Ala Ile Gln Gln Val Ile Ser Leu Lys Ala Leu Leu Glu
    50                  55                  60

Pro Thr Asp Asp Asp Ile Pro Ala Thr Val Gly Val Gly Val Ser Ser
65                  70                  75                  80

Ala Ile His His His His His His His Pro Pro Gln Pro Pro Pro Lys
                85                  90                  95

Ala Leu Asp Pro Glu Asp Thr Ala Leu Glu Leu Gln Lys Ser Thr Ser
            100                 105                 110

Pro Val Ala Glu Arg Pro Thr Glu Thr Asn Asp Ala Asn Val Val Asn
        115                 120                 125

Asn Pro Gly Gly Cys Ala Pro Ser Gly Ser Phe Gly Gln Met Thr Ile
    130                 135                 140

Phe Tyr Cys Gly Lys Val Asn Val Tyr Asp Gly Val Ser Pro Asp Lys
145                 150                 155                 160

Ala Arg Ser Ile Met Gln Leu Ala Ala Ala Cys Pro Ser Ser Phe Pro
                165                 170                 175

Gln Asp Asn Pro Ser Asn Lys Asn Ala Ala Val Trp Ala Ser Pro Cys
            180                 185                 190

Asn Leu Pro Ile Asp Lys Glu Val Leu Phe Pro Thr Asp Thr Ala Ile
        195                 200                 205

Leu Gln Val Ala Gln Thr Asp Lys Met Val Glu Tyr Pro Leu Gln Tyr
    210                 215                 220

Arg Glu Lys Gly Ser Thr Ala Arg Asp Ala Glu Gly Gln Ala Ser Arg
225                 230                 235                 240

Lys Val Ser Leu Gln Arg Tyr Leu Glu Lys Arg Lys Asp Arg Gly Arg
                245                 250                 255

Ser Lys Gly Lys Lys Leu Thr Gly Ile Thr Ser Ser Asn Phe Glu Met
            260                 265                 270

Tyr Leu Asn Leu Pro Val Lys Leu His Ala Ser Asn Gly Asn Ser Ser
        275                 280                 285

Arg Ser Ser Thr Asp Ser Pro Pro Gln Pro Arg Leu Pro Leu Val Ser
    290                 295                 300

Ser Gly Ser Ala Glu Asn Gln Pro Lys Val Thr Leu Pro Ile Asp Leu
305                 310                 315                 320

Asn Asp Lys Asp Val Gln Glu Cys
                325
```

<210> SEQ ID NO 10
<211> LENGTH: 339
<212> TYPE: PRT
<213> ORGANISM: Solanum lycopersicum

<400> SEQUENCE: 10

-continued

Met Ser Leu Glu Gln Thr Val Tyr Lys Ser Pro Leu Asp Lys Pro Leu
1 5 10 15

Tyr Leu Leu Thr Asp Asp Asp Ile Ser Gln Leu Thr Arg Glu Asp Cys
20 25 30

Arg Arg Phe Leu Lys Ala Lys Gly Met Arg Lys Pro Ser Trp Asn Lys
35 40 45

Ser Gln Ala Ile Gln Gln Val Ile Ser Leu Lys Ala Leu Phe Glu Thr
50 55 60

Thr Pro Glu Ser Asp Thr Gly Gln Arg Lys Lys Arg His Ile Pro Arg
65 70 75 80

Pro Asp Thr Ser Leu Gln Arg Val Gln Lys Glu Thr Ser Ile Asp Ala
85 90 95

Glu Phe Ala Glu Ser Ala Glu Glu Thr Val Pro Tyr Gly Arg Lys Pro
100 105 110

Pro Asn Lys Pro Asp Leu Ser Gly Asp Lys Ala Ala Ser Ala Val Ala
115 120 125

Val Val Asn Asn Leu Ala Pro Ser Arg Thr Thr Asp Ser Gly Asn Ala
130 135 140

Ser Ser Gly Gln Leu Thr Ile Phe Tyr Cys Gly Lys Val Asn Val Tyr
145 150 155 160

Asp Asp Val Pro Ala Glu Lys Ala Glu Ala Ile Met His Leu Ala Ala
165 170 175

Ser Pro Leu Phe Val Pro Ser Glu Thr Pro Leu Asp Ala Asn Arg Ala
180 185 190

Ala Gln His Ser Glu Cys His Leu Gln Ala Ala Asn Val Lys Leu Gly
195 200 205

Gln Asp Ser Pro Met Val Phe Met Pro Thr Met Gln Thr Gly Lys Ile
210 215 220

Thr Glu Val Thr Arg Leu His Leu Glu Glu Ser Asn Thr Ser Tyr Glu
225 230 235 240

Asp Asn Pro Glu Ala Val Asn His Val Ser Arg Lys Ala Leu Leu Glu
245 250 255

Arg Tyr Arg Glu Lys Arg Lys Asp Arg Phe Lys Arg Lys Met Gly Met
260 265 270

Pro Ser Ser Ala Ser Leu Asp Ile Tyr Leu Asn His Arg Thr Ile Asn
275 280 285

His Thr Gln Ser Glu Leu Ser Ser Arg Ser Asn Thr Cys Ser Pro Pro
290 295 300

Ala Ile Arg Leu Ser Ala Ala Pro Ala Pro Ser Gly Ser Met Asp Asn
305 310 315 320

Ile Leu Gln Met Asp Ala Asn Ala Ser Gly Phe Leu Asp Asp Lys Asp
325 330 335

Gly Lys Glu

<210> SEQ ID NO 11
<211> LENGTH: 338
<212> TYPE: PRT
<213> ORGANISM: Trifolium repens

<400> SEQUENCE: 11

Met Asn Gly Gly Ser Thr Val Ser Phe Arg Ser Ile Leu Asp Lys Pro
1 5 10 15

Leu Asn Gln Leu Thr Glu Asp Asp Ile Ser Gln Leu Thr Arg Glu Asp
20 25 30

```
Cys Arg Arg Phe Leu Lys Asp Lys Gly Met Arg Arg Pro Ser Trp Asn
        35                  40                  45

Lys Ser Gln Ala Ile Gln Gln Val Ile Ser Leu Lys Ala Leu Leu Glu
    50                  55                  60

Pro Thr Asp Asp Asp Leu Pro Ala Pro Val Gly Val Ser Ser Ala Ile
65                  70                  75                  80

His His His His His His His Pro Gln Pro Pro Gln Arg Asn Leu Asn
                85                  90                  95

Glu Ala Pro Val Lys Gly Ser Asp Leu Asp Asp Thr Gly Phe His Thr
            100                 105                 110

Ala Glu Asp Leu Asn Lys Ser Thr Ser Thr Ala Val Glu Ile Pro Thr
        115                 120                 125

Glu Thr Asn Asp Ala Asn Val Val Lys Ser Ser Gly Gly Cys Val Ala
    130                 135                 140

Ser Gly Ser Phe Gly Gln Met Thr Ile Phe Tyr Cys Gly Lys Val Asn
145                 150                 155                 160

Val Tyr Asp Gly Val Ser Pro Asp Lys Ala Arg Ser Ile Met Gln Leu
                165                 170                 175

Ala Ala Cys Pro Ser Ser Phe Pro Gln Asp Asn Leu Leu Asn Lys Asn
            180                 185                 190

Ala Ala Val Trp Ala Ser Pro Cys Asn Ile Pro Ile Asp Lys Asp Val
        195                 200                 205

Leu Phe Pro Asn Asp Thr Ala Ile Leu Gln Val Ala Gln Thr Asp Lys
    210                 215                 220

Met Val Glu Tyr Pro Leu Gln Tyr Arg Glu Lys Gly Ser Ile Ala Arg
225                 230                 235                 240

Asp Ala Asp Val Glu Gly Gln Ala Ser Arg Asn Ala Ser Leu Gln Arg
                245                 250                 255

Tyr Arg Glu Lys Arg Lys Asp Arg Gly Arg Ser Lys Gly Asn Lys Leu
            260                 265                 270

Thr Gly Ile Thr Ser Ser Asn Phe Glu Met Tyr Leu Asn Leu Pro Val
        275                 280                 285

Lys Leu His Ala Ser Asn Gly Asn Ser Ser Arg Ser Ser Thr Asp Ser
    290                 295                 300

Pro Pro Gln Pro Arg Leu Pro Leu Val Ser Gly Gly Ser Ala Glu Asn
305                 310                 315                 320

Gln Pro Lys Val Thr Leu Pro Ile Asp Leu Asn Asp Lys Asp Val Gln
                325                 330                 335

Glu Cys


<210> SEQ ID NO 12
<211> LENGTH: 311
<212> TYPE: PRT
<213> ORGANISM: Amborella trichopoda

<400> SEQUENCE: 12

Met Thr Ala Gly Asp Gly Ser Ile Arg Ser Ile Leu Asp Lys Pro Leu
1               5                   10                  15

Glu Glu Leu Thr Glu Glu Asp Ile Ser Gln Leu Thr Arg Glu Asp Cys
            20                  25                  30

Arg Arg Tyr Leu Lys Glu Lys Gly Met Arg Arg Pro Ser Trp Asn Lys
        35                  40                  45

Tyr Gln Ala Ile Gln Gln Val Leu Ser Leu Lys Gly Leu Leu Glu Gly
    50                  55                  60
```

Lys Pro Cys Asp Asp Asn Ser Asp Val Phe Ser His Arg Ser Pro Ile
65 70 75 80

Thr Val Ile Pro Asn Val Gly Ser Met Arg Glu Lys Glu Lys Ala Val
85 90 95

Asn Ile Ala Asp Pro Glu Ile Ser Gly Ser His Gln Pro Asn Phe Arg
100 105 110

Arg Glu Ile His Glu Thr Thr Arg Glu Arg Ala Leu Pro Ala Ser Asp
115 120 125

Trp Pro Pro Ser Gln Glu Pro Val Ser Gln Met Thr Ile Phe Tyr Ala
130 135 140

Gly Ala Val Asn Val Tyr Asn Asp Ile Pro Glu Asp Lys Val Gln Ala
145 150 155 160

Ile Ile Tyr Leu Ala Gly Lys Ser Asp Ser Leu Gln Gln Thr Asn Val
165 170 175

Ile Arg Thr Gly Pro Asp Gln Cys Ile Ala Ser Ala Ala Ser Pro Ser
180 185 190

Leu Asn Asp Leu His Ser Arg Arg Ile His Pro Thr Ser Asn Ile Thr
195 200 205

Thr Ser Gln Ser Leu Arg Val Ala Thr Ser Leu Pro Val Gly Pro His
210 215 220

Ser Glu Val Pro Lys Thr Arg Lys Thr Ser Val Gln Arg Phe Leu Glu
225 230 235 240

Lys Arg Lys Asp Arg Gly Arg Leu Lys Gly Thr Leu Ala Ser Gly Gly
245 250 255

Ser Ser Lys Arg Gly Ser Ser Cys Leu Glu Leu Tyr Ala Thr Ser Arg
260 265 270

Leu Lys Ser Glu Gly Val Ala Thr Thr Thr Thr Gln Ser Asn Met Asn
275 280 285

Asn Val Val Val Ser Pro Ser Asn Pro Arg Met Pro Leu Asn Pro Gly
290 295 300

Ser Cys Ser Trp Val Glu Asn
305 310

<210> SEQ ID NO 13
<211> LENGTH: 416
<212> TYPE: PRT
<213> ORGANISM: Selaginella moellendorffii

<400> SEQUENCE: 13

Met Ala Ala Ser Ile Leu Gly Cys Gly Ser Ser Asn Gly Val Ala Val
1 5 10 15

Thr Gly Asn Pro Ala Pro Ala Ala Ala Ala Glu Val Pro Ala Pro Leu
20 25 30

Arg Pro Leu Glu Glu Leu Thr Glu Leu Asp Ile Arg Gln Leu Thr Arg
35 40 45

Glu Asp Cys Arg Arg Tyr Leu Lys Glu Arg Gly Met Arg Arg Pro Ser
50 55 60

Trp Asn Lys Ala Gln Ala Ile Gln Gln Val Leu Ser Leu Arg Ser Leu
65 70 75 80

Leu Cys Pro Ser Asn Pro Val Gly Pro Ser Ser Lys Asn Pro Gly Ser
85 90 95

Ala Ala Asn Ala Pro Pro Ala Glu Ala Ala Ala Ala Gly His Thr Lys
100 105 110

Gln Leu Leu Asp Lys Val Ser Gln Gln Ser Met Pro Asp Ser Cys Pro
115 120 125

Ser Asn Asn Ala Ser Asp Pro Arg Pro Leu Ala Gly Cys Phe Gly Ser
    130                 135                 140

Leu Ala Pro Thr Leu Ser Val Leu Asn Pro Asp Ala Lys Arg Asn Pro
145                 150                 155                 160

Leu Ser Ser Lys Pro Ala Ser Thr Thr Lys Pro His Ser Ala Gln Leu
                165                 170                 175

Thr Ile Phe Tyr Ser Gly Ile Val Asn Val Tyr Asp Asp Val Pro Leu
            180                 185                 190

Asp Lys Ala Gln Ala Ile Met Leu Leu Ala Ala Ser Lys Thr Phe His
        195                 200                 205

Val Pro Thr Ser Ser Val Pro Gly His Pro Pro Phe Thr Ser Ala Thr
    210                 215                 220

Gln Gln Gln Gln Gln Gln Gln Arg Glu Leu Asn Gln Gln Thr Glu Ala
225                 230                 235                 240

Thr Gln Lys Tyr Pro Met Gln His Gln Gln Ala Pro Gln Ile Tyr Leu
                245                 250                 255

Ser Ser Gly Ser Ala Leu Pro Asp Glu Ser Cys Thr Glu Pro Gly Leu
            260                 265                 270

Pro Gln Val Arg Ser Ala Ser Leu Gln Arg Phe Leu Ala Lys Arg Arg
        275                 280                 285

Asp Arg Leu Ser Gly Asn Pro Ser Ser Ser Arg Arg Asn Asp Arg Ser
    290                 295                 300

Lys Lys Arg Arg Phe Ser Pro Pro Pro Ser Pro Leu Thr Ser Ala Ser
305                 310                 315                 320

Phe Gln Phe Pro Pro Ser Ala Arg Thr Ser Gln Val Leu Arg Tyr Ser
                325                 330                 335

Thr Thr Ser Thr Thr Thr Ile Thr Thr Ala Thr Ala Thr Ala Ala Thr
            340                 345                 350

Thr Thr Thr Thr Thr Gly Thr Thr Asn Gly Gly His Cys Ser Asn Ser
        355                 360                 365

Asn Gln Ala Ser Glu Asn Ala Gly Ser Asp Thr Ser Gly Gly Ser Ser
    370                 375                 380

Gly Thr Pro Asp Thr Ser Asp Thr Thr Arg Asp Asn Asp Asn Gly Arg
385                 390                 395                 400

Val Ser Asn Glu Asn Gly Arg Val Ser Thr Thr Cys Leu Ala Ala Thr
                405                 410                 415

<210> SEQ ID NO 14
<211> LENGTH: 234
<212> TYPE: PRT
<213> ORGANISM: Selaginella moellendorffii

<400> SEQUENCE: 14

Met Ser Ser Met Val Asp Phe Leu Gly Ile Glu Glu Lys Val Ser Thr
1               5                   10                  15

Ser Val Ser Ala Glu Arg Leu Lys Lys Leu Glu Glu Leu Thr Asp Glu
            20                  25                  30

Asp Val Met Gln Leu Thr Arg Glu Asp Cys Arg Arg Tyr Leu Lys Glu
        35                  40                  45

Lys Gly Met Arg Arg Pro Ser Trp Asn Lys Ala Gln Ala Val Gln Gln
    50                  55                  60

Leu Leu Ser Leu Lys Ser Leu Cys Asp Pro Ser Pro Ala Ser Ser Gly
65                  70                  75                  80

Ala Ala Lys Arg Ser Pro Ser Pro Pro Leu Asp Glu Ala Pro Ala Lys

-continued

```
                85                  90                  95

Lys Pro Met Ala Met Thr Ser Ile Asp Leu Lys Ala Ala Ala Ala Val
            100                 105                 110

Asp Ala Ala Asn Leu Thr Met Phe Tyr Asp Gly Ala Val Ser Val Phe
        115                 120                 125

Asp Asp Val Ser Pro Asp Lys Ala Ser Leu Phe Pro Leu Ala Tyr Ala
    130                 135                 140

Ile Met Leu Leu Ala Gly Asn Val Lys Ser Trp Pro Ser Ile Asn Val
145                 150                 155                 160

Ala Ala Asn Thr Asn Lys Val Val Ile Ser Ser Tyr Glu Leu Pro Gln
                165                 170                 175

Ala Arg Lys Ala Ser Leu Gln Arg Phe Leu Gln Arg Arg Arg Glu Lys
            180                 185                 190

Thr Ala Lys Glu Ala Ala Ser Lys Gly Asn Ser Asn Lys Ser Pro Cys
        195                 200                 205

His Gly Glu Ser Ser Gly Lys His Ala Ser Asp Ala Thr Asp Pro Ala
    210                 215                 220

Thr Ser Pro Leu Leu Thr Glu Val Ser Ser
225                 230


<210> SEQ ID NO 15
<211> LENGTH: 271
<212> TYPE: PRT
<213> ORGANISM: Nicotiana tabacum

<400> SEQUENCE: 15

Met Pro Pro Glu Glu Thr Val Ser Lys Ser Pro Leu Asp Lys Pro Leu
1               5                   10                  15

His Leu Leu Thr Asp Asp Asp Ile Ser Gln Leu Thr Arg Glu Asp Cys
            20                  25                  30

Arg Arg Tyr Leu Lys Glu Lys Gly Met Arg Arg Pro Ser Trp Asn Lys
        35                  40                  45

Ser Gln Ala Ile Gln Gln Val Ile Ser Leu Lys Ala Leu Leu Glu Thr
    50                  55                  60

Thr Pro Asp Ser Asp Thr Gly Pro Arg Arg Lys Leu His Ile Pro Arg
65                  70                  75                  80

Pro Asp Thr Arg Val Gln Gln Val Gln Lys Gly Thr Asp Thr Asp Ala
                85                  90                  95

Glu Phe Ser Lys Ser Ala Glu Gly Met Val Pro Tyr Gly Arg Lys His
            100                 105                 110

Ser Lys Lys Pro Asp Ile Pro Gly Asp Ile Ala Ala Gly Ser Val Ala
        115                 120                 125

Val Ala Ala Gly Asn Asn Leu Ala Pro Ser Arg Thr Thr Asp Leu Gly
    130                 135                 140

Asn Thr Pro Ala Ser Gln Leu Thr Ile Phe Tyr Cys Gly Lys Val Asn
145                 150                 155                 160

Val Tyr Asp Asp Val Pro Ala Glu Lys Ala Gln Ala Ile Met His Leu
                165                 170                 175

Ala Ala Thr Pro Leu Phe Val Pro Ser Glu Thr Pro Leu Gly Ala Thr
            180                 185                 190

Leu Ala Ala Arg His Ser Glu Cys His Leu Gln Ala Ala Ser Val Lys
        195                 200                 205

Gln Gly Pro Asp Ser Ala Met Val Leu Met Pro Thr Met Gln Thr Gly
    210                 215                 220
```

```
Lys Met Ser Glu Val Thr Arg Leu Arg Leu Glu Glu Ser Asn Thr Phe
225                 230                 235                 240

Tyr Glu Asp Asn Ser Ala Asn Tyr Ala Glu Ala Val Glu Gly His Pro
                245                 250                 255

Ser Arg Lys Ala Ser Val Gln Arg Tyr Leu Glu Lys Arg Lys Asp
            260                 265                 270


<210> SEQ ID NO 16
<211> LENGTH: 327
<212> TYPE: PRT
<213> ORGANISM: Solanum tuberosum

<400> SEQUENCE: 16

Met Pro Pro Glu Glu Thr Val Ser Lys Ser Pro Leu Asp Lys Pro Leu
1               5                   10                  15

Asn Gln Leu Thr Asp Asp Asp Ile Ser Gln Leu Thr Arg Glu Asp Cys
            20                  25                  30

Arg Arg Tyr Leu Lys Gln Lys Gly Met Arg Lys Pro Ser Trp Asn Lys
        35                  40                  45

Ser Gln Ala Ile Gln Gln Val Ile Ser Leu Lys Ala Leu Leu Glu Pro
    50                  55                  60

Asp Thr Asp Ala Gly Thr Arg Lys Lys Leu His Ile Pro Arg Ala Asp
65                  70                  75                  80

Thr His Val Gln Ser Gly Lys Asn Thr Tyr Gly Glu Pro Ser Glu Pro
                85                  90                  95

Val Pro Asp Arg Arg Asn Gln Gln Asp Arg Pro Asp Leu Ser Ser His
            100                 105                 110

Ile Thr Ala Leu Pro Val Ala Val Val Asp Asn Ser Ala Pro Ser Arg
        115                 120                 125

Thr Ile Gly Ser Ala Asp Lys Pro Val Gly Gln Met Thr Ile Phe Tyr
    130                 135                 140

Arg Gly Lys Val Asn Val Tyr Asp Asp Val Pro Ala Asp Lys Ala Gln
145                 150                 155                 160

Lys Ile Met Cys Leu Ala Ser Ser Pro Leu Cys Val Pro Ser Glu Thr
                165                 170                 175

Pro Ser Asn Ala Thr Val Ala Ala Arg His Ser Ala Cys Cys Leu Gln
            180                 185                 190

Ala Ala Asn Ser Lys Leu Arg Leu Asp Thr Asn Ile Val Pro Thr Ile
        195                 200                 205

Gln Thr Val Lys Met Ser Glu Val Ser Arg Val Pro Ile Glu Glu Ser
    210                 215                 220

Asn Arg Leu Tyr Asn Asp Asn Pro Glu Ala Val Glu Ser Pro Ala Ser
225                 230                 235                 240

Arg Lys Ala Ser Val Gln Arg Tyr Leu Glu Lys Arg Lys Glu Arg Phe
                245                 250                 255

Lys Trp Lys Arg Lys Val Glu Thr Thr Ser Ser Ala Ser Leu Asp Ile
            260                 265                 270

Tyr Leu Ser Asp Arg Ile Gly Thr Arg Thr Pro Ser Asp Tyr Ala Ser
        275                 280                 285

Gly Ala Asp Leu Cys Phe Thr Pro His Ile Thr Pro Thr Gly Ser Gly
    290                 295                 300

Pro Ile Gln Asp Asn Ile Gln Met Asn Pro Thr Phe Ser Ser Asp Leu
305                 310                 315                 320

Asn Asp Arg Asp Val Arg Glu
                325
```

<210> SEQ ID NO 17
<211> LENGTH: 348
<212> TYPE: PRT
<213> ORGANISM: Glycine max

<400> SEQUENCE: 17

Met Asn Gly Gly Ala Thr Thr Ala Thr Phe Arg Ser Ile Leu Asp Lys
1 5 10 15

Pro Leu Asn Gln Leu Thr Glu Asp Asp Ile Ser Gln Leu Thr Arg Glu
20 25 30

Asp Cys Arg Arg Phe Leu Lys Glu Lys Gly Met Arg Arg Pro Ser Trp
35 40 45

Asn Lys Ser Gln Ala Ile Gln Gln Val Ile Ser Leu Lys Ala Leu Leu
50 55 60

Glu Pro Ser Asp Asp Asp Thr Pro Pro Pro Thr Ala Met His His Arg
65 70 75 80

Ser His Ala Pro Pro Pro Pro Pro Gln Pro Gln Ser Gln Val Asn Leu
85 90 95

Thr Glu Pro Pro Pro Pro Pro Lys Ala Pro Pro Pro Glu Glu Ser Ser
100 105 110

Phe His Ala Ala Glu Asp Ile Gln Lys Pro Ala Ser Ser Gly Glu Lys
115 120 125

Pro Ser Glu Thr Asn Asp Thr Asn Thr Asn Val Ala Ser Pro Lys Gly
130 135 140

Cys Ala Thr Ser Gly Ser Phe Gly Gln Met Thr Ile Phe Tyr Cys Gly
145 150 155 160

Lys Val Asn Val Tyr Asp Gly Val Ser Pro Asp Lys Ala Arg Ala Ile
165 170 175

Met Gln Leu Ala Val Ser Pro Val Gln Phe Thr Gln Asp Asp Pro Ser
180 185 190

Asn Gly Asn Ala Ala Val Trp Pro Ser Pro Cys His Leu Pro Met Asp
195 200 205

Lys Asp Val Leu Ile Pro Val Asp Thr Thr Ile Leu Gln Val Ala Gln
210 215 220

Ser Asp Lys Met Met Glu Tyr Pro Leu Gln Tyr Arg Glu Lys Gly Ser
225 230 235 240

Ile Ala Arg Asp Ala Glu Gly Gln Ala Ser Arg Lys Val Ser Leu Gln
245 250 255

Arg Tyr Leu Glu Lys Arg Lys Asp Arg Gly Arg Leu Lys Gly Lys Lys
260 265 270

Leu Thr Gly Ile Thr Ser Ser Asn Phe Glu Met Tyr Leu Asn Leu Pro
275 280 285

Val Lys Val His Ala Ser Asn Gly Asn Ser Ser Arg Ser Ser Thr Ser
290 295 300

Ser Pro Pro Gln Pro Arg Leu Pro Leu Val Ser Ser Gly Ser Ala Asp
305 310 315 320

Asn Gln Leu Lys Val Ala Leu Pro Ile Asp Leu Asn Asp Lys Val Ser
325 330 335

Leu Gln Met Phe Lys Asn Ala Lys Thr Leu Thr Arg
340 345

<210> SEQ ID NO 18
<211> LENGTH: 338
<212> TYPE: PRT

<213> ORGANISM: Citrus clementine

<400> SEQUENCE: 18

Met Asp Val Asp Gly Gly Val Thr Ser Cys Arg Ser Ile Leu Glu Lys
1 5 10 15

Pro Leu Ser Gln Leu Thr Glu Glu Asp Ile Thr Gln Leu Thr Arg Glu
20 25 30

Asp Cys Arg Lys Phe Leu Lys Glu Lys Gly Met Arg Arg Pro Ser Trp
35 40 45

Asn Lys Ser Gln Ala Ile Gln Gln Val Ile Ser Leu Lys Ala Leu Leu
50 55 60

Glu Ser Ser Gly Asp Ser Gly Ser Gly Val Leu Arg Arg Val Leu Val
65 70 75 80

Ser Pro Pro Glu Ser Met Pro Pro Arg Val Asn Val Thr Ser Asn Ser
85 90 95

Ala Asp Leu Val Lys Glu Pro Thr Ile Ser Val Ser Gly Asp Gln Asn
100 105 110

Ser Ala Tyr Arg Arg Lys Tyr Pro Arg Asn Cys Ala Val Asp Ala Asp
115 120 125

Asn Lys Thr Ile Ser Asn Arg Asn Pro Cys Glu Ala Asn Gly Ser Ile
130 135 140

Gly Gln Met Thr Ile Phe Tyr Cys Gly Lys Val Asn Val Tyr Glu Gly
145 150 155 160

Val Pro Thr Asp Lys Ala Gln Glu Ile Met His Leu Ala Ala Thr Pro
165 170 175

Ile Asp Phe Ser Gln Asn Gly Ser Phe Gly Gly Ile Thr Ala Tyr Arg
180 185 190

Ala Ile Pro Cys His Leu Gln Val Thr Ser Asn Arg His Val Ser Leu
195 200 205

Pro Leu Arg Pro Ala Ala Met Ile Ser Gln Phe Met Gln Thr Gly Lys
210 215 220

Ile Ala Asp Tyr Ser Gln Glu Tyr Arg Glu Lys Ala Ile Ser Thr His
225 230 235 240

Asp Ser Asp Val Asp Gly Gln Val Asn Arg Lys Val Ser Leu Gln Arg
245 250 255

Tyr Leu Glu Lys Arg Lys Asp Arg Gly Arg Phe Phe Lys Gly Lys Lys
260 265 270

Asn Thr Gly Pro Thr Pro Ser Leu Glu Met Tyr Leu Asn His Pro Gly
275 280 285

Lys Thr His Ala Ser Asn Gly Gln Gln Ser Gln Ser Asn Thr Ser Ser
290 295 300

Pro Thr Gln Pro Glu Leu Ser Asn Thr Leu Gly Thr Ser Pro Asp Asn
305 310 315 320

Gln Ala Lys Thr Val Met Leu Pro Val Asp Leu Asn Asn Glu Asp Ile
325 330 335

Gln Asp

<210> SEQ ID NO 19
<211> LENGTH: 335
<212> TYPE: PRT
<213> ORGANISM: Ricinus communis

<400> SEQUENCE: 19

Met Asp Ala Gly Val Thr Ser Phe Arg Ser Ile Leu Asp Lys Pro Leu
1 5 10 15

Thr Gln Leu Thr Glu Glu Asp Ile Ser Gln Leu Thr Arg Glu Asp Cys
20 25 30

Arg Lys Tyr Leu Lys Glu Lys Gly Met Arg Arg Pro Ser Trp Asn Lys
35 40 45

Ser Gln Ala Ile Gln Gln Val Ile Ser Leu Lys Ala Leu Leu Glu Thr
50 55 60

Ser Glu Asp Ser Gly Ala Gly Ala Leu Arg Arg Ile Leu Val Ser Lys
65 70 75 80

Pro Pro Val Thr Ser Asn Ser Val Asp Ser Ala Lys Glu Pro Ser Asp
85 90 95

Ser Asn Asn Asn Asn Leu Leu Asp Glu Thr Ala Pro His Asp Ser Pro
100 105 110

Lys Ser Pro Pro Pro Ala Pro Ser Leu Asp Cys Pro Leu Glu Glu Ala
115 120 125

Asp Asn Lys Val Ile Ser Ser Arg Ser Pro Gly Ala Thr Asp Gly Leu
130 135 140

Val Gly Gln Met Thr Ile Phe Tyr Cys Gly Lys Val Asn Val Tyr Asp
145 150 155 160

Gly Val Pro Pro Asp Lys Ala Gln Ala Ile Met His Leu Ala Ala Thr
165 170 175

Pro Ile His Ser Pro Leu Asp Asp Pro Ile Arg Arg Pro Val Phe Ala
180 185 190

Phe Pro Tyr His Leu Gln Thr Pro Ser Asp Lys His Val Phe Val Pro
195 200 205

Ser Asn Ala Ala Ile Ser Pro Thr Thr Pro Thr Glu Lys Val Thr Glu
210 215 220

Tyr Ser Gln Gln Cys Arg Glu Lys Gly Asn Val Thr Tyr Asp His Asp
225 230 235 240

Val Glu Gly Gln Ala Asn Arg Lys Met Ser Leu Gln Arg Tyr Leu Glu
245 250 255

Lys Lys Lys Asp Arg Gly Arg Phe Lys Gly Arg Lys Asn Leu Gly Pro
260 265 270

Asn Ser Ser Ser Leu Asp Ala Tyr Leu Asn His Gln Met Arg Thr His
275 280 285

Ile Ser Asn Glu Gln Ser Thr Arg Ser Ser Thr Ser Ser Pro Thr Gln
290 295 300

Pro Gly Val Pro His Thr Ser Ser Asn Ser Ala Glu Asp Gln Leu Lys
305 310 315 320

Thr Ala Ser Phe Ala Val Asp Leu Asn Glu Asp Val Gln Glu Pro
325 330 335

<210> SEQ ID NO 20
<211> LENGTH: 393
<212> TYPE: PRT
<213> ORGANISM: Vitis vinifera

<400> SEQUENCE: 20

Met Asn Pro Gly Val Thr Thr Leu Arg Ser Ile Leu Asp Lys Pro Leu
1 5 10 15

His Glu Leu Thr Glu Glu Asp Ile Ser Gln Leu Thr Arg Glu Asp Cys
20 25 30

Arg Lys Tyr Leu Lys Glu Lys Gly Met Arg Arg Pro Ser Trp Asn Lys
35 40 45

Ser Gln Ala Ile Gln Gln Val Ile Ser Leu Lys Ser Leu Leu Glu Thr

-continued

```
    50                  55                  60

Ser Glu Gly Ser Gly Ala Gly Val Leu Arg Lys Ile Thr Asp Ser Pro
65                  70                  75                  80

Pro Ala Glu Asn Leu Pro Pro Val Thr Ser Asn Ser Ala Asp Ser Gly
                85                  90                  95

Lys Glu Leu Ser Ala Asp Ile Gln Ile Ser Val Ser Ala Asp Glu Leu
            100                 105                 110

Val Pro Leu Pro Pro Lys Asp His His Pro Glu Ser Thr Pro Ser Gly
        115                 120                 125

Glu Leu Ala Ser Arg Pro Pro Glu Ala Asp Thr Lys His Thr Cys Pro
    130                 135                 140

Arg Ser Pro Gly Ala Thr Asn Cys Leu Val Gly Gln Met Thr Ile Phe
145                 150                 155                 160

Tyr Cys Gly Lys Val Asn Val Tyr Asp Gly Val Pro Asp Asp Lys Ala
                165                 170                 175

Gln Ala Ile Met His Leu Ala Ala Ser Pro Phe His Leu Pro Ser Asp
            180                 185                 190

Asp Pro Phe Ser Gly Ala Ala Met Leu Cys Ser Ser Pro Cys His Leu
        195                 200                 205

His Thr Ala Asn Val Lys His Gly His Ile Pro Pro Arg Ala Met Val
    210                 215                 220

Ser Gln Thr Met Gln Thr Glu Lys Phe Thr Glu Tyr Ser Gln Gln Tyr
225                 230                 235                 240

Arg Glu Glu Val Asn Phe Thr Arg Gly His Gly Ser Glu Ala Leu Ser
                245                 250                 255

Gly Leu Arg Thr Val Gly Ser Pro Thr Ala Arg Pro Thr Glu Asp Met
            260                 265                 270

Glu Gln Thr Thr Cys Leu Thr Ile Trp Gly Thr Phe Arg Tyr Lys Val
        275                 280                 285

Met Pro Phe Glu Ile Tyr Glu Gly Ile Met Asp Val Glu Gly Gln Val
    290                 295                 300

Asp Arg Lys Leu Ser Leu Gln Arg Tyr Phe Glu Lys Arg Lys Asp Arg
305                 310                 315                 320

Phe Lys Ser Arg Lys Lys Ile Gly Leu Pro Ser Gly Ser Leu Glu Met
                325                 330                 335

Tyr Val Asn His Gln Ala Arg Thr Gln Pro Ser Asn Gly Gln Ser Ser
            340                 345                 350

Arg Ser Gly Thr Ser Ser Pro Pro Gln His Gly Leu Ser His Thr Leu
        355                 360                 365

Cys Ser Ser Ala Asp Asn His Thr Lys Asn Phe Thr Pro Phe Val Asp
    370                 375                 380

Leu Asn Ser Lys Asp Ile Gln Glu Ser
385                 390


<210> SEQ ID NO 21
<211> LENGTH: 343
<212> TYPE: PRT
<213> ORGANISM: Morus notabilis

<400> SEQUENCE: 21

Met Ser Ala Gly Thr Thr Ala Phe Arg Ser Ile Leu Asp Lys Pro Leu
1               5                   10                  15

Asn Gln Leu Thr Glu Asp Asp Ile Ser Gln Leu Thr Arg Glu Asp Cys
            20                  25                  30
```

-continued

```
Arg Lys Tyr Leu Lys Glu Lys Gly Met Arg Arg Pro Ser Trp Asn Lys
        35                  40                  45

Ser Gln Ala Ile Gln Gln Val Ile Ser Leu Lys Ala Leu Leu Glu Pro
    50                  55                  60

Cys Asp Asp Ser Gly Ala Gly Ala Leu Arg Arg Ile Val Ala Ser Thr
65                  70                  75                  80

Pro Pro Pro Pro Pro Thr Gln Asn Ala Pro Arg Val Ser Thr Phe Ser
                85                  90                  95

Val Thr Ser Asn Ser Ala Asp Ser Gly Lys Glu Ala Ser Val Asp Val
            100                 105                 110

Gln Val Ser Ala Glu Glu Ser Gly Pro Cys Gln Arg Lys Glu Gln Ala
        115                 120                 125

Lys Ser Ala Pro Glu Thr Glu Glu Arg Pro Ala Asp Ala Gly Glu Arg
    130                 135                 140

Ala Ser Pro Arg Ser His Cys Ala Thr Asp Ala Leu Val Gly Gln Met
145                 150                 155                 160

Thr Ile Phe Tyr Cys Gly Lys Val Asn Val Tyr Glu Gly Val Pro Pro
                165                 170                 175

Glu Lys Ala Arg Ala Ile Met His Leu Ala Ala Ser Pro Ile Pro Leu
            180                 185                 190

Ser Arg Glu Asn Ser Phe Gly Val Leu Ala Ala Pro Arg Ser Phe Pro
        195                 200                 205

Trp His Leu His Ala Ala Ser Asp Lys Gly Gly Leu Leu Pro Pro Ser
    210                 215                 220

Ala Thr Ile Ser Gln Pro Met Gln Thr Asp Lys Leu Ala Asp Tyr Ser
225                 230                 235                 240

Gln Gln Cys Trp Glu Lys Glu Asn Asp Gly Gln Ala Ser Arg Lys Leu
                245                 250                 255

Ser Leu Gln Lys Tyr Arg Glu Lys Lys Lys Asp Arg Gly Arg Leu Lys
            260                 265                 270

Thr Lys Arg Ser Thr Gly Phe Asn Ser Ser Ser Met Glu Val Tyr Phe
        275                 280                 285

Asn His Gln Val Lys Thr His Met Ser Asn Gly Asn Ser Ser Arg Ser
    290                 295                 300

Ser Thr Ser Ser Pro Thr Gln Pro Gly Leu Pro Gln Thr Leu Cys Ser
305                 310                 315                 320

Thr Val Asp Asn Gln Pro Lys Ile Pro Cys Leu Pro Val Asp Leu Asn
                325                 330                 335

Glu Lys Leu Thr Ile Glu Met
            340
```

<210> SEQ ID NO 22
<211> LENGTH: 364
<212> TYPE: PRT
<213> ORGANISM: Phoenix dactylifera

<400> SEQUENCE: 22

```
Met Tyr Trp Val Gly Ser Ala Gln Glu Arg Arg Arg Asp Gly Gly Arg
1               5                   10                  15

Ser Pro Leu Asp Lys Pro Leu Ser Leu Leu Thr Glu Glu Asp Ile Ala
            20                  25                  30

Gln Leu Thr Arg Glu Asp Cys Arg Arg Phe Leu Lys Glu Lys Gly Met
        35                  40                  45

Arg Arg Pro Ser Trp Asn Lys Ser Gln Ala Ile Gln Gln Val Ile Ser
    50                  55                  60
```

-continued

```
Leu Lys Ala Leu Leu Glu Gly Arg Pro Glu Ser Gly Glu Leu Pro Val
65                  70                  75                  80

Gly Ala Gly Tyr Arg Gln Lys Pro Pro Pro Arg Arg Pro Ala Ser Leu
                85                  90                  95

Pro Ser Leu Gln Glu Ala Ala Gly Asp Ser Thr Ala Ala Ala Lys Glu
            100                 105                 110

Pro Ser Pro Ser Ser Ser Leu Ser Pro Tyr Arg Arg Arg Asp Pro Ile
        115                 120                 125

Pro Pro Ile Ile Ser Ala Gly Gly Pro Ser Cys Arg Phe Pro Val Ala
    130                 135                 140

Gly Arg Asp Gln Gln Pro Pro Glu Thr Pro Ser Pro Ser Leu Arg Val
145                 150                 155                 160

Thr Ala Glu Val Pro Ala Gly Gln Met Thr Ile Phe Tyr Asp Gly Lys
                165                 170                 175

Val Asn Val Tyr Ser Asp Val Thr Val Asp Lys Ala Arg Ala Ile Leu
            180                 185                 190

Leu Leu Ala Gly Arg Arg Asp Cys Tyr Gly Ala Ala Ala Leu Pro Gly
        195                 200                 205

Pro Val His Ser Pro Gln Pro Ala Phe Leu Gly Pro Gly Gln Gly Pro
    210                 215                 220

Val Pro Thr Ala Pro Pro Leu Ala Ala Ala Leu Pro Thr Ser Pro Ala
225                 230                 235                 240

Gly Arg Leu Ala His Arg Phe Glu Gly Pro Ser Gly Val Pro Arg Gly
                245                 250                 255

Lys Ser Ser Leu Val Arg Glu Arg Ser Thr Ser Pro Glu Gly Pro Thr
            260                 265                 270

Ser Arg Lys Ala Ser Leu Gln Arg Tyr Leu Glu Lys Arg Lys Asp Arg
        275                 280                 285

Leu Lys Gly Arg Lys Thr Leu Gly Gly Ala Ser Ser Ser Ser Met Glu
    290                 295                 300

Ile Met Phe Leu Ser Gln Lys Phe Gly Gly Gln Ile Pro Asn Glu Gln
305                 310                 315                 320

Leu Ser Arg Ser Asn Thr Ser Ser Pro Thr Gln Pro Arg Pro Pro Gly
                325                 330                 335

Thr Pro Thr Arg Cys Ser Ser Ile Glu Asn Gln Ala Gln Lys Asn His
            340                 345                 350

Leu Ser Val Asp Leu Asn Asp Asp Gly Cys Gly Asn
        355                 360


<210> SEQ ID NO 23
<211> LENGTH: 354
<212> TYPE: PRT
<213> ORGANISM: Theobroma cacao

<400> SEQUENCE: 23

Met Glu Ala Gly Val Ala Thr Thr Thr Thr Thr Thr Glu Ser Phe Arg
1               5                   10                  15

Ser Ile Leu Asp Lys Pro Leu Ser Gln Leu Thr Glu Glu Asp Ile Ser
            20                  25                  30

Gln Leu Thr Arg Glu Asp Cys Arg Lys Phe Leu Lys Glu Lys Gly Met
        35                  40                  45

Arg Arg Pro Ser Trp Asn Lys Ser Gln Ala Ile Gln Gln Val Ile Ser
    50                  55                  60

Leu Lys Ala Leu Leu Glu Ser Asn Glu Asp Ser Gly Ala Gly Ala Ile
```

65 70 75 80

Arg Lys Ile Leu Val Ser Pro Pro Ser Pro Ser Val Pro Pro Gln Asn
85 90 95

Ala Ala Ala Arg Val Ala Ser Asn Ser Cys Asp Ser Val Lys Glu Ala
100 105 110

Val Val Gly Glu Glu Gly Ser Pro Tyr Arg Arg Lys Asp Pro Pro Leu
115 120 125

Lys Pro Ser Pro Val Gly Glu Ile Asn Cys Leu Gly Gly Asp Thr Asp
130 135 140

Asn Lys Asn Leu Ser Pro Arg Ser Pro Cys Glu Ser Asn Glu Leu Gly
145 150 155 160

Gly Gln Met Thr Ile Phe Tyr Cys Gly Lys Val Asn Val Tyr Asp Gly
165 170 175

Val Pro Leu Asp Lys Ala Arg Ala Ile Met His Leu Ala Ala Thr Pro
180 185 190

Ile Asp Phe Pro Gln Asp Asn Gln Cys Ser Gly Asn Ala Ala Leu Arg
195 200 205

Ser Phe Met Cys His Val Gln Ala Val Gly Asp Lys Asn Gly Leu Val
210 215 220

Ala Ser Thr Ala Leu Asn Ser His Thr Met Gln Thr Glu Lys Leu Thr
225 230 235 240

Glu Tyr Gln His Gln Phe Arg Glu Lys Gly Asn Ile Ala Arg Asp Ala
245 250 255

Asp Val Asp Gly Gln Val Asn Arg Lys Val Ser Leu Gln Arg Tyr Arg
260 265 270

Glu Lys Arg Lys Asp Arg Gly Arg Phe Phe Lys Gly Arg Lys Asn Thr
275 280 285

Gly Gln Ala Ser Ser Ser Leu Glu Met Tyr Leu Asn His Gln Ile Arg
290 295 300

Thr His Asn Ser Asn Gly Gln Ser Ser Arg Ser Ser Thr Gly Ser Pro
305 310 315 320

Pro Gln Ser Gly Leu Pro His Ala Phe Cys Ser Ser Ala Asp Asn Gln
325 330 335

Ala Lys Leu Val Asn Leu Ser Val Asp Leu Asn Asp Lys Ser Val Gln
340 345 350

Glu His

<210> SEQ ID NO 24
<211> LENGTH: 293
<212> TYPE: PRT
<213> ORGANISM: Spirodela polyrrhiza

<400> SEQUENCE: 24

Met Ala Gly Ser Glu Ala Ala Ala Pro Glu Glu Ala Gly Arg Ala Gly
1 5 10 15

Glu Glu Glu Val Arg Ala Ala Ala Gly Ala Ala Ala Val Lys Ser Pro
20 25 30

Leu Glu Lys Pro Leu Ser Glu Leu Thr Glu Glu Asp Ile Ala Gln Val
35 40 45

Thr Arg Glu Asp Cys Arg Arg Phe Leu Lys Glu Lys Gly Met Arg Arg
50 55 60

Pro Ser Trp Asn Lys Ser Gln Ala Val Gln Gln Val Ile Ser Leu Lys
65 70 75 80

Ala Leu Leu Glu Pro Cys His Asp Ala Asp Asp Asp Ala Pro Ser Ala

```
                85                  90                  95

Gly Ala Val Pro Ser Ile Ser Ser Phe Phe Ser Lys Arg Pro Ser Asp
            100                 105                 110

Ala Leu Leu Pro Ala Ala Ala Ala Gln Phe Pro Val Ser Ser Pro Met
        115                 120                 125

Arg Gly Glu Pro Ala Gly Gly Ala Pro Gln Ile Val Ser Glu Arg Pro
    130                 135                 140

His Gly Arg Asp Pro Leu Ala Asn Val Phe Thr Cys Ser Asp Ala Leu
145                 150                 155                 160

Gly Arg Phe Pro Ala Thr Gly Asn Gly Ala Leu Pro Pro Asn Ser Ala
                165                 170                 175

Thr Leu Pro Pro Arg Gly Val Ala Ser Ala Glu Thr Leu Glu Gly Gln
            180                 185                 190

Leu Thr Ile Phe Tyr Asp Gly Lys Ile Asn Val Tyr Asp Gly Val Thr
        195                 200                 205

Pro Glu Lys Val Arg Ser Gly Gln Lys Gly Pro Thr Ser Arg Ala Ala
    210                 215                 220

Ser Leu Gln Arg Tyr Leu Glu Lys Arg Lys Asp Arg Arg Asp Pro Gly
225                 230                 235                 240

Pro Ala Ala Val Ala Thr Leu Tyr Arg Lys Val Phe Leu Ser Ala Thr
                245                 250                 255

Ala Leu Leu Ile Gly Cys Ser Ser Gly Ala Asn Val Val Leu Pro Arg
            260                 265                 270

Ala Glu Gly Pro Thr Ser Arg Ala Ala Ser Leu Gln Arg Tyr Leu Glu
        275                 280                 285

Lys Arg Lys Asp Arg
    290


<210> SEQ ID NO 25
<211> LENGTH: 293
<212> TYPE: PRT
<213> ORGANISM: Musa acuminata

<400> SEQUENCE: 25

Met Asn Pro Gly Glu Thr Thr Pro Pro Ser Pro Leu Asp Lys Pro Leu
1               5                   10                  15

Ala Glu Leu Thr Glu Glu Asp Ile Ala Gln Leu Thr Arg Glu Asp Cys
            20                  25                  30

Arg Arg Phe Leu Lys Ala Lys Gly Met Arg Arg Pro Ser Trp Asn Lys
        35                  40                  45

Ser Gln Ala Ile Gln Gln Val Ile Ser Leu Lys Ala Leu Leu Glu Gly
    50                  55                  60

Arg Pro Gly Cys Asp Asp Cys Pro Ala Gly Gly Gly Ile Leu Gln Lys
65                  70                  75                  80

Leu Leu Thr Ser Ser Pro Ser Glu Pro Leu Ser Pro Pro Gln Asp Ser
                85                  90                  95

Pro Pro Pro Ala Pro Lys Glu Gly Gly Ser Gly Ser Gln Pro Leu Ala
            100                 105                 110

Lys Glu Pro Ser Pro Tyr Arg Arg Arg Asp Pro Ile Pro Pro Pro Tyr
        115                 120                 125

Ser Ala Gly Asn Pro Thr Cys Gln Thr Pro Ile Ala Gly Ala Asp Leu
    130                 135                 140

Pro His Pro Pro Glu Lys Arg Cys Pro Ser Pro Arg Leu Thr Ala Glu
145                 150                 155                 160
```

```
Val Pro Val Gly Gln Met Thr Ile Phe Tyr Asp Gly Met Val Asn Val
                165                 170                 175

Tyr Asp Gly Val Ser Ala Asp Gln Ala Arg Ser Ile Met Glu Leu Ala
            180                 185                 190

Ala Ser Pro Val Cys Phe Asp Asp Pro Thr Gly Ala Phe Ser Pro Ala
        195                 200                 205

Arg Pro Pro Ala Phe Arg Phe Pro Pro Gly Leu Pro Arg Pro Ala Pro
    210                 215                 220

Val Pro Thr Ala Pro Ser Phe Val Gly Thr Phe Pro Ile Ser Pro Ala
225                 230                 235                 240

Gly Lys Arg Cys Tyr Ser Tyr Cys Ser Phe Arg Ser Ser Val Ser Leu
                245                 250                 255

Leu Thr Thr Thr Glu Gly Pro Thr Ser Arg Lys Ala Ser Leu Gln Arg
            260                 265                 270

Tyr Leu Glu Lys Arg Lys Asp Arg Tyr Gly His Leu Pro Thr Glu Ser
        275                 280                 285

Ile Leu Leu Val Ser
    290


<210> SEQ ID NO 26
<211> LENGTH: 171
<212> TYPE: PRT
<213> ORGANISM: Phalaenopsis aphrodite
<220> FEATURE:
<221> NAME/KEY: misc_feature
<222> LOCATION: (72)..(87)
<223> OTHER INFORMATION: Xaa can be any naturally occurring amino acid

<400> SEQUENCE: 26

Met Asn Ser Asp Ala Ile Thr Met Gly Lys Ser Leu Leu Glu Lys Pro
1               5                   10                  15

Leu Ser Leu Leu Thr Glu Asp Asp Ile Ala Gln Ile Thr Arg Glu Glu
            20                  25                  30

Cys Arg Arg Phe Leu Lys Asp Arg Gly Met Arg Arg Pro Ser Trp Asn
        35                  40                  45

Lys Ser Gln Ala Ile Gln Gln Val Ile Ser Leu Lys Ala Leu Phe Glu
    50                  55                  60

Asn Arg Ser Asp Leu Glu Asp Xaa Xaa Xaa Xaa Xaa Xaa Xaa Xaa Xaa
65                  70                  75                  80

Xaa Xaa Xaa Xaa Xaa Xaa Xaa Phe Pro Glu His Ala Asp Leu Ser Ser
                85                  90                  95

Ile Ser Pro Thr Ala Glu Ala Lys Glu Pro Glu Lys Ala Gln Leu Thr
            100                 105                 110

Ile Phe Tyr Gly Gly Lys Val Leu Val Phe Asp Asn Phe Pro Val Asn
        115                 120                 125

Lys Ala Gln Asp Leu Met Gln Ile Ala Gly Lys Glu Gln Asn Gln Asn
    130                 135                 140

Tyr Gly Thr Ala Asn Thr Val Ala Pro Ser Ala Pro Ala Ala Asp Leu
145                 150                 155                 160

His Ser Leu Pro Leu Pro Ala Lys Pro Pro Ala
                165                 170


<210> SEQ ID NO 27
<211> LENGTH: 46
<212> TYPE: PRT
<213> ORGANISM: Artificial Sequence
<220> FEATURE:
<223> OTHER INFORMATION: Consensus sequence
```

-continued

<400> SEQUENCE: 27

Leu Lys Leu Leu Thr Glu Glu Asp Ile Ser Gln Leu Thr Arg Glu Asp
1               5                   10                  15

Cys Arg Lys Phe Leu Lys Asp Lys Gly Met Arg Arg Pro Ser Trp Asn
            20                  25                  30

Lys Ser Gln Ala Ile Gln Gln Val Leu Ser Leu Lys Ala Leu
        35                  40                  45

<210> SEQ ID NO 28
<211> LENGTH: 46
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(24)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (37)..(38)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid
<220> FEATURE:
<221> NAME/KEY: misc_feature
<222> LOCATION: (43)..(45)
<223> OTHER INFORMATION: Xaa can be any naturally occurring amino acid

<400> SEQUENCE: 28

Leu Xaa Xaa Leu Xaa Xaa Xaa Asp Xaa Xaa Gln Xaa Thr Arg Glu Xaa
1               5                   10                  15

Cys Arg Xaa Xaa Leu Xaa Xaa Xaa Gly Met Arg Xaa Pro Ser Trp Asn
            20                  25                  30

Lys Xaa Gln Ala Xaa Xaa Gln Xaa Xaa Ser Xaa Xaa Xaa Leu
        35                  40                  45

<210> SEQ ID NO 29
<211> LENGTH: 46
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Xaa is Glu, Phe, His, Tyr, Asn, Trp, Ser, Lys or Thr
<220> FEATURE:
<221> NAME/KEY: MISC_FEATURE
<222> LOCATION: (3)..(3)
<223> OTHER INFORMATION: Xaa is Glu, Gln or Leu
<220> FEATURE:
<221> NAME/KEY: MISC_FEATURE
<222> LOCATION: (5)..(5)
<223> OTHER INFORMATION: Xaa is Thr or Ser
<220> FEATURE:
<221> NAME/KEY: MISC_FEATURE
<222> LOCATION: (6)..(6)
<223> OTHER INFORMATION: Xaa is Glu or Asp
<220> FEATURE:
<221> NAME/KEY: MISC_FEATURE
<222> LOCATION: (7)..(7)
<223> OTHER INFORMATION: Xaa is Glu, Leu or Asp
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Ser, Phe, Arg, Met or Thr
<220> FEATURE:
<221> NAME/KEY: MISC_FEATURE
<222> LOCATION: (12)..(12)
<223> OTHER INFORMATION: Xaa is Leu or Val
<220> FEATURE:
<221> NAME/KEY: MISC_FEATURE
<222> LOCATION: (16)..(16)
<223> OTHER INFORMATION: Xaa is Asp or Glu
<220> FEATURE:
<221> NAME/KEY: MISC_FEATURE
<222> LOCATION: (19)..(19)
<223> OTHER INFORMATION: Xaa is Arg or Lys
<220> FEATURE:
<221> NAME/KEY: MISC_FEATURE
<222> LOCATION: (20)..(20)
<223> OTHER INFORMATION: Xaa is Tyr or Phe
<220> FEATURE:
<221> NAME/KEY: MISC_FEATURE
<222> LOCATION: (22)..(22)
<223> OTHER INFORMATION: Xaa is Lys or Arg
<220> FEATURE:
<221> NAME/KEY: MISC_FEATURE
<222> LOCATION: (23)..(23)
<223> OTHER INFORMATION: Xaa is Glu, Asp, Gln or Ala
<220> FEATURE:
<221> NAME/KEY: MISC_FEATURE
<222> LOCATION: (24)..(24)
<223> OTHER INFORMATION: Xaa is Lys or Arg
<220> FEATURE:
<221> NAME/KEY: MISC_FEATURE
<222> LOCATION: (28)..(28)
<223> OTHER INFORMATION: Xaa is Lys or Arg
<220> FEATURE:
<221> NAME/KEY: MISC_FEATURE
<222> LOCATION: (34)..(34)
<223> OTHER INFORMATION: Xaa is Tyr, Ser or Ala
<220> FEATURE:
<221> NAME/KEY: MISC_FEATURE
<222> LOCATION: (37)..(37)
<223> OTHER INFORMATION: Xaa is Ile or Val
<220> FEATURE:
<221> NAME/KEY: MISC_FEATURE
<222> LOCATION: (38)..(38)

<223> OTHER INFORMATION: Xaa is Gln or Glu
<220> FEATURE:
<221> NAME/KEY: MISC_FEATURE
<222> LOCATION: (40)..(40)
<223> OTHER INFORMATION: Xaa is Val or Leu
<220> FEATURE:
<221> NAME/KEY: MISC_FEATURE
<222> LOCATION: (41)..(41)
<223> OTHER INFORMATION: Xaa is Leu or Ile
<220> FEATURE:
<221> NAME/KEY: MISC_FEATURE
<222> LOCATION: (43)..(43)
<223> OTHER INFORMATION: Xaa is Leu or Phe
<220> FEATURE:
<221> NAME/KEY: MISC_FEATURE
<222> LOCATION: (44)..(44)
<223> OTHER INFORMATION: Xaa is Lys or Arg
<220> FEATURE:
<221> NAME/KEY: MISC_FEATURE
<222> LOCATION: (45)..(45)
<223> OTHER INFORMATION: Xaa is Gly, Ser, Thr or Ala

<400> SEQUENCE: 29

```
Leu Xaa Xaa Leu Xaa Xaa Xaa Asp Xaa Xaa Gln Xaa Thr Arg Glu Xaa
1               5                   10                  15

Cys Arg Xaa Xaa Leu Xaa Xaa Xaa Gly Met Arg Xaa Pro Ser Trp Asn
            20                  25                  30

Lys Xaa Gln Ala Xaa Xaa Gln Xaa Xaa Ser Xaa Xaa Xaa Leu
        35                  40                  45
```

<210> SEQ ID NO 30
<211> LENGTH: 27
<212> TYPE: PRT
<213> ORGANISM: Artificial Sequence
<220> FEATURE:
<223> OTHER INFORMATION: Consensus sequence

<400> SEQUENCE: 30

```
Thr Arg Glu Asp Cys Arg Lys Phe Leu Lys Asp Lys Gly Met Arg Arg
1               5                   10                  15

Pro Ser Trp Asn Lys Ser Gln Ala Ile Gln Gln
            20                  25
```

<210> SEQ ID NO 31
<211> LENGTH: 27
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (25)..(26)

<223> OTHER INFORMATION: Xaa can be any naturally occurring amino acid

<400> SEQUENCE: 31

Thr Arg Glu Xaa Cys Arg Xaa Xaa Leu Xaa Xaa Xaa Gly Met Arg Xaa
1               5                   10                  15

Pro Ser Trp Asn Lys Xaa Gln Ala Xaa Xaa Gln
            20                  25

<210> SEQ ID NO 32
<211> LENGTH: 27
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (4)..(4)
<223> OTHER INFORMATION: Xaa is Asp or Glu
<220> FEATURE:
<221> NAME/KEY: MISC_FEATURE
<222> LOCATION: (7)..(7)
<223> OTHER INFORMATION: Xaa is Lys or Arg
<220> FEATURE:
<221> NAME/KEY: MISC_FEATURE
<222> LOCATION: (8)..(8)
<223> OTHER INFORMATION: Xaa is Phe or Tyr
<220> FEATURE:
<221> NAME/KEY: MISC_FEATURE
<222> LOCATION: (10)..(10)
<223> OTHER INFORMATION: Xaa is Lys or Arg
<220> FEATURE:
<221> NAME/KEY: MISC_FEATURE
<222> LOCATION: (11)..(11)
<223> OTHER INFORMATION: Xaa is Asp, Ala, Glu or Gln
<220> FEATURE:
<221> NAME/KEY: MISC_FEATURE
<222> LOCATION: (12)..(12)
<223> OTHER INFORMATION: Xaa is Lys or Arg
<220> FEATURE:
<221> NAME/KEY: MISC_FEATURE
<222> LOCATION: (16)..(16)
<223> OTHER INFORMATION: Xaa is Lys or Arg
<220> FEATURE:
<221> NAME/KEY: MISC_FEATURE
<222> LOCATION: (22)..(22)
<223> OTHER INFORMATION: Xaa is Tyr, Ser or Ala
<220> FEATURE:
<221> NAME/KEY: MISC_FEATURE
<222> LOCATION: (25)..(25)
<223> OTHER INFORMATION: Xaa is Ile or Val
<220> FEATURE:
<221> NAME/KEY: MISC_FEATURE
<222> LOCATION: (26)..(26)
<223> OTHER INFORMATION: Xaa is Gln or Glu

<400> SEQUENCE: 32

Thr Arg Glu Xaa Cys Arg Xaa Xaa Leu Xaa Xaa Xaa Gly Met Arg Xaa
1               5                   10                  15

Pro Ser Trp Asn Lys Xaa Gln Ala Xaa Xaa Gln
            20                  25

<210> SEQ ID NO 33
<211> LENGTH: 6
<212> TYPE: PRT
<213> ORGANISM: Artificial Sequence
<220> FEATURE:
<223> OTHER INFORMATION: Consensus sequence

<400> SEQUENCE: 33

Thr Ile Phe Tyr Ser Gly
1               5

<210> SEQ ID NO 34
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 34

```
Thr Xaa Phe Tyr Xaa Gly
1               5
```

<210> SEQ ID NO 35
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: Xaa is Ile or Met
<220> FEATURE:
<221> NAME/KEY: MISC_FEATURE
<222> LOCATION: (5)..(5)
<223> OTHER INFORMATION: Xaa is Ala, Ser, Asp, Cys, Arg or Gly

<400> SEQUENCE: 35

```
Thr Xaa Phe Tyr Xaa Gly
1               5
```

<210> SEQ ID NO 36
<211> LENGTH: 355
<212> TYPE: PRT
<213> ORGANISM: Artificial Sequence
<220> FEATURE:
<223> OTHER INFORMATION: Consensus sequence

<400> SEQUENCE: 36

```
Met Asp Val Gly Val Ser Pro Ala Lys Ser Ile Leu Ala Lys Pro Leu
1               5                   10                  15

Lys Leu Leu Thr Glu Glu Asp Ile Ser Gln Leu Thr Arg Glu Asp Cys
            20                  25                  30

Arg Lys Phe Leu Lys Asp Lys Gly Met Arg Arg Pro Ser Trp Asn Lys
        35                  40                  45

Ser Gln Ala Ile Gln Gln Val Leu Ser Leu Lys Ala Leu Tyr Glu Pro
    50                  55                  60

Gly Asp Asp Ser Gly Ala Gly Ile Phe Arg Lys Ile Leu Val Ser Gln
65                  70                  75                  80

Pro Val Asn Pro Pro Arg Val Thr Thr Thr Leu Ile Glu Pro Ser Asn
                85                  90                  95

Glu Leu Glu Ala Cys Gly Arg Val Ser Tyr Pro Glu Asp Asn Gly Ala
            100                 105                 110

Cys His Arg Met Asp Ser Pro Arg Ser Ala Glu Phe Ser Gly Gly Ser
        115                 120                 125

Gly His Phe Val Ser Glu Lys Asp Gly His Lys Thr Thr Ile Ser Pro
    130                 135                 140
```

Arg Ser Pro Ala Glu Thr Ser Glu Leu Val Gly Gln Met Thr Ile Phe
145 150 155 160

Tyr Ser Gly Lys Val Asn Val Tyr Asp Gly Ile Pro Pro Glu Lys Ala
165 170 175

Arg Ser Ile Met His Phe Ala Ala Asn Pro Ile Asp Leu Pro Glu Asn
180 185 190

Gly Ile Phe Ala Ser Ser Arg Met Ile Ser Lys Leu Ile Ser Lys Glu
195 200 205

Lys Met Met Glu Leu Pro Gln Lys Gly Leu Glu Lys Ala Asn Ser Ser
210 215 220

Arg Asp Ser Gly Met Glu Gly Gln Ala Asn Arg Lys Val Ser Leu Gln
225 230 235 240

Arg Tyr Arg Glu Lys Arg Lys Asp Arg Lys Phe Ser Lys Ala Lys Lys
245 250 255

Cys Pro Gly Val Ala Ser Ser Ser Leu Glu Met Phe Leu Asn Cys Gln
260 265 270

Pro Arg Met Lys Ala Ala Tyr Ser Gln Asn Leu Gly Cys Thr Gly Ser
275 280 285

Pro Leu His Ser Gln Ser Pro Glu Ser Gln Thr Lys Ser Pro Asn Leu
290 295 300

Ser Val Asp Leu Asn Ser Glu Gly Ile Gly Ser Gly Gly Gly Ser Ala
305 310 315 320

Lys Gly Glu Leu Arg Gly His Pro Phe Glu Gly Lys Pro Ile Pro Asn
325 330 335

Pro Leu Leu Gly Leu Asp Ser Thr Arg Thr Gly His His His His His
340 345 350

His Gly Ser
355

<210> SEQ ID NO 37
<211> LENGTH: 42
<212> TYPE: PRT
<213> ORGANISM: Artificial Sequence
<220> FEATURE:
<223> OTHER INFORMATION: Consensus sequence

<400> SEQUENCE: 37

Gly Ser Gly Gly Gly Ser Ala Lys Gly Glu Leu Arg Gly His Pro Phe
1 5 10 15

Glu Gly Lys Pro Ile Pro Asn Pro Leu Leu Gly Leu Asp Ser Thr Arg
20 25 30

Thr Gly His His His His His His Gly Ser
35 40

<210> SEQ ID NO 38
<211> LENGTH: 315
<212> TYPE: PRT
<213> ORGANISM: Artificial Sequence
<220> FEATURE:
<223> OTHER INFORMATION: Consensus sequence

<400> SEQUENCE: 38

Met Asp Val Gly Val Ser Pro Ala Lys Ser Ile Leu Ala Lys Pro Leu
1 5 10 15

Lys Leu Leu Thr Glu Glu Asp Ile Ser Gln Leu Thr Arg Glu Asp Cys
20 25 30

Arg Lys Phe Leu Lys Asp Lys Gly Met Arg Arg Pro Ser Trp Asn Lys
35 40 45

```
Ser Gln Ala Ile Gln Gln Val Leu Ser Leu Lys Ala Leu Tyr Glu Pro
    50                  55                  60

Gly Asp Asp Ser Gly Ala Gly Ile Phe Arg Lys Ile Leu Val Ser Gln
65                  70                  75                  80

Pro Val Asn Pro Pro Arg Val Thr Thr Thr Leu Ile Glu Pro Ser Asn
                85                  90                  95

Glu Leu Glu Ala Cys Gly Arg Val Ser Tyr Pro Glu Asp Asn Gly Ala
            100                 105                 110

Cys His Arg Met Asp Ser Pro Arg Ser Ala Glu Phe Ser Gly Gly Ser
        115                 120                 125

Gly His Phe Val Ser Glu Lys Asp Gly His Lys Thr Thr Ile Ser Pro
    130                 135                 140

Arg Ser Pro Ala Glu Thr Ser Glu Leu Val Gly Gln Met Thr Ile Phe
145                 150                 155                 160

Tyr Ser Gly Lys Val Asn Val Tyr Asp Gly Ile Pro Pro Glu Lys Ala
                165                 170                 175

Arg Ser Ile Met His Phe Ala Ala Asn Pro Ile Asp Leu Pro Glu Asn
            180                 185                 190

Gly Ile Phe Ala Ser Ser Arg Met Ile Ser Lys Leu Ile Ser Lys Glu
        195                 200                 205

Lys Met Met Glu Leu Pro Gln Lys Gly Leu Glu Lys Ala Asn Ser Ser
    210                 215                 220

Arg Asp Ser Gly Met Glu Gly Gln Ala Asn Arg Lys Val Ser Leu Gln
225                 230                 235                 240

Arg Tyr Arg Glu Lys Arg Lys Asp Arg Lys Phe Ser Lys Ala Lys Lys
                245                 250                 255

Cys Pro Gly Val Ala Ser Ser Ser Leu Glu Met Phe Leu Asn Cys Gln
            260                 265                 270

Pro Arg Met Lys Ala Ala Tyr Ser Gln Asn Leu Gly Cys Thr Gly Ser
        275                 280                 285

Pro Leu His Ser Gln Ser Pro Glu Ser Gln Thr Lys Ser Pro Asn Leu
    290                 295                 300

Ser Val Asp Leu Asn Ser Glu Gly Ile Gly Ser
305                 310                 315
```

<210> SEQ ID NO 39
<211> LENGTH: 86
<212> TYPE: DNA
<213> ORGANISM: Lolium perenne

<400> SEQUENCE: 39

```
gtaatgttca gctctgctat agtgtgtgcc accctgcttg tttaataatg cgttctcttc      60

gtttttatga tatcttattc ttccag                                          86
```

<210> SEQ ID NO 40
<211> LENGTH: 1157
<212> TYPE: DNA
<213> ORGANISM: Artificial Sequence
<220> FEATURE:
<223> OTHER INFORMATION: Consensus sequence

<400> SEQUENCE: 40

```
atggacgtgg gcgtgtcccc ggccaagtct attctcgcca agccggtaat gttcagctct      60

gctatagtgt gtgccaccct gcttgtttaa taatgcgttc tcttcgtttt tatgatatct     120

tattcttcca gctcaagctc ctcaccgagg aggacatctc tcagctcaca agagaggact     180
```

gccgcaagtt cctgaaggac aaggggatga gaaggccttc ctggaacaag tcccaggcca 240
tccagcaagt gctcagcctc aaggcccttt acgagccagg cgacgactcc ggcgctggca 300
ttttcagaaa gatcctcgtg tcccagccgg tgaacccacc aagggtgacc accacactca 360
tcgagccgtc caatgagctt gaggcttgcg gcagagtgtc ctacccagag gataatggcg 420
cctgccacag gatggattct ccaaggtctg ctgagttctc tggcggctcc ggccatttcg 480
tgtctgagaa ggatggccac aagaccacca tctccccaag atccccagcc gagacatctg 540
agcttgtggg ccagatgacc atcttctact ccggcaaggt gaacgtgtac gacggcatcc 600
caccagagaa ggcccgctcc attatgcact tcgccgccaa cccaatcgac ctcccagaga 660
atggcatctt cgcctccagc cgcatgatct ccaagctcat ctccaaggag aagatgatgg 720
agctgccgca gaagggcctc gagaaggcta attcctctcg cgactccggc atggagggcc 780
aggctaatag aaaggtgtcc ctccaacgct accgcgagaa gaggaaggac cgcaagttct 840
ccaaggccaa gaagtgccca ggcgttgcct cttccagcct cgagatgttc ctcaactgcc 900
agccgagaat gaaggccgcc tactcccaaa atctcggctg cacaggctcc ccactccatt 960
ctcagtcccc agagtctcag accaagtccc cgaacctctc cgtggacctt aactccgagg 1020
gcatcggatc cggcggcggc tctgctaagg gcgagctgag gggccacccg ttcgagggca 1080
agccaattcc aaatccactc ctcggcctcg actctaccag gaccggccac catcaccatc 1140
accacggatc ctaatga 1157

<210> SEQ ID NO 41
<211> LENGTH: 2921
<212> TYPE: DNA
<213> ORGANISM: Artificial Sequence
<220> FEATURE:
<223> OTHER INFORMATION: Consensus sequence

<400> SEQUENCE: 41
gcggccgctc tagaactagt ccccttattg tacttcaatt aattatcatt atatcagcat 60
aaacattata ataagtttct tgcgtgttgg aacgtcattt tagttattct aaagaggaaa 120
tagtttcttt tttgctcatg acatcagaca tctggactac tatactggag tttacctttt 180
cttctcctct ttttcttatt gttcctctaa aaaaaattat cactttttaa atgcattagt 240
taaacttatc tcaacaacgt ttaaaattca tttcttgaat gcccattaca atgtaatagt 300
ataacttaat tagtcgtctc catgaaccat taatacgtac ggagtaatat aaaacaccat 360
tggggagttc aatttgcaat aatttcttgc aaaaatgtaa agtacctttt tgttcttgca 420
aaattttaca aataaaaatt tgcagctctt ttttttctct ctctccaaat actagctcaa 480
aacccacaaa tatttttgaa tttatggcat acttttagaa tgcgtttgat gcaactattt 540
tcctttagga aatattcaca acaatctaag acaatcaaaa agtagaaaat agtttgtaaa 600
aagggatgtg gaggacatct taatcaaata ttttcagttt aaaacttgaa aatgaaaaaa 660
cacccgaaag gaaatgattc gttctttaat atgtcctaca caatgtgaat ttgaattagt 720
ttggtcatac ggtatatcat atgattataa ataaaaaaaa ttagcaaaag aatataattt 780
attaaatatt ttacaccata ccaaacacaa ccgcattata tataatctta attatcatta 840
tcaccagcat caacattata atgattcccc tatgcgttgg aacgtcatta tagttattct 900
aaacaagaaa gaaatttgtt cttgacatca gacatctagt attataactc tagtggagct 960
tacctttctt tttccttctt ttttttcttc ttaaaaaaat tatcactttt taaatcttgt 1020
atattagtta agcttatcta aacaaagttt taaattcatt tcttaaacgt ccattacaat 1080
gtaatataac ttagtcgtct caattaaacc attaatgtga aatataaatc aaaaaaagcc 1140
aaagggcggt gggacggcgc caatcatttg tcctagtcca ctcaaataag gcccatggtc 1200
ggcaaaacca aacacaaaat gtgttatttt taattttttc ctcttttatt gttaaagttg 1260
caaaatgtgt tatttttggt aagaccctat ggatatataa agacaggtta tgtgaaactt 1320
ggaaaaccat caagttttaa gcaaaaccct cttaagaact taaattgagc ttcttttggg 1380
gcatttttct agtgagaact aaaaacaagt ttgtacaaaa aagcaggcta aaaaaaacca 1440
tggacgtggg cgtgtccccg gccaagtcta ttctcgccaa gccggtaatg ttcagctctg 1500
ctatagtgtg tgccaccctg cttgtttaat aatgcgttct cttcgttttt atgatatctt 1560
attcttccag ctcaagctcc tcaccgagga ggacatctct cagctcacaa gagaggactg 1620
ccgcaagttc ctgaaggaca aggggatgag aaggccttcc tggaacaagt cccaggccat 1680
ccagcaagtg ctcagcctca aggcccttta cgagccaggc gacgactccg gcgctggcat 1740
tttcagaaag atcctcgtgt cccagccggt gaacccacca agggtgacca ccacactcat 1800
cgagccgtcc aatgagcttg aggcttgcgg cagagtgtcc tacccagagg ataatggcgc 1860
ctgccacagg atggattctc caaggtctgc tgagttctct ggcggctccg gccatttcgt 1920
gtctgagaag gatggccaca agaccaccat ctccccaaga tccccagccg agacatctga 1980
gcttgtgggc cagatgacca tcttctactc cggcaaggtg aacgtgtacg acggcatccc 2040
accagagaag gcccgctcca ttatgcactt cgccgccaac ccaatcgacc tcccagagaa 2100
tggcatcttc gcctccagcc gcatgatctc caagctcatc tccaaggaga agatgatgga 2160
gctgccgcag aagggcctcg agaaggctaa ttcctctcgc gactccggca tggagggcca 2220
ggctaataga aaggtgtccc tccaacgcta ccgcgagaag aggaaggacc gcaagttctc 2280
caaggccaag aagtgcccag gcgttgcctc ttccagcctc gagatgttcc tcaactgcca 2340
gccgagaatg aaggccgcct actcccaaaa tctcggctgc acaggctccc cactccattc 2400
tcagtcccca gagtctcaga ccaagtcccc gaacctctcc gtggacctta actccgaggg 2460
catcggatcc ggcggcggct ctgctaaggg cgagctgagg ggccacccgt tcgagggcaa 2520
gccaattcca aatccactcc tcggcctcga ctctaccagg accggccacc atcaccatca 2580
ccacggatcc taatgaaccc agctttcttg tacaaagtgg tctagtgggt accgcgaatt 2640
tccccgatcg ttcaaacatt tggcaataaa gtttcttaag attgaatcct gttgccggtc 2700
ttgcgatgat tatcatataa tttctgttga attacgttaa gcatgtaata attaacatgt 2760
aatgcatgac gttatttatg agatgggttt ttatgattag agtcccgcaa ttatacattt 2820
aatacgcgat agaaaacaaa atatagcgcg caaactagga taaattatcg cgcgcggtgt 2880
catctatgtt actagatcga agcggccgct ctagaactag t 2921

<210> SEQ ID NO 42
<211> LENGTH: 2249
<212> TYPE: DNA
<213> ORGANISM: Artificial Sequence
<220> FEATURE:
<223> OTHER INFORMATION: Consensus sequence

<400> SEQUENCE: 42
gcggccgctc tagaactagt gtcctacaca atgtgaattt gaattagttt ggtcatacgg 60
tatatcatat gattataaat aaaaaaaatt agcaaaagaa tataatttat taaatatttt 120
acaccatacc aaacacaacc gcattatata taatcttaat tatcattatc accagcatca 180

-continued

```
acattataat gattccccta tgcgttggaa cgtcattata gttattctaa acaagaaaga    240

aatttgttct tgacatcaga catctagtat tataactcta gtggagctta ccttttcttt    300

tccttctttt ttttcttctt aaaaaaatta tcacttttta aatcttgtat attagttaag    360

cttatctaaa caaagtttta aattcatttc ttaaacgtcc attacaatgt aatataactt    420

agtcgtctca attaaaccat taatgtgaaa tataaatcaa aaaaagccaa agggcggtgg    480

gacggcgcca atcatttgtc ctagtccact caaataaggc ccatggtcgg caaaaccaaa    540

cacaaaatgt gttattttta attttttcct cttttattgt taaagttgca aaatgtgtta    600

tttttggtaa gaccctatgg atatataaag acaggttatg tgaaacttgg aaaaccatca    660

agttttaagc aaaaccctct taagaactta aattgagctt cttttggggc atttttctag    720

tgagaactaa aaacaagttt gtacaaaaaa gcaggctaaa aaaaaccatg gacgtgggcg    780

tgtccccggc caagtctatt ctcgccaagc cggtaatgtt cagctctgct atagtgtgtg    840

ccaccctgct tgtttaataa tgcgttctct tcgtttttat gatatcttat tcttccagct    900

caagctcctc accgaggagg acatctctca gctcacaaga gaggactgcc gcaagttcct    960

gaaggacaag ggatgagaa ggccttcctg gaacaagtcc caggccatcc agcaagtgct   1020

cagcctcaag gccctttacg agccaggcga cgactccggc gctggcattt tcagaaagat   1080

cctcgtgtcc cagccggtga acccaccaag ggtgaccacc acactcatcg agccgtccaa   1140

tgagcttgag gcttgcggca gagtgtccta cccagaggat aatggcgcct gccacaggat   1200

ggattctcca aggtctgctg agttctctgg cggctccggc catttcgtgt ctgagaagga   1260

tggccacaag accaccatct ccccaagatc cccagccgag acatctgagc ttgtgggcca   1320

gatgaccatc ttctactccg gcaaggtgaa cgtgtacgac ggcatcccac cagagaaggc   1380

ccgctccatt atgcacttcg ccgccaaccc aatcgacctc ccagagaatg gcatcttcgc   1440

ctccagccgc atgatctcca agctcatctc caaggagaag atgatggagc tgccgcagaa   1500

gggcctcgag aaggctaatt cctctcgcga ctccggcatg gagggccagg ctaatagaaa   1560

ggtgtccctc caacgctacc gcgagaagag gaaggaccgc aagttctcca aggccaagaa   1620

gtgcccaggc gttgcctctt ccagcctcga gatgttcctc aactgccagc cgagaatgaa   1680

ggccgcctac tcccaaaatc tcggctgcac aggctcccca ctccattctc agtccccaga   1740

gtctcagacc aagtccccga acctctccgt ggaccttaac tccgagggca tcggatccgg   1800

cggcggctct gctaagggcg agctgagggg ccacccgttc gagggcaagc caattccaaa   1860

tccactcctc ggcctcgact ctaccaggac cggccaccat caccatcacc acggatccta   1920

atgaacccag ctttcttgta caaagtggtc tagtgggtac cgcgaatttc cccgatcgtt   1980

caaacatttg gcaataaagt ttcttaagat tgaatcctgt tgccggtctt gcgatgatta   2040

tcatataatt tctgttgaat tacgttaagc atgtaataat taacatgtaa tgcatgacgt   2100

tatttatgag atgggttttt atgattagag tcccgcaatt atacatttaa tacgcgatag   2160

aaaacaaaat atagcgcgca aactaggata aattatcgcg cgcggtgtca tctatgttac   2220

tagatcgaag cggccgctct agaactagt                                    2249
```

<210> SEQ ID NO 43
<211> LENGTH: 2852
<212> TYPE: DNA
<213> ORGANISM: Artificial Sequence
<220> FEATURE:
<223> OTHER INFORMATION: Consensus sequence -continued

<400> SEQUENCE: 43

```
gcggccgctc tagaactagt tcacgtggaa cgcgccgcag taaacggagc ggtggatcaa     60
acttttcgtc cgtttgatca aacagaagag aactagtcaa tgctctttct tcatatcaca    120
atttaatagt ctcaagacga ttacgccaca taaccatttt ctcgtgattt cgacatcaaa    180
atttaataaa aggaactgat tgattggtca tcatgttaca agtgtcaaat gagctaatcc    240
gttttacagt ggcatagttt acgatcaatt tacaaatttt tggttttata acatacttgt    300
agttaaaact atttataagc tatttatagt gagttagctt ataaaaccct attcttttat    360
ctaaaattat gttttgactc gtttcatgat aaaattttat ccttttcatc ggaataaaaa    420
actttattat ttatttggca aaataattgg tgtaaaaatt atgtatatgt taataacaaa    480
aaatattaat ctgattcata atcttaaaaa agaaaaattt cttgaaataa actttagaca    540
ttgtaaataa aaaaacatta tttttatata atgggatgtt tatatgtaat tttttataaa    600
aaaataaaag ttgtttacta gtaatccgat tggctttaac tatcgtcgcc aaaagaataa    660
tgtagaactg actttgaggt aaaactaaaa gaaatttgta agataatagt cacattaaat    720
gctaaaatta atacatactg atatatcgta taaaatttat gaaaactaca ccttaacctg    780
aatcatacac tgtaataaaa aaaacaaatt atatataaac cctaaaaact aatcataaat    840
cccaaacggt gtactctcta ttagctttga aaggattgcc caattgtttg ttaaaaattt    900
ctaataatag tacaatgttt tgtttcattt ttccttttcg tcaacctgtt acccaatagc    960
aaatgaagtt tttatgtgtg tgtgtgtgtg tgaatttcca tgaaaatgaa acgggcttag   1020
aatcccggtg tattatgggt cgggtcgtaa ccgggcaatg acgcaggatc tgacgtaaaa   1080
ctcccaagaa tttttttaaa aagtctccgg aaaataaaat caaagttcat taacttaaaa   1140
agaaaaaaca aaatcggtcc acgtcccaaa cccttttttat aggagagtct tatgttctgg   1200
cagaagactt cacagactct ttcttaatct ctctctcttt caaccaaacc cctaaacaaa   1260
aaaaaaatac attttctgat ctctctaaaa atctttctcc ttcgttaatc tcgtgatctc   1320
tttctttttc tatatacaag tttgtacaaa aaagcaggct aaaaaaaacc atggacgtgg   1380
gcgtgtcccc ggccaagtct attctcgcca agccggtaat gttcagctct gctatagtgt   1440
gtgccaccct gcttgtttaa taatgcgttc tcttcgtttt tatgatatct tattcttcca   1500
gctcaagctc ctcaccgagg aggacatctc tcagctcaca agagaggact gccgcaagtt   1560
cctgaaggac aaggggatga gaaggccttc ctggaacaag tcccaggcca tccagcaagt   1620
gctcagcctc aaggcccttt acgagccagg cgacgactcc ggcgctggca ttttcagaaa   1680
gatcctcgtg tcccagccgg tgaacccacc aagggtgacc accacactca tcgagccgtc   1740
caatgagctt gaggcttgcg gcagagtgtc ctacccagag gataatggcg cctgccacag   1800
gatggattct ccaaggtctg ctgagttctc tggcggctcc ggccatttcg tgtctgagaa   1860
ggatggccac aagaccacca tctccccaag atccccagcc gagacatctg agcttgtggg   1920
ccagatgacc atcttctact ccggcaaggt gaacgtgtac gacggcatcc caccagagaa   1980
ggcccgctcc attatgcact tcgccgccaa cccaatcgac ctcccagaga atggcatctt   2040
cgcctccagc cgcatgatct ccaagctcat ctccaaggag aagatgatgg agctgccgca   2100
gaagggcctc gagaaggcta attcctctcg cgactccggc atggagggcc aggctaatag   2160
aaaggtgtcc ctccaacgct accgcgagaa gaggaaggac cgcaagttct ccaaggccaa   2220
gaagtgccca ggcgttgcct cttccagcct cgagatgttc ctcaactgcc agccgagaat   2280
gaaggccgcc tactcccaaa atctcggctg cacaggctcc ccactccatt ctcagtcccc   2340
```

agagtctcag accaagtccc cgaacctctc cgtggacctt aactccgagg gcatcggatc 2400
cggcggcggc tctgctaagg gcgagctgag gggccacccg ttcgagggca agccaattcc 2460
aaatccactc ctcggcctcg actctaccag gaccggccac catcaccatc accacggatc 2520
ctaatgaacc cagctttctt gtacaaagtg gtctagtggg taccgcgaat ttccccgatc 2580
gttcaaacat ttggcaataa agtttcttaa gattgaatcc tgttgccggt cttgcgatga 2640
ttatcatata atttctgttg aattacgtta agcatgtaat aattaacatg taatgcatga 2700
cgttatttat gagatgggtt tttatgatta gagtcccgca attatacatt taatacgcga 2760
tagaaaacaa aatatagcgc gcaaactagg ataaattatc gcgcgcggtg tcatctatgt 2820
tactagatcg aagcggccgc tctagaacta gt 2852

<210> SEQ ID NO 44
<211> LENGTH: 2801
<212> TYPE: DNA
<213> ORGANISM: Artificial Sequence
<220> FEATURE:
<223> OTHER INFORMATION: Consensus sequence

<400> SEQUENCE: 44
gcggccgctc tagaactagt ccccttattg tacttcaatt aattatcatt atatcagcat 60
aaacattata ataagtttct tgcgtgttgg aacgtcattt tagttattct aaagaggaaa 120
tagtttcttt tttgctcatg acatcagaca tctggactac tatactggag tttacctttt 180
cttctcctct ttttcttatt gttcctctaa aaaaaattat cactttttaa atgcattagt 240
taaacttatc tcaacaacgt ttaaaattca tttcttgaat gcccattaca atgtaatagt 300
ataacttaat tagtcgtctc catgaaccat taatacgtac ggagtaatat aaaacaccat 360
tggggagttc aatttgcaat aatttcttgc aaaaatgtaa agtacctttt tgttcttgca 420
aaattttaca aataaaaatt tgcagctctt ttttttctct ctctccaaat actagctcaa 480
aacccacaaa tatttttgaa tttatggcat acttttagaa tgcgtttgat gcaactattt 540
tcctttagga aatattcaca acaatctaag acaatcaaaa agtagaaaat agtttgtaaa 600
aagggatgtg gaggacatct taatcaaata ttttcagttt aaaacttgaa aatgaaaaaa 660
cacccgaaag gaaatgattc gttctttaat atgtcctaca caatgtgaat ttgaattagt 720
ttggtcatac ggtatatcat atgattataa ataaaaaaaa ttagcaaaag aatataattt 780
attaaatatt ttacaccata ccaaacacaa ccgcattata tataatctta attatcatta 840
tcaccagcat caacattata atgattcccc tatgcgttgg aacgtcatta tagttattct 900
aaacaagaaa gaaatttgtt cttgacatca gacatctagt attataactc tagtggagct 960
taccttttct tttccttctt ttttttcttc ttaaaaaaat tatcactttt taaatcttgt 1020
atattagtta agcttatcta aacaaagttt taaattcatt tcttaaacgt ccattacaat 1080
gtaatataac ttagtcgtct caattaaacc attaatgtga aatataaatc aaaaaaagcc 1140
aaagggcggt gggacggcgc caatcatttg tcctagtcca ctcaaataag gcccatggtc 1200
ggcaaaacca aacacaaaat gtgttatttt taattttttc ctcttttatt gttaaagttg 1260
caaaatgtgt tatttttggt aagaccctat ggatatataa agacaggtta tgtgaaactt 1320
ggaaaaccat caagttttaa gcaaaaccct cttaagaact taaattgagc ttcttttggg 1380
gcatttttct agtgagaact aaaaacaagt ttgtacaaaa aagcaggcta aaaaaaacca 1440
tggacgtggg cgtgtccccg gccaagtcta ttctcgccaa gccggtaatg ttcagctctg 1500

-continued

```
ctatagtgtg tgccaccctg cttgtttaat aatgcgttct cttcgttttt atgatatctt   1560
attcttccag ctcaagctcc tcaccgagga ggacatctct cagctcacaa gagaggactg   1620
ccgcaagttc ctgaaggaca aggggatgag aaggccttcc tggaacaagt cccaggccat   1680
ccagcaagtg ctcagcctca aggccccttta cgagccaggc gacgactccg gcgctggcat   1740
tttcagaaag atcctcgtgt cccagccggt gaacccacca agggtgacca ccacactcat   1800
cgagccgtcc aatgagcttg aggcttgcgg cagagtgtcc tacccagagg ataatggcgc   1860
ctgccacagg atggattctc caaggtctgc tgagttctct ggcggctccg gccatttcgt   1920
gtctgagaag gatggccaca agaccaccat ctccccaaga tccccagccg agacatctga   1980
gcttgtgggc cagatgacca tcttctactc cggcaaggtg aacgtgtacg acggcatccc   2040
accagagaag gcccgctcca ttatgcactt cgccgccaac ccaatcgacc tcccagagaa   2100
tggcatcttc gcctccagcc gcatgatctc caagctcatc tccaaggaga agatgatgga   2160
gctgccgcag aagggcctcg agaaggctaa ttcctctcgc gactccggca tggagggcca   2220
ggctaataga aaggtgtccc tccaacgcta ccgcgagaag aggaaggacc gcaagttctc   2280
caaggccaag aagtgcccag gcgttgcctc ttccagcctc gagatgttcc tcaactgcca   2340
gccgagaatg aaggccgcct actcccaaaa tctcggctgc acaggctccc cactccattc   2400
tcagtcccca gagtctcaga ccaagtcccc gaacctctcc gtggacctta actccgaggg   2460
catcggatcc taatgaaccc agctttcttg tacaaagtgg tctagtgggt accgcgaatt   2520
tccccgatcg ttcaaacatt tggcaataaa gtttcttaag attgaatcct gttgccggtc   2580
ttgcgatgat tatcatataa tttctgttga attacgttaa gcatgtaata attaacatgt   2640
aatgcatgac gttatttatg agatgggttt ttatgattag agtcccgcaa ttatacattt   2700
aatacgcgat agaaaacaaa atatagcgcg caaactagga taaattatcg cgcgcggtgt   2760
catctatgtt actagatcga agcggccgct ctagaactag t                       2801
```

```
<210> SEQ ID NO 45
<211> LENGTH: 2129
<212> TYPE: DNA
<213> ORGANISM: Artificial Sequence
<220> FEATURE:
<223> OTHER INFORMATION: Consensus sequence

<400> SEQUENCE: 45
```

```
gcggccgctc tagaactagt gtcctacaca atgtgaattt gaattagttt ggtcatacgg     60
tatatcatat gattataaat aaaaaaaatt agcaaaagaa tataatttat taaatatttt    120
acaccatacc aaacacaacc gcattatata taatcttaat tatcattatc accagcatca    180
acattataat gattccccta tgcgttggaa cgtcattata gttattctaa acaagaaaga    240
aatttgttct tgacatcaga catctagtat tataactcta gtggagctta ccttttcttt    300
tccttctttt ttttcttctt aaaaaaatta tcacttttta aatcttgtat attagttaag    360
cttatctaaa caaagtttta aattcatttc ttaaacgtcc attacaatgt aatataactt    420
agtcgtctca attaaaccat taatgtgaaa tataaatcaa aaaaagccaa agggcggtgg    480
gacggcgcca atcatttgtc ctagtccact caaataaggc ccatggtcgg caaaaccaaa    540
cacaaaatgt gttatttttta atttttttcct cttttattgt taaagttgca aaatgtgtta    600
tttttggtaa gaccctatgg atatataaag acaggttatg tgaaacttgg aaaaccatca    660
agttttaagc aaaaccctct taagaactta aattgagctt cttttggggc atttttctag    720
tgagaactaa aaacaagttt gtacaaaaaa gcaggctaaa aaaaaccatg gacgtgggcg    780
```

```
tgtccccggc caagtctatt ctcgccaagc cggtaatgtt cagctctgct atagtgtgtg    840

ccaccctgct tgtttaataa tgcgttctct tcgtttttat gatatcttat tcttccagct    900

caagctcctc accgaggagg acatctctca gctcacaaga gaggactgcc gcaagttcct    960

gaaggacaag gggatgagaa ggccttcctg gaacaagtcc caggccatcc agcaagtgct   1020

cagcctcaag gccctttacg agccaggcga cgactccggc gctggcattt tcagaaagat   1080

cctcgtgtcc cagccggtga acccaccaag ggtgaccacc acactcatcg agccgtccaa   1140

tgagcttgag gcttgcggca gagtgtccta cccagaggat aatggcgcct gccacaggat   1200

ggattctcca aggtctgctg agttctctgg cggctccggc catttcgtgt ctgagaagga   1260

tggccacaag accaccatct ccccaagatc cccagccgag acatctgagc ttgtgggcca   1320

gatgaccatc ttctactccg gcaaggtgaa cgtgtacgac ggcatcccac cagagaaggc   1380

ccgctccatt atgcacttcg ccgccaaccc aatcgacctc ccagagaatg gcatcttcgc   1440

ctccagccgc atgatctcca agctcatctc caaggagaag atgatggagc tgccgcagaa   1500

gggcctcgag aaggctaatt cctctcgcga ctccggcatg gagggccagg ctaatagaaa   1560

ggtgtccctc caacgctacc gcgagaagag gaaggaccgc aagttctcca aggccaagaa   1620

gtgcccaggc gttgcctctt ccagcctcga gatgttcctc aactgccagc cgagaatgaa   1680

ggccgcctac tcccaaaatc tcggctgcac aggctcccca ctccattctc agtccccaga   1740

gtctcagacc aagtccccga acctctccgt ggaccttaac tccgagggca tcggatccta   1800

atgaacccag ctttcttgta caaagtggtc tagtgggtac cgcgaatttc cccgatcgtt   1860

caaacatttg gcaataaagt ttcttaagat tgaatcctgt tgccggtctt gcgatgatta   1920

tcatataatt tctgttgaat tacgttaagc atgtaataat taacatgtaa tgcatgacgt   1980

tatttatgag atgggttttt atgattagag tcccgcaatt atacatttaa tacgcgatag   2040

aaaacaaaat atagcgcgca aactaggata aattatcgcg cgcggtgtca tctatgttac   2100

tagatcgaag cggccgctct agaactagt                                     2129


<210> SEQ ID NO 46
<211> LENGTH: 2732
<212> TYPE: DNA
<213> ORGANISM: Artificial Sequence
<220> FEATURE:
<223> OTHER INFORMATION: Consensus sequence

<400> SEQUENCE: 46

gcggccgctc tagaactagt tcacgtggaa cgcgccgcag taaacggagc ggtggatcaa     60

acttttcgtc cgtttgatca aacagaagag aactagtcaa tgctctttct tcatatcaca    120

atttaatagt ctcaagacga ttacgccaca taaccatttt ctcgtgattt cgacatcaaa    180

atttaataaa aggaactgat tgattggtca tcatgttaca agtgtcaaat gagctaatcc    240

gttttacagt ggcatagttt acgatcaatt tacaaatttt tggttttata acatacttgt    300

agttaaaact atttataagc tatttatagt gagttagctt ataaaaccct attcttttat    360

ctaaaattat gttttgactc gtttcatgat aaaattttat ccttttcatc ggaataaaaa    420

actttattat ttatttggca aaataattgg tgtaaaaatt atgtatatgt taataacaaa    480

aaatattaat ctgattcata atcttaaaaa agaaaaattt cttgaaataa actttagaca    540

ttgtaaataa aaaaacatta tttttatata atgggatgtt tatatgtaat tttttataaa    600

aaaataaaag ttgtttacta gtaatccgat tggctttaac tatcgtcgcc aaaagaataa    660
```

-continued

```
tgtagaactg actttgaggt aaaactaaaa gaaatttgta agataatagt cacattaaat    720

gctaaaatta atacatactg atatatcgta taaaatttat gaaaactaca ccttaacctg    780

aatcatacac tgtaataaaa aaaacaaatt atatataaac cctaaaaact aatcataaat    840

cccaaacggt gtactctcta ttagctttga aaggattgcc caattgtttg ttaaaaattt    900

ctaataatag tacaatgttt tgtttcattt ttccttttcg tcaacctgtt acccaatagc    960

aaatgaagtt tttatgtgtg tgtgtgtgtg tgaatttcca tgaaaatgaa acgggcttag   1020

aatcccggtg tattatgggt cgggtcgtaa ccgggcaatg acgcaggatc tgacgtaaaa   1080

ctcccaagaa tttttttaaa aagtctccgg aaaataaaat caaagttcat taacttaaaa   1140

agaaaaaaca aaatcggtcc acgtcccaaa cccttttat aggagagtct tatgttctgg    1200

cagaagactt cacagactct ttcttaatct ctctctcttt caaccaaacc cctaaacaaa   1260

aaaaaaatac attttctgat ctctctaaaa atctttctcc ttcgttaatc tcgtgatctc   1320

tttcttttc tatatacaag tttgtacaaa aaagcaggct aaaaaaaacc atggacgtgg    1380

gcgtgtcccc ggccaagtct attctcgcca agccggtaat gttcagctct gctatagtgt   1440

gtgccaccct gcttgtttaa taatgcgttc tcttcgtttt tatgatatct tattcttcca   1500

gctcaagctc ctcaccgagg aggacatctc tcagctcaca agagaggact gccgcaagtt   1560

cctgaaggac aaggggatga gaaggccttc ctggaacaag tcccaggcca tccagcaagt   1620

gctcagcctc aaggcccttt acgagccagg cgacgactcc ggcgctggca ttttcagaaa   1680

gatcctcgtg tcccagccgg tgaacccacc aagggtgacc accacactca tcgagccgtc   1740

caatgagctt gaggcttgcg gcagagtgtc ctacccagag gataatggcg cctgccacag   1800

gatggattct ccaaggtctg ctgagttctc tggcggctcc ggccatttcg tgtctgagaa   1860

ggatggccac aagaccacca tctccccaag atccccagcc gagacatctg agcttgtggg   1920

ccagatgacc atcttctact ccggcaaggt gaacgtgtac gacggcatcc caccagagaa   1980

ggcccgctcc attatgcact tcgccgccaa cccaatcgac ctcccagaga atggcatctt   2040

cgcctccagc cgcatgatct ccaagctcat ctccaaggag aagatgatgg agctgccgca   2100

gaagggcctc gagaaggcta attcctctcg cgactccggc atggagggcc aggctaatag   2160

aaaggtgtcc ctccaacgct accgcgagaa gaggaaggac cgcaagttct ccaaggccaa   2220

gaagtgccca ggcgttgcct cttccagcct cgagatgttc ctcaactgcc agccgagaat   2280

gaaggccgcc tactcccaaa atctcggctg cacaggctcc ccactccatt ctcagtcccc   2340

agagtctcag accaagtccc cgaacctctc cgtggacctt aactccgagg gcatcggatc   2400

ctaatgaacc cagctttctt gtacaaagtg gtctagtggg taccgcgaat ttccccgatc   2460

gttcaaacat ttggcaataa agtttcttaa gattgaatcc tgttgccggt cttgcgatga   2520

ttatcatata atttctgttg aattacgtta agcatgtaat aattaacatg taatgcatga   2580

cgttatttat gagatgggtt tttatgatta gagtcccgca attatacatt taatacgcga   2640

tagaaaacaa aatatagcgc gcaaactagg ataaattatc gcgcgcggtg tcatctatgt   2700

tactagatcg aagcggccgc tctagaacta gt                                 2732
```

```
<210> SEQ ID NO 47
<211> LENGTH: 102
<212> TYPE: DNA
<213> ORGANISM: Arabidopsis thaliana

<400> SEQUENCE: 47

gtaaaagaag atgtttttta tttccagcaa tgttacattg ttatacgtat aatgatgagt     60
```

ttagtgatca agttcctctt tgattcttct ttcttgttgc ag 102

<210> SEQ ID NO 48
<211> LENGTH: 1173
<212> TYPE: DNA
<213> ORGANISM: Artificial Sequence
<220> FEATURE:
<223> OTHER INFORMATION: Consensus sequence

<400> SEQUENCE: 48
atggatgtcg gagtttcacc ggcgaagtct atacttgcga aacctctgaa gctactcact 60
gaagaggaca tttctcagct cactcgcgaa gactgcgtaa aagaagatgt tttttatttc 120
cagcaatgtt acattgttat acgtataatg atgagtttag tgatcaagtt cctctttgat 180
tcttctttct tgttgcagcg caaattcctc aaagacaaag gaatgcgaag accgtcgtgg 240
aacaaatctc aggcgatcca gcaagtttta tctcttaaag ctctctatga gcctggagac 300
gattccggcg ccggtatctt ccgcaagatc ctcgtttctc agccagtaaa tccgcctcgc 360
gtcacaacaa cgttgattga gccaagcaac gagctggaag cttgtggccg ggtttcttat 420
ccggaagata acggcgcgtg ccatagaatg gattctccaa gatcagctga gttttccggt 480
gggtctggtc actttgtatc cgagaaagat ggccacaaga cgactatttc tcccagaagc 540
ccagctgaaa caagtgagct cgttgggcaa atgacgatat tctatagtgg aaaagtgaat 600
gtgtatgatg gaataccacc tgaaaaggcc cggtcaatca tgcactttgc agccaatcca 660
attgatttgc ctgaaaacgg tatttttgct tccagtagaa tgatttcaaa gctcataagt 720
aaagagaaga tgatggaact tccccaaaaa ggccttgaga aggcgaattc ttctcgtgat 780
tctggtatgg agggccaggc gaacagaaag gtatctttgc aaagatatcg tgaaaagcgg 840
aaagacagaa aattctcaaa ggccaaaaag tgtccaggag ttgcgtcctc tagcttggag 900
atgtttctga attgtcagcc acggatgaaa gctgcatatt cgcaaaacct aggctgcacc 960
ggatctccac tgcatagcca gtcacctgaa agccagacaa aaagtcccaa tctttcagtt 1020
gatctaaaca gtgaaggcat tggatccgga ggtggatctg ctaagggaga acttagagga 1080
catccatttg aaggaaagcc aattccaaat ccacttcttg gacttgattc tactagaact 1140
ggacatcacc atcaccatca tggatcctaa tga 1173

<210> SEQ ID NO 49
<211> LENGTH: 1173
<212> TYPE: DNA
<213> ORGANISM: Artificial Sequence
<220> FEATURE:
<223> OTHER INFORMATION: Consensus sequence

<400> SEQUENCE: 49
atggatgtcg gagtttcacc ggtaaaagaa gatgtttttt atttccagca atgttacatt 60
gttatacgta taatgatgag tttagtgatc aagttcctct ttgattcttc tttcttgttg 120
caggcgaagt ctatacttgc gaaacctctg aagctactca ctgaagagga catttctcag 180
ctcactcgcg aagactgccg caaattcctc aaagacaaag gaatgcgaag accgtcgtgg 240
aacaaatctc aggcgatcca gcaagtttta tctcttaaag ctctctatga gcctggagac 300
gattccggcg ccggtatctt ccgcaagatc ctcgtttctc agccagtaaa tccgcctcgc 360
gtcacaacaa cgttgattga gccaagcaac gagctggaag cttgtggccg ggtttcttat 420
ccggaagata acggcgcgtg ccatagaatg gattctccaa gatcagctga gttttccggt 480

```
gggtctggtc actttgtatc cgagaaagat ggccacaaga cgactatttc tcccagaagc    540

ccagctgaaa caagtgagct cgttgggcaa atgacgatat tctatagtgg aaaagtgaat    600

gtgtatgatg gaataccacc tgaaaaggcc cggtcaatca tgcactttgc agccaatcca    660

attgatttgc ctgaaaacgg tatttttgct tccagtagaa tgatttcaaa gctcataagt    720

aaagagaaga tgatggaact tccccaaaaa ggccttgaga aggcgaattc ttctcgtgat    780

tctggtatgg agggccaggc gaacagaaag gtatctttgc aaagatatcg tgaaaagcgg    840

aaagacagaa aattctcaaa ggccaaaaag tgtccaggag ttgcgtcctc tagcttggag    900

atgtttctga attgtcagcc acggatgaaa gctgcatatt cgcaaaacct aggctgcacc    960

ggatctccac tgcatagcca gtcacctgaa agccagacaa aaagtcccaa tctttcagtt   1020

gatctaaaca gtgaaggcat tggatccgga ggtggatctg ctaagggaga acttagagga   1080

catccatttg aaggaaagcc aattccaaat ccacttcttg gacttgattc tactagaact   1140

ggacatcacc atcaccatca tggatcctaa tga                                1173
```

<210> SEQ ID NO 50
<211> LENGTH: 2897
<212> TYPE: DNA
<213> ORGANISM: Artificial Sequence
<220> FEATURE:
<223> OTHER INFORMATION: Consensus sequence

<400> SEQUENCE: 50

```
ccccttattg tacttcaatt aattatcatt atatcagcat aaacattata ataagtttct     60

tgcgtgttgg aacgtcattt tagttattct aaagaggaaa tagtttcttt tttgctcatg    120

acatcagaca tctggactac tatactggag tttacctttt cttctcctct ttttcttatt    180

gttcctctaa aaaaaattat cactttttaa atgcattagt taaacttatc tcaacaacgt    240

ttaaaattca tttcttgaat gcccattaca atgtaatagt ataacttaat tagtcgtctc    300

catgaaccat taatacgtac ggagtaatat aaaacaccat tggggagttc aatttgcaat    360

aatttcttgc aaaaatgtaa agtacctttt tgttcttgca aaattttaca aataaaaatt    420

tgcagctctt ttttttctct ctctccaaat actagctcaa aacccacaaa tatttttgaa    480

tttatggcat acttttagaa tgcgtttgat gcaactattt tcctttagga aatattcaca    540

acaatctaag acaatcaaaa agtagaaaat agtttgtaaa aagggatgtg gaggacatct    600

taatcaaata ttttcagttt aaaacttgaa aatgaaaaaa cacccgaaag gaaatgattc    660

gttctttaat atgtcctaca caatgtgaat ttgaattagt ttggtcatac ggtatatcat    720

atgattataa ataaaaaaaa ttagcaaaag aatataattt attaaatatt ttacaccata    780

ccaaacacaa ccgcattata tataatctta attatcatta tcaccagcat caacattata    840

atgattcccc tatgcgttgg aacgtcatta tagttattct aaacaagaaa gaaatttgtt    900

cttgacatca gacatctagt attataactc tagtggagct taccttttct tttccttctt    960

ttttttcttc ttaaaaaaat tatcactttt taaatcttgt atattagtta agcttatcta   1020

aacaaagttt taaattcatt tcttaaacgt ccattacaat gtaatataac ttagtcgtct   1080

caattaaacc attaatgtga aatataaatc aaaaaaagcc aaagggcggt gggacggcgc   1140

caatcatttg tcctagtcca ctcaaataag gcccatggtc ggcaaaacca aacacaaaat   1200

gtgttatttt taattttttc ctcttttatt gttaaagttg caaaatgtgt tatttttggt   1260

aagaccctat ggatatataa agacaggtta tgtgaaactt ggaaaaccat caagttttaa   1320

gcaaaaccct cttaagaact taaattgagc ttcttttggg gcatttttct agtgagaact   1380
```

-continued

```
aaaaacaagt ttgtacaaaa aagcaggcta aaaaaaacca tggatgtcgg agtttcaccg   1440

gcgaagtcta tacttgcgaa acctctgaag ctactcactg aagaggacat ttctcagctc   1500

actcgcgaag actgcgtaaa agaagatgtt ttttatttcc agcaatgtta cattgttata   1560

cgtataatga tgagtttagt gatcaagttc ctctttgatt cttctttctt gttgcagcgc   1620

aaattcctca aagacaaagg aatgcgaaga ccgtcgtgga acaaatctca ggcgatccag   1680

caagttttat ctcttaaagc tctctatgag cctggagacg attccggcgc cggtatcttc   1740

cgcaagatcc tcgtttctca gccagtaaat ccgcctcgcg tcacaacaac gttgattgag   1800

ccaagcaacg agctggaagc ttgtggccgg gtttcttatc cggaagataa cggcgcgtgc   1860

catagaatgg attctccaag atcagctgag ttttccggtg ggtctggtca ctttgtatcc   1920

gagaaagatg gccacaagac gactatttct cccagaagcc cagctgaaac aagtgagctc   1980

gttgggcaaa tgacgatatt ctatagtgga aaagtgaatg tgtatgatgg aataccacct   2040

gaaaaggccc ggtcaatcat gcactttgca gccaatccaa ttgatttgcc tgaaaacggt   2100

atttttgctt ccagtagaat gatttcaaag ctcataagta aagagaagat gatggaactt   2160

ccccaaaaag gccttgagaa ggcgaattct tctcgtgatt ctggtatgga gggccaggcg   2220

aacagaaagg tatctttgca aagatatcgt gaaaagcgga aagacagaaa attctcaaag   2280

gccaaaaagt gtccaggagt tgcgtcctct agcttggaga tgtttctgaa ttgtcagcca   2340

cggatgaaag ctgcatattc gcaaaaccta ggctgcaccg gatctccact gcatagccag   2400

tcacctgaaa gccagacaaa aagtcccaat ctttcagttg atctaaacag tgaaggcatt   2460

ggatccggag gtggatctgc taagggagaa cttagaggac atccatttga aggaaagcca   2520

attccaaatc cacttcttgg acttgattct actagaactg gacatcacca tcaccatcat   2580

ggatcctaat gaacccagct ttcttgtaca aagtggtcta gtgggtaccg cgaatttccc   2640

cgatcgttca aacatttggc aataaagttt cttaagattg aatcctgttg ccggtcttgc   2700

gatgattatc atataatttc tgttgaatta cgttaagcat gtaataatta acatgtaatg   2760

catgacgtta tttatgagat gggtttttat gattagagtc ccgcaattat acatttaata   2820

cgcgatagaa aacaaaatat agcgcgcaaa ctaggataaa ttatcgcgcg cggtgtcatc   2880

tatgttacta gatcgaa                                                  2897
```

<210> SEQ ID NO 51
<211> LENGTH: 2225
<212> TYPE: DNA
<213> ORGANISM: Artificial Sequence
<220> FEATURE:
<223> OTHER INFORMATION: Consensus sequence

<400> SEQUENCE: 51

```
gtcctacaca atgtgaattt gaattagttt ggtcatacgg tatatcatat gattataaat     60

aaaaaaaatt agcaaaagaa tataatttat taaatatttt acaccatacc aaacacaacc    120

gcattatata taatcttaat tatcattatc accagcatca acattataat gattccccta    180

tgcgttggaa cgtcattata gttattctaa acaagaaaga aatttgttct tgacatcaga    240

catctagtat tataactcta gtggagctta ccttttcttt tccttctttt ttttcttctt    300

aaaaaaatta tcacttttta aatcttgtat attagttaag cttatctaaa caaagtttta    360

aattcatttc ttaaacgtcc attacaatgt aatataactt agtcgtctca attaaaccat    420

taatgtgaaa tataaatcaa aaaaagccaa agggcggtgg gacggcgcca atcatttgtc    480
```

ctagtccact caaataaggc ccatggtcgg caaaaccaaa cacaaaatgt gttattttta 540 atttttttcct cttttattgt taaagttgca aaatgtgtta tttttggtaa gaccctatgg 600
atatataaag acaggttatg tgaaacttgg aaaaccatca agttttaagc aaaaccctct 660
taagaactta aattgagctt cttttggggc atttttctag tgagaactaa aaacaagttt 720
gtacaaaaaa gcaggctaaa aaaaaccatg gatgtcggag tttcaccggc gaagtctata 780
cttgcgaaac ctctgaagct actcactgaa gaggacattt ctcagctcac tcgcgaagac 840
tgcgtaaaag aagatgtttt ttatttccag caatgttaca ttgttatacg tataatgatg 900
agtttagtga tcaagttcct ctttgattct tctttcttgt tgcagcgcaa attcctcaaa 960
gacaaaggaa tgcgaagacc gtcgtggaac aaatctcagg cgatccagca agttttatct 1020
cttaaagctc tctatgagcc tggagacgat tccggcgccg gtatcttccg caagatcctc 1080
gtttctcagc cagtaaatcc gcctcgcgtc acaacaacgt tgattgagcc aagcaacgag 1140
ctggaagctt gtggccgggt ttcttatccg gaagataacg gcgcgtgcca tagaatggat 1200
tctccaagat cagctgagtt ttccggtggg tctggtcact ttgtatccga gaaagatggc 1260
cacaagacga ctatttctcc cagaagccca gctgaaacaa gtgagctcgt tgggcaaatg 1320
acgatattct atagtggaaa agtgaatgtg tatgatggaa taccacctga aaaggcccgg 1380
tcaatcatgc actttgcagc caatccaatt gatttgcctg aaaacggtat ttttgcttcc 1440
agtagaatga tttcaaagct cataagtaaa gagaagatga tggaacttcc ccaaaaaggc 1500
cttgagaagg cgaattcttc tcgtgattct ggtatggagg gccaggcgaa cagaaaggta 1560
tctttgcaaa gatatcgtga aaagcggaaa gacagaaaat tctcaaaggc caaaaagtgt 1620
ccaggagttg cgtcctctag cttggagatg tttctgaatt gtcagccacg gatgaaagct 1680
gcatattcgc aaaacctagg ctgcaccgga tctccactgc atagccagtc acctgaaagc 1740
cagacaaaaa gtcccaatct ttcagttgat ctaaacagtg aaggcattgg atccggaggt 1800
ggatctgcta agggagaact tagaggacat ccatttgaag gaaagccaat tccaaatcca 1860
cttcttggac ttgattctac tagaactgga catcaccatc accatcatgg atcctaatga 1920
acccagcttt cttgtacaaa gtggtctagt gggtaccgcg aatttccccg atcgttcaaa 1980
catttggcaa taaagtttct taagattgaa tcctgttgcc ggtcttgcga tgattatcat 2040
ataatttctg ttgaattacg ttaagcatgt aataattaac atgtaatgca tgacgttatt 2100
tatgagatgg gtttttatga ttagagtccc gcaattatac atttaatacg cgatagaaaa 2160
caaaatatag cgcgcaaact aggataaatt atcgcgcgcg gtgtcatcta tgttactaga 2220
tcgaa 2225

<210> SEQ ID NO 52
<211> LENGTH: 2828
<212> TYPE: DNA
<213> ORGANISM: Artificial Sequence
<220> FEATURE:
<223> OTHER INFORMATION: Consensus sequence

<400> SEQUENCE: 52
tcacgtggaa cgcgccgcag taaacggagc ggtggatcaa acttttcgtc cgtttgatca 60
aacagaagag aactagtcaa tgctctttct tcatatcaca atttaatagt ctcaagacga 120
ttacgccaca taaccatttt ctcgtgattt cgacatcaaa atttaataaa aggaactgat 180
tgattggtca tcatgttaca agtgtcaaat gagctaatcc gttttacagt ggcatagttt 240
acgatcaatt tacaaatttt tggttttata acatacttgt agttaaaact atttataagc 300

-continued

```
tatttatagt gagttagctt ataaaaccct attcttttat ctaaaattat gttttgactc    360
gtttcatgat aaaattttat ccttttcatc ggaataaaaa actttattat ttatttggca    420
aaataattgg tgtaaaaatt atgtatatgt taataacaaa aaatattaat ctgattcata    480
atcttaaaaa agaaaaattt cttgaaataa actttagaca ttgtaaataa aaaaacatta    540
tttttatata atgggatgtt tatatgtaat tttttataaa aaaataaaag ttgtttacta    600
gtaatccgat tggctttaac tatcgtcgcc aaaagaataa tgtagaactg actttgaggt    660
aaaactaaaa gaaatttgta agataatagt cacattaaat gctaaaatta atacatactg    720
atatatcgta taaaatttat gaaaactaca ccttaacctg aatcatacac tgtaataaaa    780
aaaacaaatt atatataaac cctaaaaact aatcataaat cccaaacggt gtactctcta    840
ttagctttga aaggattgcc caattgtttg ttaaaaattt ctaataatag tacaatgttt    900
tgtttcattt ttccttttcg tcaacctgtt acccaatagc aaatgaagtt tttatgtgtg    960
tgtgtgtgtg tgaatttcca tgaaaatgaa acgggcttag aatcccggtg tattatgggt   1020
cgggtcgtaa ccgggcaatg acgcaggatc tgacgtaaaa ctcccaagaa tttttttaaa   1080
aagtctccgg aaaataaaat caaagttcat taacttaaaa agaaaaaaca aaatcggtcc   1140
acgtcccaaa cccttttat aggagagtct tatgttctgg cagaagactt cacagactct    1200
ttcttaatct ctctctcttt caaccaaacc cctaaacaaa aaaaaaatac attttctgat   1260
ctctctaaaa atctttctcc ttcgttaatc tcgtgatctc tttctttttc tatatacaag   1320
tttgtacaaa aaagcaggct aaaaaaaacc atggatgtcg gagtttcacc ggtaaaagaa   1380
gatgtttttt atttccagca atgttacatt gttatacgta taatgatgag tttagtgatc   1440
aagttcctct ttgattcttc tttcttgttg caggcgaagt ctatacttgc gaaacctctg   1500
aagctactca ctgaagagga catttctcag ctcactcgcg aagactgccg caaattcctc   1560
aaagacaaag gaatgcgaag accgtcgtgg aacaaatctc aggcgatcca gcaagtttta   1620
tctcttaaag ctctctatga gcctggagac gattccggcg ccggtatctt ccgcaagatc   1680
ctcgtttctc agccagtaaa tccgcctcgc gtcacaacaa cgttgattga gccaagcaac   1740
gagctggaag cttgtggccg ggtttcttat ccggaagata acggcgcgtg ccatagaatg   1800
gattctccaa gatcagctga gttttccggt gggtctggtc actttgtatc cgagaaagat   1860
ggccacaaga cgactatttc tcccagaagc ccagctgaaa caagtgagct cgttgggcaa   1920
atgacgatat tctatagtgg aaaagtgaat gtgtatgatg gaataccacc tgaaaaggcc   1980
cggtcaatca tgcactttgc agccaatcca attgatttgc ctgaaaacgg tatttttgct   2040
tccagtagaa tgatttcaaa gctcataagt aaagagaaga tgatggaact tccccaaaaa   2100
ggccttgaga aggcgaattc ttctcgtgat tctggtatgg agggccaggc gaacagaaag   2160
gtatctttgc aaagatatcg tgaaaagcgg aaagacagaa aattctcaaa ggccaaaaag   2220
tgtccaggag ttgcgtcctc tagcttggag atgtttctga attgtcagcc acggatgaaa   2280
gctgcatatt cgcaaaacct aggctgcacc ggatctccac tgcatagcca gtcacctgaa   2340
agccagacaa aaagtcccaa tctttcagtt gatctaaaca gtgaaggcat tggatccgga   2400
ggtggatctg ctaagggaga acttagagga catccatttg aaggaaagcc aattccaaat   2460
ccacttcttg gacttgattc tactagaact ggacatcacc atcaccatca tggatcctaa   2520
tgaacccagc tttcttgtac aaagtggtct agtgggtacc gcgaatttcc ccgatcgttc   2580
aaacatttgg caataaagtt tcttaagatt gaatcctgtt gccggtcttg cgatgattat   2640
```

-continued catataattt ctgttgaatt acgttaagca tgtaataatt aacatgtaat gcatgacgtt 2700
atttatgaga tgggttttta tgattagagt cccgcaatta tacatttaat acgcgataga 2760
aaacaaaata tagcgcgcaa actaggataa attatcgcgc gcggtgtcat ctatgttact 2820
agatcgaa 2828

<210> SEQ ID NO 53
<211> LENGTH: 2777
<212> TYPE: DNA
<213> ORGANISM: Artificial Sequence
<220> FEATURE:
<223> OTHER INFORMATION: Consensus sequence

<400> SEQUENCE: 53
ccccttattg tacttcaatt aattatcatt atatcagcat aaacattata ataagtttct 60
tgcgtgttgg aacgtcattt tagttattct aaagaggaaa tagtttcttt tttgctcatg 120
acatcagaca tctggactac tatactggag tttacctttt cttctcctct ttttcttatt 180
gttcctctaa aaaaaattat cactttttaa atgcattagt taaacttatc tcaacaacgt 240
ttaaaattca tttcttgaat gcccattaca atgtaatagt ataacttaat tagtcgtctc 300
catgaaccat taatacgtac ggagtaatat aaaacaccat tggggagttc aatttgcaat 360
aatttcttgc aaaaatgtaa agtacctttt tgttcttgca aaattttaca aataaaaatt 420
tgcagctctt tttttctct ctctccaaat actagctcaa aacccacaaa tatttttgaa 480
tttatggcat acttttagaa tgcgtttgat gcaactattt tcctttagga aatattcaca 540
acaatctaag acaatcaaaa agtagaaaat agtttgtaaa aagggatgtg gaggacatct 600
taatcaaata ttttcagttt aaaacttgaa aatgaaaaaa cacccgaaag gaaatgattc 660
gttctttaat atgtcctaca caatgtgaat ttgaattagt ttggtcatac ggtatatcat 720
atgattataa ataaaaaaaa ttagcaaaag aatataattt attaaatatt ttacaccata 780
ccaaacacaa ccgcattata tataatctta attatcatta tcaccagcat caacattata 840
atgattcccc tatgcgttgg aacgtcatta tagttattct aaacaagaaa gaaatttgtt 900
cttgacatca gacatctagt attataactc tagtggagct taccttttct tttccttctt 960 tttttcttc ttaaaaaaat tatcactttt taaatcttgt atattagtta agcttatcta 1020
aacaaagttt taaattcatt tcttaaacgt ccattacaat gtaatataac ttagtcgtct 1080
caattaaacc attaatgtga aatataaatc aaaaaaagcc aaagggcggt gggacggcgc 1140
caatcatttg tcctagtcca ctcaaataag gcccatggtc ggcaaaacca aacacaaaat 1200
gtgttatttt taatttttc ctcttttatt gttaaagttg caaaatgtgt tatttttggt 1260
aagaccctat ggatatataa agacaggtta tgtgaaactt ggaaaaccat caagttttaa 1320
gcaaaaccct cttaagaact taaattgagc ttcttttggg gcatttttct agtgagaact 1380
aaaaacaagt ttgtacaaaa aagcaggcta aaaaaaacca tggatgtcgg agtttcaccg 1440
gcgaagtcta tacttgcgaa acctctgaag ctactcactg aagaggacat ttctcagctc 1500
actcgcgaag actgcgtaaa agaagatgtt ttttatttcc agcaatgtta cattgttata 1560
cgtataatga tgagtttagt gatcaagttc ctctttgatt cttctttctt gttgcagcgc 1620
aaattcctca aagacaaagg aatgcgaaga ccgtcgtgga acaaatctca ggcgatccag 1680
caagttttat ctcttaaagc tctctatgag cctggagacg attccggcgc cggtatcttc 1740
cgcaagatcc tcgtttctca gccagtaaat ccgcctcgcg tcacaacaac gttgattgag 1800
ccaagcaacg agctggaagc ttgtggccgg gtttcttatc cggaagataa cggcgcgtgc 1860

```
catagaatgg attctccaag atcagctgag ttttccggtg ggtctggtca ctttgtatcc   1920
gagaaagatg gccacaagac gactatttct cccagaagcc cagctgaaac aagtgagctc   1980
gttgggcaaa tgacgatatt ctatagtgga aaagtgaatg tgtatgatgg aataccacct   2040
gaaaaggccc ggtcaatcat gcactttgca gccaatccaa ttgatttgcc tgaaaacggt   2100
atttttgctt ccagtagaat gatttcaaag ctcataagta aagagaagat gatggaactt   2160
ccccaaaaag gccttgagaa ggcgaattct tctcgtgatt ctggtatgga gggccaggcg   2220
aacagaaagg tatctttgca aagatatcgt gaaaagcgga aagacagaaa attctcaaag   2280
gccaaaaagt gtccaggagt tgcgtcctct agcttggaga tgtttctgaa ttgtcagcca   2340
cggatgaaag ctgcatattc gcaaaaccta ggctgcaccg gatctccact gcatagccag   2400
tcacctgaaa gccagacaaa aagtcccaat ctttcagttg atctaaacag tgaaggcatt   2460
ggatcctaat gaacccagct ttcttgtaca aagtggtcta gtgggtaccg cgaatttccc   2520
cgatcgttca aacatttggc aataaagttt cttaagattg aatcctgttg ccggtcttgc   2580
gatgattatc atataatttc tgttgaatta cgttaagcat gtaataatta acatgtaatg   2640
catgacgtta tttatgagat gggtttttat gattagagtc ccgcaattat acatttaata   2700
cgcgatagaa aacaaaatat agcgcgcaaa ctaggataaa ttatcgcgcg cggtgtcatc   2760
tatgttacta gatcgaa                                                  2777
```

<210> SEQ ID NO 54
<211> LENGTH: 2105
<212> TYPE: DNA
<213> ORGANISM: Artificial Sequence
<220> FEATURE:
<223> OTHER INFORMATION: Consensus sequence

<400> SEQUENCE: 54

```
gtcctacaca atgtgaattt gaattagttt ggtcatacgg tatatcatat gattataaat     60
aaaaaaaatt agcaaaagaa tataatttat taaatatttt acaccatacc aaacacaacc    120
gcattatata taatcttaat tatcattatc accagcatca acattataat gattccccta    180
tgcgttggaa cgtcattata gttattctaa acaagaaaga aatttgttct tgacatcaga    240
catctagtat tataactcta gtggagctta cctttttcttt tccttctttt ttttcttctt    300
aaaaaaatta tcacttttta aatcttgtat attagttaag cttatctaaa caaagtttta    360
aattcatttc ttaaacgtcc attacaatgt aatataactt agtcgtctca attaaaccat    420
taatgtgaaa tataaatcaa aaaaagccaa agggcggtgg gacggcgcca atcatttgtc    480
ctagtccact caaataaggc ccatggtcgg caaaaccaaa cacaaaatgt gttattttta    540
atttttcct cttttattgt taaagttgca aaatgtgtta tttttggtaa gaccctatgg    600
atatataaag acaggttatg tgaaacttgg aaaaccatca agttttaagc aaaaccctct    660
taagaactta aattgagctt cttttggggc atttttctag tgagaactaa aaacaagttt    720
gtacaaaaaa gcaggctaaa aaaaaccatg gatgtcggag tttcaccggc gaagtctata    780
cttgcgaaac ctctgaagct actcactgaa gaggacattt ctcagctcac tcgcgaagac    840
tgcgtaaaag aagatgtttt ttatttccag caatgttaca ttgttatacg tataatgatg    900
agtttagtga tcaagttcct ctttgattct tctttcttgt tgcagcgcaa attcctcaaa    960
gacaaaggaa tgcgaagacc gtcgtggaac aaatctcagg cgatccagca agttttatct   1020
cttaaagctc tctatgagcc tggagacgat tccggcgccg gtatcttccg caagatcctc   1080
```

-continued

```
gtttctcagc cagtaaatcc gcctcgcgtc acaacaacgt tgattgagcc aagcaacgag   1140

ctggaagctt gtggccgggt ttcttatccg gaagataacg gcgcgtgcca tagaatggat   1200

tctccaagat cagctgagtt ttccggtggg tctggtcact ttgtatccga gaaagatggc   1260

cacaagacga ctatttctcc cagaagccca gctgaaacaa gtgagctcgt tgggcaaatg   1320

acgatattct atagtggaaa agtgaatgtg tatgatggaa taccacctga aaaggcccgg   1380

tcaatcatgc actttgcagc caatccaatt gatttgcctg aaaacggtat ttttgcttcc   1440

agtagaatga tttcaaagct cataagtaaa gagaagatga tggaacttcc ccaaaaaggc   1500

cttgagaagg cgaattcttc tcgtgattct ggtatggagg gccaggcgaa cagaaaggta   1560

tctttgcaaa gatatcgtga aaagcggaaa gacagaaaat tctcaaaggc caaaaagtgt   1620

ccaggagttg cgtcctctag cttggagatg tttctgaatt gtcagccacg gatgaaagct   1680

gcatattcgc aaaacctagg ctgcaccgga tctccactgc atagccagtc acctgaaagc   1740

cagacaaaaa gtcccaatct ttcagttgat ctaaacagtg aaggcattgg atcctaatga   1800

acccagcttt cttgtacaaa gtggtctagt gggtaccgcg aatttccccg atcgttcaaa   1860

catttggcaa taaagtttct taagattgaa tcctgttgcc ggtcttgcga tgattatcat   1920

ataatttctg ttgaattacg ttaagcatgt aataattaac atgtaatgca tgacgttatt   1980

tatgagatgg gtttttatga ttagagtccc gcaattatac atttaatacg cgatagaaaa   2040

caaaatatag cgcgcaaact aggataaatt atcgcgcgcg gtgtcatcta tgttactaga   2100

tcgaa                                                              2105
```

<210> SEQ ID NO 55
<211> LENGTH: 2708
<212> TYPE: DNA
<213> ORGANISM: Artificial Sequence
<220> FEATURE:
<223> OTHER INFORMATION: Consensus sequence

<400> SEQUENCE: 55

```
tcacgtggaa cgcgccgcag taaacggagc ggtggatcaa acttttcgtc cgtttgatca     60

aacagaagag aactagtcaa tgctctttct tcatatcaca atttaatagt ctcaagacga    120

ttacgccaca taaccatttt ctcgtgattt cgacatcaaa atttaataaa aggaactgat    180

tgattggtca tcatgttaca agtgtcaaat gagctaatcc gttttacagt ggcatagttt    240

acgatcaatt tacaaatttt tggttttata acatacttgt agttaaaact atttataagc    300

tatttatagt gagttagctt ataaaaccct attcttttat ctaaaattat gttttgactc    360

gtttcatgat aaaattttat ccttttcatc ggaataaaaa actttattat ttatttggca    420

aaataattgg tgtaaaaatt atgtatatgt taataacaaa aaatattaat ctgattcata    480

atcttaaaaa agaaaaattt cttgaaataa actttagaca ttgtaaataa aaaaacatta    540

tttttatata atgggatgtt tatatgtaat tttttataaa aaaataaaag ttgtttacta    600

gtaatccgat tggctttaac tatcgtcgcc aaaagaataa tgtagaactg actttgaggt    660

aaaactaaaa gaaatttgta agataatagt cacattaaat gctaaaatta atacatactg    720

atatatcgta taaaatttat gaaaactaca ccttaacctg aatcatacac tgtaataaaa    780

aaaacaaatt atatataaac cctaaaaact aatcataaat cccaaacggt gtactctcta    840

ttagctttga aaggattgcc caattgtttg ttaaaaattt ctaataatag tacaatgttt    900

tgtttcattt ttccttttcg tcaacctgtt acccaatagc aaatgaagtt tttatgtgtg    960

tgtgtgtgtg tgaatttcca tgaaaatgaa acgggcttag aatcccggtg tattatgggt   1020
```

cgggtcgtaa ccgggcaatg acgcaggatc tgacgtaaaa ctcccaagaa ttttttttaaa 1080 aagtctccgg aaaataaaat caaagttcat taacttaaaa agaaaaaaca aaatcggtcc 1140
acgtcccaaa cccttttttat aggagagtct tatgttctgg cagaagactt cacagactct 1200
ttcttaatct ctctctcttt caaccaaacc cctaaacaaa aaaaaaatac attttctgat 1260
ctctctaaaa atctttctcc ttcgttaatc tcgtgatctc tttctttttc tatatacaag 1320
tttgtacaaa aaagcaggct aaaaaaaacc atggatgtcg gagtttcacc ggtaaaagaa 1380
gatgtttttt atttccagca atgttacatt gttatacgta taatgatgag tttagtgatc 1440
aagttcctct ttgattcttc tttcttgttg caggcgaagt ctatacttgc gaaacctctg 1500
aagctactca ctgaagagga catttctcag ctcactcgcg aagactgccg caaattcctc 1560
aaagacaaag gaatgcgaag accgtcgtgg aacaaatctc aggcgatcca gcaagtttta 1620
tctcttaaag ctctctatga gcctggagac gattccggcg ccggtatctt ccgcaagatc 1680
ctcgtttctc agccagtaaa tccgcctcgc gtcacaacaa cgttgattga gccaagcaac 1740
gagctggaag cttgtggccg ggtttcttat ccggaagata acggcgcgtg ccatagaatg 1800
gattctccaa gatcagctga gttttccggt gggtctggtc actttgtatc cgagaaagat 1860
ggccacaaga cgactatttc tcccagaagc ccagctgaaa caagtgagct cgttgggcaa 1920
atgacgatat tctatagtgg aaaagtgaat gtgtatgatg gaataccacc tgaaaaggcc 1980
cggtcaatca tgcactttgc agccaatcca attgatttgc ctgaaaacgg tatttttgct 2040
tccagtagaa tgatttcaaa gctcataagt aaagagaaga tgatggaact tccccaaaaa 2100
ggccttgaga aggcgaattc ttctcgtgat tctggtatgg agggccaggc gaacagaaag 2160
gtatctttgc aaagatatcg tgaaaagcgg aaagacagaa aattctcaaa ggccaaaaag 2220
tgtccaggag ttgcgtcctc tagcttggag atgtttctga attgtcagcc acggatgaaa 2280
gctgcatatt cgcaaaacct aggctgcacc ggatctccac tgcatagcca gtcacctgaa 2340
agccagacaa aaagtcccaa tctttcagtt gatctaaaca gtgaaggcat tggatcctaa 2400
tgaacccagc tttcttgtac aaagtggtct agtgggtacc gcgaatttcc ccgatcgttc 2460
aaacatttgg caataaagtt tcttaagatt gaatcctgtt gccggtcttg cgatgattat 2520
catataattt ctgttgaatt acgttaagca tgtaataatt aacatgtaat gcatgacgtt 2580
atttatgaga tgggtttttta tgattagagt cccgcaatta tacatttaat acgcgataga 2640
aaacaaaata tagcgcgcaa actaggataa attatcgcgc gcggtgtcat ctatgttact 2700
agatcgaa 2708

<210> SEQ ID NO 56
<211> LENGTH: 161
<212> TYPE: PRT
<213> ORGANISM: Artificial Sequence
<220> FEATURE:
<223> OTHER INFORMATION: Consensus sequence

<400> SEQUENCE: 56

Met Lys Leu Leu Ser Ser Ile Glu Glu Ala Cys Asn Ile Cys Arg Leu
1 5 10 15

Lys Lys Leu Lys Cys Ser Lys Glu Lys Pro Lys Cys Ala Lys Cys Leu
20 25 30

Lys Asn Asn Trp Glu Cys Arg Tyr Ser Pro Lys Thr Lys Arg Ser Pro
35 40 45

Leu Thr Arg Ala His Leu Thr Glu Val Glu Ser Arg Leu Glu Arg Leu

```
    50                  55                  60

Glu Gln Leu Phe Leu Leu Ile Phe Pro Arg Glu Asn Leu Asn Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ser Arg Ser Asn Gln Thr Ser Leu Tyr Lys Lys Ala Gly
145                 150                 155                 160

Ser


<210> SEQ ID NO 57
<211> LENGTH: 139
<212> TYPE: PRT
<213> ORGANISM: Artificial Sequence
<220> FEATURE:
<223> OTHER INFORMATION: Consensus sequence

<400> SEQUENCE: 57

Met Pro Lys Lys Lys Arg Lys Val Ser Ser Gly Ala Asn Phe Asn Gln
1               5                   10                  15

Ser Gly Asn Ile Ala Asp Ser Ser Leu Ser Phe Thr Phe Thr Asn Ser
            20                  25                  30

Ser Asn Gly Pro Asn Leu Ile Thr Thr Gln Thr Asn Ser Gln Ala Leu
        35                  40                  45

Ser Gln Pro Ile Ala Ser Ser Asn Val His Asp Asn Phe Met Asn Asn
    50                  55                  60

Glu Ile Thr Ala Ser Lys Ile Asp Asp Gly Asn Asn Ser Lys Pro Leu
65                  70                  75                  80

Ser Pro Gly Trp Thr Asp Gln Thr Ala Tyr Asn Ala Phe Gly Ile Thr
                85                  90                  95

Thr Gly Met Phe Asn Thr Thr Thr Met Asp Asp Val Tyr Asn Tyr Leu
            100                 105                 110

Phe Asp Asp Glu Asp Thr Pro Pro Asn Pro Lys Lys Glu Gly Gly Ser
        115                 120                 125

Asn Gln Thr Ser Leu Tyr Lys Lys Ala Gly Ser
    130                 135


<210> SEQ ID NO 58
<211> LENGTH: 474
<212> TYPE: PRT
<213> ORGANISM: Artificial Sequence
<220> FEATURE:
<223> OTHER INFORMATION: Consensus sequence

<400> SEQUENCE: 58

Met Lys Leu Leu Ser Ser Ile Glu Glu Ala Cys Asn Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
```

```
    50                  55                  60

Glu Gln Leu Phe Leu Leu Ile Phe Pro Arg Glu Asn Leu Asn Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ser Arg Ser Asn Gln Thr Ser Leu Tyr Lys Lys Ala Gly
145                 150                 155                 160

Ser Met Asp Val Gly Val Ser Pro Ala Lys Ser Ile Leu Ala Lys Pro
                165                 170                 175

Leu Lys Leu Leu Thr Glu Glu Asp Ile Ser Gln Leu Thr Arg Glu Asp
            180                 185                 190

Cys Arg Lys Phe Leu Lys Asp Lys Gly Met Arg Arg Pro Ser Trp Asn
        195                 200                 205

Lys Ser Gln Ala Ile Gln Gln Val Leu Ser Leu Lys Ala Leu Tyr Glu
    210                 215                 220

Pro Gly Asp Asp Ser Gly Ala Gly Ile Phe Arg Lys Ile Leu Val Ser
225                 230                 235                 240

Gln Pro Val Asn Pro Pro Arg Val Thr Thr Thr Leu Ile Glu Pro Ser
                245                 250                 255

Asn Glu Leu Glu Ala Cys Gly Arg Val Ser Tyr Pro Glu Asp Asn Gly
            260                 265                 270

Ala Cys His Arg Met Asp Ser Pro Arg Ser Ala Glu Phe Ser Gly Gly
        275                 280                 285

Ser Gly His Phe Val Ser Glu Lys Asp Gly His Lys Thr Thr Ile Ser
    290                 295                 300

Pro Arg Ser Pro Ala Glu Thr Ser Glu Leu Val Gly Gln Met Thr Ile
305                 310                 315                 320

Phe Tyr Ser Gly Lys Val Asn Val Tyr Asp Gly Ile Pro Pro Glu Lys
                325                 330                 335

Ala Arg Ser Ile Met His Phe Ala Ala Asn Pro Ile Asp Leu Pro Glu
            340                 345                 350

Asn Gly Ile Phe Ala Ser Ser Arg Met Ile Ser Lys Leu Ile Ser Lys
        355                 360                 365

Glu Lys Met Met Glu Leu Pro Gln Lys Gly Leu Glu Lys Ala Asn Ser
    370                 375                 380

Ser Arg Asp Ser Gly Met Glu Gly Gln Ala Asn Arg Lys Val Ser Leu
385                 390                 395                 400

Gln Arg Tyr Arg Glu Lys Arg Lys Asp Arg Lys Phe Ser Lys Ala Lys
                405                 410                 415

Lys Cys Pro Gly Val Ala Ser Ser Ser Leu Glu Met Phe Leu Asn Cys
            420                 425                 430

Gln Pro Arg Met Lys Ala Ala Tyr Ser Gln Asn Leu Gly Cys Thr Gly
        435                 440                 445

Ser Pro Leu His Ser Gln Ser Pro Glu Ser Gln Thr Lys Ser Pro Asn
    450                 455                 460

Leu Ser Val Asp Leu Asn Ser Glu Gly Ile
465                 470
```

<210> SEQ ID NO 59
<211> LENGTH: 452
<212> TYPE: PRT
<213> ORGANISM: Artificial Sequence
<220> FEATURE:
<223> OTHER INFORMATION: Consensus sequence

<400> SEQUENCE: 59

Met Pro Lys Lys Lys Arg Lys Val Ser Ser Gly Ala Asn Phe Asn Gln
1               5                   10                  15

Ser Gly Asn Ile Ala Asp Ser Ser Leu Ser Phe Thr Phe Thr Asn Ser
            20                  25                  30

Ser Asn Gly Pro Asn Leu Ile Thr Thr Gln Thr Asn Ser Gln Ala Leu
        35                  40                  45

Ser Gln Pro Ile Ala Ser Ser Asn Val His Asp Asn Phe Met Asn Asn
    50                  55                  60

Glu Ile Thr Ala Ser Lys Ile Asp Asp Gly Asn Asn Ser Lys Pro Leu
65                  70                  75                  80

Ser Pro Gly Trp Thr Asp Gln Thr Ala Tyr Asn Ala Phe Gly Ile Thr
                85                  90                  95

Thr Gly Met Phe Asn Thr Thr Thr Met Asp Asp Val Tyr Asn Tyr Leu
            100                 105                 110

Phe Asp Asp Glu Asp Thr Pro Pro Asn Pro Lys Lys Glu Gly Gly Ser
        115                 120                 125

Asn Gln Thr Ser Leu Tyr Lys Lys Ala Gly Ser Met Asp Val Gly Val
    130                 135                 140

Ser Pro Ala Lys Ser Ile Leu Ala Lys Pro Leu Lys Leu Leu Thr Glu
145                 150                 155                 160

Glu Asp Ile Ser Gln Leu Thr Arg Glu Asp Cys Arg Lys Phe Leu Lys
                165                 170                 175

Asp Lys Gly Met Arg Arg Pro Ser Trp Asn Lys Ser Gln Ala Ile Gln
            180                 185                 190

Gln Val Leu Ser Leu Lys Ala Leu Tyr Glu Pro Gly Asp Asp Ser Gly
        195                 200                 205

Ala Gly Ile Phe Arg Lys Ile Leu Val Ser Gln Pro Val Asn Pro Pro
    210                 215                 220

Arg Val Thr Thr Thr Leu Ile Glu Pro Ser Asn Glu Leu Glu Ala Cys
225                 230                 235                 240

Gly Arg Val Ser Tyr Pro Glu Asp Asn Gly Ala Cys His Arg Met Asp
                245                 250                 255

Ser Pro Arg Ser Ala Glu Phe Ser Gly Gly Ser Gly His Phe Val Ser
            260                 265                 270

Glu Lys Asp Gly His Lys Thr Thr Ile Ser Pro Arg Ser Pro Ala Glu
        275                 280                 285

Thr Ser Glu Leu Val Gly Gln Met Thr Ile Phe Tyr Ser Gly Lys Val
    290                 295                 300

Asn Val Tyr Asp Gly Ile Pro Pro Glu Lys Ala Arg Ser Ile Met His
305                 310                 315                 320

Phe Ala Ala Asn Pro Ile Asp Leu Pro Glu Asn Gly Ile Phe Ala Ser
                325                 330                 335

Ser Arg Met Ile Ser Lys Leu Ile Ser Lys Glu Lys Met Met Glu Leu
            340                 345                 350

Pro Gln Lys Gly Leu Glu Lys Ala Asn Ser Ser Arg Asp Ser Gly Met
        355                 360                 365

```
Glu Gly Gln Ala Asn Arg Lys Val Ser Leu Gln Arg Tyr Arg Glu Lys
    370                 375                 380

Arg Lys Asp Arg Lys Phe Ser Lys Ala Lys Lys Cys Pro Gly Val Ala
385                 390                 395                 400

Ser Ser Ser Leu Glu Met Phe Leu Asn Cys Gln Pro Arg Met Lys Ala
                405                 410                 415

Ala Tyr Ser Gln Asn Leu Gly Cys Thr Gly Ser Pro Leu His Ser Gln
            420                 425                 430

Ser Pro Glu Ser Gln Thr Lys Ser Pro Asn Leu Ser Val Asp Leu Asn
        435                 440                 445

Ser Glu Gly Ile
    450


<210> SEQ ID NO 60
<211> LENGTH: 391
<212> TYPE: PRT
<213> ORGANISM: Artificial Sequence
<220> FEATURE:
<223> OTHER INFORMATION: Consensus sequence

<400> SEQUENCE: 60

Met Pro Lys Lys Lys Arg Lys Val Ser Ser Gly Ala Asn Phe Asn Gln
1               5                   10                  15

Ser Gly Asn Ile Ala Asp Ser Ser Leu Ser Phe Thr Phe Thr Asn Ser
            20                  25                  30

Ser Asn Gly Pro Asn Leu Ile Thr Thr Gln Thr Asn Ser Gln Ala Leu
        35                  40                  45

Ser Gln Pro Ile Ala Ser Ser Asn Val His Asp Asn Phe Met Asn Asn
    50                  55                  60

Glu Ile Thr Ala Ser Lys Ile Asp Asp Gly Asn Asn Ser Lys Pro Leu
65                  70                  75                  80

Ser Pro Gly Trp Thr Asp Gln Thr Ala Tyr Asn Ala Phe Gly Ile Thr
                85                  90                  95

Thr Gly Met Phe Asn Thr Thr Thr Met Asp Asp Val Tyr Asn Tyr Leu
            100                 105                 110

Phe Asp Asp Glu Asp Thr Pro Pro Asn Pro Lys Lys Glu Gly Gly Ser
        115                 120                 125

Asn Gln Thr Ser Leu Tyr Lys Lys Ala Gly Ser Tyr Glu Pro Gly Asp
    130                 135                 140

Asp Ser Gly Ala Gly Ile Phe Arg Lys Ile Leu Val Ser Gln Pro Val
145                 150                 155                 160

Asn Pro Pro Arg Val Thr Thr Thr Leu Ile Glu Pro Ser Asn Glu Leu
                165                 170                 175

Glu Ala Cys Gly Arg Val Ser Tyr Pro Glu Asp Asn Gly Ala Cys His
            180                 185                 190

Arg Met Asp Ser Pro Arg Ser Ala Glu Phe Ser Gly Gly Ser Gly His
        195                 200                 205

Phe Val Ser Glu Lys Asp Gly His Lys Thr Thr Ile Ser Pro Arg Ser
    210                 215                 220

Pro Ala Glu Thr Ser Glu Leu Val Gly Gln Met Thr Ile Phe Tyr Ser
225                 230                 235                 240

Gly Lys Val Asn Val Tyr Asp Gly Ile Pro Pro Glu Lys Ala Arg Ser
                245                 250                 255

Ile Met His Phe Ala Ala Asn Pro Ile Asp Leu Pro Glu Asn Gly Ile
            260                 265                 270
```

Phe Ala Ser Ser Arg Met Ile Ser Lys Leu Ile Ser Lys Glu Lys Met
275 280 285

Met Glu Leu Pro Gln Lys Gly Leu Glu Lys Ala Asn Ser Ser Arg Asp
290 295 300

Ser Gly Met Glu Gly Gln Ala Asn Arg Lys Val Ser Leu Gln Arg Tyr
305 310 315 320

Arg Glu Lys Arg Lys Asp Arg Lys Phe Ser Lys Ala Lys Lys Cys Pro
325 330 335

Gly Val Ala Ser Ser Ser Leu Glu Met Phe Leu Asn Cys Gln Pro Arg
340 345 350

Met Lys Ala Ala Tyr Ser Gln Asn Leu Gly Cys Thr Gly Ser Pro Leu
355 360 365

His Ser Gln Ser Pro Glu Ser Gln Thr Lys Ser Pro Asn Leu Ser Val
370 375 380

Asp Leu Asn Ser Glu Gly Ile
385 390

<210> SEQ ID NO 61
<211> LENGTH: 427
<212> TYPE: PRT
<213> ORGANISM: Artificial Sequence
<220> FEATURE:
<223> OTHER INFORMATION: Consensus sequence

<400> SEQUENCE: 61

Met Pro Lys Lys Lys Arg Lys Val Ser Ser Gly Ala Asn Phe Asn Gln
1 5 10 15

Ser Gly Asn Ile Ala Asp Ser Ser Leu Ser Phe Thr Phe Thr Asn Ser
20 25 30

Ser Asn Gly Pro Asn Leu Ile Thr Thr Gln Thr Asn Ser Gln Ala Leu
35 40 45

Ser Gln Pro Ile Ala Ser Ser Asn Val His Asp Asn Phe Met Asn Asn
50 55 60

Glu Ile Thr Ala Ser Lys Ile Asp Asp Gly Asn Asn Ser Lys Pro Leu
65 70 75 80

Ser Pro Gly Trp Thr Asp Gln Thr Ala Tyr Asn Ala Phe Gly Ile Thr
85 90 95

Thr Gly Met Phe Asn Thr Thr Thr Met Asp Asp Val Tyr Asn Tyr Leu
100 105 110

Phe Asp Asp Glu Asp Thr Pro Pro Asn Pro Lys Lys Glu Gly Gly Ser
115 120 125

Asn Gln Thr Ser Leu Tyr Lys Lys Ala Gly Ser Met Asp Val Gly Val
130 135 140

Ser Pro Ala Lys Ser Ile Leu Ala Lys Pro Leu Lys Leu Leu Thr Glu
145 150 155 160

Glu Asp Ile Ser Gln Leu Thr Arg Glu Asp Cys Arg Lys Phe Leu Lys
165 170 175

Asp Lys Gly Met Arg Arg Pro Ser Trp Asn Lys Ser Gln Ala Ile Gln
180 185 190

Gln Val Leu Ser Leu Lys Ala Leu Tyr Glu Pro Gly Asp Asp Ser Gly
195 200 205

Ala Gly Ile Phe Arg Lys Ile Leu Val Ser Gln Pro Val Asn Pro Pro
210 215 220

Arg Val Thr Thr Thr Leu Ile Glu Pro Ser Asn Glu Leu Glu Ala Cys
225 230 235 240

-continued

```
Gly Arg Val Ser Tyr Pro Glu Asp Asn Gly Ala Cys His Arg Met Asp
                245                 250                 255

Ser Pro Arg Ser Ala Glu Phe Ser Gly Gly Ser Gly His Phe Val Ser
            260                 265                 270

Glu Lys Asp Gly His Lys Thr Thr Ile Ser Pro Arg Ser Pro Ala Glu
        275                 280                 285

Thr Ser Glu Leu Ile Met His Phe Ala Ala Asn Pro Ile Asp Leu Pro
    290                 295                 300

Glu Asn Gly Ile Phe Ala Ser Ser Arg Met Ile Ser Lys Leu Ile Ser
305                 310                 315                 320

Lys Glu Lys Met Met Glu Leu Pro Gln Lys Gly Leu Glu Lys Ala Asn
                325                 330                 335

Ser Ser Arg Asp Ser Gly Met Glu Gly Gln Ala Asn Arg Lys Val Ser
            340                 345                 350

Leu Gln Arg Tyr Arg Glu Lys Arg Lys Asp Arg Lys Phe Ser Lys Ala
        355                 360                 365

Lys Lys Cys Pro Gly Val Ala Ser Ser Ser Leu Glu Met Phe Leu Asn
    370                 375                 380

Cys Gln Pro Arg Met Lys Ala Ala Tyr Ser Gln Asn Leu Gly Cys Thr
385                 390                 395                 400

Gly Ser Pro Leu His Ser Gln Ser Pro Glu Ser Gln Thr Lys Ser Pro
                405                 410                 415

Asn Leu Ser Val Asp Leu Asn Ser Glu Gly Ile
            420                 425


<210> SEQ ID NO 62
<211> LENGTH: 368
<212> TYPE: PRT
<213> ORGANISM: Artificial Sequence
<220> FEATURE:
<223> OTHER INFORMATION: Consensus sequence

<400> SEQUENCE: 62

Met Pro Lys Lys Lys Arg Lys Val Ser Ser Gly Ala Asn Phe Asn Gln
1               5                   10                  15

Ser Gly Asn Ile Ala Asp Ser Ser Leu Ser Phe Thr Phe Thr Asn Ser
            20                  25                  30

Ser Asn Gly Pro Asn Leu Ile Thr Thr Gln Thr Asn Ser Gln Ala Leu
        35                  40                  45

Ser Gln Pro Ile Ala Ser Ser Asn Val His Asp Asn Phe Met Asn Asn
    50                  55                  60

Glu Ile Thr Ala Ser Lys Ile Asp Asp Gly Asn Asn Ser Lys Pro Leu
65                  70                  75                  80

Ser Pro Gly Trp Thr Asp Gln Thr Ala Tyr Asn Ala Phe Gly Ile Thr
                85                  90                  95

Thr Gly Met Phe Asn Thr Thr Thr Met Asp Asp Val Tyr Asn Tyr Leu
            100                 105                 110

Phe Asp Asp Glu Asp Thr Pro Pro Asn Pro Lys Lys Glu Gly Gly Ser
        115                 120                 125

Asn Gln Thr Ser Leu Tyr Lys Lys Ala Gly Ser Met Asp Val Gly Val
    130                 135                 140

Ser Pro Ala Lys Ser Ile Leu Ala Lys Pro Leu Lys Leu Leu Thr Glu
145                 150                 155                 160

Glu Asp Ile Ser Gln Leu Thr Arg Glu Asp Cys Arg Lys Phe Leu Lys
                165                 170                 175
```

Asp Lys Gly Met Arg Arg Pro Ser Trp Asn Lys Ser Gln Ala Ile Gln
180 185 190

Gln Val Leu Ser Leu Lys Ala Leu Tyr Glu Pro Gly Asp Asp Ser Gly
195 200 205

Ala Gly Ile Phe Arg Lys Ile Leu Val Ser Gln Pro Val Asn Pro Pro
210 215 220

Arg Val Thr Thr Thr Leu Ile Glu Pro Ser Asn Glu Leu Glu Ala Cys
225 230 235 240

Gly Arg Val Ser Tyr Pro Glu Asp Asn Gly Ala Cys His Arg Met Asp
245 250 255

Ser Pro Arg Ser Ala Glu Phe Ser Gly Gly Ser Gly His Phe Val Ser
260 265 270

Glu Lys Asp Gly His Lys Thr Thr Ile Ser Pro Arg Ser Pro Ala Glu
275 280 285

Thr Ser Glu Leu Val Gly Gln Met Thr Ile Phe Tyr Ser Gly Lys Val
290 295 300

Asn Val Tyr Asp Gly Ile Pro Pro Glu Lys Ala Arg Ser Ile Met His
305 310 315 320

Phe Ala Ala Asn Pro Ile Asp Leu Pro Glu Asn Gly Ile Phe Ala Ser
325 330 335

Ser Arg Met Ile Ser Lys Leu Ile Ser Lys Glu Lys Met Met Glu Leu
340 345 350

Pro Gln Lys Gly Leu Glu Lys Ala Asn Ser Ser Arg Asp Ser Gly Met
355 360 365

<210> SEQ ID NO 63
<211> LENGTH: 1131
<212> TYPE: PRT
<213> ORGANISM: Artificial Sequence
<220> FEATURE:
<223> OTHER INFORMATION: Consensus sequence

<400> SEQUENCE: 63

Met Ser Ser Leu Ser Arg Glu Leu Val Phe Leu Ile Leu Gln Phe Leu
1 5 10 15

Asp Glu Glu Lys Phe Lys Glu Thr Val His Lys Leu Glu Gln Glu Ser
20 25 30

Gly Phe Phe Phe Asn Met Lys Tyr Phe Glu Asp Glu Val His Asn Gly
35 40 45

Asn Trp Asp Glu Val Glu Lys Tyr Leu Ser Gly Phe Thr Lys Val Asp
50 55 60

Asp Asn Arg Tyr Ser Met Lys Ile Phe Phe Glu Ile Arg Lys Gln Lys
65 70 75 80

Tyr Leu Glu Ala Leu Asp Lys His Asp Arg Pro Lys Ala Val Asp Ile
85 90 95

Leu Val Lys Asp Leu Lys Val Phe Ser Thr Phe Asn Glu Glu Leu Phe
100 105 110

Lys Glu Ile Thr Gln Leu Leu Thr Leu Glu Asn Phe Arg Glu Asn Glu
115 120 125

Gln Leu Ser Lys Tyr Gly Asp Thr Lys Ser Ala Arg Ala Ile Met Leu
130 135 140

Val Glu Leu Lys Lys Leu Ile Glu Ala Asn Pro Leu Phe Arg Asp Lys
145 150 155 160

Leu Gln Phe Pro Thr Leu Arg Asn Ser Arg Leu Arg Thr Leu Ile Asn
165 170 175

-continued

```
Gln Ser Leu Asn Trp Gln His Gln Leu Cys Lys Asn Pro Arg Pro Asn
            180                 185                 190

Pro Asp Ile Lys Thr Leu Phe Val Asp His Ser Cys Gly Pro Pro Asn
        195                 200                 205

Gly Ala Arg Ala Pro Ser Pro Val Asn Asn Pro Leu Leu Gly Gly Ile
    210                 215                 220

Pro Lys Ala Gly Gly Phe Pro Pro Leu Gly Ala His Gly Pro Phe Gln
225                 230                 235                 240

Pro Thr Ala Ser Pro Val Pro Thr Pro Leu Ala Gly Trp Met Ser Ser
                245                 250                 255

Pro Ser Ser Val Pro His Pro Ala Val Ser Ala Gly Ala Ile Ala Leu
            260                 265                 270

Gly Gly Pro Ser Ile Pro Ala Ala Leu Lys His Pro Arg Thr Pro Pro
        275                 280                 285

Thr Asn Ala Ser Leu Asp Tyr Pro Ser Ala Asp Ser Glu His Val Ser
    290                 295                 300

Lys Arg Thr Arg Pro Met Gly Ile Ser Asp Glu Val Asn Leu Gly Val
305                 310                 315                 320

Asn Met Leu Pro Met Ser Phe Ser Gly Gln Ala His Gly His Ser Pro
                325                 330                 335

Ala Phe Lys Ala Pro Asp Asp Leu Pro Lys Thr Val Ala Arg Thr Leu
            340                 345                 350

Ser Gln Gly Ser Ser Pro Met Ser Met Asp Phe His Pro Ile Lys Gln
        355                 360                 365

Thr Leu Leu Leu Val Gly Thr Asn Val Gly Asp Ile Gly Leu Trp Glu
    370                 375                 380

Val Gly Ser Arg Glu Arg Leu Val Gln Lys Thr Phe Lys Val Trp Asp
385                 390                 395                 400

Leu Ser Lys Cys Ser Met Pro Leu Gln Ala Ala Leu Val Lys Glu Pro
                405                 410                 415

Val Val Ser Val Asn Arg Val Ile Trp Ser Pro Asp Gly Ser Leu Phe
            420                 425                 430

Gly Val Ala Tyr Ser Arg His Ile Val Gln Leu Tyr Ser Tyr His Gly
        435                 440                 445

Gly Glu Asp Met Arg Gln His Leu Glu Ile Asp Ala His Val Gly Gly
    450                 455                 460

Val Asn Asp Ile Ser Phe Ser Thr Pro Asn Lys Gln Leu Cys Val Ile
465                 470                 475                 480

Thr Cys Gly Asp Asp Lys Thr Ile Lys Val Trp Asp Ala Ala Thr Gly
                485                 490                 495

Val Lys Arg His Thr Phe Glu Gly His Glu Ala Pro Val Tyr Ser Val
            500                 505                 510

Cys Pro His Tyr Lys Glu Asn Ile Gln Phe Ile Phe Ser Thr Ala Leu
        515                 520                 525

Asp Gly Lys Ile Lys Ala Trp Leu Tyr Asp Asn Met Gly Ser Arg Val
    530                 535                 540

Asp Tyr Asp Ala Pro Gly Arg Trp Cys Thr Thr Met Ala Tyr Ser Ala
545                 550                 555                 560

Asp Gly Thr Arg Leu Phe Ser Cys Gly Thr Ser Lys Asp Gly Glu Ser
                565                 570                 575

Phe Ile Val Glu Trp Asn Glu Ser Glu Gly Ala Val Lys Arg Thr Tyr
            580                 585                 590
```

```
Gln Gly Phe His Lys Arg Ser Leu Gly Val Val Gln Phe Asp Thr Thr
        595                 600                 605

Lys Asn Arg Tyr Leu Ala Ala Gly Asp Asp Phe Ser Ile Lys Phe Trp
    610                 615                 620

Asp Met Asp Ala Val Gln Leu Leu Thr Ala Ile Asp Gly Asp Gly Gly
625                 630                 635                 640

Leu Gln Ala Ser Pro Arg Ile Arg Phe Asn Lys Glu Gly Ser Leu Leu
                645                 650                 655

Ala Val Ser Gly Asn Glu Asn Val Ile Lys Ile Met Ala Asn Ser Asp
            660                 665                 670

Gly Leu Arg Leu Leu His Thr Phe Glu Asn Ile Ser Ser Glu Ser Ser
        675                 680                 685

Lys Pro Ala Ile Asn Ser Ile Ala Ala Ala Ala Ala Ala Ala Ala Thr
    690                 695                 700

Ser Ala Gly His Ala Asp Arg Ser Ala Asn Val Val Ser Ile Gln Gly
705                 710                 715                 720

Met Asn Gly Asp Ser Arg Asn Met Val Asp Val Lys Pro Val Ile Thr
                725                 730                 735

Glu Glu Ser Asn Asp Lys Ser Lys Ile Trp Lys Leu Thr Glu Val Ser
            740                 745                 750

Glu Pro Ser Gln Cys Arg Ser Leu Arg Leu Pro Glu Asn Leu Arg Val
        755                 760                 765

Ala Lys Ile Ser Arg Leu Ile Phe Thr Asn Ser Gly Asn Ala Ile Leu
    770                 775                 780

Ala Leu Ala Ser Asn Ala Ile His Leu Leu Trp Lys Trp Gln Arg Asn
785                 790                 795                 800

Glu Arg Asn Ala Thr Gly Lys Ala Thr Ala Ser Leu Pro Pro Gln Gln
                805                 810                 815

Trp Gln Pro Ala Ser Gly Ile Leu Met Thr Asn Asp Val Ala Glu Thr
            820                 825                 830

Asn Pro Glu Glu Ala Val Pro Cys Phe Ala Leu Ser Lys Asn Asp Ser
        835                 840                 845

Tyr Val Met Ser Ala Ser Gly Gly Lys Ile Ser Leu Phe Asn Met Met
    850                 855                 860

Thr Phe Lys Thr Met Ala Thr Phe Met Pro Pro Pro Pro Ala Ala Thr
865                 870                 875                 880

Phe Leu Ala Phe His Pro Gln Asp Asn Asn Ile Ile Ala Ile Gly Met
                885                 890                 895

Asp Asp Ser Thr Ile Gln Ile Tyr Asn Val Arg Val Asp Glu Val Lys
            900                 905                 910

Ser Lys Leu Lys Gly His Ser Lys Arg Ile Thr Gly Leu Ala Phe Ser
        915                 920                 925

Asn Val Leu Asn Val Leu Val Ser Ser Gly Ala Asp Ala Gln Leu Cys
    930                 935                 940

Val Trp Asn Thr Asp Gly Trp Glu Lys Gln Arg Ser Lys Val Leu Pro
945                 950                 955                 960

Leu Pro Gln Gly Arg Pro Asn Ser Ala Pro Ser Asp Thr Arg Val Gln
                965                 970                 975

Phe His Gln Asp Gln Ala His Phe Leu Val Val His Glu Thr Gln Leu
            980                 985                 990

Ala Ile Tyr Glu Thr Thr Lys Leu  Glu Cys Met Lys Gln  Trp Ala Val
        995                 1000                1005

Arg Glu  Ser Leu Ala Pro Ile  Thr His Ala Thr Phe  Ser Cys Asp
```

```
    1010                1015                1020

Ser Gln  Leu Val Tyr Ala Ser  Phe Met Asp Ala Thr  Val Cys Val
    1025                1030                1035

Phe Ser  Ser Ala Asn Leu Arg  Leu Arg Cys Arg Val  Asn Pro Ser
    1040                1045                1050

Ala Tyr  Leu Pro Ala Ser Leu  Ser Asn Ser Asn Val  His Pro Leu
    1055                1060                1065

Val Ile  Ala Ala His Pro Gln  Glu Pro Asn Met Phe  Ala Val Gly
    1070                1075                1080

Leu Ser  Asp Gly Gly Val His  Ile Phe Glu Pro Leu  Glu Ser Glu
    1085                1090                1095

Gly Lys  Trp Gly Val Ala Pro  Pro Ala Glu Asn Gly  Ser Ala Ser
    1100                1105                1110

Gly Ala  Pro Thr Ala Pro Ser  Val Gly Ala Ser Ala  Ser Asp Gln
    1115                1120                1125

Pro Gln  Arg
    1130


<210> SEQ ID NO 64
<211> LENGTH: 1292
<212> TYPE: PRT
<213> ORGANISM: Artificial Sequence
<220> FEATURE:
<223> OTHER INFORMATION: Consensus sequence

<400> SEQUENCE: 64

Met Lys Leu Leu Ser Ser Ile Glu Glu Ala Cys Asn Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asn Leu Asn Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ser Arg Ser Asn Gln Thr Ser Leu Tyr Lys Lys Ala Gly
145                 150                 155                 160

Ser Met Ser Ser Leu Ser Arg Glu Leu Val Phe Leu Ile Leu Gln Phe
                165                 170                 175

Leu Asp Glu Glu Lys Phe Lys Glu Thr Val His Lys Leu Glu Gln Glu
            180                 185                 190

Ser Gly Phe Phe Phe Asn Met Lys Tyr Phe Glu Asp Glu Val His Asn
        195                 200                 205

Gly Asn Trp Asp Glu Val Glu Lys Tyr Leu Ser Gly Phe Thr Lys Val
    210                 215                 220

Asp Asp Asn Arg Tyr Ser Met Lys Ile Phe Phe Glu Ile Arg Lys Gln
```

-continued

```
225                 230                 235                 240

Lys Tyr Leu Glu Ala Leu Asp Lys His Asp Arg Pro Lys Ala Val Asp
                245                 250                 255

Ile Leu Val Lys Asp Leu Lys Val Phe Ser Thr Phe Asn Glu Glu Leu
            260                 265                 270

Phe Lys Glu Ile Thr Gln Leu Leu Thr Leu Glu Asn Phe Arg Glu Asn
        275                 280                 285

Glu Gln Leu Ser Lys Tyr Gly Asp Thr Lys Ser Ala Arg Ala Ile Met
    290                 295                 300

Leu Val Glu Leu Lys Lys Leu Ile Glu Ala Asn Pro Leu Phe Arg Asp
305                 310                 315                 320

Lys Leu Gln Phe Pro Thr Leu Arg Asn Ser Arg Leu Arg Thr Leu Ile
                325                 330                 335

Asn Gln Ser Leu Asn Trp Gln His Gln Leu Cys Lys Asn Pro Arg Pro
            340                 345                 350

Asn Pro Asp Ile Lys Thr Leu Phe Val Asp His Ser Cys Gly Pro Pro
        355                 360                 365

Asn Gly Ala Arg Ala Pro Ser Pro Val Asn Asn Pro Leu Leu Gly Gly
    370                 375                 380

Ile Pro Lys Ala Gly Gly Phe Pro Pro Leu Gly Ala His Gly Pro Phe
385                 390                 395                 400

Gln Pro Thr Ala Ser Pro Val Pro Thr Pro Leu Ala Gly Trp Met Ser
                405                 410                 415

Ser Pro Ser Ser Val Pro His Pro Ala Val Ser Ala Gly Ala Ile Ala
            420                 425                 430

Leu Gly Gly Pro Ser Ile Pro Ala Ala Leu Lys His Pro Arg Thr Pro
        435                 440                 445

Pro Thr Asn Ala Ser Leu Asp Tyr Pro Ser Ala Asp Ser Glu His Val
    450                 455                 460

Ser Lys Arg Thr Arg Pro Met Gly Ile Ser Asp Glu Val Asn Leu Gly
465                 470                 475                 480

Val Asn Met Leu Pro Met Ser Phe Ser Gly Gln Ala His Gly His Ser
                485                 490                 495

Pro Ala Phe Lys Ala Pro Asp Asp Leu Pro Lys Thr Val Ala Arg Thr
            500                 505                 510

Leu Ser Gln Gly Ser Ser Pro Met Ser Met Asp Phe His Pro Ile Lys
        515                 520                 525

Gln Thr Leu Leu Leu Val Gly Thr Asn Val Gly Asp Ile Gly Leu Trp
    530                 535                 540

Glu Val Gly Ser Arg Glu Arg Leu Val Gln Lys Thr Phe Lys Val Trp
545                 550                 555                 560

Asp Leu Ser Lys Cys Ser Met Pro Leu Gln Ala Ala Leu Val Lys Glu
                565                 570                 575

Pro Val Val Ser Val Asn Arg Val Ile Trp Ser Pro Asp Gly Ser Leu
            580                 585                 590

Phe Gly Val Ala Tyr Ser Arg His Ile Val Gln Leu Tyr Ser Tyr His
        595                 600                 605

Gly Gly Glu Asp Met Arg Gln His Leu Glu Ile Asp Ala His Val Gly
    610                 615                 620

Gly Val Asn Asp Ile Ser Phe Ser Thr Pro Asn Lys Gln Leu Cys Val
625                 630                 635                 640

Ile Thr Cys Gly Asp Asp Lys Thr Ile Lys Val Trp Asp Ala Ala Thr
                645                 650                 655
```

Gly Val Lys Arg His Thr Phe Glu Gly His Glu Ala Pro Val Tyr Ser
660 665 670

Val Cys Pro His Tyr Lys Glu Asn Ile Gln Phe Ile Phe Ser Thr Ala
675 680 685

Leu Asp Gly Lys Ile Lys Ala Trp Leu Tyr Asp Asn Met Gly Ser Arg
690 695 700

Val Asp Tyr Asp Ala Pro Gly Arg Trp Cys Thr Thr Met Ala Tyr Ser
705 710 715 720

Ala Asp Gly Thr Arg Leu Phe Ser Cys Gly Thr Ser Lys Asp Gly Glu
725 730 735

Ser Phe Ile Val Glu Trp Asn Glu Ser Glu Gly Ala Val Lys Arg Thr
740 745 750

Tyr Gln Gly Phe His Lys Arg Ser Leu Gly Val Val Gln Phe Asp Thr
755 760 765

Thr Lys Asn Arg Tyr Leu Ala Ala Gly Asp Asp Phe Ser Ile Lys Phe
770 775 780

Trp Asp Met Asp Ala Val Gln Leu Leu Thr Ala Ile Asp Gly Asp Gly
785 790 795 800

Gly Leu Gln Ala Ser Pro Arg Ile Arg Phe Asn Lys Glu Gly Ser Leu
805 810 815

Leu Ala Val Ser Gly Asn Glu Asn Val Ile Lys Ile Met Ala Asn Ser
820 825 830

Asp Gly Leu Arg Leu Leu His Thr Phe Glu Asn Ile Ser Ser Glu Ser
835 840 845

Ser Lys Pro Ala Ile Asn Ser Ile Ala Ala Ala Ala Ala Ala Ala Ala
850 855 860

Thr Ser Ala Gly His Ala Asp Arg Ser Ala Asn Val Val Ser Ile Gln
865 870 875 880

Gly Met Asn Gly Asp Ser Arg Asn Met Val Asp Val Lys Pro Val Ile
885 890 895

Thr Glu Glu Ser Asn Asp Lys Ser Lys Ile Trp Lys Leu Thr Glu Val
900 905 910

Ser Glu Pro Ser Gln Cys Arg Ser Leu Arg Leu Pro Glu Asn Leu Arg
915 920 925

Val Ala Lys Ile Ser Arg Leu Ile Phe Thr Asn Ser Gly Asn Ala Ile
930 935 940

Leu Ala Leu Ala Ser Asn Ala Ile His Leu Leu Trp Lys Trp Gln Arg
945 950 955 960

Asn Glu Arg Asn Ala Thr Gly Lys Ala Thr Ala Ser Leu Pro Pro Gln
965 970 975

Gln Trp Gln Pro Ala Ser Gly Ile Leu Met Thr Asn Asp Val Ala Glu
980 985 990

Thr Asn Pro Glu Glu Ala Val Pro Cys Phe Ala Leu Ser Lys Asn Asp
995 1000 1005

Ser Tyr Val Met Ser Ala Ser Gly Gly Lys Ile Ser Leu Phe Asn
1010 1015 1020

Met Met Thr Phe Lys Thr Met Ala Thr Phe Met Pro Pro Pro Pro
1025 1030 1035

Ala Ala Thr Phe Leu Ala Phe His Pro Gln Asp Asn Asn Ile Ile
1040 1045 1050

Ala Ile Gly Met Asp Asp Ser Thr Ile Gln Ile Tyr Asn Val Arg
1055 1060 1065

-continued

Val Asp Glu Val Lys Ser Lys Leu Lys Gly His Ser Lys Arg Ile
1070 1075 1080

Thr Gly Leu Ala Phe Ser Asn Val Leu Asn Val Leu Val Ser Ser
1085 1090 1095

Gly Ala Asp Ala Gln Leu Cys Val Trp Asn Thr Asp Gly Trp Glu
1100 1105 1110

Lys Gln Arg Ser Lys Val Leu Pro Leu Pro Gln Gly Arg Pro Asn
1115 1120 1125

Ser Ala Pro Ser Asp Thr Arg Val Gln Phe His Gln Asp Gln Ala
1130 1135 1140

His Phe Leu Val Val His Glu Thr Gln Leu Ala Ile Tyr Glu Thr
1145 1150 1155

Thr Lys Leu Glu Cys Met Lys Gln Trp Ala Val Arg Glu Ser Leu
1160 1165 1170

Ala Pro Ile Thr His Ala Thr Phe Ser Cys Asp Ser Gln Leu Val
1175 1180 1185

Tyr Ala Ser Phe Met Asp Ala Thr Val Cys Val Phe Ser Ser Ala
1190 1195 1200

Asn Leu Arg Leu Arg Cys Arg Val Asn Pro Ser Ala Tyr Leu Pro
1205 1210 1215

Ala Ser Leu Ser Asn Ser Asn Val His Pro Leu Val Ile Ala Ala
1220 1225 1230

His Pro Gln Glu Pro Asn Met Phe Ala Val Gly Leu Ser Asp Gly
1235 1240 1245

Gly Val His Ile Phe Glu Pro Leu Glu Ser Glu Gly Lys Trp Gly
1250 1255 1260

Val Ala Pro Pro Ala Glu Asn Gly Ser Ala Ser Gly Ala Pro Thr
1265 1270 1275

Ala Pro Ser Val Gly Ala Ser Ala Ser Asp Gln Pro Gln Arg
1280 1285 1290

<210> SEQ ID NO 65
<211> LENGTH: 425
<212> TYPE: PRT
<213> ORGANISM: Artificial Sequence
<220> FEATURE:
<223> OTHER INFORMATION: Consensus sequence

<400> SEQUENCE: 65

Met Asp Asp Asp Asn Gly Leu Glu Leu Ser Leu Gly Leu Ser Cys Gly
1 5 10 15

Gly Ser Thr Gly Lys Ala Lys Gly Asn Asn Asn Asn Asn Ala Gly Ser
20 25 30

Ser Ser Glu Asn Tyr Arg Ala Glu Gly Gly Asp Arg Ser Ala Lys Val
35 40 45

Ile Asp Asp Phe Lys Asn Phe Leu His Pro Thr Ser Gln Arg Pro Ala
50 55 60

Glu Pro Ser Ser Gly Ser Gln Arg Ser Asp Ser Gly Gln Gln Pro Pro
65 70 75 80

Gln Asn Phe Phe Asn Asp Leu Ser Lys Ala Pro Thr Thr Glu Ala Glu
85 90 95

Ala Ser Thr Lys Pro Leu Trp Val Glu Asp Glu Ser Arg Lys Glu Ala
100 105 110

Gly Asn Lys Arg Lys Phe Gly Phe Pro Gly Met Asn Asp Asp Lys Lys
115 120 125

-continued

```
Lys Glu Lys Asp Ser Ser His Val Asp Met His Glu Lys Lys Thr Lys
    130                 135                 140

Ala Ser His Val Ser Thr Ala Thr Asp Glu Gly Ser Thr Ala Glu Asn
145                 150                 155                 160

Glu Asp Val Ala Glu Ser Glu Val Gly Gly Gly Ser Ser Ser Asn His
                165                 170                 175

Ala Lys Glu Val Val Arg Pro Pro Thr Asp Thr Asn Ile Val Asp Asn
            180                 185                 190

Leu Thr Gly Gln Arg Arg Ser Asn His Gly Gly Ser Gly Thr Glu Glu
        195                 200                 205

Phe Thr Met Arg Asn Met Ser Tyr Thr Val Pro Phe Thr Val His Pro
    210                 215                 220

Gln Asn Val Val Thr Ser Met Pro Tyr Ser Leu Pro Thr Lys Glu Ser
225                 230                 235                 240

Gly Gln His Ala Ala Ala Thr Ser Leu Leu Gln Pro Asn Ala Asn Ala
                245                 250                 255

Gly Asn Leu Pro Ile Met Phe Gly Tyr Ser Pro Val Gln Leu Pro Met
            260                 265                 270

Leu Asp Lys Asp Gly Ser Gly Gly Ile Val Ala Leu Ser Gln Ser Pro
        275                 280                 285

Phe Ala Gly Arg Val Pro Ser Asn Ser Ala Thr Ala Lys Gly Glu Gly
    290                 295                 300

Lys Gln Pro Val Ala Glu Glu Gly Ser Ser Glu Asp Ala Ser Glu Arg
305                 310                 315                 320

Pro Thr Gly Asp Asn Ser Asn Leu Asn Thr Ala Phe Ser Phe Asp Phe
                325                 330                 335

Ser Ala Ile Lys Pro Gly Met Ala Ala Asp Val Lys Phe Gly Gly Ser
            340                 345                 350

Gly Ala Arg Pro Asn Leu Pro Trp Val Ser Thr Thr Gly Ser Gly Pro
        355                 360                 365

His Gly Arg Thr Ile Ser Gly Val Thr Tyr Arg Tyr Asn Ala Asn Gln
    370                 375                 380

Ile Lys Ile Val Cys Ala Cys His Gly Ser His Met Ser Pro Glu Glu
385                 390                 395                 400

Phe Val Arg His Ala Ser Glu Glu Tyr Val Ser Pro Glu Ser Ser Met
                405                 410                 415

Gly Met Thr Ala Ala Ser Ala His Thr
            420                 425
```

<210> SEQ ID NO 66
<211> LENGTH: 564
<212> TYPE: PRT
<213> ORGANISM: Artificial Sequence
<220> FEATURE:
<223> OTHER INFORMATION: Consensus sequence

<400> SEQUENCE: 66

```
Met Pro Lys Lys Lys Arg Lys Val Ser Ser Gly Ala Asn Phe Asn Gln
1               5                   10                  15

Ser Gly Asn Ile Ala Asp Ser Ser Leu Ser Phe Thr Phe Thr Asn Ser
            20                  25                  30

Ser Asn Gly Pro Asn Leu Ile Thr Thr Gln Thr Asn Ser Gln Ala Leu
        35                  40                  45

Ser Gln Pro Ile Ala Ser Ser Asn Val His Asp Asn Phe Met Asn Asn
    50                  55                  60
```

-continued

```
Glu Ile Thr Ala Ser Lys Ile Asp Asp Gly Asn Asn Ser Lys Pro Leu
65                  70                  75                  80

Ser Pro Gly Trp Thr Asp Gln Thr Ala Tyr Asn Ala Phe Gly Ile Thr
                85                  90                  95

Thr Gly Met Phe Asn Thr Thr Thr Met Asp Asp Val Tyr Asn Tyr Leu
            100                 105                 110

Phe Asp Asp Glu Asp Thr Pro Pro Asn Pro Lys Lys Glu Gly Gly Ser
        115                 120                 125

Asn Gln Thr Ser Leu Tyr Lys Lys Ala Gly Ser Met Asp Asp Asp Asn
    130                 135                 140

Gly Leu Glu Leu Ser Leu Gly Leu Ser Cys Gly Gly Ser Thr Gly Lys
145                 150                 155                 160

Ala Lys Gly Asn Asn Asn Asn Asn Ala Gly Ser Ser Ser Glu Asn Tyr
                165                 170                 175

Arg Ala Glu Gly Gly Asp Arg Ser Ala Lys Val Ile Asp Asp Phe Lys
            180                 185                 190

Asn Phe Leu His Pro Thr Ser Gln Arg Pro Ala Glu Pro Ser Ser Gly
        195                 200                 205

Ser Gln Arg Ser Asp Ser Gly Gln Gln Pro Pro Gln Asn Phe Phe Asn
    210                 215                 220

Asp Leu Ser Lys Ala Pro Thr Thr Glu Ala Glu Ala Ser Thr Lys Pro
225                 230                 235                 240

Leu Trp Val Glu Asp Glu Ser Arg Lys Glu Ala Gly Asn Lys Arg Lys
                245                 250                 255

Phe Gly Phe Pro Gly Met Asn Asp Asp Lys Lys Lys Glu Lys Asp Ser
            260                 265                 270

Ser His Val Asp Met His Glu Lys Lys Thr Lys Ala Ser His Val Ser
        275                 280                 285

Thr Ala Thr Asp Glu Gly Ser Thr Ala Glu Asn Glu Asp Val Ala Glu
    290                 295                 300

Ser Glu Val Gly Gly Gly Ser Ser Ser Asn His Ala Lys Glu Val Val
305                 310                 315                 320

Arg Pro Pro Thr Asp Thr Asn Ile Val Asp Asn Leu Thr Gly Gln Arg
                325                 330                 335

Arg Ser Asn His Gly Gly Ser Gly Thr Glu Glu Phe Thr Met Arg Asn
            340                 345                 350

Met Ser Tyr Thr Val Pro Phe Thr Val His Pro Gln Asn Val Val Thr
        355                 360                 365

Ser Met Pro Tyr Ser Leu Pro Thr Lys Glu Ser Gly Gln His Ala Ala
    370                 375                 380

Ala Thr Ser Leu Leu Gln Pro Asn Ala Asn Ala Gly Asn Leu Pro Ile
385                 390                 395                 400

Met Phe Gly Tyr Ser Pro Val Gln Leu Pro Met Leu Asp Lys Asp Gly
                405                 410                 415

Ser Gly Gly Ile Val Ala Leu Ser Gln Ser Pro Phe Ala Gly Arg Val
            420                 425                 430

Pro Ser Asn Ser Ala Thr Ala Lys Gly Glu Gly Lys Gln Pro Val Ala
        435                 440                 445

Glu Glu Gly Ser Ser Glu Asp Ala Ser Glu Arg Pro Thr Gly Asp Asn
    450                 455                 460

Ser Asn Leu Asn Thr Ala Phe Ser Phe Asp Phe Ser Ala Ile Lys Pro
465                 470                 475                 480

Gly Met Ala Ala Asp Val Lys Phe Gly Gly Ser Gly Ala Arg Pro Asn
```

-continued 485 490 495

Leu Pro Trp Val Ser Thr Thr Gly Ser Gly Pro His Gly Arg Thr Ile
500 505 510

Ser Gly Val Thr Tyr Arg Tyr Asn Ala Asn Gln Ile Lys Ile Val Cys
515 520 525

Ala Cys His Gly Ser His Met Ser Pro Glu Glu Phe Val Arg His Ala
530 535 540

Ser Glu Glu Tyr Val Ser Pro Glu Ser Ser Met Gly Met Thr Ala Ala
545 550 555 560

Ser Ala His Thr

<210> SEQ ID NO 67
<211> LENGTH: 475
<212> TYPE: PRT
<213> ORGANISM: Artificial Sequence
<220> FEATURE:
<223> OTHER INFORMATION: Consensus sequence

<400> SEQUENCE: 67

Met Pro Lys Lys Lys Arg Lys Val Ser Ser Gly Ala Asn Phe Asn Gln
1 5 10 15

Ser Gly Asn Ile Ala Asp Ser Ser Leu Ser Phe Thr Phe Thr Asn Ser
20 25 30

Ser Asn Gly Pro Asn Leu Ile Thr Thr Gln Thr Asn Ser Gln Ala Leu
35 40 45

Ser Gln Pro Ile Ala Ser Ser Asn Val His Asp Asn Phe Met Asn Asn
50 55 60

Glu Ile Thr Ala Ser Lys Ile Asp Asp Gly Asn Asn Ser Lys Pro Leu
65 70 75 80

Ser Pro Gly Trp Thr Asp Gln Thr Ala Tyr Asn Ala Phe Gly Ile Thr
85 90 95

Thr Gly Met Phe Asn Thr Thr Thr Met Asp Asp Val Tyr Asn Tyr Leu
100 105 110

Phe Asp Asp Glu Asp Thr Pro Pro Asn Pro Lys Lys Glu Gly Gly Ser
115 120 125

Asn Gln Thr Ser Leu Tyr Lys Lys Ala Gly Ser Met Thr Ser Asp Gly
130 135 140

Ala Thr Ser Thr Ser Ala Ala Ala Ala Ala Ala Ala Ala Ala Ala Ala
145 150 155 160

Arg Arg Lys Pro Ser Trp Arg Glu Arg Glu Asn Asn Arg Arg Arg Glu
165 170 175

Arg Arg Arg Arg Ala Val Ala Ala Lys Ile Tyr Thr Gly Leu Arg Ala
180 185 190

Gln Gly Asp Tyr Asn Leu Pro Lys His Cys Asp Asn Asn Glu Val Leu
195 200 205

Lys Ala Leu Cys Val Glu Ala Gly Trp Val Val Glu Glu Asp Gly Thr
210 215 220

Thr Tyr Arg Lys Gly Cys Lys Pro Leu Pro Gly Glu Ile Ala Gly Thr
225 230 235 240

Ser Ser Arg Val Thr Pro Tyr Ser Ser Gln Asn Gln Ser Pro Leu Ser
245 250 255

Ser Ala Phe Gln Ser Pro Ile Pro Ser Tyr Gln Val Ser Pro Ser Ser
260 265 270

Ser Ser Phe Pro Ser Pro Ser Arg Gly Glu Pro Asn Asn Asn Met Ser
275 280 285

Ser Thr Phe Phe Pro Phe Leu Arg Asn Gly Gly Ile Pro Ser Ser Leu
290 295 300

Pro Ser Leu Arg Ile Ser Asn Ser Cys Pro Val Thr Pro Pro Val Ser
305 310 315 320

Ser Pro Thr Ser Lys Asn Pro Lys Pro Leu Pro Asn Trp Glu Ser Ile
325 330 335

Ala Lys Gln Ser Met Ala Ile Ala Lys Gln Ser Met Ala Ser Phe Asn
340 345 350

Tyr Pro Phe Tyr Ala Val Ser Ala Pro Ala Ser Pro Thr His Arg His
355 360 365

Gln Phe His Thr Pro Ala Thr Ile Pro Glu Cys Asp Glu Ser Asp Ser
370 375 380

Ser Thr Val Asp Ser Gly His Trp Ile Ser Phe Gln Lys Phe Ala Gln
385 390 395 400

Gln Gln Pro Phe Ser Ala Ser Met Val Pro Thr Ser Pro Thr Phe Asn
405 410 415

Leu Val Lys Pro Ala Pro Gln Gln Met Ser Pro Asn Thr Ala Ala Phe
420 425 430

Gln Glu Ile Gly Gln Ser Ser Glu Phe Lys Phe Glu Asn Ser Gln Val
435 440 445

Lys Pro Trp Glu Gly Glu Arg Ile His Asp Val Gly Met Glu Asp Leu
450 455 460

Glu Leu Thr Leu Gly Asn Gly Lys Ala Arg Gly
465 470 475

<210> SEQ ID NO 68
<211> LENGTH: 587
<212> TYPE: PRT
<213> ORGANISM: Artificial Sequence
<220> FEATURE:
<223> OTHER INFORMATION: Consensus sequence

<400> SEQUENCE: 68

Met Lys Arg Asp His His Gln Phe Gln Gly Arg Leu Ser Asn His Gly
1 5 10 15

Thr Ser Ser Ser Ser Ser Ser Ile Ser Lys Asp Lys Met Met Met Val
20 25 30

Lys Lys Glu Glu Asp Gly Gly Gly Asn Met Asp Asp Glu Leu Leu Ala
35 40 45

Val Leu Gly Tyr Lys Val Arg Ser Ser Glu Met Ala Glu Val Ala Leu
50 55 60

Lys Leu Glu Gln Leu Glu Thr Met Met Ser Asn Val Gln Glu Asp Gly
65 70 75 80

Leu Ser His Leu Ala Thr Asp Thr Val His Tyr Asn Pro Ser Glu Leu
85 90 95

Tyr Ser Trp Leu Asp Asn Met Leu Ser Glu Leu Asn Pro Pro Pro Leu
100 105 110

Pro Ala Ser Ser Asn Gly Leu Asp Pro Val Leu Pro Ser Pro Glu Ile
115 120 125

Cys Gly Phe Pro Ala Ser Asp Tyr Asp Leu Lys Val Ile Pro Gly Asn
130 135 140

Ala Ile Tyr Gln Phe Pro Ala Ile Asp Ser Ser Ser Ser Ser Asn Asn
145 150 155 160

Gln Asn Lys Arg Leu Lys Ser Cys Ser Ser Pro Asp Ser Met Val Thr
165 170 175

-continued

```
Ser Thr Ser Thr Gly Thr Gln Ile Gly Gly Val Ile Gly Thr Thr Val
            180                 185                 190

Thr Thr Thr Thr Thr Thr Thr Thr Ala Ala Gly Glu Ser Thr Arg Ser
        195                 200                 205

Val Ile Leu Val Asp Ser Gln Glu Asn Gly Val Arg Leu Val His Ala
    210                 215                 220

Leu Met Ala Cys Ala Glu Ala Ile Gln Gln Asn Asn Leu Thr Leu Ala
225                 230                 235                 240

Glu Ala Leu Val Lys Gln Ile Gly Cys Leu Ala Val Ser Gln Ala Gly
                245                 250                 255

Ala Met Arg Lys Val Ala Thr Tyr Phe Ala Glu Ala Leu Ala Arg Arg
            260                 265                 270

Ile Tyr Arg Leu Ser Pro Pro Gln Asn Gln Ile Asp His Cys Leu Ser
        275                 280                 285

Asp Thr Leu Gln Met His Phe Tyr Glu Thr Cys Pro Tyr Leu Lys Phe
    290                 295                 300

Ala His Phe Thr Ala Asn Gln Ala Ile Leu Glu Ala Phe Glu Gly Lys
305                 310                 315                 320

Lys Arg Val His Val Ile Asp Phe Ser Met Asn Gln Gly Leu Gln Trp
                325                 330                 335

Pro Ala Leu Met Gln Ala Leu Ala Leu Arg Glu Gly Gly Pro Pro Thr
            340                 345                 350

Phe Arg Leu Thr Gly Ile Gly Pro Pro Ala Pro Asp Asn Ser Asp His
        355                 360                 365

Leu His Glu Val Gly Cys Lys Leu Ala Gln Leu Ala Glu Ala Ile His
    370                 375                 380

Val Glu Phe Glu Tyr Arg Gly Phe Val Ala Asn Ser Leu Ala Asp Leu
385                 390                 395                 400

Asp Ala Ser Met Leu Glu Leu Arg Pro Ser Asp Thr Glu Ala Val Ala
                405                 410                 415

Val Asn Ser Val Phe Glu Leu His Lys Leu Leu Gly Arg Pro Gly Gly
            420                 425                 430

Ile Glu Lys Val Leu Gly Val Val Lys Gln Ile Lys Pro Val Ile Phe
        435                 440                 445

Thr Val Val Glu Gln Glu Ser Asn His Asn Gly Pro Val Phe Leu Asp
    450                 455                 460

Arg Phe Thr Glu Ser Leu His Tyr Tyr Ser Thr Leu Phe Asp Ser Leu
465                 470                 475                 480

Glu Gly Val Pro Asn Ser Gln Asp Lys Val Met Ser Glu Val Tyr Leu
                485                 490                 495

Gly Lys Gln Ile Cys Asn Leu Val Ala Cys Glu Gly Pro Asp Arg Val
            500                 505                 510

Glu Arg His Glu Thr Leu Ser Gln Trp Gly Asn Arg Phe Gly Ser Ser
        515                 520                 525

Gly Leu Ala Pro Ala His Leu Gly Ser Asn Ala Phe Lys Gln Ala Ser
    530                 535                 540

Met Leu Leu Ser Val Phe Asn Ser Gly Gln Gly Tyr Arg Val Glu Glu
545                 550                 555                 560

Ser Asn Gly Cys Leu Met Leu Gly Trp His Thr Arg Pro Leu Ile Thr
                565                 570                 575

Thr Ser Ala Trp Lys Leu Ser Thr Ala Ala Tyr
            580                 585
```

<210> SEQ ID NO 69
<211> LENGTH: 726
<212> TYPE: PRT
<213> ORGANISM: Artificial Sequence
<220> FEATURE:
<223> OTHER INFORMATION: Consensus sequence

<400> SEQUENCE: 69

Met Pro Lys Lys Lys Arg Lys Val Ser Ser Gly Ala Asn Phe Asn Gln
1 5 10 15

Ser Gly Asn Ile Ala Asp Ser Ser Leu Ser Phe Thr Phe Thr Asn Ser
20 25 30

Ser Asn Gly Pro Asn Leu Ile Thr Thr Gln Thr Asn Ser Gln Ala Leu
35 40 45

Ser Gln Pro Ile Ala Ser Ser Asn Val His Asp Asn Phe Met Asn Asn
50 55 60

Glu Ile Thr Ala Ser Lys Ile Asp Asp Gly Asn Asn Ser Lys Pro Leu
65 70 75 80

Ser Pro Gly Trp Thr Asp Gln Thr Ala Tyr Asn Ala Phe Gly Ile Thr
85 90 95

Thr Gly Met Phe Asn Thr Thr Thr Met Asp Asp Val Tyr Asn Tyr Leu
100 105 110

Phe Asp Asp Glu Asp Thr Pro Pro Asn Pro Lys Lys Glu Gly Gly Ser
115 120 125

Asn Gln Thr Ser Leu Tyr Lys Lys Ala Gly Ser Met Lys Arg Asp His
130 135 140

His Gln Phe Gln Gly Arg Leu Ser Asn His Gly Thr Ser Ser Ser Ser
145 150 155 160

Ser Ser Ile Ser Lys Asp Lys Met Met Met Val Lys Lys Glu Glu Asp
165 170 175

Gly Gly Gly Asn Met Asp Asp Glu Leu Leu Ala Val Leu Gly Tyr Lys
180 185 190

Val Arg Ser Ser Glu Met Ala Glu Val Ala Leu Lys Leu Glu Gln Leu
195 200 205

Glu Thr Met Met Ser Asn Val Gln Glu Asp Gly Leu Ser His Leu Ala
210 215 220

Thr Asp Thr Val His Tyr Asn Pro Ser Glu Leu Tyr Ser Trp Leu Asp
225 230 235 240

Asn Met Leu Ser Glu Leu Asn Pro Pro Pro Leu Pro Ala Ser Ser Asn
245 250 255

Gly Leu Asp Pro Val Leu Pro Ser Pro Glu Ile Cys Gly Phe Pro Ala
260 265 270

Ser Asp Tyr Asp Leu Lys Val Ile Pro Gly Asn Ala Ile Tyr Gln Phe
275 280 285

Pro Ala Ile Asp Ser Ser Ser Ser Ser Asn Asn Gln Asn Lys Arg Leu
290 295 300

Lys Ser Cys Ser Ser Pro Asp Ser Met Val Thr Ser Thr Ser Thr Gly
305 310 315 320

Thr Gln Ile Gly Gly Val Ile Gly Thr Thr Val Thr Thr Thr Thr Thr
325 330 335

Thr Thr Thr Ala Ala Gly Glu Ser Thr Arg Ser Val Ile Leu Val Asp
340 345 350

Ser Gln Glu Asn Gly Val Arg Leu Val His Ala Leu Met Ala Cys Ala
355 360 365

-continued

Glu Ala Ile Gln Gln Asn Asn Leu Thr Leu Ala Glu Ala Leu Val Lys
    370                 375                 380

Gln Ile Gly Cys Leu Ala Val Ser Gln Ala Gly Ala Met Arg Lys Val
385                 390                 395                 400

Ala Thr Tyr Phe Ala Glu Ala Leu Ala Arg Arg Ile Tyr Arg Leu Ser
                405                 410                 415

Pro Pro Gln Asn Gln Ile Asp His Cys Leu Ser Asp Thr Leu Gln Met
            420                 425                 430

His Phe Tyr Glu Thr Cys Pro Tyr Leu Lys Phe Ala His Phe Thr Ala
        435                 440                 445

Asn Gln Ala Ile Leu Glu Ala Phe Glu Gly Lys Lys Arg Val His Val
    450                 455                 460

Ile Asp Phe Ser Met Asn Gln Gly Leu Gln Trp Pro Ala Leu Met Gln
465                 470                 475                 480

Ala Leu Ala Leu Arg Glu Gly Gly Pro Pro Thr Phe Arg Leu Thr Gly
                485                 490                 495

Ile Gly Pro Pro Ala Pro Asp Asn Ser Asp His Leu His Glu Val Gly
            500                 505                 510

Cys Lys Leu Ala Gln Leu Ala Glu Ala Ile His Val Glu Phe Glu Tyr
        515                 520                 525

Arg Gly Phe Val Ala Asn Ser Leu Ala Asp Leu Asp Ala Ser Met Leu
    530                 535                 540

Glu Leu Arg Pro Ser Asp Thr Glu Ala Val Ala Val Asn Ser Val Phe
545                 550                 555                 560

Glu Leu His Lys Leu Leu Gly Arg Pro Gly Gly Ile Glu Lys Val Leu
                565                 570                 575

Gly Val Val Lys Gln Ile Lys Pro Val Ile Phe Thr Val Val Glu Gln
            580                 585                 590

Glu Ser Asn His Asn Gly Pro Val Phe Leu Asp Arg Phe Thr Glu Ser
        595                 600                 605

Leu His Tyr Tyr Ser Thr Leu Phe Asp Ser Leu Glu Gly Val Pro Asn
    610                 615                 620

Ser Gln Asp Lys Val Met Ser Glu Val Tyr Leu Gly Lys Gln Ile Cys
625                 630                 635                 640

Asn Leu Val Ala Cys Glu Gly Pro Asp Arg Val Glu Arg His Glu Thr
                645                 650                 655

Leu Ser Gln Trp Gly Asn Arg Phe Gly Ser Ser Gly Leu Ala Pro Ala
            660                 665                 670

His Leu Gly Ser Asn Ala Phe Lys Gln Ala Ser Met Leu Leu Ser Val
        675                 680                 685

Phe Asn Ser Gly Gln Gly Tyr Arg Val Glu Glu Ser Asn Gly Cys Leu
    690                 695                 700

Met Leu Gly Trp His Thr Arg Pro Leu Ile Thr Thr Ser Ala Trp Lys
705                 710                 715                 720

Leu Ser Thr Ala Ala Tyr
                725

<210> SEQ ID NO 70
<211> LENGTH: 413
<212> TYPE: PRT
<213> ORGANISM: Artificial Sequence
<220> FEATURE:
<223> OTHER INFORMATION: Consensus sequence

<400> SEQUENCE: 70

-continued

```
Met Lys Leu Leu Ser Ser Ile Glu Glu Ala Cys Asn Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asn Leu Asn Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ser Arg Ser Asn Gln Thr Ser Leu Tyr Lys Lys Ala Gly
145                 150                 155                 160

Ser Tyr Glu Pro Gly Asp Asp Ser Gly Ala Gly Ile Phe Arg Lys Ile
                165                 170                 175

Leu Val Ser Gln Pro Val Asn Pro Pro Arg Val Thr Thr Thr Leu Ile
            180                 185                 190

Glu Pro Ser Asn Glu Leu Glu Ala Cys Gly Arg Val Ser Tyr Pro Glu
        195                 200                 205

Asp Asn Gly Ala Cys His Arg Met Asp Ser Pro Arg Ser Ala Glu Phe
    210                 215                 220

Ser Gly Gly Ser Gly His Phe Val Ser Glu Lys Asp Gly His Lys Thr
225                 230                 235                 240

Thr Ile Ser Pro Arg Ser Pro Ala Glu Thr Ser Glu Leu Val Gly Gln
                245                 250                 255

Met Thr Ile Phe Tyr Ser Gly Lys Val Asn Val Tyr Asp Gly Ile Pro
            260                 265                 270

Pro Glu Lys Ala Arg Ser Ile Met His Phe Ala Ala Asn Pro Ile Asp
        275                 280                 285

Leu Pro Glu Asn Gly Ile Phe Ala Ser Ser Arg Met Ile Ser Lys Leu
    290                 295                 300

Ile Ser Lys Glu Lys Met Met Glu Leu Pro Gln Lys Gly Leu Glu Lys
305                 310                 315                 320

Ala Asn Ser Ser Arg Asp Ser Gly Met Glu Gly Gln Ala Asn Arg Lys
                325                 330                 335

Val Ser Leu Gln Arg Tyr Arg Glu Lys Arg Lys Asp Arg Lys Phe Ser
            340                 345                 350

Lys Ala Lys Lys Cys Pro Gly Val Ala Ser Ser Ser Leu Glu Met Phe
        355                 360                 365

Leu Asn Cys Gln Pro Arg Met Lys Ala Ala Tyr Ser Gln Asn Leu Gly
    370                 375                 380

Cys Thr Gly Ser Pro Leu His Ser Gln Ser Pro Glu Ser Gln Thr Lys
385                 390                 395                 400

Ser Pro Asn Leu Ser Val Asp Leu Asn Ser Glu Gly Ile
                405                 410
```

<210> SEQ ID NO 71
<211> LENGTH: 449
<212> TYPE: PRT
<213> ORGANISM: Artificial Sequence
<220> FEATURE:
<223> OTHER INFORMATION: Consensus sequence

<400> SEQUENCE: 71

```
Met Lys Leu Leu Ser Ser Ile Glu Glu Ala Cys Asn Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asn Leu Asn Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ser Arg Ser Asn Gln Thr Ser Leu Tyr Lys Lys Ala Gly
145                 150                 155                 160

Ser Met Asp Val Gly Val Ser Pro Ala Lys Ser Ile Leu Ala Lys Pro
                165                 170                 175

Leu Lys Leu Leu Thr Glu Glu Asp Ile Ser Gln Leu Thr Arg Glu Asp
            180                 185                 190

Cys Arg Lys Phe Leu Lys Asp Lys Gly Met Arg Arg Pro Ser Trp Asn
        195                 200                 205

Lys Ser Gln Ala Ile Gln Gln Val Leu Ser Leu Lys Ala Leu Tyr Glu
    210                 215                 220

Pro Gly Asp Asp Ser Gly Ala Gly Ile Phe Arg Lys Ile Leu Val Ser
225                 230                 235                 240

Gln Pro Val Asn Pro Pro Arg Val Thr Thr Thr Leu Ile Glu Pro Ser
                245                 250                 255

Asn Glu Leu Glu Ala Cys Gly Arg Val Ser Tyr Pro Glu Asp Asn Gly
            260                 265                 270

Ala Cys His Arg Met Asp Ser Pro Arg Ser Ala Glu Phe Ser Gly Gly
        275                 280                 285

Ser Gly His Phe Val Ser Glu Lys Asp Gly His Lys Thr Thr Ile Ser
    290                 295                 300

Pro Arg Ser Pro Ala Glu Thr Ser Glu Leu Ile Met His Phe Ala Ala
305                 310                 315                 320

Asn Pro Ile Asp Leu Pro Glu Asn Gly Ile Phe Ala Ser Ser Arg Met
                325                 330                 335

Ile Ser Lys Leu Ile Ser Lys Glu Lys Met Met Glu Leu Pro Gln Lys
            340                 345                 350

Gly Leu Glu Lys Ala Asn Ser Ser Arg Asp Ser Gly Met Glu Gly Gln
        355                 360                 365

Ala Asn Arg Lys Val Ser Leu Gln Arg Tyr Arg Glu Lys Arg Lys Asp
```

```
370                 375                 380

Arg Lys Phe Ser Lys Ala Lys Lys Cys Pro Gly Val Ala Ser Ser Ser
385                 390                 395                 400

Leu Glu Met Phe Leu Asn Cys Gln Pro Arg Met Lys Ala Ala Tyr Ser
                405                 410                 415

Gln Asn Leu Gly Cys Thr Gly Ser Pro Leu His Ser Gln Ser Pro Glu
            420                 425                 430

Ser Gln Thr Lys Ser Pro Asn Leu Ser Val Asp Leu Asn Ser Glu Gly
        435                 440                 445

Ile


<210> SEQ ID NO 72
<211> LENGTH: 390
<212> TYPE: PRT
<213> ORGANISM: Artificial Sequence
<220> FEATURE:
<223> OTHER INFORMATION: Consensus sequence

<400> SEQUENCE: 72

Met Lys Leu Leu Ser Ser Ile Glu Glu Ala Cys Asn Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asn Leu Asn Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ser Arg Ser Asn Gln Thr Ser Leu Tyr Lys Lys Ala Gly
145                 150                 155                 160

Ser Met Asp Val Gly Val Ser Pro Ala Lys Ser Ile Leu Ala Lys Pro
                165                 170                 175

Leu Lys Leu Leu Thr Glu Glu Asp Ile Ser Gln Leu Thr Arg Glu Asp
            180                 185                 190

Cys Arg Lys Phe Leu Lys Asp Lys Gly Met Arg Arg Pro Ser Trp Asn
        195                 200                 205

Lys Ser Gln Ala Ile Gln Gln Val Leu Ser Leu Lys Ala Leu Tyr Glu
    210                 215                 220

Pro Gly Asp Asp Ser Gly Ala Gly Ile Phe Arg Lys Ile Leu Val Ser
225                 230                 235                 240

Gln Pro Val Asn Pro Pro Arg Val Thr Thr Thr Leu Ile Glu Pro Ser
                245                 250                 255

Asn Glu Leu Glu Ala Cys Gly Arg Val Ser Tyr Pro Glu Asp Asn Gly
            260                 265                 270

Ala Cys His Arg Met Asp Ser Pro Arg Ser Ala Glu Phe Ser Gly Gly
        275                 280                 285
```

```
Ser Gly His Phe Val Ser Glu Lys Asp Gly His Lys Thr Thr Ile Ser
    290                 295                 300

Pro Arg Ser Pro Ala Glu Thr Ser Glu Leu Val Gly Gln Met Thr Ile
305                 310                 315                 320

Phe Tyr Ser Gly Lys Val Asn Val Tyr Asp Gly Ile Pro Pro Glu Lys
                325                 330                 335

Ala Arg Ser Ile Met His Phe Ala Ala Asn Pro Ile Asp Leu Pro Glu
            340                 345                 350

Asn Gly Ile Phe Ala Ser Ser Arg Met Ile Ser Lys Leu Ile Ser Lys
        355                 360                 365

Glu Lys Met Met Glu Leu Pro Gln Lys Gly Leu Glu Lys Ala Asn Ser
    370                 375                 380

Ser Arg Asp Ser Gly Met
385                 390


<210> SEQ ID NO 73
<211> LENGTH: 142
<212> TYPE: PRT
<213> ORGANISM: Artificial Sequence
<220> FEATURE:
<223> OTHER INFORMATION: Consensus sequence

<400> SEQUENCE: 73

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Asp Asp Gly Asn
        35                  40                  45

Tyr Lys Thr Arg Ala Glu Val Lys Phe Glu Gly Asp Thr Leu Val Asn
    50                  55                  60

Arg Ile Glu Leu Lys Gly Ile Asp Phe Lys Glu Asp Gly Asn Ile Leu
65                  70                  75                  80

Gly His Lys Leu Glu Tyr Asn Tyr Asn Ser His Asn Val Tyr Ile Thr
                85                  90                  95

Ala Asp Lys Gln Lys Asn Gly Ile Lys Ala Asn Phe Lys Ile Arg His
            100                 105                 110

Asn Ile Glu Glu Gln Lys Leu Ile Ser Glu Glu Asp Leu Gly Pro Arg
        115                 120                 125

Pro Thr Ser Gly Ser Val Asp Leu Glu Gly Thr Ala Pro Gly
    130                 135                 140


<210> SEQ ID NO 74
<211> LENGTH: 111
<212> TYPE: PRT
<213> ORGANISM: Artificial Sequence
<220> FEATURE:
<223> OTHER INFORMATION: Consensus sequence

<400> SEQUENCE: 74

Met Asp Lys Gln Lys Asn Gly Ile Lys Ala Asn Phe Lys Ile Arg His
1               5                   10                  15

Asn Ile Glu Asp Gly Gly Val Gln Leu Ala Asp His Tyr Gln Gln Asn
            20                  25                  30

Thr Pro Ile Gly Asp Gly Pro Val Leu Leu Pro Asp Asn His Tyr Leu
        35                  40                  45

Ser Tyr Gln Ser Ala Leu Ser Lys Asp Pro Asn Glu Lys Arg Asp His
```

```
    50                  55                  60

Met Val Leu Leu Glu Phe Val Thr Ala Ala Gly Ile Thr Leu Gly Met
65                  70                  75                  80

Asp Glu Leu Tyr Lys Tyr Pro Tyr Asp Val Pro Asp Tyr Ala Gly Pro
                85                  90                  95

Arg Pro Thr Ser Gly Ser Val Asp Leu Glu Gly Thr Ala Pro Gly
            100                 105                 110


<210> SEQ ID NO 75
<211> LENGTH: 568
<212> TYPE: PRT
<213> ORGANISM: Artificial Sequence
<220> FEATURE:
<223> OTHER INFORMATION: Consensus sequence

<400> SEQUENCE: 75

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Asp Asp Gly Asn
        35                  40                  45

Tyr Lys Thr Arg Ala Glu Val Lys Phe Glu Gly Asp Thr Leu Val Asn
    50                  55                  60

Arg Ile Glu Leu Lys Gly Ile Asp Phe Lys Glu Asp Gly Asn Ile Leu
65                  70                  75                  80

Gly His Lys Leu Glu Tyr Asn Tyr Asn Ser His Asn Val Tyr Ile Thr
                85                  90                  95

Ala Asp Lys Gln Lys Asn Gly Ile Lys Ala Asn Phe Lys Ile Arg His
            100                 105                 110

Asn Ile Glu Glu Gln Lys Leu Ile Ser Glu Glu Asp Leu Gly Pro Arg
        115                 120                 125

Pro Thr Ser Gly Ser Val Asp Leu Glu Gly Thr Ala Pro Gly Ser Met
    130                 135                 140

Asp Asp Asp Asn Gly Leu Glu Leu Ser Leu Gly Leu Ser Cys Gly Gly
145                 150                 155                 160

Ser Thr Gly Lys Ala Lys Gly Asn Asn Asn Asn Asn Ala Gly Ser Ser
                165                 170                 175

Ser Glu Asn Tyr Arg Ala Glu Gly Gly Asp Arg Ser Ala Lys Val Ile
            180                 185                 190

Asp Asp Phe Lys Asn Phe Leu His Pro Thr Ser Gln Arg Pro Ala Glu
        195                 200                 205

Pro Ser Ser Gly Ser Gln Arg Ser Asp Ser Gly Gln Gln Pro Pro Gln
    210                 215                 220

Asn Phe Phe Asn Asp Leu Ser Lys Ala Pro Thr Thr Glu Ala Glu Ala
225                 230                 235                 240

Ser Thr Lys Pro Leu Trp Val Glu Asp Glu Ser Arg Lys Glu Ala Gly
                245                 250                 255

Asn Lys Arg Lys Phe Gly Phe Pro Gly Met Asn Asp Asp Lys Lys Lys
            260                 265                 270

Glu Lys Asp Ser Ser His Val Asp Met His Glu Lys Lys Thr Lys Ala
        275                 280                 285

Ser His Val Ser Thr Ala Thr Asp Glu Gly Ser Thr Ala Glu Asn Glu
    290                 295                 300

Asp Val Ala Glu Ser Glu Val Gly Gly Gly Ser Ser Ser Asn His Ala
```

305 310 315 320

Lys Glu Val Val Arg Pro Pro Thr Asp Thr Asn Ile Val Asp Asn Leu
325 330 335

Thr Gly Gln Arg Arg Ser Asn His Gly Gly Ser Gly Thr Glu Glu Phe
340 345 350

Thr Met Arg Asn Met Ser Tyr Thr Val Pro Phe Thr Val His Pro Gln
355 360 365

Asn Val Val Thr Ser Met Pro Tyr Ser Leu Pro Thr Lys Glu Ser Gly
370 375 380

Gln His Ala Ala Ala Thr Ser Leu Leu Gln Pro Asn Ala Asn Ala Gly
385 390 395 400

Asn Leu Pro Ile Met Phe Gly Tyr Ser Pro Val Gln Leu Pro Met Leu
405 410 415

Asp Lys Asp Gly Ser Gly Gly Ile Val Ala Leu Ser Gln Ser Pro Phe
420 425 430

Ala Gly Arg Val Pro Ser Asn Ser Ala Thr Ala Lys Gly Glu Gly Lys
435 440 445

Gln Pro Val Ala Glu Glu Gly Ser Ser Glu Asp Ala Ser Glu Arg Pro
450 455 460

Thr Gly Asp Asn Ser Asn Leu Asn Thr Ala Phe Ser Phe Asp Phe Ser
465 470 475 480

Ala Ile Lys Pro Gly Met Ala Ala Asp Val Lys Phe Gly Gly Ser Gly
485 490 495

Ala Arg Pro Asn Leu Pro Trp Val Ser Thr Thr Gly Ser Gly Pro His
500 505 510

Gly Arg Thr Ile Ser Gly Val Thr Tyr Arg Tyr Asn Ala Asn Gln Ile
515 520 525

Lys Ile Val Cys Ala Cys His Gly Ser His Met Ser Pro Glu Glu Phe
530 535 540

Val Arg His Ala Ser Glu Glu Tyr Val Ser Pro Glu Ser Ser Met Gly
545 550 555 560

Met Thr Ala Ala Ser Ala His Thr
565

<210> SEQ ID NO 76
<211> LENGTH: 479
<212> TYPE: PRT
<213> ORGANISM: Artificial Sequence
<220> FEATURE:
<223> OTHER INFORMATION: Consensus sequence

<400> SEQUENCE: 76

Met Val Ser Lys Gly Glu Glu Leu Phe Thr Gly Val Val Pro Ile Leu
1 5 10 15

Val Glu Leu Asp Gly Asp Val Asn Gly His Lys Phe Ser Val Ser Gly
20 25 30

Glu Gly Glu Gly Asp Ala Thr Tyr Gly Lys Leu Thr Asp Asp Gly Asn
35 40 45

Tyr Lys Thr Arg Ala Glu Val Lys Phe Glu Gly Asp Thr Leu Val Asn
50 55 60

Arg Ile Glu Leu Lys Gly Ile Asp Phe Lys Glu Asp Gly Asn Ile Leu
65 70 75 80

Gly His Lys Leu Glu Tyr Asn Tyr Asn Ser His Asn Val Tyr Ile Thr
85 90 95

Ala Asp Lys Gln Lys Asn Gly Ile Lys Ala Asn Phe Lys Ile Arg His

```
            100                 105                 110

Asn Ile Glu Glu Gln Lys Leu Ile Ser Glu Glu Asp Leu Gly Pro Arg
        115                 120                 125

Pro Thr Ser Gly Ser Val Asp Leu Glu Gly Thr Ala Pro Gly Ser Met
    130                 135                 140

Thr Ser Asp Gly Ala Thr Ser Thr Ser Ala Ala Ala Ala Ala Ala Ala
145                 150                 155                 160

Ala Ala Ala Ala Arg Arg Lys Pro Ser Trp Arg Glu Arg Glu Asn Asn
                165                 170                 175

Arg Arg Arg Glu Arg Arg Arg Arg Ala Val Ala Ala Lys Ile Tyr Thr
            180                 185                 190

Gly Leu Arg Ala Gln Gly Asp Tyr Asn Leu Pro Lys His Cys Asp Asn
        195                 200                 205

Asn Glu Val Leu Lys Ala Leu Cys Val Glu Ala Gly Trp Val Val Glu
    210                 215                 220

Glu Asp Gly Thr Thr Tyr Arg Lys Gly Cys Lys Pro Leu Pro Gly Glu
225                 230                 235                 240

Ile Ala Gly Thr Ser Ser Arg Val Thr Pro Tyr Ser Ser Gln Asn Gln
                245                 250                 255

Ser Pro Leu Ser Ser Ala Phe Gln Ser Pro Ile Pro Ser Tyr Gln Val
            260                 265                 270

Ser Pro Ser Ser Ser Ser Phe Pro Ser Pro Ser Arg Gly Glu Pro Asn
        275                 280                 285

Asn Asn Met Ser Ser Thr Phe Phe Pro Phe Leu Arg Asn Gly Gly Ile
    290                 295                 300

Pro Ser Ser Leu Pro Ser Leu Arg Ile Ser Asn Ser Cys Pro Val Thr
305                 310                 315                 320

Pro Pro Val Ser Ser Pro Thr Ser Lys Asn Pro Lys Pro Leu Pro Asn
                325                 330                 335

Trp Glu Ser Ile Ala Lys Gln Ser Met Ala Ile Ala Lys Gln Ser Met
            340                 345                 350

Ala Ser Phe Asn Tyr Pro Phe Tyr Ala Val Ser Ala Pro Ala Ser Pro
        355                 360                 365

Thr His Arg His Gln Phe His Thr Pro Ala Thr Ile Pro Glu Cys Asp
    370                 375                 380

Glu Ser Asp Ser Ser Thr Val Asp Ser Gly His Trp Ile Ser Phe Gln
385                 390                 395                 400

Lys Phe Ala Gln Gln Gln Pro Phe Ser Ala Ser Met Val Pro Thr Ser
                405                 410                 415

Pro Thr Phe Asn Leu Val Lys Pro Ala Pro Gln Gln Met Ser Pro Asn
            420                 425                 430

Thr Ala Ala Phe Gln Glu Ile Gly Gln Ser Ser Glu Phe Lys Phe Glu
        435                 440                 445

Asn Ser Gln Val Lys Pro Trp Glu Gly Glu Arg Ile His Asp Val Gly
    450                 455                 460

Met Glu Asp Leu Glu Leu Thr Leu Gly Asn Gly Lys Ala Arg Gly
465                 470                 475
```

<210> SEQ ID NO 77
<211> LENGTH: 425
<212> TYPE: PRT
<213> ORGANISM: Artificial Sequence
<220> FEATURE:
<223> OTHER INFORMATION: Consensus sequence

<400> SEQUENCE: 77

```
Met Asp Lys Gln Lys Asn Gly Ile Lys Ala Asn Phe Lys Ile Arg His
1               5                   10                  15

Asn Ile Glu Asp Gly Gly Val Gln Leu Ala Asp His Tyr Gln Gln Asn
            20                  25                  30

Thr Pro Ile Gly Asp Gly Pro Val Leu Leu Pro Asp Asn His Tyr Leu
        35                  40                  45

Ser Tyr Gln Ser Ala Leu Ser Lys Asp Pro Asn Glu Lys Arg Asp His
    50                  55                  60

Met Val Leu Leu Glu Phe Val Thr Ala Ala Gly Ile Thr Leu Gly Met
65                  70                  75                  80

Asp Glu Leu Tyr Lys Tyr Pro Tyr Asp Val Pro Asp Tyr Ala Gly Pro
                85                  90                  95

Arg Pro Thr Ser Gly Ser Val Asp Leu Glu Gly Thr Ala Pro Gly Ser
            100                 105                 110

Met Asp Val Gly Val Ser Pro Ala Lys Ser Ile Leu Ala Lys Pro Leu
        115                 120                 125

Lys Leu Leu Thr Glu Glu Asp Ile Ser Gln Leu Thr Arg Glu Asp Cys
    130                 135                 140

Arg Lys Phe Leu Lys Asp Lys Gly Met Arg Arg Pro Ser Trp Asn Lys
145                 150                 155                 160

Ser Gln Ala Ile Gln Gln Val Leu Ser Leu Lys Ala Leu Tyr Glu Pro
                165                 170                 175

Gly Asp Asp Ser Gly Ala Gly Ile Phe Arg Lys Ile Leu Val Ser Gln
            180                 185                 190

Pro Val Asn Pro Pro Arg Val Thr Thr Thr Leu Ile Glu Pro Ser Asn
        195                 200                 205

Glu Leu Glu Ala Cys Gly Arg Val Ser Tyr Pro Glu Asp Asn Gly Ala
    210                 215                 220

Cys His Arg Met Asp Ser Pro Arg Ser Ala Glu Phe Ser Gly Gly Ser
225                 230                 235                 240

Gly His Phe Val Ser Glu Lys Asp Gly His Lys Thr Thr Ile Ser Pro
                245                 250                 255

Arg Ser Pro Ala Glu Thr Ser Glu Leu Val Gly Gln Met Thr Ile Phe
            260                 265                 270

Tyr Ser Gly Lys Val Asn Val Tyr Asp Gly Ile Pro Pro Glu Lys Ala
        275                 280                 285

Arg Ser Ile Met His Phe Ala Ala Asn Pro Ile Asp Leu Pro Glu Asn
    290                 295                 300

Gly Ile Phe Ala Ser Ser Arg Met Ile Ser Lys Leu Ile Ser Lys Glu
305                 310                 315                 320

Lys Met Met Glu Leu Pro Gln Lys Gly Leu Glu Lys Ala Asn Ser Ser
                325                 330                 335

Arg Asp Ser Gly Met Glu Gly Gln Ala Asn Arg Lys Val Ser Leu Gln
            340                 345                 350

Arg Tyr Arg Glu Lys Arg Lys Asp Arg Lys Phe Ser Lys Ala Lys Lys
        355                 360                 365

Cys Pro Gly Val Ala Ser Ser Ser Leu Glu Met Phe Leu Asn Cys Gln
    370                 375                 380

Pro Arg Met Lys Ala Ala Tyr Ser Gln Asn Leu Gly Cys Thr Gly Ser
385                 390                 395                 400

Pro Leu His Ser Gln Ser Pro Glu Ser Gln Thr Lys Ser Pro Asn Leu
                405                 410                 415
```

```
Ser Val Asp Leu Asn Ser Glu Gly Ile
            420                 425


<210> SEQ ID NO 78
<211> LENGTH: 537
<212> TYPE: PRT
<213> ORGANISM: Artificial Sequence
<220> FEATURE:
<223> OTHER INFORMATION: Consensus sequence

<400> SEQUENCE: 78

Met Asp Lys Gln Lys Asn Gly Ile Lys Ala Asn Phe Lys Ile Arg His
1               5                   10                  15

Asn Ile Glu Asp Gly Gly Val Gln Leu Ala Asp His Tyr Gln Gln Asn
            20                  25                  30

Thr Pro Ile Gly Asp Gly Pro Val Leu Leu Pro Asp Asn His Tyr Leu
        35                  40                  45

Ser Tyr Gln Ser Ala Leu Ser Lys Asp Pro Asn Glu Lys Arg Asp His
    50                  55                  60

Met Val Leu Leu Glu Phe Val Thr Ala Ala Gly Ile Thr Leu Gly Met
65                  70                  75                  80

Asp Glu Leu Tyr Lys Tyr Pro Tyr Asp Val Pro Asp Tyr Ala Gly Pro
                85                  90                  95

Arg Pro Thr Ser Gly Ser Val Asp Leu Glu Gly Thr Ala Pro Gly Ser
            100                 105                 110

Met Asp Asp Asp Asn Gly Leu Glu Leu Ser Leu Gly Leu Ser Cys Gly
        115                 120                 125

Gly Ser Thr Gly Lys Ala Lys Gly Asn Asn Asn Asn Asn Ala Gly Ser
    130                 135                 140

Ser Ser Glu Asn Tyr Arg Ala Glu Gly Gly Asp Arg Ser Ala Lys Val
145                 150                 155                 160

Ile Asp Asp Phe Lys Asn Phe Leu His Pro Thr Ser Gln Arg Pro Ala
                165                 170                 175

Glu Pro Ser Ser Gly Ser Gln Arg Ser Asp Ser Gly Gln Gln Pro Pro
            180                 185                 190

Gln Asn Phe Phe Asn Asp Leu Ser Lys Ala Pro Thr Thr Glu Ala Glu
        195                 200                 205

Ala Ser Thr Lys Pro Leu Trp Val Glu Asp Glu Ser Arg Lys Glu Ala
    210                 215                 220

Gly Asn Lys Arg Lys Phe Gly Phe Pro Gly Met Asn Asp Asp Lys Lys
225                 230                 235                 240

Lys Glu Lys Asp Ser Ser His Val Asp Met His Glu Lys Lys Thr Lys
                245                 250                 255

Ala Ser His Val Ser Thr Ala Thr Asp Glu Gly Ser Thr Ala Glu Asn
            260                 265                 270

Glu Asp Val Ala Glu Ser Glu Val Gly Gly Gly Ser Ser Ser Asn His
        275                 280                 285

Ala Lys Glu Val Val Arg Pro Pro Thr Asp Thr Asn Ile Val Asp Asn
    290                 295                 300

Leu Thr Gly Gln Arg Arg Ser Asn His Gly Gly Ser Gly Thr Glu Glu
305                 310                 315                 320

Phe Thr Met Arg Asn Met Ser Tyr Thr Val Pro Phe Thr Val His Pro
                325                 330                 335

Gln Asn Val Val Thr Ser Met Pro Tyr Ser Leu Pro Thr Lys Glu Ser
            340                 345                 350
```

Gly Gln His Ala Ala Ala Thr Ser Leu Leu Gln Pro Asn Ala Asn Ala
        355                 360                 365

Gly Asn Leu Pro Ile Met Phe Gly Tyr Ser Pro Val Gln Leu Pro Met
    370                 375                 380

Leu Asp Lys Asp Gly Ser Gly Gly Ile Val Ala Leu Ser Gln Ser Pro
385                 390                 395                 400

Phe Ala Gly Arg Val Pro Ser Asn Ser Ala Thr Ala Lys Gly Glu Gly
                405                 410                 415

Lys Gln Pro Val Ala Glu Glu Gly Ser Ser Glu Asp Ala Ser Glu Arg
            420                 425                 430

Pro Thr Gly Asp Asn Ser Asn Leu Asn Thr Ala Phe Ser Phe Asp Phe
        435                 440                 445

Ser Ala Ile Lys Pro Gly Met Ala Ala Asp Val Lys Phe Gly Gly Ser
    450                 455                 460

Gly Ala Arg Pro Asn Leu Pro Trp Val Ser Thr Thr Gly Ser Gly Pro
465                 470                 475                 480

His Gly Arg Thr Ile Ser Gly Val Thr Tyr Arg Tyr Asn Ala Asn Gln
                485                 490                 495

Ile Lys Ile Val Cys Ala Cys His Gly Ser His Met Ser Pro Glu Glu
            500                 505                 510

Phe Val Arg His Ala Ser Glu Glu Tyr Val Ser Pro Glu Ser Ser Met
        515                 520                 525

Gly Met Thr Ala Ala Ser Ala His Thr
    530                 535

<210> SEQ ID NO 79
<211> LENGTH: 448
<212> TYPE: PRT
<213> ORGANISM: Artificial Sequence
<220> FEATURE:
<223> OTHER INFORMATION: Consensus sequence

<400> SEQUENCE: 79

Met Asp Lys Gln Lys Asn Gly Ile Lys Ala Asn Phe Lys Ile Arg His
1               5                   10                  15

Asn Ile Glu Asp Gly Gly Val Gln Leu Ala Asp His Tyr Gln Gln Asn
            20                  25                  30

Thr Pro Ile Gly Asp Gly Pro Val Leu Leu Pro Asp Asn His Tyr Leu
        35                  40                  45

Ser Tyr Gln Ser Ala Leu Ser Lys Asp Pro Asn Glu Lys Arg Asp His
    50                  55                  60

Met Val Leu Leu Glu Phe Val Thr Ala Ala Gly Ile Thr Leu Gly Met
65                  70                  75                  80

Asp Glu Leu Tyr Lys Tyr Pro Tyr Asp Val Pro Asp Tyr Ala Gly Pro
                85                  90                  95

Arg Pro Thr Ser Gly Ser Val Asp Leu Glu Gly Thr Ala Pro Gly Ser
            100                 105                 110

Met Thr Ser Asp Gly Ala Thr Ser Thr Ser Ala Ala Ala Ala Ala Ala
        115                 120                 125

Ala Ala Ala Ala Ala Arg Arg Lys Pro Ser Trp Arg Glu Arg Glu Asn
    130                 135                 140

Asn Arg Arg Arg Glu Arg Arg Arg Arg Ala Val Ala Ala Lys Ile Tyr
145                 150                 155                 160

Thr Gly Leu Arg Ala Gln Gly Asp Tyr Asn Leu Pro Lys His Cys Asp
                165                 170                 175

Asn Asn Glu Val Leu Lys Ala Leu Cys Val Glu Ala Gly Trp Val Val
180 185 190

Glu Glu Asp Gly Thr Thr Tyr Arg Lys Gly Cys Lys Pro Leu Pro Gly
195 200 205

Glu Ile Ala Gly Thr Ser Ser Arg Val Thr Pro Tyr Ser Ser Gln Asn
210 215 220

Gln Ser Pro Leu Ser Ser Ala Phe Gln Ser Pro Ile Pro Ser Tyr Gln
225 230 235 240

Val Ser Pro Ser Ser Ser Ser Phe Pro Ser Pro Ser Arg Gly Glu Pro
245 250 255

Asn Asn Asn Met Ser Ser Thr Phe Phe Pro Phe Leu Arg Asn Gly Gly
260 265 270

Ile Pro Ser Ser Leu Pro Ser Leu Arg Ile Ser Asn Ser Cys Pro Val
275 280 285

Thr Pro Pro Val Ser Ser Pro Thr Ser Lys Asn Pro Lys Pro Leu Pro
290 295 300

Asn Trp Glu Ser Ile Ala Lys Gln Ser Met Ala Ile Ala Lys Gln Ser
305 310 315 320

Met Ala Ser Phe Asn Tyr Pro Phe Tyr Ala Val Ser Ala Pro Ala Ser
325 330 335

Pro Thr His Arg His Gln Phe His Thr Pro Ala Thr Ile Pro Glu Cys
340 345 350

Asp Glu Ser Asp Ser Ser Thr Val Asp Ser Gly His Trp Ile Ser Phe
355 360 365

Gln Lys Phe Ala Gln Gln Gln Pro Phe Ser Ala Ser Met Val Pro Thr
370 375 380

Ser Pro Thr Phe Asn Leu Val Lys Pro Ala Pro Gln Gln Met Ser Pro
385 390 395 400

Asn Thr Ala Ala Phe Gln Glu Ile Gly Gln Ser Ser Glu Phe Lys Phe
405 410 415

Glu Asn Ser Gln Val Lys Pro Trp Glu Gly Glu Arg Ile His Asp Val
420 425 430

Gly Met Glu Asp Leu Glu Leu Thr Leu Gly Asn Gly Lys Ala Arg Gly
435 440 445

<210> SEQ ID NO 80
<211> LENGTH: 364
<212> TYPE: PRT
<213> ORGANISM: Artificial Sequence
<220> FEATURE:
<223> OTHER INFORMATION: Consensus sequence

<400> SEQUENCE: 80

Met Asp Lys Gln Lys Asn Gly Ile Lys Ala Asn Phe Lys Ile Arg His
1 5 10 15

Asn Ile Glu Asp Gly Gly Val Gln Leu Ala Asp His Tyr Gln Gln Asn
20 25 30

Thr Pro Ile Gly Asp Gly Pro Val Leu Leu Pro Asp Asn His Tyr Leu
35 40 45

Ser Tyr Gln Ser Ala Leu Ser Lys Asp Pro Asn Glu Lys Arg Asp His
50 55 60

Met Val Leu Leu Glu Phe Val Thr Ala Ala Gly Ile Thr Leu Gly Met
65 70 75 80

Asp Glu Leu Tyr Lys Tyr Pro Tyr Asp Val Pro Asp Tyr Ala Gly Pro
85 90 95

-continued

```
Arg Pro Thr Ser Gly Ser Val Asp Leu Glu Gly Thr Ala Pro Gly Ser
            100                 105                 110

Tyr Glu Pro Gly Asp Asp Ser Gly Ala Gly Ile Phe Arg Lys Ile Leu
        115                 120                 125

Val Ser Gln Pro Val Asn Pro Pro Arg Val Thr Thr Thr Leu Ile Glu
    130                 135                 140

Pro Ser Asn Glu Leu Glu Ala Cys Gly Arg Val Ser Tyr Pro Glu Asp
145                 150                 155                 160

Asn Gly Ala Cys His Arg Met Asp Ser Pro Arg Ser Ala Glu Phe Ser
                165                 170                 175

Gly Gly Ser Gly His Phe Val Ser Glu Lys Asp Gly His Lys Thr Thr
            180                 185                 190

Ile Ser Pro Arg Ser Pro Ala Glu Thr Ser Glu Leu Val Gly Gln Met
        195                 200                 205

Thr Ile Phe Tyr Ser Gly Lys Val Asn Val Tyr Asp Gly Ile Pro Pro
    210                 215                 220

Glu Lys Ala Arg Ser Ile Met His Phe Ala Ala Asn Pro Ile Asp Leu
225                 230                 235                 240

Pro Glu Asn Gly Ile Phe Ala Ser Ser Arg Met Ile Ser Lys Leu Ile
                245                 250                 255

Ser Lys Glu Lys Met Met Glu Leu Pro Gln Lys Gly Leu Glu Lys Ala
            260                 265                 270

Asn Ser Ser Arg Asp Ser Gly Met Glu Gly Gln Ala Asn Arg Lys Val
        275                 280                 285

Ser Leu Gln Arg Tyr Arg Glu Lys Arg Lys Asp Arg Lys Phe Ser Lys
    290                 295                 300

Ala Lys Lys Cys Pro Gly Val Ala Ser Ser Ser Leu Glu Met Phe Leu
305                 310                 315                 320

Asn Cys Gln Pro Arg Met Lys Ala Ala Tyr Ser Gln Asn Leu Gly Cys
                325                 330                 335

Thr Gly Ser Pro Leu His Ser Gln Ser Pro Glu Ser Gln Thr Lys Ser
            340                 345                 350

Pro Asn Leu Ser Val Asp Leu Asn Ser Glu Gly Ile
        355                 360


<210> SEQ ID NO 81
<211> LENGTH: 400
<212> TYPE: PRT
<213> ORGANISM: Artificial Sequence
<220> FEATURE:
<223> OTHER INFORMATION: Consensus sequence

<400> SEQUENCE: 81

Met Asp Lys Gln Lys Asn Gly Ile Lys Ala Asn Phe Lys Ile Arg His
1               5                   10                  15

Asn Ile Glu Asp Gly Gly Val Gln Leu Ala Asp His Tyr Gln Gln Asn
            20                  25                  30

Thr Pro Ile Gly Asp Gly Pro Val Leu Leu Pro Asp Asn His Tyr Leu
        35                  40                  45

Ser Tyr Gln Ser Ala Leu Ser Lys Asp Pro Asn Glu Lys Arg Asp His
    50                  55                  60

Met Val Leu Leu Glu Phe Val Thr Ala Ala Gly Ile Thr Leu Gly Met
65                  70                  75                  80

Asp Glu Leu Tyr Lys Tyr Pro Tyr Asp Val Pro Asp Tyr Ala Gly Pro
                85                  90                  95
```

Arg Pro Thr Ser Gly Ser Val Asp Leu Glu Gly Thr Ala Pro Gly Ser
100 105 110

Met Asp Val Gly Val Ser Pro Ala Lys Ser Ile Leu Ala Lys Pro Leu
115 120 125

Lys Leu Leu Thr Glu Glu Asp Ile Ser Gln Leu Thr Arg Glu Asp Cys
130 135 140

Arg Lys Phe Leu Lys Asp Lys Gly Met Arg Arg Pro Ser Trp Asn Lys
145 150 155 160

Ser Gln Ala Ile Gln Gln Val Leu Ser Leu Lys Ala Leu Tyr Glu Pro
165 170 175

Gly Asp Asp Ser Gly Ala Gly Ile Phe Arg Lys Ile Leu Val Ser Gln
180 185 190

Pro Val Asn Pro Pro Arg Val Thr Thr Thr Leu Ile Glu Pro Ser Asn
195 200 205

Glu Leu Glu Ala Cys Gly Arg Val Ser Tyr Pro Glu Asp Asn Gly Ala
210 215 220

Cys His Arg Met Asp Ser Pro Arg Ser Ala Glu Phe Ser Gly Gly Ser
225 230 235 240

Gly His Phe Val Ser Glu Lys Asp Gly His Lys Thr Thr Ile Ser Pro
245 250 255

Arg Ser Pro Ala Glu Thr Ser Glu Leu Ile Met His Phe Ala Ala Asn
260 265 270

Pro Ile Asp Leu Pro Glu Asn Gly Ile Phe Ala Ser Ser Arg Met Ile
275 280 285

Ser Lys Leu Ile Ser Lys Glu Lys Met Met Glu Leu Pro Gln Lys Gly
290 295 300

Leu Glu Lys Ala Asn Ser Ser Arg Asp Ser Gly Met Glu Gly Gln Ala
305 310 315 320

Asn Arg Lys Val Ser Leu Gln Arg Tyr Arg Glu Lys Arg Lys Asp Arg
325 330 335

Lys Phe Ser Lys Ala Lys Lys Cys Pro Gly Val Ala Ser Ser Ser Leu
340 345 350

Glu Met Phe Leu Asn Cys Gln Pro Arg Met Lys Ala Ala Tyr Ser Gln
355 360 365

Asn Leu Gly Cys Thr Gly Ser Pro Leu His Ser Gln Ser Pro Glu Ser
370 375 380

Gln Thr Lys Ser Pro Asn Leu Ser Val Asp Leu Asn Ser Glu Gly Ile
385 390 395 400

<210> SEQ ID NO 82
<211> LENGTH: 341
<212> TYPE: PRT
<213> ORGANISM: Artificial Sequence
<220> FEATURE:
<223> OTHER INFORMATION: Consensus sequence

<400> SEQUENCE: 82

Met Asp Lys Gln Lys Asn Gly Ile Lys Ala Asn Phe Lys Ile Arg His
1 5 10 15

Asn Ile Glu Asp Gly Gly Val Gln Leu Ala Asp His Tyr Gln Gln Asn
20 25 30

Thr Pro Ile Gly Asp Gly Pro Val Leu Leu Pro Asp Asn His Tyr Leu
35 40 45

Ser Tyr Gln Ser Ala Leu Ser Lys Asp Pro Asn Glu Lys Arg Asp His
50 55 60

-continued

```
Met Val Leu Leu Glu Phe Val Thr Ala Ala Gly Ile Thr Leu Gly Met
65                  70                  75                  80

Asp Glu Leu Tyr Lys Tyr Pro Tyr Asp Val Pro Asp Tyr Ala Gly Pro
                85                  90                  95

Arg Pro Thr Ser Gly Ser Val Asp Leu Glu Gly Thr Ala Pro Gly Ser
            100                 105                 110

Met Asp Val Gly Val Ser Pro Ala Lys Ser Ile Leu Ala Lys Pro Leu
        115                 120                 125

Lys Leu Leu Thr Glu Glu Asp Ile Ser Gln Leu Thr Arg Glu Asp Cys
    130                 135                 140

Arg Lys Phe Leu Lys Asp Lys Gly Met Arg Arg Pro Ser Trp Asn Lys
145                 150                 155                 160

Ser Gln Ala Ile Gln Gln Val Leu Ser Leu Lys Ala Leu Tyr Glu Pro
                165                 170                 175

Gly Asp Asp Ser Gly Ala Gly Ile Phe Arg Lys Ile Leu Val Ser Gln
            180                 185                 190

Pro Val Asn Pro Pro Arg Val Thr Thr Thr Leu Ile Glu Pro Ser Asn
        195                 200                 205

Glu Leu Glu Ala Cys Gly Arg Val Ser Tyr Pro Glu Asp Asn Gly Ala
    210                 215                 220

Cys His Arg Met Asp Ser Pro Arg Ser Ala Glu Phe Ser Gly Gly Ser
225                 230                 235                 240

Gly His Phe Val Ser Glu Lys Asp Gly His Lys Thr Thr Ile Ser Pro
                245                 250                 255

Arg Ser Pro Ala Glu Thr Ser Glu Leu Val Gly Gln Met Thr Ile Phe
            260                 265                 270

Tyr Ser Gly Lys Val Asn Val Tyr Asp Gly Ile Pro Pro Glu Lys Ala
        275                 280                 285

Arg Ser Ile Met His Phe Ala Ala Asn Pro Ile Asp Leu Pro Glu Asn
    290                 295                 300

Gly Ile Phe Ala Ser Ser Arg Met Ile Ser Lys Leu Ile Ser Lys Glu
305                 310                 315                 320

Lys Met Met Glu Leu Pro Gln Lys Gly Leu Glu Lys Ala Asn Ser Ser
                325                 330                 335

Arg Asp Ser Gly Met
            340
```

```
<210> SEQ ID NO 83
<211> LENGTH: 942
<212> TYPE: DNA
<213> ORGANISM: Arabidopsis thaliana

<400> SEQUENCE: 83

atggatgtcg gagtttcacc ggcgaagtct atacttgcga aacctctgaa gctactcact     60

gaagaggaca tttctcagct cactcgcgaa gactgccgca aattcctcaa agacaaagga    120

atgcgaagac cgtcgtggaa caaatctcag gcgatccagc aagttttatc tcttaaagct    180

ctctatgagc ctggagacga ttccggcgcc ggtatcttcc gcaagatcct cgtttctcag    240

ccagtaaatc cgcctcgcgt cacaacaacg ttgattgagc caagcaacga gctggaagct    300

tgtggccggg tttcttatcc ggaagataac ggcgcgtgcc atagaatgga ttctccaaga    360

tcagctgagt tttccggtgg gtctggtcac tttgtatccg agaaagatgg ccacaagacg    420

actatttctc ccagaagccc agctgaaaca agtgagctcg ttgggcaaat gacgatattc    480
```

-continued

```
tatagtggaa aagtgaatgt gtatgatgga ataccacctg aaaaggcccg gtcaatcatg    540

cactttgcag ccaatccaat tgatttgcct gaaaacggta tttttgcttc cagtagaatg    600

atttcaaagc tcataagtaa agagaagatg atggaacttc cccaaaaagg ccttgagaag    660

gcgaattctt ctcgtgattc tggtatggag ggccaggcga acagaaaggt atctttgcaa    720

agatatcgtg aaaagcggaa agacagaaaa ttctcaaagg ccaaaaagtg tccaggagtt    780

gcgtcctcta gcttggagat gtttctgaat tgtcagccac ggatgaaagc tgcatattcg    840

caaaacctag gctgcaccgg atctccactg catagccagt cacctgaaag ccagacaaaa    900

agtcccaatc tttcagttga tctaaacagt gaaggcattt aa                       942
```

<210> SEQ ID NO 84
<211> LENGTH: 950
<212> TYPE: DNA
<213> ORGANISM: Arabidopsis thaliana

<400> SEQUENCE: 84

```
agggatatgg atgtaggagt tactacggcg aagtctatac ttgagaagcc tctgaagctt     60

ctcactgaag aagacatttc tcagcttact cgcgaagatt gccgcaaatt cctcaaagag    120

aaaggaatgc gcaggccttc gtggaataaa tctcaggcga tccagcaagt tttatctctt    180

aaagctctct atgaacctgg agatgattcc ggcgccggaa tcctccgcaa gatccttgtt    240

tctcagccgc caaatccgcc tcgcgttaca acaacgttga ttgagccaag gaacgagctc    300

gaagcttgtg gaaggattcc tttacaggaa gatgatggtg cgtgccatag aagggattct    360

ccaagatcag ctgagttttc tggtagttct ggtcagtttg ttgcggataa agatagccac    420

aagactgttt ctgtttcccc cagaagccca gctgaaacaa atgcggtggt tgggcaaatg    480

acgatatttt atagtggcaa agtgaatgta tatgatggag taccacctga aaaggcccgg    540

tctatcatgc attttgcagc caatccaatt gatttgcctg aaaatggtat tttgcttct     600

agtagaatga tttcgaaacc catgagtaaa gagaagatgg tggagcttcc ccaatatgga    660

cttgaaaagg cacctgcttc tcgtgattct gatgttgagg gtcaggcgaa cagaaaagta    720

tcgttgcaaa gatatcttga aaagcggaaa gacagaagat ttctaagac caagaaggct     780

ccaggagttg cgtcctctag cttggagatg tttctgaatc gtcagccacg gatgaacgct    840

gcatattcac aaaaccttag tggcacaggg cattgcgagt cacctgaaaa tcaaacaaaa    900

agtcccaata tctcagttga tctaaacagt gatctaaaca gcgaagataa               950
```

<210> SEQ ID NO 85
<211> LENGTH: 1128
<212> TYPE: DNA
<213> ORGANISM: Populus trichocarpa

<400> SEQUENCE: 85

```
atgcagccgg gagagacagt tttccggtca gctctggaca aacccctaca ccagctaaca     60

gaagatgata tttctcaggt cactcgcgaa gattgccgcc gttacctcaa agaaaaaggt    120

atgagaaggc cgtcgtggaa caaatcgcag gcaatacagc aagtgatttc actcaaaaca    180

ctcctggaag cgacgccgga gactgaatct ccaaggcgac gactctacat tccccgccct    240

cctcctcatc ctcctgataa tactcctcgt gtgcgtttct ctgccgtccc tccaaattcc    300

tctgtttcag agaggggagc aagtgctgaa acgccgatct cggtgccagc cgaggagcca    360

gttccgtgcc ggcaacacga tcctccaaat cccgatgatc ctgccgatcc tctgcctcct    420

gtccatgccg ccgtcaccga gaatgcttcg gtttcaccaa gaactacagg catggcagaa    480
```

gaatcagcag gacagatgac aattttttac tgtgggaagg taaacgtcta tgatgatgta 540
ccgggagaca aggcgcaagc aataatgcat cttgctgcaa gcccatttgc tccacctcag 600
gatgcttctt cagatgtaat tcctacatta aggcctttac aatgccagtt agacactcca 660
ggtgtcaaag ctgctccaaa ttcaattgtg gcgaactttc caaccctgcc aacagtgaaa 720
ggggcagata gtggtcagct tctctgggaa gaaagcaaca tagctcgtga agacaaccta 780
gaaggctcta caagcagaaa agcatcctta caaagatatt ttgagaagaa gaaagacagg 840
ttcaagaaca agagaaaggt ggcagtgcct tctgctagct tggacgtctt cttaagccat 900
ctggttggag atcaaatctc aaatgatcat tggaacctaa atgatgcctg ctctccttcc 960
caacccaggc ctccccaaac gcctaaccgg tgcaactctg ttgacaatgt agcaaaaaat 1020
ggcatcctca aagctgacct taacaacaaa ggtgatgcag atttatcttg ttgtcttgac 1080
tttagttcca agcagattaa tgcgtggtgc ttatgcttgg gatgttga 1128

<210> SEQ ID NO 86
<211> LENGTH: 2114
<212> TYPE: DNA
<213> ORGANISM: Picea abies

<400> SEQUENCE: 86
atgcgaggag gaggaggcgc ggacagactc cccgctagag ctaacctcga gaaacccttg 60
gaagatctca gccatgaaga cattatgcag ctcaccaggg aagactgccg gcgatacttg 120
atagaaaaag gtagcttcca aaatcttttg ctttctcctc aaataacgct ttgctctgag 180
taaatatatg aatataaatg aatgtaatct agtaatcgag ccctaagcgc gacatttaaa 240
gtatttgtaa aggtctgcgg ctgttttggc tttgtctacg gagacaaaaa tctttttttcc 300 gttgggttga gctcagaatc aatggcggtt cttctcgtgg atttgatttt gtttcgtttg 360
gcttgacttt tgccagtatt tacgccctgc cttgtcctaa aatgctttta cagaaaaaat 420
taaatcctct aaattttctt taaacctttc cagtgttaac ctctgaacat tgccaataaa 480
agcgtatagg aaaattttca attaaagctt tatataccgt aaggccatgt agaatctttt 540
aatttttgcc gtttcagaaa acggtttaaa gggataaatt tcttagaagc tcttaaaata 600
gaaaatagag cttgaaatac cactgatcca atgccagaat tgtatataat ttgacttcag 660
accttaaata ctgcttattc ggacggacat ttgctcagaa atcgttttaa tatttatgca 720
taacagattt taaatttctt tgtaggcatg cgacggcctt cgtggaacaa gtctcaggcg 780
attcagcagg tactctcgtt gaagaaattg tttgaatccg ggccgaacga tgaaaagagg 840
tcggcggcaa caaatcggcc gaatccggat gaaaacttaa atgaaaagag gtcggcggca 900
acaaatcggc cgaatccgga tgaaaactta aaggaagctg cgtccgtttc tttgctttac 960
ggttcacagc ctgaaagtcc ttcggtaggc tttttctttt aaacaatgtc gtctaatcga 1020
gcttaaacct gcagaaacgc tggcattgtc tttaatttgg ctaggtattt caaagttgaa 1080
catttctgtc tccattgtaa tgtttgttca ggttgtcttc gccagtaaag actcagacac 1140
ttttaatttg gagtggttgg cgaagacaga gttgccagta ttagcaagcc aaccccgaca 1200
catagcacag cagaatgttt tcttaagctc tttatctgct cagcaatccg gagctcagct 1260
caccattttt tactcgggaa atgttaatgt ctacgacgat gtgcctgcag aaaaggtatc 1320
tacagattta cagttcgatt ctcgtaaaga tgtgcttaaa atttccaatg atataggctt 1380
aaaattctca agatctatat ttgcaggcac aagaaataat gctgttggcc gggagcggaa 1440
attatcctcc gtcgtcgacg tgtcagtcca cacgaaatac acaacaaaac gcagtacgtg 1500
cggcgtatcc atcaaatcct acgaatacgc cgttcattca cggagtaggg ccgcctcttg 1560
caactgtggc gagctcttcc gtcatgagca gtccaataca taaaggtatc gtccattgta 1620
tcccaatgcg gaatgaaacg aaactaaaaa attgacccaa atttatcaaa atttgggcgt 1680
ccgaacataa tttggttgtt tccgatgcag agagtccgat tacaagaaaa gcatcgctgc 1740
aaagatttct ggagaaaaga aaggacaggt acagatagaa aaggttttac tccattatca 1800
tgagattcgt ggttaaaaat gcaatgaatg caattaaata tttttgattg caggagtcgt 1860
ggcaagttgg gggctcccac tatatcgaaa aagcctctgc tgatgggtat gtttatgcat 1920
ccctccattg ttcatcgtca gtattggact gatacggcca agaggaaatc cggaaaaccg 1980
gacatacctg cttctatttc tccgacccgg cctcctcaca cgccgcgtcg gacttcgtcg 2040
gacgaacaac ttagtgcacg ccatgctcgt ggtgatataa gtgcgcaggg ggggtcgcta 2100
cataattcca acta 2114

<210> SEQ ID NO 87
<211> LENGTH: 1098
<212> TYPE: DNA
<213> ORGANISM: Gossypium raimondii

<400> SEQUENCE: 87
atggaggctg ggtaacgac gacggcgact acaacagcgt cgttcagttc gatacttgat 60
aaacccctca gccaactaac cgaagaagac atttctcaac tcactcgcga agactgtcgc 120
aaattcctca aagaaaaagg aatgcgtagg ccgtcatgga acaaatcgca ggcgatccag 180
caagtgattt cgttcaaggc gttgttggaa agcaacgaag attccggcgc cggagctcgc 240
cggaaaatcc ttgtttgtcc accaccgtca cattttcctc cgcaaaatgc ggtagcttca 300
aattctggtg agtcagtaaa agaagcagtc tttggagaag aagaaagcct gtacggccaa 360
aaagatcttt ctttgaaagc tgctccggtg gtgcagatga attgtcaggg cggtgacacg 420
gatgacaaga ctctttcgcc tagtttaggc tctccacggg agtattcaaa attgcctggc 480
agaagtcaat gtgaaacaaa tgagttgggt gggcaaatga caattttttta ctgtggaaag 540 atcaatgtgt acgatggtgt accacttgct aaggcacgag caatcatgca cctggcagct 600
tctcctattg attttcctca gggcaatcta tgtaatcaaa atggtgcctt taggtccttt 660
ctgggtcatg tacaagaagc cgaagacaaa aacgacctta cttcatctat tgctttgaac 720
ttgaattctc ataccatgca cactgagaag atgacagaat atcagcagca gtttaggggga 780 aaagcaaaca tcagtcgtga ttctgatgta gatggacagg tgagcagaaa agaatcattg 840
cagcgatatc ttgaaaagcg aaaagacagg ggaagattct ttaaaggcag gaaaaatgca 900
ggacaagctt tgtctagctc ggagatgtac ctgaaccatc agataagagc tcactactta 960
aatggacaaa caaaccagag cagaacaagt tctccaccac agtctggagt gccacatgca 1020
ttttatagct cagctgacaa ccaagagctt gtgaattttt ctgtagatct caatgatgaa 1080
ggtggtcaag aacactga 1098

<210> SEQ ID NO 88
<211> LENGTH: 1074
<212> TYPE: DNA
<213> ORGANISM: Aquilegia coerulea

<400> SEQUENCE: 88
atgaaacctg acgagacagt ttcccggtca ccacttgata aacctttgtt tcaacttact 60

-continued

```
gatgaagata tttcacagct cactcgtgaa gattgccgga aatttctcag agacaaaggt    120

atgagacgtc cttcatggaa caaatctcag gcgattgaac aagtgatctc acttaaaacg    180

ttgctagaac caagaacgga atctgataca aatgccaccg gaatccggca gaaattactt    240

gtttctcggc tagaaaattc tacccaagta cctttaaatg acaagacaaa tgcctcaaat    300

ttaaagacat ctgttcaggc aataaactcc gggaaagccg atattcatgg tgacaggccg    360

tgtcgggtcc ctgttccagt ccctgacgat aacacaatca ctgttccagt ccctgacaat    420

aacacaatca ctgttccagt ccctgacaat aacatcactt catccagaaa cctgaactcc    480

accaatggac tggttggtca gatgacaatt ttctactgcg gcaaggtgat cgtctacgat    540

gatatgcctg ctgagaaggc acatgcaatc atgaaatttg caggaagcca tatcaatgtg    600

cctgaggatt cttcaccagc tggagctgca gtaattcaat cctttgcatg ccaattacag    660

gcagcatcca tcagacatgg acttgctttc ccgtcagcgg tctctccacc cttgcacaat    720

gtggtagccg atacttctca gcattgcagg gaggaagtga cagtttctcg tgaagttgaa    780

cccgagggtc cagtgagtag aaaagcatct gtacaaagat atttggagaa gcgaaaagac    840

agggggcggt ttaagaacaa gcgaaagata gagtcatctt ctagcttaga gatatacttg    900

aaccatcaac tgggggatca gtaccttaat gagaaatcaa gtcagagcag ggcatgttcc    960

ccaccccaac ctagagcacc acacactccc actcgttgca gttcagttga gaaccaggtc   1020

acaaatgtcg tgttctccat tgatctcaat gataacgatg ttcgggaagg ctga         1074
```

<210> SEQ ID NO 89
<211> LENGTH: 1044
<212> TYPE: DNA
<213> ORGANISM: Aquilegia coerulea

<400> SEQUENCE: 89

```
atgaaacctg acgagacagt ttcccggtca ccacttgata aacctttgtt tcaacttact     60

gatgaagata tttcacagct cactcgtgaa gattgccgga aatttctcag agacaaaggt    120

atgagacgtc cttcatggaa caaatctcag gcgattgaac aagtgatctc acttaaaacg    180

ttgctagaac caagaacgga atctgacaca aatgccaccg gaatccggca gaaattactt    240

gtttctcggc tagaaaattc tacccaagta cctttaaatg acaagacaaa tgcctcaaat    300

ttaaagacat ctgttcaggc aataaactcc ggggaagccg atattcatgg tgacaggccg    360

tgtcgggtcc ctgttccagt ccctgacgat aacacaatca ctgttccagt ccctgacaat    420

aacatcactt catccagaaa cctgaactcc accaatggac tggttggtca gatgacaatt    480

ttctactgcg gcaaggtgat cgtctacgat ggtatgcctg ctgagaaggc acatgcaatc    540

atgaaatttg caggaagcca tatcaatgtg cctgaggatt cttcaccagc tggagctgca    600

gtaattcaat cctttgcatg ccaattacag gcagcatcca tcagacatgg acttgctttc    660

ccgtcagcgg tctctccacc cttgcacaat gtggtagccg atacttctca gcattgcagg    720

gaggaagtga cagtttctcg tgaagttgaa cccgagggtc cagtgagtag aaaagcatct    780

gtacaaagat atttggagaa gcgaaaagac agggggcggt ttaagaacaa gcgaaagata    840

gagtcatctt ctagcttaga gatatacttg aaccatcaac tgggggatca gtaccttaat    900

gagaaatcaa gtcagagcag ggcatgttcc ccaccccaac ctagagcacc acacactccc    960

actcgttgca gttcagttga gaaccaggtc acaaatgtcg tgttctccat tgatctcaat   1020

gataacgatg ttcgggaagg ctga                                          1044
```

<210> SEQ ID NO 90
<211> LENGTH: 987
<212> TYPE: DNA
<213> ORGANISM: Medicago truncatula

<400> SEQUENCE: 90
atgaacggcg gaagcaccgt ttccttccga tccatcctcg acagacctct taaccaactc 60
actgaagatg acatttctca actcactcgc gaagactgtc gcagattcct caaagataaa 120
gggatgcgca ggccttcctg gaacaaatca caggcgatcc agcaggtgat ttctctcaaa 180
gcgcttctag aacctaccga cgatgatatc ccggctaccg tcggcgttgg tgtctcctcc 240
gccattcacc accatcacca ccaccaccct cctcaacctc cgccgaaggc tttggatccc 300
gaagatactg ctttggaact acagaaatcc acttcacctg ttgctgagag acccacggaa 360
accaatgatg ccaatgttgt taacaatccc ggagggtgcg cacctagtgg gtcatttggg 420
caaatgacaa ttttctactg tggtaaggtg aatgtctatg atggagtctc gccggataag 480
gcacgatcaa tcatgcagct tgctgctgca tgtccgtcct cctttcctca ggataatcct 540
tcaaataaaa atgcagcagt ttgggcttct ccttgcaact tacctattga taaggaagtc 600
ctcttcccta ctgacacagc aatccttcaa gttgctcaaa cagataagat ggtggaatac 660
cctctgcaat acagggagaa aggaagcaca gctcgtgatg ctgagggtca ggcaagcaga 720
aaagtgtcac tgcagcgata tcttgaaaag cgaaaggaca ggggaagatc gaagggcaag 780
aaactgactg gcataacttc atctaacttt gagatgtatt tgaaccttcc agtgaagctc 840
catgcctcaa atgggaattc aagtcgtagt agcactgact ctccaccaca gcctagactg 900
cctttagttt ccagtggctc agctgaaaac cagccaaaag ttacccttcc cattgatttg 960
aatgataaag atgttcaaga atgctaa 987

<210> SEQ ID NO 91
<211> LENGTH: 1020
<212> TYPE: DNA
<213> ORGANISM: Solanum lycopersicum

<400> SEQUENCE: 91
atgtcgctgg aacaaactgt ttacaagtct cctctggaca aaccgcttta cctacttacc 60
gatgacgaca tttctcagct cactcgcgaa gattgccgac gttttcttaa agctaaagga 120
atgagaaagc cgtcatggaa taaatcacag gcgattcagc aggtgatttc actgaaggcg 180
ttgtttgaga cgacgccgga atccgacacc ggtcagcgga aaaagcgtca cattcctcgc 240
ccggacacta gtttacagcg agtccagaaa gaaacgagta tcgatgcaga atttgctgaa 300
tcggctgaag aaacggtgcc gtacggtaga aaacctccca ataaacctga tctttccggc 360
gacaaagctg caagtgctgt tgccgttgtc aataacttag ctccttctag aaccacagat 420
tcaggaaatg catcatcagg tcaattgaca atcttctatt gtggcaaggt gaatgtgtat 480
gatgatgtac ctgctgaaaa ggcagaagca atcatgcatc ttgctgcaag cccactcttt 540
gtcccttcag aaactccatt ggatgctaac agagcagctc aacattccga atgccatttg 600
caagctgcaa atgttaaact gggtcaagat tctcctatgg tgttcatgcc aaccatgcaa 660
acagggaaaa taactgaagt tactcgcctg catttggagg aaagcaacac ttcctatgaa 720
gacaatcctg aagcagtgaa ccacgtaagc aggaaagcat tactggaaag atatcgtgag 780
aagcggaaag acaggttcaa gagaaagatg ggaatgcctt catctgctag cttggacatc 840
tatttgaacc atcgaaccat aaatcatacc caaagcgagc tctcaagtag gagcaacact 900
tgttccccgc ccgcaattag attatctgct gcgcctgctc caagtggttc aatggataac 960
attctccaaa tggatgccaa tgcttctggt tttctcgacg acaaagatgg taaagagtga 1020

<210> SEQ ID NO 92
<211> LENGTH: 1018
<212> TYPE: DNA
<213> ORGANISM: Trifolium repens

<400> SEQUENCE: 92
atgaacggcg gaagcaccgt ttccttccga tccatcctcg acaaacccct taaccagctc 60
accgaagatg acatttctca actcactcgt gaagactgtc gcagattcct caaagataaa 120
gggatgcgca ggccttcctg gaacaaatct caggcgatcc agcaagtcat ttctctcaaa 180
gcacttctag aacctaccga cgatgatctc cctgctcccg tcggtgtctc ctccgccatt 240
caccaccatc atcaccacca ccctcaacct cctcagagga atttgaatga agctccggtg 300
aagggctccg atctcgatga taccggtttt catactgcgg aggatcttaa caaatctact 360
tcaactgctg tggaaattcc tactgaaacg aatgatgcca atgttgttaa atcctctggg 420
gggtgcgtag ctagtgggtc gtttgggcaa atgacaattt tctactgtgg taaggtgaat 480
gtctatgatg gagtctcacc ggataaggca cgatcaatca tgcagcttgc tgcatgtcca 540
tcctcgtttc ctcaggataa tcttttaaat aaaaatgcag cagtgtgggc ttctccttgc 600
aacataccaa ttgataagga tgtcctcttt cccaatgaca cagcaatcct tcaggttgct 660
caaacagata agatggtgga atatcctctg caatacaggg agaaagggag catagctcgt 720
gatgctgatg tagagggtca ggcaagcaga aatgcgtcgc tgcagcgata tcgtgaaaag 780
cgaaaggaca ggggaagatc gaaaggcaac aaactgactg gcataacttc atctaacttt 840
gagatgtatt tgaaccttcc agtgaagctc catgcctcaa atggtaattc aagtcgtagt 900
agcactgact ctccaccaca gcctagactg cctctagttt ccggtggctc agctgaaaac 960
cagccaaaag ttacccttcc cattgatttg aatgataaag atgttcaaga atgctaat 1018

<210> SEQ ID NO 93
<211> LENGTH: 936
<212> TYPE: DNA
<213> ORGANISM: Amborella trichopoda

<400> SEQUENCE: 93
atgacggccg gtgatggctc catacgatca atattggaca agcccttgga agagctcacg 60
gaggaggaca tctcgcagct cactcgtgaa gactgtcgca ggtacctcaa agaaaaaggg 120
atgcgaaggc cttcgtggaa caagtatcag gcaattcagc aggttctctc tctaaaaggc 180
ctcttagagg ggaagccttg cgatgacaac agcgatgttt tcagtcaccg atcaccgatc 240
acggtcattc ccaatgttgg gagcatgaga gagaaagaaa aggccgtaaa tattgcggat 300
ccggagatat cggggtctca tcagccgaat tttcgccgag aaattcacga aaccacccgg 360
gaaagagctt taccggcttc cgactggcca ccttctcagg agccggtatc tcagatgacc 420
attttctatg ctggagccgt taacgtatac aacgacattc ctgaagataa ggtgcaagcc 480
atcatttatc ttgctgggaa gtcagactcc ttacagcaaa ctaatgttat cagaacggga 540
ccggaccaat gcatagcatc tgctgcaagc ccctcattga acgatctcca cagtagacga 600
atccacccaa cttcaaacat caccacttct cagtctcttc gtgttgcaac ttcccttcct 660
gttgggcctc attcagaggt tcctaagacg aggaaaacct cggtgcagcg attcttggag 720
aagcggaagg acagggggcg cttgaaggga acattggcga gtggtgggag ctctaagagg 780
ggttcctcat gcctagaatt gtatgcaact tcaagattaa agagtgaggg ggtggccacg 840
actacaactc aatccaatat gaacaatgtg gtcgtatcac cttctaaccc aagaatgcct 900
ctaaatcccg ggagttgcag ctgggttgag aactaa 936

<210> SEQ ID NO 94
<211> LENGTH: 1251
<212> TYPE: DNA
<213> ORGANISM: Selaginella moellendorffii

<400> SEQUENCE: 94
atggcggcct cgattctagg ttgcggttct agcaatggcg tcgcggtcac cggtaatcct 60
gctccagccg cggcggccga ggtgcccgcg cctctcaggc cgctggagga gctcacggag 120
ctggatatca ggcagctcac gcgggaggac tgtagacgct atctcaagga acggggaatg 180
cgcaggccgt cttggaacaa ggcacaggcg atccagcaag tgctgtcttt gaggagtttg 240
ctttgtcctt ccaatccggt aggcccttcc tccaagaacc cgggaagtgc cgcgaacgcc 300
cctccggctg aagcagctgc tgctggtcac accaaacaat tactggacaa ggtctctcag 360
caaagcatgc cagattcttg tccatctaac aacgcctctg atcctaggcc gctcgccgga 420
tgctttggat ctcttgcccc gacgttatca gttctcaatc ccgatgcgaa acgtaacccg 480
ctgagttcta aacccgcgtc aacgacaaag cctcacagtg cccagctgac cattttctac 540
tccggtattg tgaacgtgta cgacgatgtc ccgcttgaca aggcacaagc tataatgctt 600
cttgccgcga gtaaaacgtt tcacgttccg acaagttcag tgcctggcca tccgccgttt 660
acgagtgcaa cccaacaaca acaacaacaa caacgagagc ttaaccaaca aaccgaagcc 720
acgcaaaagt acccgatgca gcaccaacaa gctcctcaaa tatatctaag ctcgggttca 780
gctctacccg acgaaagctg cacggaacct gggcttccac aggtcagaag tgcatcgcta 840
cagagattcc tggctaaacg acgagacagg ttgtcaggga atccttcctc gtctaggcgg 900
aacgacagat ccaaaaagcg gaggttctcc ccgccaccgt caccgttaac ttcggcttcg 960
ttccagtttc ctccaagtgc tagaacatcg caagttttaa gatactccac tacttctaca 1020
actacgatca ctactgccac tgctactgcc gctactacca ctactactac gggtaccacg 1080
aatggtggac actgttccaa ttccaatcaa gcaagcgaga atgcaggcag cgatacctcc 1140
ggtggaagtt ctggaacgcc ggacacaagc gacacaacaa gggacaacga caatggacga 1200
gtttccaacg aaaatggacg agtgtccacc acttgtctcg cagcaacgtg a 1251

<210> SEQ ID NO 95
<211> LENGTH: 705
<212> TYPE: DNA
<213> ORGANISM: Selaginella moellendorffii

<400> SEQUENCE: 95
atgtctagca tggtcgattt cctggggatc gaggagaagg tgtccaccag cgtcagcgcc 60
gagaggttga agaagctgga ggagctcacg gacgaggacg tgatgcagct cactcgggag 120
gattgccggc gctacctcaa ggagaaggga atgcgtcgtc cgtcttggaa caaggcccag 180
gccgtgcagc aacttctctc gctcaagagc ctgtgcgatc cttccccggc ttccagtgga 240
gccgccaaga ggagcccatc tccgccgctc gacgaggctc cagcgaagaa acccatggca 300
atgacaagca tcgatctcaa ggctgccgct gctgtggacg ccgccaatct tacgatgttt 360
tatgatggag cagtgtccgt gtttgacgac gtttcgccag acaaggcatc tcttttccct 420

```
ttggcttatg cgatcatgct cctggccggg aatgtgaagt cgtggccttc gatcaacgtt    480

gctgctaaca ccaacaaagt tgtgatctct tcttatgagt tgccacaggc gcgaaaggca    540

tcactccagc gttttcttca gagacgccgt gagaaaactg cgaaagaggc agcatccaaa    600

gggaactcta ataagtcgcc ttgtcatggc gagagctcgg ggaagcacgc atcggatgct    660

actgatccag ccacttctcc cttgctcacg gaggtctctt cctag                    705
```

<210> SEQ ID NO 96
<211> LENGTH: 813
<212> TYPE: DNA
<213> ORGANISM: Nicotiana tabacum

<400> SEQUENCE: 96

```
atgccgccgg aagaaacagt ttccaaatca cctctggaca aaccgctcca cctacttacc     60

gatgacgaca tttctcagct tactcgcgaa gattgccgcc gttaccttaa agaaaaagga    120

atgagaaggc cgtcatggaa taaatcacag gcgattcagc aggtgatttc actgaaggcg    180

cttctcgaga cgacaccgga ttccgacacc ggccctcgga gaaaacttca cattcctcgc    240

ccagacacta gagtacaaca agtccagaaa ggaacggata ccgatgcaga attttcgaaa    300

tctgctgaag ggatggtgcc atacggaaga aaacattcga aaaaacctga tattcccggt    360

gatatagctg ccggttcagt tgccgttgcc gccggcaata acttagctcc ttctagaacc    420

acagatttgg gaaacacacc agcaagtcaa ttgacaatct tctattgtgg caaggtgaat    480

gtgtacgatg atgtgcccgc tgaaaaggca caagcaatca tgcatcttgc tgcaactcca    540

ctctttgtgc cttcagaaac tccattgggt gctaccttag cggctcgaca ttccgaatgc    600

catttgcaag ctgcaagtgt taaacagggt ccagattctg ctatggtgct catgccaacc    660

atgcaaacag ggaaaatgag tgaagtgact cgcctgcgtc tggaggaaag caataccttc    720

tatgaagaca actctgccaa ttatgcagaa gcagtggaag gccacccaag caggaaagca    780

tcagtacaaa gatatcttga gaagcggaaa gac                                813
```

<210> SEQ ID NO 97
<211> LENGTH: 984
<212> TYPE: DNA
<213> ORGANISM: Solanum tuberosum

<400> SEQUENCE: 97

```
atgccgccgg aagaaacagt ttccaagtca cctctcgata aacctctcaa tcaactcact     60

gacgatgaca tttctcagct cacacgcgaa gactgccgtc gttacctcaa acaaaaagga    120

atgagaaagc cgtcatggaa taaatcacag gcgattcagc aagttatatc gttgaaggct    180

ctcctcgagc cggatactga cgccggaact cggaagaaac ttcacattcc tcgtgcagat    240

actcatgtcc agagcgggaa aaatacctat ggcgaacctt ctgaaccagt gcctgataga    300

agaaatcagc aggacagacc tgatctttcc agtcatatta ctgcccttcc ggtcgctgtt    360

gtggataatt cagctccttc tagaacaata ggttcagcag ataaaccagt aggacaaatg    420

acaatcttct atagaggcaa ggtgaatgtc tatgatgatg tgcctgccga caaggcacaa    480

aaaatcatgt gtcttgcttc aagccctctt tgtgtgcctt cagaaactcc atcgaatgcc    540

actgtagcag ctcgacattc agcatgctgc ttacaagctg caaatagtaa actacgccta    600

gatactaata ttgtaccgac tattcaaaca gtgaaaatga gtgaggtttc tcgagttcct    660

atagaagaaa gcaaccgctt atacaatgat aatcctgaag cagtggagag ccccgcaagc    720
```

```
aggaaagcat cagtacaaag atatcttgag aagcgaaaag aaaggttcaa gtggaagaga    780

aaggtagaaa caacttcatc agctagcttg gatatctatt taagtgatcg aattgggact    840

cgtacgccaa gtgactatgc aagtggggct gatctttgct tcacacccca cattacacct    900

acaggaagtg gtcctataca agacaatatt cagatgaatc ccactttttc tagtgatctc    960

aatgacagag atgttagaga gtga                                           984
```

<210> SEQ ID NO 98
<211> LENGTH: 1047
<212> TYPE: DNA
<213> ORGANISM: Glycine max

<400> SEQUENCE: 98

```
atgaacggcg gtgccaccac cgccaccttc cgatccatcc tcgacaagcc cctcaaccag     60

ctcaccgagg atgacatttc tcagctcact cgcgaagact gtcgcagatt cctcaaagaa    120

aaagggatgc gcaggccttc ctggaacaaa tcgcaggcga tccaacaggt catttccctg    180

aaagcgctgc tggaaccttc cgacgatgat actcctcctc ctaccgccat gcaccaccgt    240

agtcatgctc ctccccctcc acctcaacct caatctcaag tgaatttgac tgaacctcct    300

cctccgccca aggctccgcc acctgaagaa tcctcttttc atgctgctga agacattcag    360

aaacctgcgt cgtctgggga aaaaccttcg gaaactaatg acaccaacac caacgttgct    420

agccccaaag ggtgtgcaac tagtggatca tttgggcaaa tgacaatttt ctattgtggt    480

aaggtgaatg tctatgatgg agtctcgcct gataaggcac gagcaatcat gcagcttgcg    540

gtgagtcctg tccagtttac tcaagatgat ccttcaaatg gaaatgcagc tgtttggcct    600

tctccttgcc acttaccaat ggataaggat gtcctcattc ctgtagatac aacaatcctt    660

caggttgctc aatcagataa gatgatggaa tatcctctgc aatatagaga gaaaggtagc    720

atagctcgtg atgctgaggg tcaggcaagc agaaaagtgt cattgcagcg atatcttgaa    780

aagcgtaagg acagggggag attgaaaggc aagaaattga ctgggataac ttcatctaac    840

ttcgagatgt atttgaacct tccagtgaag gtccatgcct caaatgggaa ttcaagccgt    900

agcagtacta gctctccacc acagcctaga ctgcctctag tatctagtgg ttcagctgac    960

aaccagctaa aggttgccct tcccattgat ctcaatgaca aagtgtcatt gcagatgttc   1020

aagaatgcta aaactctaac tagatag                                       1047
```

<210> SEQ ID NO 99
<211> LENGTH: 1017
<212> TYPE: DNA
<213> ORGANISM: Citrus clementine

<400> SEQUENCE: 99

```
atggacgtgg acggtggcgt gacgtcgtgc cggtcaatac tcgagaaacc tctcagtcag     60

ctcactgaag aggacattac gcagctcaca cgcgaagatt gccgcaaatt tctcaaggag    120

aaaggaatgc gcagaccatc gtggaacaaa tcgcaggcga tccagcaggt gatctctctc    180

aaagctttgc tcgagtccag cggcgattcc ggctcaggtg ttttacgcag agtactcgtc    240

tcgcctccgg aaagtatgcc gccgcgcgtg aatgtgactt caaattcagc tgatttagta    300

aaggaaccga ccatctcagt ttctggagac caaaacagtg cgtataggcg gaagtaccct    360

cgcaactgtg ctgttgatgc agataacaag accatctcta acagaaatcc ctgtgaagca    420

aatgggtcca tagggcagat gacgattttc tattgtggca aggtgaacgt gtacgaagga    480

gtgccaactg ataaggcaca ggagattatg caccttgcag caactccaat tgatttttcc    540
```

cagaacggtt catttggtgg aattacggca tatagggcca ttccatgcca tttacaagtg 600
acaagcaaca gacatgtgtc tctccctctt cgtcctgctg ccatgatctc tcagttcatg 660
caaacaggga agatagcaga ttattctcag gagtataggg agaaagcgat tagtactcat 720
gactctgatg tggatggtca ggttaaccga aaagtctcgt tgcagaggta tcttgaaaag 780
cggaaagaca ggggaaggtt tttcaaggga aagaaaaata caggaccaac tcctagtttg 840
gagatgtacc tgaaccatcc ggggaagaca catgcctcca atggacaaca gagccagagc 900
aacacaagct ctccgaccca gcctgagttg tccaacacat tggggacctc cccagacaac 960
caggcgaaga ctgtcatgct tccggttgat ctcaacaatg aagatattca agactga 1017

<210> SEQ ID NO 100
<211> LENGTH: 1008
<212> TYPE: DNA
<213> ORGANISM: Ricinus communis

<400> SEQUENCE: 100
atggacgccg gagtgacgtc gttcaggtca atactagata aacccctaac tcagctaact 60
gaagaagaca tttctcaact cacacgcgaa gattgccgca aatacctcaa agaaaaagga 120
atgcgaagac cttcatggaa caaatcgcaa gcgatccagc aagtgatttc tctaaaagca 180
cttcttgaaa ctagtgaaga ttccggtgcc ggtgctctcc gtagaatctt agtttctaaa 240
cctccggtta cttcaaattc tgttgattca gctaaggaac caagtgatag caacaataat 300
aacttactag atgagacagc tcctcatgat tctcccaaat ctcctcctcc ggcgccatcg 360
ttggattgtc cactggaaga ggcagataat aaagtcattt cttcaagaag tcctggtgca 420
acagatgggt tggtcgggca aatgacgatt ttctattgtg gaaaggtgaa tgtttatgat 480
ggagtcccac ccgataaggc ccaggcgatc atgcatcttg cagcgactcc aattcactca 540
cctttagacg atccaattcg tagacctgta tttgcttttc cgtatcattt acagacccca 600
agtgacaaac atgtctttgt tccttctaat gctgcaattt ctccaaccac accaacagag 660
aaggtgacag aatattctca gcagtgtagg gagaaaggaa atgtaactta tgatcatgat 720
gtagagggtc aagcaaaccg aaaaatgtca ttgcagagat atctggagaa gaaaaaggat 780
aggggaagat tcaagggtag gaaaaattta gggcctaatt cgtctagctt ggatgcatat 840
ttgaaccatc aaatgaggac acatatctca aacgagcaat caaccaggag cagtacaagc 900
tctccaaccc agcctggagt gccacatact tcgagtaact cggccgaaga tcagctgaag 960
actgccagtt ttgctgttga tcttaatgaa gatgtccaag aaccttga 1008

<210> SEQ ID NO 101
<211> LENGTH: 1182
<212> TYPE: DNA
<213> ORGANISM: Vitis vinifera

<400> SEQUENCE: 101
atgaatcccg gcgtcaccac tctccgctct atactggaca aacccettca cgaactcacc 60 gaagaagaca tttctcagct cactcgtgaa gattgtcgca aatacctcaa agaaaaagga 120
atgcgtcgtc cttcctggaa caaatcgcag gcgatccagc aggttatttc gcttaaatcg 180
ttgctcgaaa ccagtgaggg cagcggtgcc ggagttttga ggaagatcac cgattcaccg 240
ccggcggaaa atctacctcc ggttacctcc aattcagctg attcaggcaa ggagctgagt 300
gctgatatcc agatctcagt atcagctgat gaactggttc cccttccgcc aaaagatcat 360

-continued

```
catccagaat ccaccccttc tggcgaatta gccagccggc ctccagaggc agacaccaag    420

catacttgtc ccagaagtcc aggtgcaaca aattgtttgg ttgggcagat gacaattttc    480

tactgtggaa aggtgaatgt gtatgatgga gttccagatg ataaggcaca agcaatcatg    540

catcttgcag caagcccatt ccatttgcct tcagatgacc cctttagtgg tgctgctatg    600

ctttgctcct ctccatgcca tttgcatact gccaatgtta aacatggcca tattcctcct    660

cgagccatgg tttctcagac tatgcaaaca gagaaattta ctgaatattc tcaacagtac    720

agagaagaag tgaactttac ccgtggacat ggatcggaag cactttctgg gcttaggacg    780

gtaggaagcc caacggccag gcctaccgaa gatatggaac agaccacttg tctcactata    840

tggggtacct tccgctacaa ggttatgcca ttcgagatat atgagggcat catggatgtt    900

gaaggtcagg ttgacagaaa attatcattg caaagatatt tcgaaaagcg aaaagacaga    960

tttaagagca ggaaaaaaat aggactacct tctggtagct tggagatgta tgtgaaccat   1020

caagcaagga cacaaccctc gaatgggcaa tcaagccgga gtggcacaag ctctccaccc   1080

cagcatggat tgtcgcacac cctgtgcagc tcagctgaca accatacaaa gaatttcact   1140

ccttttgttg atctaaacag taaagatatc caagaaagtt ga                      1182
```

<210> SEQ ID NO 102
<211> LENGTH: 1029
<212> TYPE: DNA
<213> ORGANISM: Morus notabilis

<400> SEQUENCE: 102

```
atgagcgccg gcacgacggc gtttcggtcc atactggaca agcccctgaa ccagctcacc     60

gaggatgaca tttctcagct cacccgtgaa gattgccgca aatacctcaa ggaaaaaggg    120

atgcgaaggc cgtcgtggaa caaatcgcag gcgatccagc aagtgatttc gctcaaggct    180

ttgttggagc cctgcgacga ttccggcgcc ggagccctaa ggaggatcgt cgcttcgacg    240

ccgccgccac cgccgacaca aaacgcgcca cgtgtctcca ctttcagtgt tacttcgaac    300

tcggcagatt cgggtaagga agcaagtgtt gatgtccagg tttcggcgga ggaatcggga    360

ccgtgtcaga ggaaggagca ggcgaaatct gctccggaga ctgaggaaag accggctgat    420

gcgggtgaga gggcaagtcc aagaagtcat tgtgcaactg atgcattggt cggacaaatg    480

acaattttct attgtggcaa agtgaatgtg tacgaagggg ttccacctga gaaggcacga    540

gcaatcatgc accttgctgc aagtccaatc cctttatctc gagaaaattc atttggggtc    600

cttgcagcac ctagatcttt tccatggcat ttacatgctg cgagtgacaa gggtggcctt    660

ctccctccta gtgccacaat atcacaaccc atgcagacag ataagctagc cgactacagc    720

caacagtgct gggagaaaga aaatgatggt caggcgagca gaaaactctc attgcagaaa    780

taccgtgaaa agaaaaaaga tagggggagg ttgaagacca agagaagcac gggatttaat    840

tcttctagca tggaggtcta ttttaaccac caggtaaaga cccacatgtc aaatggtaat    900

tcaagtcgaa gtagcacaag ctctccgacc cagcctggac taccacaaac attgtgtagc    960

acagtcgaca atcagccaaa gattccctgt cttcctgttg atctcaatga aaaactaact   1020

attgagatg                                                           1029
```

<210> SEQ ID NO 103
<211> LENGTH: 1095
<212> TYPE: DNA
<213> ORGANISM: Phoenix dactylifera

<400> SEQUENCE: 103
atgtattggg ttggatcggc tcaagaacgc cgccgagacg ggggccggtc gccgctcgac 60
aagccactca gcctgctcac agaggaggat atcgcccagc tcacccgcga ggactgccgc 120
cgattcctca aagagaaagg catgcgacgg ccgtcctgga ataagtcgca ggcgatccaa 180
caggtcatct ccctcaaggc cctcctcgag ggacgaccgg agtccggcga actccccgtc 240
ggcgccggct accgccagaa gcctccccct cggcggccgg cctctcttcc ttcgctgcag 300
gaggcggccg gcgactcgac ggcggcggcg aaggagccgt cgccgtcgtc gtcgctgtct 360
ccgtaccgga gaagagatcc gatcccgccg atcatctccg ccggcgggcc gtcttgccgg 420
ttcccggtcg ccggcaggga ccaacaaccg ccagagaccc cctccccctc gctcagggtg 480
acggcggaag taccggcggg tcagatgacg atcttctacg acggcaaggt gaacgtctac 540
agcgacgtga cggtcgataa ggcgcgggcg atcctgctgc tcgcggggag acgagactgc 600
tacggcgctg cggctctacc gggtccggtt cactcgcccc agccggcttt tctcggaccg 660
ggtcagggcc cggtccccac cgctccccccg ctggccgctg ctttacccac ctcgccagct 720
gggaggttag cccaccgttt cgagggaccg agtggagtgc cgcgcgggaa atcgagcctg 780
gtaagagagc ggagcacgtc accggagggt ccaacaagta gaaaagcatc attgcagcgg 840
tacctggaga aaaggaagga caggttaaaa ggtagaaaaa ctcttggagg ggcatcttct 900
tcaagcatgg aaataatgtt cttgagccaa aaatttgggg gtcagatacc aaatgagcag 960
ttaagtagga gcaacactag ctcccctacc caacccagac cacctggcac accaactaga 1020
tgcagttcaa tagagaacca ggctcagaaa aatcatctct cagttgatct caatgatgat 1080
ggttgcggca actga 1095

<210> SEQ ID NO 104
<211> LENGTH: 1065
<212> TYPE: DNA
<213> ORGANISM: Theobroma cacao

<400> SEQUENCE: 104
atggaggcgg gggtagcgac gacgacgaca acgacggagt cgtttaggtc gatacttgat 60
aaacccctca gccaactaac agaagaagac atttctcagc tcactcggga agattgtcga 120
aaattcctca aggaaaaagg aatgcggagg ccgtcgtgga acaaatcgca ggcgatccag 180
caagtaattt cactcaaggc gttgttggag agcaacgaag attccggcgc cggagctatc 240
cggaagatcc tcgtttctcc accatcaccg tcagtgcctc cgcaaaatgc agcggcgcgt 300
gtggcttcca attcatgtga ttcagtaaaa gaagcggttg tcggagaaga aggaagcccg 360
tatcggcgaa aagatcctcc tttgaaacct tctccggtgg gggagataaa ttgccttggc 420
ggtgacacgg ataacaagaa tctctctcct agaagtccat gtgaatcaaa tgagttgggt 480
gggcaaatga caattttcta ctgtggaaag gtcaatgtgt atgatggagt accacttgat 540
aaggcacggg caatcatgca tctggcagcg actcctattg attttcctca ggacaatcaa 600
tgtagtggaa atgcagccct taggtccttt atgtgccatg tccaagcagt cggtgacaaa 660
aatggccttg ttgcttctac tgccttgaac tctcatacca tgcaaacaga gaagttgaca 720
gaatatcagc atcagtttag ggaaaaagga aatatcgctc gtgacgctga tgtagatggg 780
caggtgaaca gaaaagtatc attgcagaga tatcgtgaaa agcgaaaaga caggggaaga 840
ttttttaagg gcaggaagaa tacaggacaa gcttcctcta gcttggagat gtacctgaac 900
catcagataa gaactcacaa ctcaaatgga caatcaagcc ggagcagcac gggttctcca 960
ccacagtctg gattgccaca tgcattttgt agctcagctg acaaccaagc aaaacttgtg 1020
aatctttctg tagatctcaa tgacaaaagt gttcaagaac actga 1065

<210> SEQ ID NO 105
<211> LENGTH: 3789
<212> TYPE: DNA
<213> ORGANISM: Spirodela polyrrhiza

<400> SEQUENCE: 105
atggccggga gcgaggcggc ggcgccggag gaggccggaa gggcggggga ggaggaggtg 60
agagcggcgg cgggggctgc ggcggtgaag tcgccgctgg agaagccgct gtcggagctc 120
acggaggagg acatcgcgca ggtcacgcgc gaggactgcc gtcggttcct caaggaaaaa 180
ggtgctctag tccttttcct ttggttttcc tccttgtttc tcttcttttc ctttggaggt 240
cgcggtggag ctgatctcga tatccacgtg gccgcccgcg gtgacggcgg ctcccgtttt 300
ctctgtgcaa acgaatgcag gtatgcgccg ccccttcgtgg aacaagtcgc aggccgtcca 360
gcaggtcatc tccctcaagg cgctcctgga gccctgccac gatgcagacg acgacgcacc 420
ttccgccggt gctgttccct ccatctcctc cttcttctcg aaaaggccgt ccgacgccct 480
gcttccggcc gccgcggcgc aggtgaggag gggtatcctg ttccaaactt ccgtcgcctt 540
ctcttctagc tcgagctggc aacattttgt gaaattgttc cttctcgatt tagttggaga 600
aacgcgtgtg gtttattgtg ttctgtttac ttctcagttt cccgtctctt ctccaatgag 660
gggtgaacct gccggcggcg cgccccaaat tgtctccgaa cgtccccacg gaagggaccc 720
gctggcgaac gtcttcacct gctccgacgc cctcggtcga ttcccggcaa cggggaacgg 780
tgctcttccg ccaaacagtg ccaccctccc gcccaggtgc gtcccttctc agcacaacgc 840
cccctctatt caactctttt atttccccgg attgtccctc agatgttaac gggcgcccat 900
ggtgttgtag aggggttgct tccgctgaga cgctggaggg acagctgaca atcttctacg 960
atggcaagat taatgtctat gatggtgtga cgccggagaa ggtgaggtcc ggtcagagta 1020
agttggcggt gaccccttcc tgtggtagat ctaggcactc atggcagtgt atttcccgtc 1080
tttgaaggcg cgggtgatcg tacaatttgc ggggagcccg agctgctacg atatgccgcc 1140
gatgccttcg ccgtctttct acccaaaccg acccccctaaa tgccacgacc tggctctgcc 1200
agcgttatct caagcgacag gtggtggttc cttcaatccg ccaccgcctc cgccgccgtt 1260
gcagccaccg ccgtctcatc ctgcccagcc tatcggctat tcccaggttc cccagaacgc 1320
tggtacgttt ttttctccgt catgactttc ctgcgggttc gcctatgctt gatcacgttc 1380
acgataacgc cctgcggtgg ccctcctgct cacgttgagt tctattgccc tggcaggaag 1440
gttcccgcag caatttcggg aaggcatgga agagtggaga agctcgcgag aagttgaacc 1500
aggtgagaga ccttggaccc ttttcttcag tatcagtcgt tattctcgtt tctctctgct 1560
taactgacct atgcacccgg cctgaacagg cagggtatgc tgggtgattg aggagattac 1620
gcctatatgt cagtctatta ccatgctact gtttaagggt gtccttctgt ctaagttaac 1680
tagagtgacc ttaagctcct ggatttctta acctaccaca ccctgatggt acatggtaca 1740
ctcacagttg acctcaaagc ctttctcatt cctgcggggg aagagggtgg gggtgggcgt 1800
tgactgagaa aatttgaaa gcaaattgct aatttctgtt gttctttata atgacatttt 1860
aggcattgcg cgcaagatag ctcttttttc ctttttaaga actgtgcttc ttgattccat 1920
tagcccggga tttaggttcc gttcattgct tagttagcct ccccaattgg cgctgtttat 1980
gaacgattgg cctcgaccct cttcagcatc cttatcaggg atcttgagat tgagcttaat 2040
cttatcgcct cttctcaaat gattatggct gccgcgtttt tttccaattt ccagttgatt 2100
tacctatttt ttggggagag gatgactggt acagtatggc aacttatcca gttttgaatt 2160
gatgctgata ctgttcttct ttataaggcc tagaaattga tggtaattaa agtaacgtgt 2220
cagtgattcc atggatcaca ttaatgccct aaacttctgt gtcttatgct attccaaatc 2280
tgaaaacctt atgaatcaga ccaacaatag tatgaagaaa atttatttca tgctagggtc 2340
catggtgttc tattcaagaa ctaccctttt tttggatcat gcagatgatc tattaagaga 2400
acaaaatgca gtagaaataa gttaacgaaa gacaacaagg tcatgtcatt tgacgaatga 2460
agaatttcag aatcaaattg aagcacatta catcttctca tgagttaaaa aaaatgctca 2520
tgcactgctt ttaatgctcc tttataatac ctgtcatagg ctgaattatt tcaaagtttc 2580
cttgtatggg aagttctact gggtggttct tttgtatgaa tcttcgtaaa taatcaaagc 2640
ctgtttattg ttcttcatga cgtggaaata attattttta tgtatcactc acgaaatgga 2700
tacagcacct atggttacat gatatttaac ttacgtccgc tcaaataaat gagcaataat 2760
aagataacct accatttctc tccttcattc ccattttgca aagcgtctgt tggtcgtatg 2820
ggaaaccaca tttctacaag aggaatccat catcttctat cacatctccc ttgagtgggc 2880
gcattttatg tggatccaaa tatctcaatt aataataatg tttactggat cattatatag 2940 tttttttat gcattcctct gatgatctta gtggctctcg gaaatttttt attcatgaat 3000
agaaattttg tcatccctga aagctgctgc tcctttgcgt tcatcatttc tattctatta 3060
ttctcccttc ttcctgtatg gcctcctgaa gagttcttct tcatgcgaga gaaaaactat 3120
ggtcttaccc gaatagggtg ggatatttgt atgatcttcc caaggttttg tgtgggcccc 3180
atatgggggc ggtggcgaag cgggctttcg ggccggcgag cctagagaga cccgggcccg 3240
gcggctgttg ctaccctcta tagaaaagtt ttcctcagtg ctaccgcgct actgattggt 3300
tgctcttctg gtgccaatgt cgtcttgccg cgagcagagg gccccaccag cagagccgca 3360
tcgctccagc ggtacctgga gaaacggaag gataggtaaa gatggtgggc gtgggggtt 3420 gaccgactgg ttgactgccg ccgccgctgg ctgacttcgc cctctttccc tgtcggaagg 3480
ttcaagtgca agaagcacgc cggcgggggc tcttccggcg tggagctcct cctgagccag 3540
cggatcaggg accagattcc ggccgcccac ctctcatgcg gagagatgta cgcggcggcg 3600
ccgccggccc cgcggccccc tcccccgccg gcccgctgta gcgccgccgg ccacctccgc 3660
ttctccatcg acctcaacga cggcggtgag cgctctctct atctctctca cctcttttc 3720 atcgcctctg cttttgaaga gagtacccat gccaccgccg cctgcgtttc agatgtccgg 3780
gaagcttga 3789

<210> SEQ ID NO 106
<211> LENGTH: 882
<212> TYPE: DNA
<213> ORGANISM: Musa acuminata

<400> SEQUENCE: 106
atgaaccccg gggagaccac gccccccgtcg ccgctcgaca agcccctcgc cgagctcacc 60
gaggaggaca tcgcccagct cacccgcgag gactgccgcc gcttcctcaa agcgaaaggc 120
atgcgacggc cgtcgtggaa caagtcgcag gcgatccagc aggtcatctc tctcaaggcc 180
cttctcgagg ggcggcccgg ctgtgacgac tgccctgctg gcggcggaat cctccaaaag 240
ctgctcactt cttctccttc ggagccgcta tcgccaccgc aggactcacc tcctcccgcg 300

-continued

```
ccgaaggagg gcggtagcgg atcacagccg ctggcgaagg agccgtcgcc gtatcgaagg    360

agggacccga tcccaccgcc ctattcagcc ggaaatccga cgtgccagac cccaattgcc    420

ggagctgacc ttccccaccc gccggagaag cgctgcccct cccccaggtt gacggcggaa    480

gtaccggtcg gccagatgac gatcttctac gacgggatgg tcaacgtata cgacggcgtc    540

tcggccgatc aggccaggtc gatcatggaa cttgcggcca gcccggtctg cttcgacgat    600

ccgaccggtg cattctctcc ggcccggccg ccggccttcc gcttccctcc gggtctcccc    660

cgaccggccc cggtccccac cgctccctcg ttcgtgggga ccttcccgat ctcgccggct    720

ggtaaacgtt gctactccta ctgttcgttc cggtcaagcg tcagcctttt aaccacaaca    780

gagggcccaa caagcagaaa agcatcattg cagagatact tggagaaaag gaaagacagg    840

tatggtcatt taccaacaga aagtatacta cttgttagct ga                       882


<210> SEQ ID NO 107
<211> LENGTH: 498
<212> TYPE: DNA
<213> ORGANISM: Phalaenopsis aphrodite
<220> FEATURE:
<221> NAME/KEY: misc_feature
<222> LOCATION: (214)..(243)
<223> OTHER INFORMATION: n is a, c, g, or t

<400> SEQUENCE: 107

atgaactccg atgcaataac catggggaaa tctctgcttg agaaacccct tagccttcta     60

accgaagacg atatcgcaca gattacaaga gaagaatgcc gtagattcct caaagataga    120

ggcatgcgtc gcccctcttg gaacaagtcg caggcgatcc agcaagtgat ttctctcaaa    180

gccctgttcg aaaaccgatc agatctagaa gatnnnnnnn nnnnnnnnnn nnnnnnnnnn    240

nnntttcccg aacacgcaga tctcagttcg atctcgccga ctgcggaggc caaggaacca    300

gagaaagctc agctcactat attctacggg gggaaggtgc ttgtgttcga caattttccg    360

gttaataagg cacaggattt gatgcagatt gcaggaaaag agcagaatca aaattacggg    420

acagcaaaca ctgtggctcc atctgcccct gcagcagacc tccatagttt acctctgccg    480

gctaagcctc cggcgtaa                                                  498


<210> SEQ ID NO 108
<211> LENGTH: 238
<212> TYPE: DNA
<213> ORGANISM: Arabidopsis thaliana
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
```

<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t

<400> SEQUENCE: 108
mdvgvsaksa kktdstrdcr kkdkgmrrsw nksavskayg ddsgagrkvs vnrvtttsna 60
cgrvsydnga chrmdsrsas ggsghvskdg hkttsrsats vgmtysgkvn vydgkarsmh 120
aandngassr mskskkmmkg kanssrdsgm ganrkvsryr krkdrkskak kcgvasssmn 180
crmkaaysng ctgshssstk snsvdnsggs gggsakgrgh gkngdstrtg hhhhhhgs 238

<210> SEQ ID NO 109
<211> LENGTH: 380
<212> TYPE: PRT
<213> ORGANISM: Trifolium repens

<400> SEQUENCE: 109

Met Asn Gly Gly Ser Thr Val Ser Phe Arg Ser Ile Leu Asp Lys Pro
1 5 10 15

Leu Asn Gln Leu Thr Glu Asp Asp Ile Ser Gln Leu Thr Arg Glu Asp
20 25 30

Cys Arg Arg Phe Leu Lys Asp Lys Gly Met Arg Arg Pro Ser Trp Asn
35 40 45

Lys Ser Gln Ala Ile Gln Gln Val Ile Ser Leu Lys Ala Leu Leu Glu
50 55 60

Pro Thr Asp Asp Asp Leu Pro Ala Pro Val Gly Val Ser Ser Ala Ile
65 70 75 80

His His His His His His His Pro Gln Pro Pro Gln Arg Asn Leu Asn
85 90 95

Glu Ala Pro Val Lys Gly Ser Asp Leu Asp Asp Thr Gly Phe His Thr
100 105 110

Ala Glu Asp Leu Asn Lys Ser Thr Ser Thr Ala Val Glu Ile Pro Thr
115 120 125

Glu Thr Asn Asp Ala Asn Val Val Lys Ser Ser Gly Gly Cys Val Ala
130 135 140

Ser Gly Ser Phe Gly Gln Met Thr Ile Phe Tyr Cys Gly Lys Val Asn

```
145                 150                 155                 160

Val Tyr Asp Gly Val Ser Pro Asp Lys Ala Arg Ser Ile Met Gln Leu
                165                 170                 175

Ala Ala Cys Pro Ser Ser Phe Pro Gln Asp Asn Leu Leu Asn Lys Asn
            180                 185                 190

Ala Ala Val Trp Ala Ser Pro Cys Asn Ile Pro Ile Asp Lys Asp Val
        195                 200                 205

Leu Phe Pro Asn Asp Thr Ala Ile Leu Gln Val Ala Gln Thr Asp Lys
    210                 215                 220

Met Val Glu Tyr Pro Leu Gln Tyr Arg Glu Lys Gly Ser Ile Ala Arg
225                 230                 235                 240

Asp Ala Asp Val Glu Gly Gln Ala Ser Arg Asn Ala Ser Leu Gln Arg
                245                 250                 255

Tyr Arg Glu Lys Arg Lys Asp Arg Gly Arg Ser Lys Gly Asn Lys Leu
            260                 265                 270

Thr Gly Ile Thr Ser Ser Asn Phe Glu Met Tyr Leu Asn Leu Pro Val
        275                 280                 285

Lys Leu His Ala Ser Asn Gly Asn Ser Ser Arg Ser Ser Thr Asp Ser
    290                 295                 300

Pro Pro Gln Pro Arg Leu Pro Leu Val Ser Gly Gly Ser Ala Glu Asn
305                 310                 315                 320

Gln Pro Lys Val Thr Leu Pro Ile Asp Leu Asn Asp Lys Asp Val Gln
                325                 330                 335

Glu Cys Gly Ser Gly Gly Gly Ser Ala Lys Gly Glu Leu Arg Gly His
            340                 345                 350

Pro Phe Glu Gly Lys Pro Ile Pro Asn Pro Leu Leu Gly Leu Asp Ser
        355                 360                 365

Thr Arg Thr Gly His His His His His His Gly Ser
    370                 375                 380
```

<210> SEQ ID NO 110
<211> LENGTH: 353
<212> TYPE: PRT
<213> ORGANISM: Amborella trichopoda

<400> SEQUENCE: 110

```
Met Thr Ala Gly Asp Gly Ser Ile Arg Ser Ile Leu Asp Lys Pro Leu
1               5                   10                  15

Glu Glu Leu Thr Glu Glu Asp Ile Ser Gln Leu Thr Arg Glu Asp Cys
            20                  25                  30

Arg Arg Tyr Leu Lys Glu Lys Gly Met Arg Arg Pro Ser Trp Asn Lys
        35                  40                  45

Tyr Gln Ala Ile Gln Gln Val Leu Ser Leu Lys Gly Leu Leu Glu Gly
    50                  55                  60

Lys Pro Cys Asp Asp Asn Ser Asp Val Phe Ser His Arg Ser Pro Ile
65                  70                  75                  80

Thr Val Ile Pro Asn Val Gly Ser Met Arg Glu Lys Glu Lys Ala Val
                85                  90                  95

Asn Ile Ala Asp Pro Glu Ile Ser Gly Ser His Gln Pro Asn Phe Arg
            100                 105                 110

Arg Glu Ile His Glu Thr Thr Arg Glu Arg Ala Leu Pro Ala Ser Asp
        115                 120                 125

Trp Pro Pro Ser Gln Glu Pro Val Ser Gln Met Thr Ile Phe Tyr Ala
    130                 135                 140
```

Gly Ala Val Asn Val Tyr Asn Asp Ile Pro Glu Asp Lys Val Gln Ala
145 150 155 160

Ile Ile Tyr Leu Ala Gly Lys Ser Asp Ser Leu Gln Gln Thr Asn Val
165 170 175

Ile Arg Thr Gly Pro Asp Gln Cys Ile Ala Ser Ala Ala Ser Pro Ser
180 185 190

Leu Asn Asp Leu His Ser Arg Arg Ile His Pro Thr Ser Asn Ile Thr
195 200 205

Thr Ser Gln Ser Leu Arg Val Ala Thr Ser Leu Pro Val Gly Pro His
210 215 220

Ser Glu Val Pro Lys Thr Arg Lys Thr Ser Val Gln Arg Phe Leu Glu
225 230 235 240

Lys Arg Lys Asp Arg Gly Arg Leu Lys Gly Thr Leu Ala Ser Gly Gly
245 250 255

Ser Ser Lys Arg Gly Ser Ser Cys Leu Glu Leu Tyr Ala Thr Ser Arg
260 265 270

Leu Lys Ser Glu Gly Val Ala Thr Thr Thr Thr Gln Ser Asn Met Asn
275 280 285

Asn Val Val Val Ser Pro Ser Asn Pro Arg Met Pro Leu Asn Pro Gly
290 295 300

Ser Cys Ser Trp Val Glu Asn Gly Ser Gly Gly Gly Ser Ala Lys Gly
305 310 315 320

Glu Leu Arg Gly His Pro Phe Glu Gly Lys Pro Ile Pro Asn Pro Leu
325 330 335

Leu Gly Leu Asp Ser Thr Arg Thr Gly His His His His His His Gly
340 345 350

Ser

<210> SEQ ID NO 111
<211> LENGTH: 335
<212> TYPE: PRT
<213> ORGANISM: Musa acuminata

<400> SEQUENCE: 111

Met Asn Pro Gly Glu Thr Thr Pro Pro Ser Pro Leu Asp Lys Pro Leu
1 5 10 15

Ala Glu Leu Thr Glu Glu Asp Ile Ala Gln Leu Thr Arg Glu Asp Cys
20 25 30

Arg Arg Phe Leu Lys Ala Lys Gly Met Arg Arg Pro Ser Trp Asn Lys
35 40 45

Ser Gln Ala Ile Gln Gln Val Ile Ser Leu Lys Ala Leu Leu Glu Gly
50 55 60

Arg Pro Gly Cys Asp Asp Cys Pro Ala Gly Gly Gly Ile Leu Gln Lys
65 70 75 80

Leu Leu Thr Ser Ser Pro Ser Glu Pro Leu Ser Pro Pro Gln Asp Ser
85 90 95

Pro Pro Pro Ala Pro Lys Glu Gly Gly Ser Gly Ser Gln Pro Leu Ala
100 105 110

Lys Glu Pro Ser Pro Tyr Arg Arg Arg Asp Pro Ile Pro Pro Pro Tyr
115 120 125

Ser Ala Gly Asn Pro Thr Cys Gln Thr Pro Ile Ala Gly Ala Asp Leu
130 135 140

Pro His Pro Pro Glu Lys Arg Cys Pro Ser Pro Arg Leu Thr Ala Glu
145 150 155 160

-continued

```
Val Pro Val Gly Gln Met Thr Ile Phe Tyr Asp Gly Met Val Asn Val
                165                 170                 175

Tyr Asp Gly Val Ser Ala Asp Gln Ala Arg Ser Ile Met Glu Leu Ala
            180                 185                 190

Ala Ser Pro Val Cys Phe Asp Asp Pro Thr Gly Ala Phe Ser Pro Ala
        195                 200                 205

Arg Pro Pro Ala Phe Arg Phe Pro Pro Gly Leu Pro Arg Pro Ala Pro
    210                 215                 220

Val Pro Thr Ala Pro Ser Phe Val Gly Thr Phe Pro Ile Ser Pro Ala
225                 230                 235                 240

Gly Lys Arg Cys Tyr Ser Tyr Cys Ser Phe Arg Ser Ser Val Ser Leu
                245                 250                 255

Leu Thr Thr Thr Glu Gly Pro Thr Ser Arg Lys Ala Ser Leu Gln Arg
            260                 265                 270

Tyr Leu Glu Lys Arg Lys Asp Arg Tyr Gly His Leu Pro Thr Glu Ser
        275                 280                 285

Ile Leu Leu Val Ser Gly Ser Gly Gly Gly Ser Ala Lys Gly Glu Leu
    290                 295                 300

Arg Gly His Pro Phe Glu Gly Lys Pro Ile Pro Asn Pro Leu Leu Gly
305                 310                 315                 320

Leu Asp Ser Thr Arg Thr Gly His His His His His His Gly Ser
                325                 330                 335


<210> SEQ ID NO 112
<211> LENGTH: 264
<212> TYPE: PRT
<213> ORGANISM: Picea sitchensis

<400> SEQUENCE: 112

Met Arg Gly Gly Glu Arg Ala Pro Gly Ser Arg Pro Ser Leu Asp Lys
1               5                   10                  15

Pro Leu Glu Glu Leu Thr Glu Glu Asp Ile Phe Gln Leu Thr Arg Glu
            20                  25                  30

Asp Cys Arg Arg Tyr Leu Lys Glu Lys Gly Met Arg Arg Pro Ser Trp
        35                  40                  45

Asn Lys Ser Gln Ala Ile Gln Gln Val Leu Ser Leu Lys Ser Leu Phe
    50                  55                  60

Glu Ser Lys Pro Asn Gln Gln Ser Lys Lys Pro Ser Lys His Lys Pro
65                  70                  75                  80

Ala Thr Leu Gln Phe Glu Thr Ala Arg Asp Ser Thr Phe Ala Gln Ser
                85                  90                  95

Ser Val Ser Gln Glu Gln Ser Leu Gly Phe Ser Trp Ser Lys Glu Val
            100                 105                 110

Leu Asp Lys Gly Thr Ala Glu Arg Gln Arg Leu Cys Ser Asp Ser Gln
        115                 120                 125

Glu Ala His Glu Ile Pro Arg Leu Gly Ser Lys Pro Pro Gln Ser Asn
    130                 135                 140

Thr Glu Gly Lys Arg Cys Ala His Asp Gly His Gly Arg Lys Ser Ala
145                 150                 155                 160

Gln Pro Leu Val Arg Leu Pro Ala Asn Phe Lys Asn Asp Cys Ser Asn
                165                 170                 175

Arg Gln Ser Ser His Thr Ser Glu Ser Gln Pro Asp Thr Leu Leu Arg
            180                 185                 190

Ser Asp Ser Phe Gln Gln Pro Thr Ala Gln Leu Thr Ile Phe Tyr Ala
        195                 200                 205
```

```
Gly Met Val Asn Val Tyr Asp Asp Val Pro Leu Asp Lys Ala Gly Ser
    210                 215                 220

Gly Gly Gly Ser Ala Lys Gly Glu Leu Arg Gly His Pro Phe Glu Gly
225                 230                 235                 240

Lys Pro Ile Pro Asn Pro Leu Leu Gly Leu Asp Ser Thr Arg Thr Gly
                245                 250                 255

His His His His His His Gly Ser
            260
```

<210> SEQ ID NO 113
<211> LENGTH: 276
<212> TYPE: PRT
<213> ORGANISM: Selaginella moellendorffii

<400> SEQUENCE: 113

```
Met Ser Ser Met Val Asp Phe Leu Gly Ile Glu Glu Lys Val Ser Thr
1               5                   10                  15

Ser Val Ser Ala Glu Arg Leu Lys Lys Leu Glu Glu Leu Thr Asp Glu
            20                  25                  30

Asp Val Met Gln Leu Thr Arg Glu Asp Cys Arg Arg Tyr Leu Lys Glu
        35                  40                  45

Lys Gly Met Arg Arg Pro Ser Trp Asn Lys Ala Gln Ala Val Gln Gln
    50                  55                  60

Leu Leu Ser Leu Lys Ser Leu Cys Asp Pro Ser Pro Ala Ser Ser Gly
65                  70                  75                  80

Ala Ala Lys Arg Ser Pro Ser Pro Pro Leu Asp Glu Ala Pro Ala Lys
                85                  90                  95

Lys Pro Met Ala Met Thr Ser Ile Asp Leu Lys Ala Ala Ala Ala Val
            100                 105                 110

Asp Ala Ala Asn Leu Thr Met Phe Tyr Asp Gly Ala Val Ser Val Phe
        115                 120                 125

Asp Asp Val Ser Pro Asp Lys Ala Ser Leu Phe Pro Leu Ala Tyr Ala
    130                 135                 140

Ile Met Leu Leu Ala Gly Asn Val Lys Ser Trp Pro Ser Ile Asn Val
145                 150                 155                 160

Ala Ala Asn Thr Asn Lys Val Val Ile Ser Ser Tyr Glu Leu Pro Gln
                165                 170                 175

Ala Arg Lys Ala Ser Leu Gln Arg Phe Leu Gln Arg Arg Arg Glu Lys
            180                 185                 190

Thr Ala Lys Glu Ala Ala Ser Lys Gly Asn Ser Asn Lys Ser Pro Cys
        195                 200                 205

His Gly Glu Ser Ser Gly Lys His Ala Ser Asp Ala Thr Asp Pro Ala
    210                 215                 220

Thr Ser Pro Leu Leu Thr Glu Val Ser Ser Gly Ser Gly Gly Gly Ser
225                 230                 235                 240

Ala Lys Gly Glu Leu Arg Gly His Pro Phe Glu Gly Lys Pro Ile Pro
                245                 250                 255

Asn Pro Leu Leu Gly Leu Asp Ser Thr Arg Thr Gly His His His His
            260                 265                 270

His His Gly Ser
        275
```

<210> SEQ ID NO 114
<211> LENGTH: 315
<212> TYPE: PRT

<213> ORGANISM: Arabidopsis thaliana

<400> SEQUENCE: 114

Met Asp Val Gly Val Ser Pro Ala Lys Ser Ile Leu Ala Lys Pro Leu
1               5                   10                  15

Lys Leu Leu Thr Glu Glu Asp Ile Ser Gln Leu Thr Arg Glu Asp Cys
            20                  25                  30

Arg Lys Phe Leu Lys Asp Lys Gly Met Arg Arg Pro Ser Trp Asn Lys
        35                  40                  45

Ser Gln Ala Ile Gln Gln Val Leu Ser Leu Lys Ala Leu Tyr Glu Pro
    50                  55                  60

Gly Asp Asp Ser Gly Ala Gly Ile Phe Arg Lys Ile Leu Val Ser Gln
65                  70                  75                  80

Pro Val Asn Pro Pro Arg Val Thr Thr Thr Leu Ile Glu Pro Ser Asn
                85                  90                  95

Glu Leu Glu Ala Cys Gly Arg Val Ser Tyr Pro Glu Asp Asn Gly Ala
            100                 105                 110

Cys His Arg Met Asp Ser Pro Arg Ser Ala Glu Phe Ser Gly Gly Ser
        115                 120                 125

Gly His Phe Val Ser Glu Lys Asp Gly His Lys Thr Thr Ile Ser Pro
    130                 135                 140

Arg Ser Pro Ala Glu Thr Ser Glu Leu Val Gly Gln Met Thr Ile Phe
145                 150                 155                 160

Tyr Ser Gly Lys Val Asn Val Tyr Asp Gly Ile Pro Pro Glu Lys Ala
                165                 170                 175

Arg Ser Ile Met His Phe Ala Ala Asn Pro Ile Asp Leu Pro Glu Asn
            180                 185                 190

Gly Ile Phe Ala Ser Ser Arg Met Ile Ser Lys Leu Ile Ser Lys Glu
        195                 200                 205

Lys Met Met Glu Leu Pro Gln Lys Gly Leu Glu Lys Ala Asn Ser Ser
    210                 215                 220

Arg Asp Ser Gly Met Glu Gly Gln Ala Asn Arg Lys Val Ser Leu Gln
225                 230                 235                 240

Arg Tyr Arg Glu Lys Arg Lys Asp Arg Lys Phe Ser Lys Ala Lys Lys
                245                 250                 255

Cys Pro Gly Val Ala Ser Ser Ser Leu Glu Met Phe Leu Asn Cys Gln
            260                 265                 270

Pro Arg Met Lys Ala Ala Tyr Ser Gln Asn Leu Gly Cys Thr Gly Ser
        275                 280                 285

Pro Leu His Ser Gln Ser Pro Glu Ser Gln Thr Lys Ser Pro Asn Leu
    290                 295                 300

Ser Val Asp Leu Asn Ser Glu Gly Ile Gly Ser
305                 310                 315

<210> SEQ ID NO 115
<211> LENGTH: 340
<212> TYPE: PRT
<213> ORGANISM: Trifolium repens

<400> SEQUENCE: 115

Met Asn Gly Gly Ser Thr Val Ser Phe Arg Ser Ile Leu Asp Lys Pro
1               5                   10                  15

Leu Asn Gln Leu Thr Glu Asp Asp Ile Ser Gln Leu Thr Arg Glu Asp
            20                  25                  30

Cys Arg Arg Phe Leu Lys Asp Lys Gly Met Arg Arg Pro Ser Trp Asn 35 40 45

Lys Ser Gln Ala Ile Gln Gln Val Ile Ser Leu Lys Ala Leu Leu Glu
50 55 60

Pro Thr Asp Asp Asp Leu Pro Ala Pro Val Gly Val Ser Ser Ala Ile
65 70 75 80

His His His His His His His Pro Gln Pro Pro Gln Arg Asn Leu Asn
85 90 95

Glu Ala Pro Val Lys Gly Ser Asp Leu Asp Asp Thr Gly Phe His Thr
100 105 110

Ala Glu Asp Leu Asn Lys Ser Thr Ser Thr Ala Val Glu Ile Pro Thr
115 120 125

Glu Thr Asn Asp Ala Asn Val Val Lys Ser Ser Gly Gly Cys Val Ala
130 135 140

Ser Gly Ser Phe Gly Gln Met Thr Ile Phe Tyr Cys Gly Lys Val Asn
145 150 155 160

Val Tyr Asp Gly Val Ser Pro Asp Lys Ala Arg Ser Ile Met Gln Leu
165 170 175

Ala Ala Cys Pro Ser Ser Phe Pro Gln Asp Asn Leu Leu Asn Lys Asn
180 185 190

Ala Ala Val Trp Ala Ser Pro Cys Asn Ile Pro Ile Asp Lys Asp Val
195 200 205

Leu Phe Pro Asn Asp Thr Ala Ile Leu Gln Val Ala Gln Thr Asp Lys
210 215 220

Met Val Glu Tyr Pro Leu Gln Tyr Arg Glu Lys Gly Ser Ile Ala Arg
225 230 235 240

Asp Ala Asp Val Glu Gly Gln Ala Ser Arg Asn Ala Ser Leu Gln Arg
245 250 255

Tyr Arg Glu Lys Arg Lys Asp Arg Gly Arg Ser Lys Gly Asn Lys Leu
260 265 270

Thr Gly Ile Thr Ser Ser Asn Phe Glu Met Tyr Leu Asn Leu Pro Val
275 280 285

Lys Leu His Ala Ser Asn Gly Asn Ser Ser Arg Ser Ser Thr Asp Ser
290 295 300

Pro Pro Gln Pro Arg Leu Pro Leu Val Ser Gly Gly Ser Ala Glu Asn
305 310 315 320

Gln Pro Lys Val Thr Leu Pro Ile Asp Leu Asn Asp Lys Asp Val Gln
325 330 335

Glu Cys Gly Ser
340

<210> SEQ ID NO 116
<211> LENGTH: 313
<212> TYPE: PRT
<213> ORGANISM: Amborella trichopoda

<400> SEQUENCE: 116

Met Thr Ala Gly Asp Gly Ser Ile Arg Ser Ile Leu Asp Lys Pro Leu
1 5 10 15

Glu Glu Leu Thr Glu Glu Asp Ile Ser Gln Leu Thr Arg Glu Asp Cys
20 25 30

Arg Arg Tyr Leu Lys Glu Lys Gly Met Arg Arg Pro Ser Trp Asn Lys
35 40 45

Tyr Gln Ala Ile Gln Gln Val Leu Ser Leu Lys Gly Leu Leu Glu Gly
50 55 60

Lys Pro Cys Asp Asp Asn Ser Asp Val Phe Ser His Arg Ser Pro Ile
65 70 75 80

Thr Val Ile Pro Asn Val Gly Ser Met Arg Glu Lys Glu Lys Ala Val
85 90 95

Asn Ile Ala Asp Pro Glu Ile Ser Gly Ser His Gln Pro Asn Phe Arg
100 105 110

Arg Glu Ile His Glu Thr Thr Arg Glu Arg Ala Leu Pro Ala Ser Asp
115 120 125

Trp Pro Pro Ser Gln Glu Pro Val Ser Gln Met Thr Ile Phe Tyr Ala
130 135 140

Gly Ala Val Asn Val Tyr Asn Asp Ile Pro Glu Asp Lys Val Gln Ala
145 150 155 160

Ile Ile Tyr Leu Ala Gly Lys Ser Asp Ser Leu Gln Gln Thr Asn Val
165 170 175

Ile Arg Thr Gly Pro Asp Gln Cys Ile Ala Ser Ala Ala Ser Pro Ser
180 185 190

Leu Asn Asp Leu His Ser Arg Arg Ile His Pro Thr Ser Asn Ile Thr
195 200 205

Thr Ser Gln Ser Leu Arg Val Ala Thr Ser Leu Pro Val Gly Pro His
210 215 220

Ser Glu Val Pro Lys Thr Arg Lys Thr Ser Val Gln Arg Phe Leu Glu
225 230 235 240

Lys Arg Lys Asp Arg Gly Arg Leu Lys Gly Thr Leu Ala Ser Gly Gly
245 250 255

Ser Ser Lys Arg Gly Ser Ser Cys Leu Glu Leu Tyr Ala Thr Ser Arg
260 265 270

Leu Lys Ser Glu Gly Val Ala Thr Thr Thr Thr Gln Ser Asn Met Asn
275 280 285

Asn Val Val Val Ser Pro Ser Asn Pro Arg Met Pro Leu Asn Pro Gly
290 295 300

Ser Cys Ser Trp Val Glu Asn Gly Ser
305 310

<210> SEQ ID NO 117
<211> LENGTH: 295
<212> TYPE: PRT
<213> ORGANISM: Musa acuminata

<400> SEQUENCE: 117

Met Asn Pro Gly Glu Thr Thr Pro Pro Ser Pro Leu Asp Lys Pro Leu
1 5 10 15

Ala Glu Leu Thr Glu Glu Asp Ile Ala Gln Leu Thr Arg Glu Asp Cys
20 25 30

Arg Arg Phe Leu Lys Ala Lys Gly Met Arg Arg Pro Ser Trp Asn Lys
35 40 45

Ser Gln Ala Ile Gln Gln Val Ile Ser Leu Lys Ala Leu Leu Glu Gly
50 55 60

Arg Pro Gly Cys Asp Asp Cys Pro Ala Gly Gly Gly Ile Leu Gln Lys
65 70 75 80

Leu Leu Thr Ser Ser Pro Ser Glu Pro Leu Ser Pro Pro Gln Asp Ser
85 90 95

Pro Pro Pro Ala Pro Lys Glu Gly Gly Ser Gly Ser Gln Pro Leu Ala
100 105 110

Lys Glu Pro Ser Pro Tyr Arg Arg Arg Asp Pro Ile Pro Pro Pro Tyr
115 120 125

```
Ser Ala Gly Asn Pro Thr Cys Gln Thr Pro Ile Ala Gly Ala Asp Leu
    130                 135                 140

Pro His Pro Pro Glu Lys Arg Cys Pro Ser Pro Arg Leu Thr Ala Glu
145                 150                 155                 160

Val Pro Val Gly Gln Met Thr Ile Phe Tyr Asp Gly Met Val Asn Val
                165                 170                 175

Tyr Asp Gly Val Ser Ala Asp Gln Ala Arg Ser Ile Met Glu Leu Ala
            180                 185                 190

Ala Ser Pro Val Cys Phe Asp Asp Pro Thr Gly Ala Phe Ser Pro Ala
        195                 200                 205

Arg Pro Pro Ala Phe Arg Phe Pro Pro Gly Leu Pro Arg Pro Ala Pro
    210                 215                 220

Val Pro Thr Ala Pro Ser Phe Val Gly Thr Phe Pro Ile Ser Pro Ala
225                 230                 235                 240

Gly Lys Arg Cys Tyr Ser Tyr Cys Ser Phe Arg Ser Ser Val Ser Leu
                245                 250                 255

Leu Thr Thr Thr Glu Gly Pro Thr Ser Arg Lys Ala Ser Leu Gln Arg
            260                 265                 270

Tyr Leu Glu Lys Arg Lys Asp Arg Tyr Gly His Leu Pro Thr Glu Ser
        275                 280                 285

Ile Leu Leu Val Ser Gly Ser
    290                 295


<210> SEQ ID NO 118
<211> LENGTH: 224
<212> TYPE: PRT
<213> ORGANISM: Picea abies

<400> SEQUENCE: 118

Met Arg Gly Gly Glu Arg Ala Pro Gly Ser Arg Pro Ser Leu Asp Lys
1               5                   10                  15

Pro Leu Glu Glu Leu Thr Glu Glu Asp Ile Phe Gln Leu Thr Arg Glu
            20                  25                  30

Asp Cys Arg Arg Tyr Leu Lys Glu Lys Gly Met Arg Arg Pro Ser Trp
        35                  40                  45

Asn Lys Ser Gln Ala Ile Gln Gln Val Leu Ser Leu Lys Ser Leu Phe
    50                  55                  60

Glu Ser Lys Pro Asn Gln Gln Ser Lys Lys Pro Ser Lys His Lys Pro
65                  70                  75                  80

Ala Thr Leu Gln Phe Glu Thr Ala Arg Asp Ser Thr Phe Ala Gln Ser
                85                  90                  95

Ser Val Ser Gln Glu Gln Ser Leu Gly Phe Ser Trp Ser Lys Glu Val
            100                 105                 110

Leu Asp Lys Gly Thr Ala Glu Arg Gln Arg Leu Cys Ser Asp Ser Gln
        115                 120                 125

Glu Ala His Glu Ile Pro Arg Leu Gly Ser Lys Pro Pro Gln Ser Asn
    130                 135                 140

Thr Glu Gly Lys Arg Cys Ala His Asp Gly His Gly Arg Lys Ser Ala
145                 150                 155                 160

Gln Pro Leu Val Arg Leu Pro Ala Asn Phe Lys Asn Asp Cys Ser Asn
                165                 170                 175

Arg Gln Ser Ser His Thr Ser Glu Ser Gln Pro Asp Thr Leu Leu Arg
            180                 185                 190

Ser Asp Ser Phe Gln Gln Pro Thr Ala Gln Leu Thr Ile Phe Tyr Ala
```

```
        195                 200                 205

Gly Met Val Asn Val Tyr Asp Asp Val Pro Leu Asp Lys Ala Gly Ser
    210                 215                 220


<210> SEQ ID NO 119
<211> LENGTH: 236
<212> TYPE: PRT
<213> ORGANISM: Selaginella moellendorffii

<400> SEQUENCE: 119

Met Ser Ser Met Val Asp Phe Leu Gly Ile Glu Glu Lys Val Ser Thr
1               5                   10                  15

Ser Val Ser Ala Glu Arg Leu Lys Lys Leu Glu Glu Leu Thr Asp Glu
            20                  25                  30

Asp Val Met Gln Leu Thr Arg Glu Asp Cys Arg Arg Tyr Leu Lys Glu
        35                  40                  45

Lys Gly Met Arg Arg Pro Ser Trp Asn Lys Ala Gln Ala Val Gln Gln
    50                  55                  60

Leu Leu Ser Leu Lys Ser Leu Cys Asp Pro Ser Pro Ala Ser Ser Gly
65                  70                  75                  80

Ala Ala Lys Arg Ser Pro Ser Pro Pro Leu Asp Glu Ala Pro Ala Lys
                85                  90                  95

Lys Pro Met Ala Met Thr Ser Ile Asp Leu Lys Ala Ala Ala Ala Val
            100                 105                 110

Asp Ala Ala Asn Leu Thr Met Phe Tyr Asp Gly Ala Val Ser Val Phe
        115                 120                 125

Asp Asp Val Ser Pro Asp Lys Ala Ser Leu Phe Pro Leu Ala Tyr Ala
    130                 135                 140

Ile Met Leu Leu Ala Gly Asn Val Lys Ser Trp Pro Ser Ile Asn Val
145                 150                 155                 160

Ala Ala Asn Thr Asn Lys Val Val Ile Ser Ser Tyr Glu Leu Pro Gln
                165                 170                 175

Ala Arg Lys Ala Ser Leu Gln Arg Phe Leu Gln Arg Arg Arg Glu Lys
            180                 185                 190

Thr Ala Lys Glu Ala Ala Ser Lys Gly Asn Ser Asn Lys Ser Pro Cys
        195                 200                 205

His Gly Glu Ser Ser Gly Lys His Ala Ser Asp Ala Thr Asp Pro Ala
    210                 215                 220

Thr Ser Pro Leu Leu Thr Glu Val Ser Ser Gly Ser
225                 230                 235


<210> SEQ ID NO 120
<211> LENGTH: 1226
<212> TYPE: DNA
<213> ORGANISM: Arabidopsis thaliana

<400> SEQUENCE: 120

acaagtttgt acaaaaaagc aggctcaaaa aaaaccatgg acgtgggcgt gtccccggcc      60

aagtctattc tcgccaagcc ggtaatgttc agctctgcta tagtgtgtgc caccctgctt     120

gtttaataat gcgttctctt cgtttttatg atatcttatt cttccagctc aagctcctca     180

ccgaggagga catctctcag ctcacaagag aggactgccg caagttcctc aaggacaagg     240

gcatgagaag gccgtcctgg aacaagtccc aggccatcca acaagtgctc agcctcaagg     300

ccctctacga gccaggcgac gactccggcg ctggcatttt cagaaagatc ctcgtgtccc     360

agccggtgaa cccaccaagg gtgaccacca cactcatcga gccgtccaat gagcttgagg     420
```

```
cctgcggcag agtttcctac ccagaggata atggcgcctg ccacaggatg gattctccaa    480
ggtctgctga gttctctggc ggctccggcc atttcgtgtc tgagaaggat ggccacaaga    540
ccaccatctc cccaagatcc ccagccgaga catctgagct tgtgggccag atgaccatct    600
tctactccgg caaggtgaac gtgtacgacg gcatcccacc agagaaggcc cgctccatta    660
tgcacttcgc cgccaaccca atcgacctcc cagagaatgg catcttcgcc tccagccgca    720
tgatctccaa gctcatctcc aaggagaaga tgatggagct gccgcagaag ggcctcgaga    780
aggctaattc ctctcgcgac tccggcatgg agggccaggc taatagaaag gtgtccctcc    840
aacgctaccg cgagaagagg aaggaccgca agttctccaa ggccaagaag tgcccaggcg    900
ttgcctcttc cagcctcgag atgttcctca actgccagcc gagaatgaag gccgcctact    960
cccaaaatct cggctgcaca ggctccccac tccattctca gtccccagag tctcagacca   1020
agtccccgaa cctctccgtg gaccttaact ccgagggcat cggatccggc ggcggctctg   1080
ctaagggcga gctgaggggc cacccgttcg agggcaagcc aattccaaat ccactcctcg   1140
gcctcgactc taccaggacc ggccaccatc accatcacca cggatcctaa tgaagaccca   1200
gctttcttgt acaaagtggt caggct                                         1226
```

<210> SEQ ID NO 121
<211> LENGTH: 1295
<212> TYPE: DNA
<213> ORGANISM: Trifolium repens

<400> SEQUENCE: 121

```
acaagtttgt acaaaaaagc aggctcaaaa aaaaccatga acggcggctc caccgtgtcc     60
ttcagatcca tcctcgataa gccggtaatg ttcagctctg ctatagtgtg tgccaccctg    120
cttgtttaat aatgcgttct cttcgttttt atgatatctt attcttccag ctcaaccagc    180
tcaccgagga cgacatctct cagctcacac gcgaggattg ccgccgcttc cttaaggaca    240
agggcatgag aaggccgtcc tggaacaagt cccaggccat ccagcaagtg atctccctca    300
aggctctcct cgagccgacc gacgatgatc tcccagcccc ggtgggcgtg tcatctgcca    360
tccaccatca ccaccaccac catcctcaac cgccacagag gaacctcaat gaggccccag    420
ttaagggctc cgacctcgac gataccggct tccatacagc cgaggacctc aacaagtcta    480
cctccaccgc cgtcgagatc ccgaccgaga caaacgatgc caacgtggtg aagtctagcg    540
gcggctgcgt ggcctccggc tccttcggcc agatgaccat tttctactgc ggcaaggtga    600
acgtgtacga cggcgtgtca ccagataagg cccgctccat tatgcaactc gccgcttgcc    660
catctagctt cccgcaggat aacctcctca acaagaacgc cgccgtttgg gcctccccat    720
gcaacatccc gatcgacaag gatgtcctct tcccgaacga caccgccatt ctccaggtgg    780
cccagaccga taagatggtc gagtacccac tccagtaccg cgagaagggc tctattgcca    840
gggatgccga tgttgagggc caggcctcca gaaatgcttc cctgcaacgc tatcgcgaga    900
agcgcaagga cagaggcaga tccaagggca acaagctgac cggcatcacc tcctccaact    960
tcgagatgta cctcaacctc ccggtgaagc tccatgcctc caacggcaac tcctctaggt   1020
cctccacaga ttccccaccg cagccaagac tcccactcgt gtccggcggc tctgccgaga   1080
accagccaaa ggtgaccctc ccgatcgacc tcaacgacaa ggacgtgcaa gagtgcggat   1140
ccggcggcgg ctctgctaag ggcgagctga ggggccaccc gttcgagggc aagccaattc   1200
caaatccact cctcggcctc gactctacca ggaccggcca ccatcaccat caccacggat   1260
```

cctaatgaag acccagcttt cttgtacaaa gtggt 1295

<210> SEQ ID NO 122
<211> LENGTH: 1214
<212> TYPE: DNA
<213> ORGANISM: Amborella trichopoda

<400> SEQUENCE: 122
acaagtttgt acaaaaaagc aggctcaaaa aaaaccatga cagccggcga cggctccatc 60
cgctctatcc ttgacaagcc ggtaatgttc agctctgcta tagtgtgtgc caccctgctt 120
gtttaataat gcgttctctt cgtttttatg atatcttatt cttccagctc gaggagctga 180
ccgaggagga catctctcaa ctcacccgcg aggattgccg ccgctacctc aaggagaagg 240
ggatgcgcag gccatcctgg aacaagtacc aggccatcca gcaggtcctc agcctcaagg 300
gcctcctcga gggcaagcca tgcgacgata actccgacgt gttctcccac aggtccccga 360
tcaccgtgat cccaaatgtt ggctccatgc gcgagaagga gaaggccgtc aatatcgccg 420
acccagagat ctccggctcc caccagccga actttaggcg cgagatccat gagacaacac 480
gcgagagagc cctcccagct tctgattggc cgccgtcaca agagccagtg tcccagatga 540
ccatcttcta cgctggcgcc gtgaacgtgt acaacgacat cccagaggac aaggtgcagg 600
ccatcatcta cctcgccggc aagtctgatt ccctccagca gaccaacgtg atcaggaccg 660
gcccagatca gtgcattgct tctgctgctt ccccgtccct caacgacctc cattctaggc 720
gcatccaccc gacctccaac atcaccacat ctcagtctct ccgcgtggcc acatctctcc 780
cagtgggccc gcactccgag gtgccaaaga ccagaaagac aagcgtgcag cgcttcctcg 840
agaagaggaa ggataggggc aggctcaagg gcacactcgc ctccggcggc tcctccaaga 900
ggggctcctc ctgcctcgag ctttacgcta catcccgcct taagtctgag ggcgtggcca 960
ccacaaccac ccagtccaac atgaacaacg tggtggtgtc cccgtccaac ccgaggatgc 1020
cgctcaaccc gggctcctgc tcctgggtcg agaacggatc cggcggcggc tctgctaagg 1080
gcgagctgag gggccacccg ttcgagggca agccaattcc aaatccactc ctcggcctcg 1140
actctaccag gaccggccac catcaccatc accacggatc ctaatgaaga cccagctttc 1200
ttgtacaaag tggt 1214

<210> SEQ ID NO 123
<211> LENGTH: 1160
<212> TYPE: DNA
<213> ORGANISM: Musa acuminata

<400> SEQUENCE: 123
acaagtttgt acaaaaaagc aggctcaaaa aaaaccatga acccgggcga gacaaccccg 60
ccatctccac ttgacaagcc ggtaatgttc agctctgcta tagtgtgtgc caccctgctt 120
gtttaataat gcgttctctt cgtttttatg atatcttatt cttccagctc gccgagctga 180
ccgaggagga tattgctcaa ctcacccgcg aggactgccg cagattcctt aaggctaagg 240
gcatgcgcag gccgtcctgg aacaagtctc aggccatcca gcaagtgatc tccctcaagg 300
ctctcctcga gggcaggcca ggttgcgatg actgcccggc cggcggcggc atcctccaga 360
agctcctcac ctccagcccg tctgagccgc tctccccgcc acaggactcc ccgccaccgg 420
ctccaaaaga gggcggctcc ggctcccagc ctctcgccaa ggagccgtcc ccgtacaggc 480
gcagggaccc gatcccgcca ccgtactccg ccggcaaccc gacctgccag accccgatcg 540
ctggcgccga cctcccgcac ccgccagaga agaggtgccc gtccccgagg ctcacagccg 600
aggtgccggt gggccagatg accattttct acgacggcat ggtgaacgtg tacgacggcg 660
tgtcagctga tcaggcccgc tccattatgg agcttgccgc ttctccggtg tgcttcgatg 720
atccaacagg cgcctttagc ccagccagac caccagcttt cagattccca ccaggcctcc 780
caaggccagc tccggtgccg accgccccgt ccttcgtggg caccttcccg atctccccag 840
ccggcaagag atgctactcc tactgctcct tccgctcctc cgtgtcactc ctcacaacaa 900
ccgagggccc aacatctagg aaggcctcac tccaacgcta cctcgagaag cgcaaggaca 960
ggtacggcca tctcccaacc gagtccattc tcctcgtgtc cggatccggc ggcggctctg 1020
ctaagggcga gctgaggggc cacccgttcg agggcaagcc aattccaaat ccactcctcg 1080
gcctcgactc taccaggacc ggccaccatc accatcacca cggatcctaa tgaagaccca 1140
gctttcttgt acaaagtggt 1160

<210> SEQ ID NO 124
<211> LENGTH: 947
<212> TYPE: DNA
<213> ORGANISM: Picea abies

<400> SEQUENCE: 124
acaagtttgt acaaaaaagc aggctcaaaa aaaaccatga gaggcggcga gagagcccca 60
ggctccaggc cggtaatgtt cagctctgct atagtgtgtg ccaccctgct tgtttaataa 120
tgcgttctct tcgtttttat gatatcttat tcttccagtc cctcgacaag ccgctcgagg 180
agcttaccga ggaggacatc ttccagctca cccgcgagga ttgcaggcgc tacctcaagg 240
agaaggggat gagaaggccg tcctggaaca agtcccaggc catccaacaa gtgctcagcc 300
tcaagagcct cttcgagtcc aagccgaacc agcagtccaa gaagccgtcc aagcacaagc 360
cagccaccct ccaattcgag acagccaggg attctacctt cgcccagtcc tccgtgtccc 420
aagagcaatc tctcggcttc tcctggtcca aggaggtgct cgataagggc acagccgaga 480
gacaaaggct ctgctccgat tcccaagagg cccacgagat tccaaggctc ggctctaagc 540
caccgcagtc caacaccgag ggcaagagat gcgctcatga tggccatggg agaaagtccg 600
cccaaccact cgttaggctc ccggccaact tcaagaacga ctgctccaac aggcagtcct 660
cccacacatc tgagtcccag ccagataccc tcctccgctc cgattctttc cagcagccaa 720
cagcccagct caccatcttc tacgccggca tggtgaacgt gtacgacgac gtgccactcg 780
acaaggccgg atccggcggc ggctctgcta agggcgagct gaggggccac ccgttcgagg 840
gcaagccaat tccaaatcca ctcctcggcc tcgactctac caggaccggc caccatcacc 900
atcaccacgg atcctaatga agacccagct ttcttgtaca aagtggt 947

<210> SEQ ID NO 125
<211> LENGTH: 897
<212> TYPE: DNA
<213> ORGANISM: Selaginella moellendorffii

<400> SEQUENCE: 125
acaagtttgt acaaaaaagc aggctcaaaa aaaaccatgt cctcgatggt ggacttcctc 60
ggcatcgagg agaaggtgtc cacctccgtg tccgccgaga ggctcaagaa gctcgaggag 120
ctgaccgacg aggacgtgat gcaactcaca cgcgaggatt gccgccgcta ccttaaggag 180
aaggggatga gaaggccgtc ctggaacaag gcccaagccg tgcaacaact cctcagcctc 240
aagtccctct gcgatccatc tccggcctcc agcggagctg ccaagaggtc cccgtccccg 300

```
ccactcgacg aggccccagc caagaagccg atggccatga cctccatcga tctcaaggcc    360

gctgccgccg ttgatgccgc caatctcacc atgttctacg acggcgccgt gtccgtgttc    420

gatgatgtgt ctccagacaa ggcctccctc ttcccactcg cctacgccat tatgctcctc    480

gccggcaatg tgaagtcctg gccgtctatc aacgtggccg ccaacaccaa caaggtggtg    540

atctccagct acgagctgcc gcaagctaga aaggcttccc tccagcgctt ccttcagaga    600

aggcgcgaga agacagccaa ggaggccgct tctaagggca actccaacaa gtccccatgc    660

cacggcgagt ctagcggcaa gcacgcctct gatgctaccg atccagctac ctctccactc    720

ctcacagagg tgtcatccgg atccggcggc ggctctgcta agggcgagct gaggggccac    780

ccgttcgagg gcaagccaat tccaaatcca ctcctcggcc tcgactctac caggaccggc    840

caccatcacc atcaccacgg atcctaatga agacccagct ttcttgtaca aagtggt       897
```

<210> SEQ ID NO 126
<211> LENGTH: 1134
<212> TYPE: DNA
<213> ORGANISM: Arabidopsis thaliana

<400> SEQUENCE: 126

```
acaagtttgt acaaaaaagc aggctcaaaa aaaaccatgg atgtgggagt gtctccagct     60

aagtctatcc ttgctaagcc tctcaagctc ctcaccgaag aggatatctc tcagctcact    120

agagaggatt gcagaaagtt cctcaaggat aagggaatga gaaggccatc ttggaacaag    180

tctcaggcta tccagcaggt tctcagtctc aaggctcttt acgagcctgg tgatgattct    240

ggtgctggaa tcttcagaaa gatcctcgtg tctcagcctg tgaaccctcc tagagttact    300

actactctca tcgagccttc taacgagctt gaggcttgcg gaagagtttc ttaccctgag    360

gataacggtg cttgccacag gatggattct ccaagatctg ctgagttctc tggtggatct    420

ggacacttcg tgtctgagaa ggatggacac aagactacta tctctccaag aagtcctgct    480

gagacttctg agcttgtggg acagatgacc atcttctact ctggaaaggt gaacgtgtac    540

gatggaatcc ctcctgagaa ggctagatct atcatgcact tcgctgctaa ccctatcgat    600

ctccctgaga acggaatctt cgcttcttct aggatgatct ctaagctcat ctctaaagaa    660

aagatgatgg aactccctca gaagggactc gagaaggcta actcttctag ggattctgga    720

atggaaggac aggctaacag aaaggtgtca ctccagaggt acagagagaa gaggaaggat    780

aggaagttct ctaaggctaa gaaatgccct ggtgtggctt cttcatctct cgagatgttc    840

cttaactgcc agcctaggat gaaggctgct tactctcaga acctcggatg tactggatct    900

ccactccatt ctcagtctcc agagtctcag accaagtctc ctaacctctc tgtggatctc    960

aactctgagg gaatcggatc cggtggtgga tctgctaagg gtgagcttag aggtcatcct   1020

ttcgagggta agcctatccc taaccctctt ctcggtctcg attctactag aactggtcat   1080

catcatcacc atcacggatc ctaatgaaga cccagctttc ttgtacaaag tggt         1134
```

<210> SEQ ID NO 127
<211> LENGTH: 1209
<212> TYPE: DNA
<213> ORGANISM: Trifolium repens

<400> SEQUENCE: 127

```
acaagtttgt acaaaaaagc aggctcaaaa aaaaccatga acggtggatc taccgtgtct     60

ttcagatcta tcctcgataa gcctctcaac cagctcaccg aggatgatat ctctcagctc    120

actagagagg attgcagaag attcctcaag gataagggaa tgagaaggcc atcttggaac    180
```

aagtctcagg ctatccagca ggttatctct ctcaaggctc tcctcgagcc taccgatgat 240
gatcttcctg ctcctgtggg agtgtcatct gctatccatc atcatcacca tcaccaccct 300
caacctccac agagaaatct taacgaggct cctgtgaagg gatctgatct cgatgatact 360
ggattccaca ccgctgagga tctcaacaag tctacttcta ccgctgttga gatccctacc 420
gagactaacg atgctaacgt ggtgaagtca tctggtggat gtgtggcttc tggatctttc 480
ggacagatga ccatcttcta ctgcggaaag gtgaacgtgt acgatggtgt gtctcctgat 540
aaggctagat ctatcatgca gctcgctgct tgcccttcta gtttccctca ggataacctc 600
ctcaacaaga acgctgctgt ttgggcttct ccttgcaaca tccctattga taaggatgtt 660
ctcttcccta acgataccgc tatcctccaa gtggctcaga ccgataagat ggttgagtac 720
cctctccagt acagagagaa gggatctatc gctagggatg ctgatgttga gggacaggct 780
tctagaaacg cttcactcca gaggtacagg gaaaagagga aggatagggg aaggtctaag 840
ggaaacaagc tcaccggaat cacctcttct aacttcgaga tgtacctcaa cctccctgtg 900
aagctccatg cttctaacgg aaactcttct aggtctagta ccgattcacc tcctcagcct 960
agactccctc ttgtttctgg tggatctgct gagaaccagc ctaaggttac actccctatc 1020
gatctcaacg ataaggatgt gcaagagtgc ggatccggtg gtggatctgc taagggtgag 1080
cttagaggtc atcctttcga gggtaagcct atccctaacc ctcttctcgg tctcgattct 1140
actagaactg gtcatcatca tcaccatcac ggatcctaat gaagacccag ctttcttgta 1200
caaagtggt 1209

<210> SEQ ID NO 128
<211> LENGTH: 1128
<212> TYPE: DNA
<213> ORGANISM: Amborella trichopoda

<400> SEQUENCE: 128
acaagtttgt acaaaaaagc aggctcaaaa aaaaccatga ccgctggtga tggatctatc 60
agatctatcc tcgataagcc tctcgaggaa ctcaccgaag aggatatctc tcagctcacc 120
agagaggatt gcagaagata cctcaaagaa aagggtatga gaaggccatc ttggaacaag 180
taccaggcta tccagcaggt tctcagtctt aagggacttc tcgagggaaa gccttgtgat 240
gataactctg atgtgttctc tcacaggtca cctatcaccg tgatccctaa cgtgggatct 300
atgagagaga aagagaaggc tgttaacatt gctgatcctg agatctctgg ttctcaccag 360
cctaacttta gaagagagat ccacgagact accagagaga gagctttgcc tgcttctgat 420
tggcctccat ctcaagagcc tgtgtctcag atgaccatct tctacgctgg tgctgtgaac 480
gtgtacaacg atatccctga ggataaggtg caggctatca tctacctcgc tggaaagtct 540
gattctctcc agcagaccaa cgtgatcaga actggacctg atcagtgtat cgcttctgct 600
gcttctcctt ctctcaacga tctccactct agaagaatcc accctacctc taacatcacc 660
acctctcagt ctctcagagt ggctacttct cttcctgtgg gacctcattc tgaggtgcca 720
aagactagaa agacctctgt gcagagattc ctcgagaaga ggaaggatag aggtaggctc 780
aagggaactc ttgcttctgg tggatcttct aagaggggat cttcttgcct cgagctttac 840
gctacctcta ggcttaagtc tgagggtgtg gctactacta ccacccagtc taacatgaac 900
aacgtggtgg tgtctccatc taaccctagg atgcctctta accctggatc ttgctcttgg 960
gttgagaacg gatccggtgg tggatctgct aagggtgagc ttagaggtca tcctttcgag 1020
ggtaagccta tccctaaccc tcttctcggt ctcgattcta ctagaactgg tcatcatcat 1080
caccatcacg gatcctaatg aagacccagc tttcttgtac aaagtggt 1128

<210> SEQ ID NO 129
<211> LENGTH: 1074
<212> TYPE: DNA
<213> ORGANISM: Musa acuminata

<400> SEQUENCE: 129
acaagtttgt acaaaaaagc aggctcaaaa aaaaccatga accctggtga gactacccct 60
ccatctccac ttgataagcc tctcgctgag cttaccgaag aggatatcgc tcagctcact 120
agagaggatt gcagaagatt cctcaaggct aagggaatga gaaggccatc ttggaacaag 180
tctcaggcta tccagcaggt tatctctctc aaggctctcc ttgaaggtag gcctggatgt 240
gatgattgtc ctgctggtgg tggaatcctc cagaagctcc ttacttctag tccttctgag 300
cctctcagtc ctcctcaaga ttctccacct cctgctccta aagagggagg atctggatct 360
cagcctcttg ctaaagagcc ttctccatac agaagaagag atcctatccc tcctccttac 420
tctgctggaa accctacttg tcagactcct atcgctggtg ctgatcttcc tcatcctcct 480
gagaagagat gcccatctcc tagacttact gctgaggttc cagtgggaca gatgaccatc 540
ttctacgatg gaatggtgaa cgtgtacgat ggtgtgtctg ctgatcaggc tagatctatt 600
atggaactcg ctgcttctcc tgtgtgcttc gatgatccta ctggtgcttt cagtcctgct 660
agacctcctg cttttagatt ccctccagga cttcctagac ctgctcctgt tcctactgct 720
ccttctttcg ttggaacctt ccctatctct cctgctggaa agaggtgcta ctcttactgc 780
tctttcaggt ctagtgtgtc tctcttgact accactgagg gacctacctc tagaaaggct 840
tcactccaga gatacctcga gaagaggaag gatagatacg gacacctccc taccgagtct 900
atccttctcg tttctggatc cggtggtgga tctgctaagg gtgagcttag aggtcatcct 960
ttcgagggta agcctatccc taaccctctt ctcggtctcg attctactag aactggtcat 1020
catcatcacc atcacggatc ctaatgaaga cccagctttc ttgtacaaag tggt 1074

<210> SEQ ID NO 130
<211> LENGTH: 1233
<212> TYPE: DNA
<213> ORGANISM: Picea abies

<400> SEQUENCE: 130
acaagtttgt acaaaaaagc aggctcaaaa aaaaccatga ggggtggtgg tggtgctgat 60
agacttcctg ctagagctaa ccttgagaag cctctcgagg atctctctca cgaggatatc 120
atgcagctca ccagagagga ttgcagaaga tacctcatcg agaagggaat gagaaggcca 180
tcttggaaca agtctcaggc tatccagcag gttctcagtc tcaagaagct tttcgagtct 240
ggacctaacg atgagaagag gtctgctgct accaacaggc ctaatcctga tgagaacctc 300
aaagaggctg cttctgtttc tctcttgtac ggatctcagc ctgagtctcc ttctgtggtg 360
ttcgcttcta aggattctga taccttcaac ctcgagtggc tcgctaagac tgagcttcct 420
gttcttgctt ctcagcctag gcatatcgct cagcagaacg tgttcctctc ttcactttct 480
gctcagcagt ctggtgctca gctcaccatt ttctactctg gaaacgtgaa cgtgtacgat 540
gatgtgcctg ctgagaaggc tcaagagatc atgcttcttg ctggatctgg aaactaccct 600
ccttcatcta cttgccagtc taccagaaac acccagcaga acgctgttag agctgcttac 660
ccttctaacc ctaccaacac ccctttcatc catggtgttg gaccacctct tgctaccgtg 720

-continued

```
gcttcttctt ctgtgatgtc atctcctatc cacaaagagt ctccaatcac cagaaaggct    780

tcactccaga gattcctcga gaagaggaag gataggtcta ggggtaagct tggtgctcct    840

actatctcta agaaacctct cctcatggga atgttcatgc acccttctat cgtgcacaga    900

cagtactgga ctgataccgc taagaggaag tctggaaagc ctgatatccc tgcttctatc    960

tctcctacca gacctcctca cactcctaga aggacatctt ctgatgagca gctctctgct   1020

agacacgcta ggggagatat ttctgctcaa ggtggaagtc tccacaactc taacggatcc   1080

ggtggtggat ctgctaaggg tgagcttaga ggtcatcctt tcgagggtaa gcctatccct   1140

aaccctcttc tcggtctcga ttctactaga actggtcatc atcatcacca tcacggatcc   1200

taatgaagac ccagctttct tgtacaaagt ggt                                1233
```

<210> SEQ ID NO 131
<211> LENGTH: 835
<212> TYPE: DNA
<213> ORGANISM: Selaginella moellendorffii

<400> SEQUENCE: 131

```
acaagtttgt acaaaaaagc aggctcaaaa aaaaccatgt caagtatggt ggatttcctc     60

ggaatcgaag agaaggtttc aacctctgtg tctgctgaga ggcttaagaa gctcgaggaa    120

ctcactgatg aggatgtgat gcagctcacc agagaggatt gcagaagata cctcaaagaa    180

aagggtatga gaaggccatc ttggaacaag gctcaagctg ttcagcagct cctcagtctt    240

aagtctctct gcgatccttc accagcttca tctggtgctg ctaagagatc tccttcacct    300

cctttggatg aggctcctgc taagaaacct atggctatga cctctatcga tctcaaggct    360

gctgctgctg ttgatgctgc taacctcacc atgttctacg atggtgctgt gtctgtgttc    420

gatgatgtgt ctcctgataa ggcttctctc ttcccactcg cttacgctat catgcttctc    480

gctggaaacg tgaagtcttg gccttctatc aacgtggcag ctaacaccaa caaggtggtg    540

atctcttctt acgaactccc tcaggctagg aaggcttcac ttcagagatt cctccagaga    600

agaagggaaa agaccgctaa agaggctgct tctaagggaa actctaacaa gtctccttgc    660

cacggtgagt ctagtggaaa gcacgcttct gatgctactg atcctgctac ttctccactc    720

ctcactgagg tgtcatctgg atccggtggt ggatctgcta agggtgagct tagaggtcat    780

cctttcgagg gtaagcctat ccctaaccct cttctcggtc tcgattctac tagaa         835
```

<210> SEQ ID NO 132
<211> LENGTH: 20
<212> TYPE: DNA
<213> ORGANISM: Artificial Sequence
<220> FEATURE:
<223> OTHER INFORMATION: Consensus sequence

<400> SEQUENCE: 132

```
gatatgcgag acgcctatga                                                  20
```

<210> SEQ ID NO 133
<211> LENGTH: 20
<212> TYPE: DNA
<213> ORGANISM: Artificial Sequence
<220> FEATURE:
<223> OTHER INFORMATION: Consensus sequence

<400> SEQUENCE: 133

```
gagttccctt cagtgaacgt                                                  20
```

<210> SEQ ID NO 134
<211> LENGTH: 26
<212> TYPE: DNA
<213> ORGANISM: Artificial Sequence
<220> FEATURE:
<223> OTHER INFORMATION: Consensus sequence

<400> SEQUENCE: 134
gctggggcgt cggtttccac tatccg 26

<210> SEQ ID NO 135
<211> LENGTH: 27
<212> TYPE: DNA
<213> ORGANISM: Artificial Sequence
<220> FEATURE:
<223> OTHER INFORMATION: Consensus sequence

<400> SEQUENCE: 135
cgcataacag cggtcattga ctggagc 27

<210> SEQ ID NO 136
<211> LENGTH: 20
<212> TYPE: DNA
<213> ORGANISM: Artificial Sequence
<220> FEATURE:
<223> OTHER INFORMATION: Consensus sequence

<400> SEQUENCE: 136
ctgttgccgg tcttgcgatg 20

<210> SEQ ID NO 137
<211> LENGTH: 20
<212> TYPE: DNA
<213> ORGANISM: Artificial Sequence
<220> FEATURE:
<223> OTHER INFORMATION: Consensus sequence

<400> SEQUENCE: 137
gtcacataga tgacaccgcg 20

<210> SEQ ID NO 138
<211> LENGTH: 24
<212> TYPE: DNA
<213> ORGANISM: Artificial Sequence
<220> FEATURE:
<223> OTHER INFORMATION: Consensus sequence

<400> SEQUENCE: 138
ctcgtgcttt cagcttcgat gtag 24

<210> SEQ ID NO 139
<211> LENGTH: 26
<212> TYPE: DNA
<213> ORGANISM: Artificial Sequence
<220> FEATURE:
<223> OTHER INFORMATION: Consensus sequence

<400> SEQUENCE: 139
gctggggcgt cggtttccac tatcgg 26

<210> SEQ ID NO 140
<211> LENGTH: 21
<212> TYPE: DNA
<213> ORGANISM: Artificial Sequence
<220> FEATURE:
<223> OTHER INFORMATION: Consensus sequence

<400> SEQUENCE: 140
cacaggatgg attctccaag g 21

<210> SEQ ID NO 141
<211> LENGTH: 20
<212> TYPE: DNA
<213> ORGANISM: Artificial Sequence
<220> FEATURE:
<223> OTHER INFORMATION: Consensus sequence

<400> SEQUENCE: 141
taaggtccac ggagaggttc 20

<210> SEQ ID NO 142
<211> LENGTH: 12
<212> TYPE: DNA
<213> ORGANISM: Artificial Sequence
<220> FEATURE:
<223> OTHER INFORMATION: Construct

<400> SEQUENCE: 142
gatctataga tc 12

<210> SEQ ID NO 143
<211> LENGTH: 12
<212> TYPE: DNA
<213> ORGANISM: Artificial Sequence
<220> FEATURE:
<223> OTHER INFORMATION: Construct

<400> SEQUENCE: 143
ctagatatct ag 12

<210> SEQ ID NO 144
<211> LENGTH: 12
<212> TYPE: DNA
<213> ORGANISM: Artificial Sequence
<220> FEATURE:
<223> OTHER INFORMATION: Construct

<400> SEQUENCE: 144
gatctataga tc 12

<210> SEQ ID NO 145
<211> LENGTH: 12
<212> TYPE: DNA
<213> ORGANISM: Artificial Sequence
<220> FEATURE:
<223> OTHER INFORMATION: Construct

<400> SEQUENCE: 145
ctagatatct ag 12

<210> SEQ ID NO 146
<211> LENGTH: 6
<212> TYPE: PRT
<213> ORGANISM: Artificial Sequence
<220> FEATURE:
<223> OTHER INFORMATION: Construct
<220> FEATURE:
<221> NAME/KEY: misc_feature
<222> LOCATION: (4)..(4)
<223> OTHER INFORMATION: Xaa can be Phe or Tyr
<220> FEATURE:
<221> NAME/KEY: misc_feature
<222> LOCATION: (5)..(5)

<223> OTHER INFORMATION: Xaa can be any naturally occurring amino acid

<400> SEQUENCE: 146

Thr Ile Phe Xaa Xaa Gly
1               5

<210> SEQ ID NO 147
<211> LENGTH: 46
<212> TYPE: PRT
<213> ORGANISM: Amborella trichopoda

<400> SEQUENCE: 147

Leu Glu Glu Leu Thr Glu Glu Asp Ile Ser Gln Leu Thr Arg Glu Asp
1               5                   10                  15

Cys Arg Arg Tyr Leu Lys Glu Lys Gly Met Arg Arg Pro Ser Trp Asn
            20                  25                  30

Lys Tyr Gln Ala Ile Gln Gln Val Leu Ser Leu Lys Gly Leu
        35                  40                  45

<210> SEQ ID NO 148
<211> LENGTH: 46
<212> TYPE: PRT
<213> ORGANISM: Picea abies

<400> SEQUENCE: 148

Leu Glu Asp Leu Ser His Glu Asp Ile Met Gln Leu Thr Arg Glu Asp
1               5                   10                  15

Cys Arg Arg Tyr Leu Ile Glu Lys Gly Met Arg Arg Pro Ser Trp Asn
            20                  25                  30

Lys Ser Gln Ala Ile Gln Gln Val Leu Ser Leu Lys Lys Leu
        35                  40                  45

<210> SEQ ID NO 149
<211> LENGTH: 46
<212> TYPE: PRT
<213> ORGANISM: Picea sitchensis

<400> SEQUENCE: 149

Leu Glu Glu Leu Thr Glu Glu Asp Ile Phe Gln Leu Thr Arg Glu Asp
1               5                   10                  15

Cys Arg Arg Tyr Leu Lys Glu Lys Gly Met Arg Arg Pro Ser Trp Asn
            20                  25                  30

Lys Ser Gln Ala Ile Gln Gln Val Leu Ser Leu Lys Ser Leu
        35                  40                  45

<210> SEQ ID NO 150
<211> LENGTH: 46
<212> TYPE: PRT
<213> ORGANISM: Spirodela polyrrhiza

<400> SEQUENCE: 150

Leu Ser Glu Leu Thr Glu Glu Asp Ile Ala Gln Val Thr Arg Glu Asp
1               5                   10                  15

Cys Arg Arg Phe Leu Lys Glu Lys Gly Met Arg Arg Pro Ser Trp Asn
            20                  25                  30

Lys Ser Gln Ala Val Gln Gln Val Ile Ser Leu Lys Ala Leu
        35                  40                  45

<210> SEQ ID NO 151
<211> LENGTH: 46
<212> TYPE: PRT

<213> ORGANISM: Selaginella moellendorffii PPD1

<400> SEQUENCE: 151

```
Leu Glu Glu Leu Thr Glu Leu Asp Ile Arg Gln Leu Thr Arg Glu Asp
1               5                   10                  15

Cys Arg Arg Tyr Leu Lys Glu Arg Gly Met Arg Arg Pro Ser Trp Asn
            20                  25                  30

Lys Ala Gln Ala Ile Gln Gln Val Leu Ser Leu Arg Ser Leu
        35                  40                  45
```

<210> SEQ ID NO 152
<211> LENGTH: 46
<212> TYPE: PRT
<213> ORGANISM: Selaginella moellendorffii PPD2

<400> SEQUENCE: 152

```
Leu Glu Glu Leu Thr Asp Glu Asp Val Met Gln Leu Thr Arg Glu Asp
1               5                   10                  15

Cys Arg Arg Tyr Leu Lys Glu Lys Gly Met Arg Arg Pro Ser Trp Asn
            20                  25                  30

Lys Ala Gln Ala Val Gln Gln Leu Leu Ser Leu Lys Ser Leu
        35                  40                  45
```

<210> SEQ ID NO 153
<211> LENGTH: 46
<212> TYPE: PRT
<213> ORGANISM: Musa species

<400> SEQUENCE: 153

```
Leu Ala Glu Leu Thr Glu Glu Asp Ile Ala Gln Leu Thr Arg Glu Asp
1               5                   10                  15

Cys Arg Arg Phe Leu Lys Ala Lys Gly Met Arg Arg Pro Ser Trp Asn
            20                  25                  30

Lys Ser Gln Ala Ile Gln Gln Val Ile Ser Leu Lys Ala Leu
        35                  40                  45
```

<210> SEQ ID NO 154
<211> LENGTH: 46
<212> TYPE: PRT
<213> ORGANISM: Phoenix dactylifera

<400> SEQUENCE: 154

```
Leu Ser Leu Leu Thr Glu Glu Asp Ile Ala Gln Leu Thr Arg Glu Asp
1               5                   10                  15

Cys Arg Arg Phe Leu Lys Glu Lys Gly Met Arg Arg Pro Ser Trp Asn
            20                  25                  30

Lys Ser Gln Ala Ile Gln Gln Val Ile Ser Leu Lys Ala Leu
        35                  40                  45
```

<210> SEQ ID NO 155
<211> LENGTH: 46
<212> TYPE: PRT
<213> ORGANISM: Phalaenopsis aphrodite

<400> SEQUENCE: 155

```
Leu Asn Leu Leu Thr Glu Asp Asp Ile Ala Gln Ile Thr Arg Glu Glu
1               5                   10                  15

Cys Arg Arg Phe Leu Lys Asp Arg Gly Met Arg Arg Pro Ser Trp Asn
            20                  25                  30

Lys Ser Gln Ala Ile Gln Gln Val Ile Ser Leu Lys Ala Leu
```

35 40 45

<210> SEQ ID NO 156
<211> LENGTH: 46
<212> TYPE: PRT
<213> ORGANISM: Nicotiana tabacum

<400> SEQUENCE: 156

Leu His Leu Leu Thr Asp Asp Asp Ile Ser Gln Leu Thr Arg Glu Asp
1 5 10 15

Cys Arg Arg Tyr Leu Lys Glu Lys Gly Met Arg Arg Pro Ser Trp Asn
20 25 30

Lys Ser Gln Ala Ile Gln Gln Val Ile Ser Leu Lys Ala Leu
35 40 45

<210> SEQ ID NO 157
<211> LENGTH: 46
<212> TYPE: PRT
<213> ORGANISM: Solanum lycopersicum

<400> SEQUENCE: 157

Leu Tyr Leu Leu Thr Asp Asp Asp Ile Ser Gln Leu Thr Arg Glu Asp
1 5 10 15

Cys Arg Arg Phe Leu Lys Ala Lys Gly Met Arg Lys Pro Ser Trp Asn
20 25 30

Lys Ser Gln Ala Ile Gln Gln Val Ile Ser Leu Lys Ala Leu
35 40 45

<210> SEQ ID NO 158
<211> LENGTH: 46
<212> TYPE: PRT
<213> ORGANISM: Solanum tuberosum

<400> SEQUENCE: 158

Leu Asn Gln Leu Thr Asp Asp Asp Ile Ser Gln Leu Thr Arg Glu Asp
1 5 10 15

Cys Arg Arg Tyr Leu Lys Gln Lys Gly Met Arg Lys Pro Ser Trp Asn
20 25 30

Lys Ser Gln Ala Ile Gln Gln Val Ile Ser Leu Lys Ala Leu
35 40 45

<210> SEQ ID NO 159
<211> LENGTH: 46
<212> TYPE: PRT
<213> ORGANISM: Aquilegia coerulea

<400> SEQUENCE: 159

Leu Phe Gln Leu Thr Asp Glu Asp Ile Ser Gln Leu Thr Arg Glu Asp
1 5 10 15

Cys Arg Lys Phe Leu Arg Asp Lys Gly Met Arg Arg Pro Ser Trp Asn
20 25 30

Lys Ser Gln Ala Ile Glu Gln Val Ile Ser Leu Lys Thr Leu
35 40 45

<210> SEQ ID NO 160
<211> LENGTH: 46
<212> TYPE: PRT
<213> ORGANISM: Populus trichocarpa

<400> SEQUENCE: 160

Leu His Gln Leu Thr Glu Asp Asp Ile Ser Gln Val Thr Arg Glu Asp

```
1               5                   10                  15

Cys Arg Arg Tyr Leu Lys Glu Lys Gly Met Arg Arg Pro Ser Trp Asn
            20                  25                  30

Lys Ser Gln Ala Ile Gln Gln Val Ile Ser Leu Lys Thr Leu
        35                  40                  45


<210> SEQ ID NO 161
<211> LENGTH: 46
<212> TYPE: PRT
<213> ORGANISM: Glycine max

<400> SEQUENCE: 161

Leu Asn Gln Leu Thr Glu Asp Asp Ile Ser Gln Leu Thr Arg Glu Asp
1               5                   10                  15

Cys Arg Arg Phe Leu Lys Glu Lys Gly Met Arg Arg Pro Ser Trp Asn
            20                  25                  30

Lys Ser Gln Ala Ile Gln Gln Val Ile Ser Leu Lys Ala Leu
        35                  40                  45


<210> SEQ ID NO 162
<211> LENGTH: 46
<212> TYPE: PRT
<213> ORGANISM: Medicago truncatula

<400> SEQUENCE: 162

Leu Trp Gln Leu Thr Glu Asp Asp Ile Ser Gln Leu Thr Arg Glu Asp
1               5                   10                  15

Cys Arg Arg Phe Leu Lys Asp Lys Gly Met Arg Arg Pro Ser Trp Asn
            20                  25                  30

Lys Ser Gln Ala Ile Gln Gln Val Ile Ser Leu Lys Ala Leu
        35                  40                  45


<210> SEQ ID NO 163
<211> LENGTH: 46
<212> TYPE: PRT
<213> ORGANISM: Trifolium repens

<400> SEQUENCE: 163

Leu Asn Gln Leu Thr Glu Asp Asp Ile Ser Gln Leu Thr Arg Glu Asp
1               5                   10                  15

Cys Arg Arg Phe Leu Lys Asp Lys Gly Met Arg Arg Pro Ser Trp Asn
            20                  25                  30

Lys Ser Gln Ala Ile Gln Gln Val Ile Ser Leu Lys Ala Leu
        35                  40                  45


<210> SEQ ID NO 164
<211> LENGTH: 46
<212> TYPE: PRT
<213> ORGANISM: Arabidopsis thaliana

<400> SEQUENCE: 164

Leu Lys Leu Leu Thr Glu Glu Asp Ile Ser Gln Leu Thr Arg Glu Asp
1               5                   10                  15

Cys Arg Lys Phe Leu Lys Asp Lys Gly Met Arg Arg Pro Ser Trp Asn
            20                  25                  30

Lys Ser Gln Ala Ile Gln Gln Val Leu Ser Leu Lys Ala Leu
        35                  40                  45


<210> SEQ ID NO 165
<211> LENGTH: 46
```

<212> TYPE: PRT
<213> ORGANISM: Arabidopsis thaliana

<400> SEQUENCE: 165

Leu Lys Leu Leu Thr Glu Glu Asp Ile Ser Gln Leu Thr Arg Glu Asp
1               5                   10                  15

Cys Arg Lys Phe Leu Lys Glu Lys Gly Met Arg Arg Pro Ser Trp Asn
            20                  25                  30

Lys Ser Gln Ala Ile Gln Gln Val Leu Ser Leu Lys Ala Leu
        35                  40                  45

<210> SEQ ID NO 166
<211> LENGTH: 46
<212> TYPE: PRT
<213> ORGANISM: Gossypium raimondii

<400> SEQUENCE: 166

Leu Ser Gln Leu Thr Glu Glu Asp Ile Ser Gln Leu Thr Arg Glu Asp
1               5                   10                  15

Cys Arg Lys Phe Leu Lys Glu Lys Gly Met Arg Arg Pro Ser Trp Asn
            20                  25                  30

Lys Ser Gln Ala Ile Gln Gln Val Ile Ser Phe Lys Ala Leu
        35                  40                  45

<210> SEQ ID NO 167
<211> LENGTH: 46
<212> TYPE: PRT
<213> ORGANISM: Theobroma cacao

<400> SEQUENCE: 167

Leu Ser Gln Leu Thr Glu Glu Asp Ile Ser Gln Leu Thr Arg Glu Asp
1               5                   10                  15

Cys Arg Lys Phe Leu Lys Glu Lys Gly Met Arg Arg Pro Ser Trp Asn
            20                  25                  30

Lys Ser Gln Ala Ile Gln Gln Val Ile Ser Leu Lys Ala Leu
        35                  40                  45

<210> SEQ ID NO 168
<211> LENGTH: 46
<212> TYPE: PRT
<213> ORGANISM: Citrus clementine

<400> SEQUENCE: 168

Leu Ser Gln Leu Thr Glu Glu Asp Ile Thr Gln Leu Thr Arg Glu Asp
1               5                   10                  15

Cys Arg Lys Phe Leu Lys Glu Lys Gly Met Arg Arg Pro Ser Trp Asn
            20                  25                  30

Lys Ser Gln Ala Ile Gln Gln Val Ile Ser Leu Lys Ala Leu
        35                  40                  45

<210> SEQ ID NO 169
<211> LENGTH: 46
<212> TYPE: PRT
<213> ORGANISM: Morus notabilis

<400> SEQUENCE: 169

Leu Asn Gln Leu Thr Glu Asp Asp Ile Ser Gln Leu Thr Arg Glu Asp
1               5                   10                  15

Cys Arg Lys Tyr Leu Lys Glu Lys Gly Met Arg Arg Pro Ser Trp Asn
            20                  25                  30

```
Lys Ser Gln Ala Ile Gln Gln Val Ile Ser Leu Lys Ala Leu
        35                  40                  45


<210> SEQ ID NO 170
<211> LENGTH: 46
<212> TYPE: PRT
<213> ORGANISM: Ricinus communis

<400> SEQUENCE: 170

Leu Thr Gln Leu Thr Glu Glu Asp Ile Ser Gln Leu Thr Arg Glu Asp
1               5                   10                  15

Cys Arg Lys Tyr Leu Lys Glu Lys Gly Met Arg Arg Pro Ser Trp Asn
            20                  25                  30

Lys Ser Gln Ala Ile Gln Gln Val Ile Ser Leu Lys Ala Leu
        35                  40                  45


<210> SEQ ID NO 171
<211> LENGTH: 46
<212> TYPE: PRT
<213> ORGANISM: Vitis vinifera

<400> SEQUENCE: 171

Leu His Glu Leu Thr Glu Glu Asp Ile Ser Gln Leu Thr Arg Glu Asp
1               5                   10                  15

Cys Arg Lys Tyr Leu Lys Glu Lys Gly Met Arg Arg Pro Ser Trp Asn
            20                  25                  30

Lys Ser Gln Ala Ile Gln Gln Val Ile Ser Leu Lys Ser Leu
        35                  40                  45


<210> SEQ ID NO 172
<211> LENGTH: 27
<212> TYPE: PRT
<213> ORGANISM: Amborella trichopoda

<400> SEQUENCE: 172

Thr Arg Glu Asp Cys Arg Arg Tyr Leu Lys Glu Lys Gly Met Arg Arg
1               5                   10                  15

Pro Ser Trp Asn Lys Tyr Gln Ala Ile Gln Gln
            20                  25


<210> SEQ ID NO 173
<211> LENGTH: 27
<212> TYPE: PRT
<213> ORGANISM: Picea abies

<400> SEQUENCE: 173

Thr Arg Glu Asp Cys Arg Arg Tyr Leu Lys Glu Lys Gly Met Arg Arg
1               5                   10                  15

Pro Ser Trp Asn Lys Ser Gln Ala Ile Gln Gln
            20                  25


<210> SEQ ID NO 174
<211> LENGTH: 27
<212> TYPE: PRT
<213> ORGANISM: Picea sitchensis

<400> SEQUENCE: 174

Thr Arg Glu Asp Cys Arg Arg Tyr Leu Lys Glu Lys Gly Met Arg Arg
1               5                   10                  15

Pro Ser Trp Asn Lys Ser Gln Ala Ile Gln Gln
            20                  25
```

<210> SEQ ID NO 175
<211> LENGTH: 27
<212> TYPE: PRT
<213> ORGANISM: Spirodela polyrrhiza

<400> SEQUENCE: 175

Thr Arg Glu Asp Cys Arg Arg Phe Leu Lys Glu Lys Gly Met Arg Arg
1 5 10 15

Pro Ser Trp Asn Lys Ser Gln Ala Val Gln Gln
20 25

<210> SEQ ID NO 176
<211> LENGTH: 27
<212> TYPE: PRT
<213> ORGANISM: Selaginella moellendorffii PPD1

<400> SEQUENCE: 176

Thr Arg Glu Asp Cys Arg Arg Tyr Leu Lys Glu Arg Gly Met Arg Arg
1 5 10 15

Pro Ser Trp Asn Lys Ala Gln Ala Ile Gln Gln
20 25

<210> SEQ ID NO 177
<211> LENGTH: 27
<212> TYPE: PRT
<213> ORGANISM: Selaginella moellendorffii PPD2

<400> SEQUENCE: 177

Thr Arg Glu Asp Cys Arg Arg Tyr Leu Lys Glu Lys Gly Met Arg Arg
1 5 10 15

Pro Ser Trp Asn Lys Ala Gln Ala Val Gln Gln
20 25

<210> SEQ ID NO 178
<211> LENGTH: 27
<212> TYPE: PRT
<213> ORGANISM: Musa species

<400> SEQUENCE: 178

Thr Arg Glu Asp Cys Arg Arg Phe Leu Lys Ala Lys Gly Met Arg Arg
1 5 10 15

Pro Ser Trp Asn Lys Ser Gln Ala Ile Gln Gln
20 25

<210> SEQ ID NO 179
<211> LENGTH: 27
<212> TYPE: PRT
<213> ORGANISM: Phoenix dactylifera

<400> SEQUENCE: 179

Thr Arg Glu Asp Cys Arg Arg Phe Leu Lys Glu Lys Gly Met Arg Arg
1 5 10 15

Pro Ser Trp Asn Lys Ser Gln Ala Ile Gln Gln
20 25

<210> SEQ ID NO 180
<211> LENGTH: 27
<212> TYPE: PRT
<213> ORGANISM: Phalaenopsis aphrodite

<400> SEQUENCE: 180

Thr Arg Glu Glu Cys Arg Arg Phe Leu Lys Asp Arg Gly Met Arg Arg 1               5                   10                  15

Pro Ser Trp Asn Lys Ser Gln Ala Ile Gln Gln
            20                  25

<210> SEQ ID NO 181
<211> LENGTH: 27
<212> TYPE: PRT
<213> ORGANISM: Nicotiana tabacum

<400> SEQUENCE: 181

Thr Arg Glu Asp Cys Arg Arg Tyr Leu Lys Glu Lys Gly Met Arg Arg
1               5                   10                  15

Pro Ser Trp Asn Lys Ser Gln Ala Ile Gln Gln
            20                  25

<210> SEQ ID NO 182
<211> LENGTH: 27
<212> TYPE: PRT
<213> ORGANISM: Solanum lycopersicum

<400> SEQUENCE: 182

Thr Arg Glu Asp Cys Arg Arg Phe Leu Lys Ala Lys Gly Met Arg Lys
1               5                   10                  15

Pro Ser Trp Asn Lys Ser Gln Ala Ile Gln Gln
            20                  25

<210> SEQ ID NO 183
<211> LENGTH: 27
<212> TYPE: PRT
<213> ORGANISM: Solanum tuberosum

<400> SEQUENCE: 183

Thr Arg Glu Asp Cys Arg Arg Tyr Leu Lys Gln Lys Gly Met Arg Lys
1               5                   10                  15

Pro Ser Trp Asn Lys Ser Gln Ala Ile Gln Gln
            20                  25

<210> SEQ ID NO 184
<211> LENGTH: 27
<212> TYPE: PRT
<213> ORGANISM: Aquilegia coerulea

<400> SEQUENCE: 184

Thr Arg Glu Asp Cys Arg Lys Phe Leu Arg Asp Lys Gly Met Arg Arg
1               5                   10                  15

Pro Ser Trp Asn Lys Ser Gln Ala Ile Glu Gln
            20                  25

<210> SEQ ID NO 185
<211> LENGTH: 27
<212> TYPE: PRT
<213> ORGANISM: Populus trichocarpa

<400> SEQUENCE: 185

Thr Arg Glu Asp Cys Arg Arg Tyr Leu Lys Glu Lys Gly Met Arg Arg
1               5                   10                  15

Pro Ser Trp Asn Lys Ser Gln Ala Ile Gln Gln
            20                  25

<210> SEQ ID NO 186
<211> LENGTH: 27
<212> TYPE: PRT

<213> ORGANISM: Glycine max

<400> SEQUENCE: 186

Thr Arg Glu Asp Cys Arg Arg Phe Leu Lys Glu Lys Gly Met Arg Arg
1               5                   10                  15

Pro Ser Trp Asn Lys Ser Gln Ala Ile Gln Gln
            20                  25

<210> SEQ ID NO 187
<211> LENGTH: 27
<212> TYPE: PRT
<213> ORGANISM: Medicago truncatula

<400> SEQUENCE: 187

Thr Arg Glu Asp Cys Arg Arg Phe Leu Lys Asp Lys Gly Met Arg Arg
1               5                   10                  15

Pro Ser Trp Asn Lys Ser Gln Ala Ile Gln Gln
            20                  25

<210> SEQ ID NO 188
<211> LENGTH: 27
<212> TYPE: PRT
<213> ORGANISM: Trifolium repens

<400> SEQUENCE: 188

Thr Arg Glu Asp Cys Arg Arg Phe Leu Lys Asp Lys Gly Met Arg Arg
1               5                   10                  15

Pro Ser Trp Asn Lys Ser Gln Ala Ile Gln Gln
            20                  25

<210> SEQ ID NO 189
<211> LENGTH: 27
<212> TYPE: PRT
<213> ORGANISM: Arabidopsis thaliana

<400> SEQUENCE: 189

Thr Arg Glu Asp Cys Arg Lys Phe Leu Lys Asp Lys Gly Met Arg Arg
1               5                   10                  15

Pro Ser Trp Asn Lys Ser Gln Ala Ile Gln Gln
            20                  25

<210> SEQ ID NO 190
<211> LENGTH: 27
<212> TYPE: PRT
<213> ORGANISM: Arabidopsis thaliana

<400> SEQUENCE: 190

Thr Arg Glu Asp Cys Arg Lys Phe Leu Lys Glu Lys Gly Met Arg Arg
1               5                   10                  15

Pro Ser Trp Asn Lys Ser Gln Ala Ile Gln Gln
            20                  25

<210> SEQ ID NO 191
<211> LENGTH: 27
<212> TYPE: PRT
<213> ORGANISM: Gossypium raimondii

<400> SEQUENCE: 191

Thr Arg Glu Asp Cys Arg Lys Phe Leu Lys Glu Lys Gly Met Arg Arg
1               5                   10                  15

Pro Ser Trp Asn Lys Ser Gln Ala Ile Gln Gln
            20                  25

<210> SEQ ID NO 192
<211> LENGTH: 27
<212> TYPE: PRT
<213> ORGANISM: Theobroma cacao

<400> SEQUENCE: 192

Thr Arg Glu Asp Cys Arg Lys Phe Leu Lys Glu Lys Gly Met Arg Arg
1 5 10 15

Pro Ser Trp Asn Lys Ser Gln Ala Ile Gln Gln
20 25

<210> SEQ ID NO 193
<211> LENGTH: 27
<212> TYPE: PRT
<213> ORGANISM: Citrus clementine

<400> SEQUENCE: 193

Thr Arg Glu Asp Cys Arg Lys Phe Leu Lys Glu Lys Gly Met Arg Arg
1 5 10 15

Pro Ser Trp Asn Lys Ser Gln Ala Ile Gln Gln
20 25

<210> SEQ ID NO 194
<211> LENGTH: 27
<212> TYPE: PRT
<213> ORGANISM: Morus notabilis

<400> SEQUENCE: 194

Thr Arg Glu Asp Cys Arg Lys Tyr Leu Lys Glu Lys Gly Met Arg Arg
1 5 10 15

Pro Ser Trp Asn Lys Ser Gln Ala Ile Gln Gln
20 25

<210> SEQ ID NO 195
<211> LENGTH: 27
<212> TYPE: PRT
<213> ORGANISM: Ricinus communis

<400> SEQUENCE: 195

Thr Arg Glu Asp Cys Arg Lys Tyr Leu Lys Glu Lys Gly Met Arg Arg
1 5 10 15

Pro Ser Trp Asn Lys Ser Gln Ala Ile Gln Gln
20 25

<210> SEQ ID NO 196
<211> LENGTH: 27
<212> TYPE: PRT
<213> ORGANISM: Vitis vinifera

<400> SEQUENCE: 196

Thr Arg Glu Asp Cys Arg Lys Tyr Leu Lys Glu Lys Gly Met Arg Arg
1 5 10 15

Pro Ser Trp Asn Lys Ser Gln Ala Ile Gln Gln
20 25

<210> SEQ ID NO 197
<211> LENGTH: 6
<212> TYPE: PRT
<213> ORGANISM: Amborella trichopoda

<400> SEQUENCE: 197

Thr Ile Phe Tyr Ala Gly
1 5

<210> SEQ ID NO 198
<211> LENGTH: 6
<212> TYPE: PRT
<213> ORGANISM: Picea sitchensis

<400> SEQUENCE: 198

Thr Ile Phe Tyr Ala Gly
1 5

<210> SEQ ID NO 199
<211> LENGTH: 6
<212> TYPE: PRT
<213> ORGANISM: Picea abies

<400> SEQUENCE: 199

Thr Ile Phe Tyr Ser Gly
1 5

<210> SEQ ID NO 200
<211> LENGTH: 6
<212> TYPE: PRT
<213> ORGANISM: Spirodela polyrrhiza

<400> SEQUENCE: 200

Thr Ile Phe Tyr Asp Gly
1 5

<210> SEQ ID NO 201
<211> LENGTH: 6
<212> TYPE: PRT
<213> ORGANISM: Selaginella moellendorffii PPD1

<400> SEQUENCE: 201

Thr Ile Phe Tyr Ser Gly
1 5

<210> SEQ ID NO 202
<211> LENGTH: 6
<212> TYPE: PRT
<213> ORGANISM: Selaginella moellendorffii PPD2

<400> SEQUENCE: 202

Thr Met Phe Tyr Asp Gly
1 5

<210> SEQ ID NO 203
<211> LENGTH: 6
<212> TYPE: PRT
<213> ORGANISM: Musa species

<400> SEQUENCE: 203

Thr Ile Phe Tyr Asp Gly
1 5

<210> SEQ ID NO 204
<211> LENGTH: 6
<212> TYPE: PRT
<213> ORGANISM: Elaeis guineensis

<400> SEQUENCE: 204

Thr Ile Phe Tyr Asp Gly
1 5

<210> SEQ ID NO 205
<211> LENGTH: 6
<212> TYPE: PRT
<213> ORGANISM: Phalaenopsis aphrodite

<400> SEQUENCE: 205

Thr Ile Phe Tyr Gly Gly
1               5

<210> SEQ ID NO 206
<211> LENGTH: 6
<212> TYPE: PRT
<213> ORGANISM: Nicotiana tabacum

<400> SEQUENCE: 206

Thr Ile Phe Tyr Cys Gly
1               5

<210> SEQ ID NO 207
<211> LENGTH: 6
<212> TYPE: PRT
<213> ORGANISM: Solanum lycopersicum

<400> SEQUENCE: 207

Thr Ile Phe Tyr Cys Gly
1               5

<210> SEQ ID NO 208
<211> LENGTH: 6
<212> TYPE: PRT
<213> ORGANISM: Solanum tuberosum

<400> SEQUENCE: 208

Thr Ile Phe Tyr Arg Gly
1               5

<210> SEQ ID NO 209
<211> LENGTH: 6
<212> TYPE: PRT
<213> ORGANISM: Aquilegia coerulea

<400> SEQUENCE: 209

Thr Ile Phe Tyr Cys Gly
1               5

<210> SEQ ID NO 210
<211> LENGTH: 6
<212> TYPE: PRT
<213> ORGANISM: Populus trichocarpa

<400> SEQUENCE: 210

Thr Ile Phe Tyr Cys Gly
1               5

<210> SEQ ID NO 211
<211> LENGTH: 6
<212> TYPE: PRT
<213> ORGANISM: Glycine max

<400> SEQUENCE: 211

Thr Ile Phe Tyr Cys Gly
1               5

<210> SEQ ID NO 212
<211> LENGTH: 6
<212> TYPE: PRT
<213> ORGANISM: Medicago truncatula

<400> SEQUENCE: 212

Thr Ile Phe Tyr Cys Gly
1 5

<210> SEQ ID NO 213
<211> LENGTH: 6
<212> TYPE: PRT
<213> ORGANISM: Trifolium repens

<400> SEQUENCE: 213

Thr Ile Phe Tyr Cys Gly
1 5

<210> SEQ ID NO 214
<211> LENGTH: 6
<212> TYPE: PRT
<213> ORGANISM: Arabidopsis thaliana

<400> SEQUENCE: 214

Thr Ile Phe Tyr Ser Gly
1 5

<210> SEQ ID NO 215
<211> LENGTH: 6
<212> TYPE: PRT
<213> ORGANISM: Arabidopsis thaliana

<400> SEQUENCE: 215

Thr Ile Phe Tyr Ser Gly
1 5

<210> SEQ ID NO 216
<211> LENGTH: 6
<212> TYPE: PRT
<213> ORGANISM: Gossypium raimondii

<400> SEQUENCE: 216

Thr Ile Phe Tyr Cys Gly
1 5

<210> SEQ ID NO 217
<211> LENGTH: 6
<212> TYPE: PRT
<213> ORGANISM: Theobroma cacao

<400> SEQUENCE: 217

Thr Ile Phe Tyr Cys Gly
1 5

<210> SEQ ID NO 218
<211> LENGTH: 6
<212> TYPE: PRT
<213> ORGANISM: Citrus clementine

<400> SEQUENCE: 218

Thr Ile Phe Tyr Cys Gly
1 5

<210> SEQ ID NO 219
<211> LENGTH: 6

<212> TYPE: PRT
<213> ORGANISM: Morus notabilis

<400> SEQUENCE: 219

```
Thr Ile Phe Tyr Cys Gly
1               5
```

<210> SEQ ID NO 220
<211> LENGTH: 6
<212> TYPE: PRT
<213> ORGANISM: Ricinus communis

<400> SEQUENCE: 220

```
Thr Ile Phe Tyr Cys Gly
1               5
```

<210> SEQ ID NO 221
<211> LENGTH: 6
<212> TYPE: PRT
<213> ORGANISM: Vitis vinifera

<400> SEQUENCE: 221

```
Thr Ile Phe Tyr Cys Gly
1               5
```

<210> SEQ ID NO 222
<211> LENGTH: 45
<212> TYPE: PRT
<213> ORGANISM: Artificial Sequence
<220> FEATURE:
<223> OTHER INFORMATION: Construct

<400> SEQUENCE: 222

```
Leu Lys Leu Leu Thr Glu Glu Asp Ile Ser Gln Leu Thr Arg Glu Asp
1               5                   10                  15

Cys Arg Lys Phe Leu Lys Asp Gly Met Arg Arg Pro Ser Trp Asn Lys
            20                  25                  30

Ser Gln Ala Ile Gln Gln Val Leu Ser Leu Lys Ala Leu
        35                  40                  45
```

<210> SEQ ID NO 223
<211> LENGTH: 26
<212> TYPE: PRT
<213> ORGANISM: Artificial Sequence
<220> FEATURE:
<223> OTHER INFORMATION: Construct

<400> SEQUENCE: 223

```
Glu Gly Gln Ala Asn Arg Lys Val Ser Leu Gln Arg Tyr Arg Glu Lys
1               5                   10                  15

Arg Lys Asp Arg Lys Phe Ser Lys Ala Lys
            20                  25
```

<210> SEQ ID NO 224
<211> LENGTH: 26
<212> TYPE: PRT
<213> ORGANISM: Artificial Sequence
<220> FEATURE:
<223> OTHER INFORMATION: Construct -continued

```
<400> SEQUENCE: 224

Val Gly Gln Thr Ile Phe Tyr Ser Gly Ser Gly Lys Val Asn Val Tyr
1               5                   10                  15

Asp Gly Ile Pro Pro Glu Lys Ala Arg Ser
            20                  25
```

METHODS OF INCREASING ROOT BIOMASS IN PLANTS

CROSS-REFERENCE TO RELATED APPLICATIONS

This application is a U.S. National Stage Application filed under 35 U.S.C. § 371 of International Application No. PCT/IB2015/058479, filed Nov. 3, 2015, which claims the benefit of New Zealand Application No. 701643, filed Nov. 4, 2014. Both of these applications are hereby incorporated by reference in their entireties.

TECHNICAL FIELD

The present invention relates methods for producing plants with increased root biomass.

BACKGROUND ART

The roots of vascular plants have multiple functions. These include: 1) absorption of water and inorganic nutrients, 2) anchoring of the plant to the ground, and supporting it, 3) storage of food and nutrients, and 4) vegetative reproduction. In response to the concentration of nutrients, roots also synthesise cytokinin, which acts as a signal influencing how fast the shoots can grow.

Plants with increased root biomass would therefore potentially have a number of advantages including better anchorage, more efficient water uptake, more efficient nutrient uptake, and improved drought tolerance. A combination of these features may also result in improved yield, including increased grain or fruit biomass and/or increased leaf biomass.

At present there is limited understanding of the genetic mechanisms controlling root biomass in plants.

It would be beneficial to have available alternative methods for controlling root biomass in plants.

It is therefore an object of the invention to provide methods and materials for increasing the production of root biomass in plants, and/or at least to provide the public with a useful choice.

SUMMARY OF THE INVENTION

Previously, White (2006) discovered two adjacent homologous genes in *Arabidopsis* (named PEAPOD, PPD1 and PPD2) that regulate the cell proliferation of meristemoids during the late stages of leaf and seed pod development. Deletion of these genes in *Arabidopsis* resulted in enlarged leaves and wide seed pods while over expression of PPD1 resulted in a reduction in the size of the leaves and siliques (White, 2006).

The applicants have now surprisingly shown that the over-expression of PEAPOD genes in plants results in an increase in the production of root biomass.

The applicant's invention therefore relates to a method for increasing root biomass in plants by ectopic expression of PEAPOD. In particular the invention relates to ectopic expression of PEAPOD proteins that are characterized by presence of consensus amino acid motifs common to all PEAPOD proteins disclosed from a wide range of plant species.

Methods

In the first aspect the invention provides a method for increasing root biomass in a plant, the method comprising the step of increasing the expression of at least one PEAPOD protein in the plant.

In one embodiment root biomass is increased relative to that in a control plant, of the same species or variety.

In one embodiment the increased expression of the at least one PEAPOD protein is a consequence of the plant, or its ancestor plant or plant cell, having been transformed with a polynucleotide encoding the PEAPOD protein.

In a further embodiment, the plant is transgenic for at least one polynucleotide encoding and expressing the PEAPOD protein.

In a further aspect the invention provides a method for producing a plant increased root biomass, the method comprising the step of increasing the expression of at least one PEAPOD protein in the plant.

In one embodiment the plant is transformed with at least one polynucleotide encoding a PEAPOD protein.

In a further embodiment the method comprises the step of transforming the plant, or transforming a plant cell which is regenerated into the plant, with a polynucleotide encoding the PEAPOD protein.

In one embodiment the method includes the additional step of testing or assessing the plant for increased root biomass.

In a further embodiment the method includes the step producing further plants with increased root biomass by asexually or sexually multiplying the plants tested for increased biomass.

PEAPOD Proteins

In one embodiment the PEAPOD protein is a polypeptide comprising the sequence of at least one of SEQ ID NO: 28, 29, 31, 32, 34 and 35.

In a further embodiment the PEAPOD protein comprises the sequence of SEQ ID NO: 28. In a further embodiment the PEAPOD protein comprises the sequence of SEQ ID NO: 29. In a further embodiment the PEAPOD protein comprises the sequence of SEQ ID NO:31. In a further embodiment the PEAPOD protein comprises the sequence of SEQ ID NO:32. In a further embodiment the PEAPOD protein comprises the sequence of SEQ ID NO:34. In a further embodiment the PEAPOD protein comprises the sequence of SEQ ID NO:35.

In a further embodiment the PEAPOD protein is a polypeptide comprising a sequence with at least 70% identity to any one of SEQ ID NO: 1 to 26.

In a further embodiment the PEAPOD protein is a polypeptide comprising a sequence selected from any one of SEQ ID NO: 1 to 26.

In a further embodiment the PEAPOD protein is a polypeptide comprising a sequence with at least 70% identity to SEQ ID NO: 1.

In a further embodiment the PEAPOD protein is a polypeptide comprising the sequence of SEQ ID NO: 1.

Expressing PEAPOD

Methods for expressing proteins in plants are well known to those skilled in the art, and are described herein. All of such methods are included within the scope of the invention.

Increasing Expression of PEAPOD by Introducing a Polynucleotide

In one embodiment expression is increased by introducing at least one polynucleotide into the plant cell or plant.

In a preferred embodiment the polynucleotide encodes a PEAPOD protein as herein defined.

In a further embodiment the polynucleotide comprises a sequence with at least 70% identity to the coding sequence of any one of SEQ ID NO: 83-107.

In a further embodiment the polynucleotide comprises a sequence with at least 70% identity to the sequence of any one of SEQ ID NO: 83-107.

In a further embodiment the polynucleotide comprises the coding sequence of any one of SEQ ID NO: 83-107.

In a further embodiment the polynucleotide comprises the sequence of any one of SEQ ID NO: 83-107.

In a further embodiment the polynucleotide comprises a fragment of the sequences described above, that is capable of encoding a polypeptide with the same function as a PEAPOD protein. In one embodiment the fragment encodes a polypeptide capable of increasing root biomass.

Expressing PEAPOD via an Expression Construct

In a preferred embodiment the polynucleotide is introduced into the plant as part of an expression construct.

In a preferred embodiment the expression construct comprises a promoter operatively linked to the polynucleotide.

Promoter for Increasing Expression of PEAPOD

In one embodiment the promoter is capable of driving, or drives, expression of the operatively linked polynucleotide constitutively in all tissues of the plant.

In a further embodiment the promoter is a tissue-preferred promoter.

In a further embodiment the promoter is capable of driving, or drives, expression of the operatively linked polynucleotide in the below ground tissues of the plant.

In one embodiment the promoter is a below ground tissues-preferred promoter.

In a further embodiment the promoter is a below ground tissue-specific promoter.

In one embodiment the promoter is a light-repressed promoter.

In a further embodiment the promoter is capable of driving, or drives, expression of the operatively linked polynucleotide in the roots of the plant.

In one embodiment the promoter is a root-preferred promoter.

In a further embodiment the promoter is a root-specific promoter.

Source of Polynucleotides and Polypeptides

The polynucleotides and variants of polynucleotides of the invention, or used in the methods of the invention, may be derived from any species. The polynucleotides and variants may also be synthetically or recombinantly produced, and also may be the products of "gene shuffling" approaches.

The polypeptides and variants of polypeptides of the invention, or used in the methods of the invention, may be derived from any species. The polypeptides and variants may also be recombinantly produced and also may also be expressed from the products of "gene shuffling" approaches.

In one embodiment the polynucleotide, polypeptide or variant, is derived from a plant species.

In a further embodiment the polynucleotide, polypeptide or variant, is derived from gymnosperm plant species.

In a further embodiment the polynucleotide, polypeptide or variant, is derived from an angiosperm plant species.

In a further embodiment the polynucleotide, polypeptide or variant, is derived from a dicotyledonous species.

In a preferred embodiment the polynucleotide, polypeptide or variant, is derived from a eudicot species.

In a further embodiment the polynucleotide, polypeptide or variant, is derived from a eudicot plant species.

In a further embodiment the polynucleotide, polypeptide or variant, is derived from a monocotyledonous species. Preferred monocot plants include: palm, banana, duckweed and orchid species.

Plant Cells and Plants to be Transformed

The plant cells and plants of the invention, or used in the methods of the invention, are from any plant species.

In one embodiment the plant cells or plants are from gymnosperm plant species.

In a further embodiment the plant cells or plants are from angiosperm plant species.

In a further embodiment the plant cells or plants are from a dicotyledonous species.

Preferred monocotyledonous genera include: *Agropyron, Allium, Alopecurus, Andropogon, Arrhenatherum, Asparagus, Avena, Bambusa, Bothrichloa, Bouteloua, Bromus, Calamovilfa, Cenchrus, Chloris, Cymbopogon, Cynodon, Dactylis, Dichanthium, Digitaria, Eleusine, Eragrostis, Fagopyrum, Festuca, Helianthus, Hordeum, Lolium, Miscanthis, Miscanthus×giganteus, Oryza, Panicum, Paspalum, Pennisetum, Phalaris, Phleum, Poa, Saccharum, Secale, Setaria, Sorgahastum, Sorghum, Triticum, Vanilla*, X *Triticosecale Triticale* and *Zea.*

Preferred monocotyledonous species include: *Agropyron cristatum, Agropyron desertorum, Agropyron elongatum, Agropyron intermedium, Agropyron smithii, Agropyron spicaturn, Agropyron trachycaulum, Agropyron trichophorum, Allium ascalonicum, Allium cepa, Allium chinense, Allium porrum, Allium schoenoprasum, Allium fistulosum, Allium sativum, Alopecurus pratensis, Andropogon gerardi, Andropogon Gerardii, Andropogon scoparious, Arrhenatherum elatius, Asparagus officinalis, Avena nuda, Avena sativa, Bambusa vulgaris, Bothrichloa barbinodis, Bothrichloa ischaemurn, Bothrichloa saccharoides, Bouteloua curipendula, Bouteloua eriopoda, Bouteloua gracilis, Bromus erectus, Bromus inermis, Bromus riparius, Calamovilfa longifilia, Cenchrus ciliaris, Chloris gayana, Cymbopogon nardus, Cynodon dactylon, Dactylis glomerata, Dichanthium annulatum, Dichanthium aristatum, Dichanthium sericeum, Digitaria decumbens, Digitaria smutsii, Dioscorea rotundata, Dicsorea alata, Dicscorea opposita, Dicscorea bulbifera, Dioscorea esculenta, Dioscorea trifida, Eleusine coracan, Elymus angustus, Elymus junceus, Eragrostis curvula, Eragrostis tef, Fagopyrum esculenturn, Fagopyrum tataricum, Festuca arundinacea, Festuca ovina, Festuca pratensis, Festuca rubra, Helianthus annuus sunflower, Hordeum distichum, Hordeum vulgare, Lolium multiflorum, Lolium perenn, Miscanthis sinensis, Miscanthus× giganteus, Oryza sativa, Panicum italicium, Panicum maximum, Panicum miliaceum, Panicum purpurascens, Panicum virgatum, Panicum virgatum, Paspalum dllatatum, Paspalum notatum, Pennisetum clandestinurn, Pennisetum glaucum, Pennisetum purpureum, Pennisetum spicaturn, Phalaris arundinacea, Phleum bertolinii, Phleum pratense, Poa fendleriana, Poa pratensis, Poa. nemoralis, Saccharum officinarum, Saccharum robustum, Saccharum sinense, Saccharum spontaneum, Secale cereale, Setaria sphacelate, Sorgahastum nutans, Sorghastrum nutans, Sorghum dochna, Sorghum halepense, Sorghum sudanense, Sorghum vulgare, Sorghum vulgare, Triticum aestivum, Triticum dicoccum, Triticum durum, Triticum monococcum, Vanilla fragrans, X Triticosecale* and *Zea mays.*

A preferred family of monocotyledonous plants is poaceae family.

Preferred poaceae subfamilies include the: Anomochlooideae, Pharoideae, Puelioideae, Bambusoideae, Pooideae, Ehrhartoideae, Aristidoideae, Arundinoideae, Chloridoideae, Panicoideae, Danthonioideae, and Micrairoideae.

A preferred poaceae family is the subfamily pooideae. Preferred pooideae plants include wheat, barley, oats, brome grass and reed grass.

Another preferred poaceae family is the subfamily Ehrhartoideae. Preferred ehrhartoideae plants include rice.

Another preferred poaceae family is the subfamily panicoideae. Preferred panicoideae plants include panic grass, maize, sorghum, sugar cane, energy cane, millet, fonio and bluestem grasses.

Another preferred poaceae family is the subfamily Arundinoideae. Preferred Arundinoideae plants include *Arundo donax.*

Another preferred poaceae family is the subfamily Bambusoideae. Preferred Bambusoideae plants include bamboo.

Preferred poaceae species include those form the *Lolium* genera. Preferred *Lolium* species include *Lolium longiflorum, Lolium multiflorum, Lolium perenne, Lolium westerwoldicum, Lolium temulentum*, and *Lolium hybridum.*

Other preferred poaceae species include those form the *Festuca* genera. Preferred *Festuca* species include *Festuca arundinacea, Festuca ovina, Festuca pratensis* and *Festuca rubra.*

Preferably the plant cells or plants are from a dicotyledonous species.

Preferred dicotyledonous genera include: *Amygdalus, Anacardium, Arachis, Brassica, Cajanus, Cannabis, Carthamus, Carya, Ceiba, Cicer, Cocos, Coriandrum, Coronilla, Cossypium, Crotalaria, Dolichos, Elaeis, lycine, Gossypium, Helianthus, Lathyrus, Lens, Lespedeza, Linum, Lotus, Lupinus, Macadamia, Medicago, Melilotus, Mucuna, Olea, Onobrychis, Ornithopus, Papaver, Phaseolus, Phoenix, Pistacia, Pisum, Prunus, Pueraria, Ribes, Ricinus, Sesamum, Theobroma, Trifolium, Trigonella, Vicia* and *Vigna.*

Preferred dicotyledonous species include: *Amygdalus communis, Anacardium occidentale, Arachis hypogaea, Arachis hypogea, Brassica napus Rape, Brassica. nigra. Brassica campestris, Cajanus cajan, Cajanus indicus, Camelina sativa, Cannabis sativa, Carthamus tinctorius, Carya illinoinensis, Ceiba pentandra, Cicer arietinum, Cocos nucifera, Coriandrum sativum, Coronilla varia, Cossypium hirsutum, Crotalaria juncea, Dolichos lablab, Elaeis guineensis, Gossypium arboreum, Gossypium nanking, Gossypium barbadense, Gossypium herbaceum, Gossypium hirsutum, Glycine max, Glycine ussuriensis, Glycine gracilis, Helianthus annus, Jatropha cuneata, Jatropha curcas, Lupinus angustifolius, Lupinus luteus, Lupinus mutabilis, Lespedeza sericea, Lespedeza striata, Lotus uliginosus, Lathyrus sativus, Lens culinaris, Lespedeza stipulacea, Linum usitatissimum, Lotus comiculatus, Lupinus albus, Lupinus angustifolius, Lupinus luteus, Medicago arborea, Medicago falcate, Medicago hispida, Medicago officinalis, Medicago. sativa Alfalfa, Medicago tribuloides, Macadamia integrifolia, Medicago arabica, Melilotus albus, Millettia pinnata, Mucuna pruriens, Olea europaea, Onobrychis viciifolia, Ornithopus sativus, Phaseolus aureus, Prunus cerasifera, Prunus cerasus, Phaseolus coccineus, Prunus domestica, Phaseolus lunatus, Prunus. maheleb, Phaseolus mungo, Prunus. persica, Prunus. pseudocerasus, Phaseolus vulgaris, Papaver somniferum, Phaseolus acutifolius, Phoenix dactylifera, Pistacia vera, Pisum sativum, Prunus amygdalus, Prunus armeniaca, Pueraria thunbergiana, Ribes nigrum, Ribes rubrum, Ribes grossularia, Ricinus communis, Sesamum indicum, Solanum tuberosum, Trifolium augustifolium, Trifolium diffusum, Trifolium hybridum, Trifolium incarnatum, Trifolium ingrescens, Trifolium pratense, Trifolium repens, Trifolium resupinatum, Trifolium subterraneum, Theobroma cacao, Trifolium alexandrinum, Trigonella foenumgraecum, Vemicia fordii, Vicia angustifolia, Vicia atropurpurea, Vicia calcarata, Vicia dasycarpa,*

*Vicia ervilia, Vaccinium oxycoccos, Vicia pannonica, Vigna sesquipedalis, Vigna sinensis, Vicia villosa, Vicia faba, Vicia sative* and *Vigna angularis.*

Plants and Plant Parts

In a further aspect the invention provides a plant that has increased root biomass as a result of having increased expression a PEAPOD protein, or fragment thereof.

In one embodiment expression of the PEAPOD protein, or fragment thereof, is increased as a consequence of the plant, or its ancestor plant or plant cell, having been transformed with a polynucleotide encoding the PEAPOD protein, or fragment thereof.

In a further embodiment plant is transgenic for a polynucleotide expressing the PEAPOD protein, or fragment thereof.

In a further embodiment the polynucleotide or fragment thereof is operatively linked polynucleotide to a tissue-preferred promoter.

In a further embodiment the promoter is a root-preferred promoter.

In a further embodiment the promoter is a root-specific promoter.

In a further embodiment the PEAPOD protein is as herein defined.

In a further embodiment the polynucleotide, encoding the PEAPOD protein, is as herein defined.

In a further aspect the invention provides a cell, part, propagule or progeny of the plant that is transgenic for at least one of:

a) the polynucleotide, and b) the polynucleotide and operatively linked promoter.

DETAILED DESCRIPTION

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

Increased Root Biomass

A plant with "increased root biomass" produces more root biomass than does a control plant of the same type and age. Thus "increased" means increased relative to a control plant of the same type and age.

Preferably the plant with "increased root biomass" produces at least 10%, preferably at least 20%, more preferably at least 30%, more preferably at least 40%, more preferably at least 50%, more preferably at least 60%, more preferably at least 70%, more preferably at least 80%, more preferably at least 90%, more preferably at least 100%, more preferably at least 150%, more preferably at least 200%, more preferably at least 300%, more preferably at least 400% more root biomass than does a control plant of the same type and age.

In one embodiment the plant with "increased root biomass" has at least one of: larger roots, more roots, or a more extensive root system, than does a control plant.

Root Biomass

The term root biomass refers to total mass of root tissue produced by the plant. This can be assessed by dry weight or wet weight.

Root

The term root as used herein means the same as standard usage of the term. The term root encompasses the primary root, secondary roots, adventitious roots, root branches and root hairs. Roots are generally below ground, but the term also encompasses aerial roots. In one embodiment the term root encompasses non-leaf, non-node bearing parts of the plant.

Increased Drought Tolerance

In one embodiment the plant with "increased root biomass" also has increased drought tolerance. Again "increased" means increased relative to a control plant of the same type and age.

The term "increased drought tolerance" is intended to describe a plant, or plants, which perform more favourably in any aspect of their growth and development under sub-optimal hydration conditions than do suitable control plants in the same conditions.

Control Plant

In one embodiment the control plant is a wild-type plant. In a further embodiment the control plant is a non-transformed plant. In a further embodiment the control plant is a plant that has not been transformed with a PEAPOD polynucleotide. In a further embodiment the control plant is a plant that has not been transformed with a construct. In a further embodiment the control plant is a plant that has been transformed with a control construct. In one embodiment the construct is an empty vector construct.

Ectopic Expression

The term "ectopic expression" is intended to be interpreted broadly. The term refers to expression of a polynucleotide or polypeptide in any one of:

- a cell, organ, tissue or plant where it is not normally expressed,
- a cell, organ, tissue or plant at a time, or developmental stage, when it is not normally expressed, and
- a cell, organ, tissue or plant at a level higher than it is normally expressed in that cell, organ, tissue or plant.

Tissue Preferred Promoters

In certain embodiments, the PEAPOD protein encoding polynucleotides are expressed under the control of tissue preferred promoters. The term "preferred" with respect to tissue preferred promoters means that the promoter primarily drives expression in that tissue. Thus, for example, a root-preferred promoter drives a higher level of expression of an operably linked polynucleotide in root tissue than it does in other tissues or organs or the plant.

Root Preferred Promoters

A root-preferred promoter drives a higher level of expression of an operably linked polynucleotide in root tissue than it does in other tissues or organs or the plant.

Root-preferred promoters may include non-photosynthetic tissue preferred promoters and light-repressed regulated promoters.

Non-photosynthetic Tissue Preferred Promoters

Non-photosynthetic tissue preferred promoters include those preferentially expressed in non-photosynthetic tissues/organs of the plant.

Non-photosynthetic tissue preferred promoters may also include light repressed promoters.

Light Repressed Promoters

An example of a light repressed promoter is found in U.S. Pat. No. 5,639,952 and in U.S. Pat. No. 5,656,496.

Root Specific Promoters

An example of a root specific promoter is found in U.S. Pat. No. 5,837,848; and US 2004/0067506 and US 2001/0047525.

The term "preferentially expressed" with respect to a promoter being preferentially expressed in a certain tissue, means that the promoter is expressed at a higher level in that tissue than in other tissues of the plant.

The term "tissue specific" with respect to a promoter, means that the promoter is expressed substantially only in that tissue, and not other tissues of the plant.

In one embodiment the root-preferred promoter is a root-specific promoter.

The term "gene" as used herein means an endogenous genomic sequence which includes a coding sequence which encodes a polypeptide or protein. The coding sequence may be interrupted by one or more introns. A gene typically also includes a promoter sequence, 5' untranslated sequence, 3' untranslated sequence, and a terminator sequence. Genomic sequences that regulate expression of the protein may also be considered part of the gene.

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide refers to a contiguous subsequence of larger a polynucleotide sequence. Preferably the fragment is at least 15 nucleotides preferably at least 16 nucleotides, more preferably at least 17 nucleotides, more preferably at least 18 nucleotides, more preferably at least 19 nucleotides, more preferably at least 20 nucleotides, more preferably at least 21 nucleotides, more preferably at least 22 nucleotides, more preferably at least 23 nucleotides, more preferably at least 24 nucleotides, more preferably at least 25 nucleotides, more preferably at least 26 nucleotides, more preferably at least 27 nucleotides, more preferably at least 28 nucleotides, more preferably at least 29 nucleotides, more preferably at least 30 nucleotides, more preferably at least 31 nucleotides, more preferably at least 32 nucleotides, more preferably at least 33 nucleotides, more preferably at least 34 nucleotides, more preferably at least 35 nucleotides, more preferably at least 36 nucleotides, more preferably at least 37 nucleotides, more preferably at least 38 nucleotides, more preferably at least 39 nucleotides, more preferably at least 40 nucleotides, more preferably at least 41 nucleotides, more preferably at least 42 nucleotides, more preferably at least 43 nucleotides, more preferably at least 44 nucleotides, more preferably at least 45 nucleotides, more preferably at least 46 nucleotides, more preferably at least 47 nucleotides, more preferably at least 48 nucleotides, more preferably at least 49 nucleotides, more preferably at least 50 nucleotides, more preferably at least 51 nucleotides, more preferably at least 52 nucleotides, more preferably at least 53 nucleotides, more preferably at least 54 nucleotides, more preferably at least 55 nucleotides, more preferably at least 56 nucleotides, more preferably at least 57 nucleotides, more preferably at least 58 nucleotides, more preferably at least 59 nucleotides, more preferably at least 60 nucleotides, more preferably at least 61 nucleotides, more preferably at least 62 nucleotides, more preferably at least 63 nucleotides, more preferably at least 64 nucleotides, more preferably at least 65 nucleotides, more preferably at least 66 nucleotides, more preferably at least 67 nucleotides, more preferably at least 68 nucleotides, more preferably at least 69 nucleotides, more preferably at least 70 nucleotides, more preferably at least 71 nucleotides, more preferably at least 72 nucleotides, more preferably at least 73 nucleotides, more preferably at least 74 nucleotides, more preferably at least 75 nucleotides, more preferably at least 76 nucleotides, more preferably at least 77 nucleotides, more preferably at least 78 nucleotides, more preferably at least 79 nucleotides, more preferably at least 80 nucleotides, more preferably at least 81 nucleotides, more preferably at least 82 nucleotides, more preferably at least 83 nucleotides, more preferably at least 84 nucleotides, more preferably at least 85 nucleotides, more preferably at least 86 nucleotides, more preferably at least 87 nucleotides, more preferably at least 88 nucleotides, more preferably at least 89 nucleotides, more preferably at least 90 nucleotides, more preferably at least 91 nucleotides, more preferably at least 92 nucleotides, more preferably at least 93 nucleotides, more preferably at least 94 nucleotides, more preferably at least 95 nucleotides, more preferably at least 96 nucleotides, more preferably at least 97 nucleotides, more preferably at least 98 nucleotides, more preferably at least 99 nucleotides, more preferably at least 100 nucleotides, more preferably at least 150 nucleotides, more preferably at least 200 nucleotides, more preferably at least 250 nucleotides, more preferably at least 300 nucleotides, more preferably at least 350 nucleotides, more preferably at least 400 nucleotides, more preferably at least 450 nucleotides and most preferably at least 500 nucleotides of contiguous nucleotides of a polynucleotide disclosed. A fragment of a polynucleotide sequence can be used in antisense, RNA interference (RNAi), gene silencing, triple helix or ribozyme technology, or as a primer, a probe, included in a microarray, or used in polynucleotide-based selection methods of the invention.

In one embodiment the fragment encodes a polypeptide that performs, or is capable of performing, the same function as the polypeptide encoded by the larger polynucleotide that the fragment is part of.

The term "primer" refers to a short polynucleotide, usually having a free 3'OH group that is, or can be, hybridized to a template and used for priming polymerization of a polynucleotide complementary to the target.

The term "probe" refers to a short polynucleotide that is, or can be, used to detect a polynucleotide sequence that is complementary to the probe, in a hybridization-based assay. The probe may consist of a "fragment" of a polynucleotide as defined herein.

Polypeptides and Fragments

The term "polypeptide", as used herein, encompasses amino acid chains of any length but preferably at least 5 amino acids, including full-length proteins, in which amino acid residues are linked by covalent peptide bonds. Polypeptides of the present invention, or used in the methods of the invention, may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polynucleotide refers to a contiguous subsequence of a larger polynucleotide sequence. Preferably the fragment A "fragment" of a polypeptide refers to a contiguous subsequence of larger a polypeptide. Preferably the fragment is at least 5, more preferably at least 10, more preferably at least 20, more preferably at least 30, more preferably at least 40, more preferably at least 50, more preferably at least 100, more preferably at least 120, more preferably at least 150, more preferably at least 200, more preferably at least 250, more preferably at least 300, more preferably at least 350, more preferably at least 400.

In one embodiment the fragment performs, or is capable of performing, the same function as the polypeptide that the fragment is part of.

Preferably the fragment performs a function that is required for the biological activity and/or provides three dimensional structure of the polypeptide.

The term "isolated" as applied to the polynucleotide or polypeptide sequences disclosed herein is used to refer to sequences that are removed from their natural cellular environment. In one embodiment the sequence is separated from its flanking sequences as found in nature. An isolated molecule may be obtained by any method or combination of methods including biochemical, recombinant, and synthetic techniques.

The term "recombinant" refers to a polynucleotide sequence that is synthetically produced or is removed from sequences that surround it in its natural context. The recombinant sequence may be recombined with sequences that are not present in its natural context.

A "recombinant" polypeptide sequence is produced by translation from a "recombinant" polynucleotide sequence.

The term "derived from" with respect to polynucleotides or polypeptides of the invention being derived from a particular genera or species, means that the polynucleotide or polypeptide has the same sequence as a polynucleotide or polypeptide found naturally in that genera or species. The polynucleotide or polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the polypeptides and polynucleotides disclosed herein possess biological activities that are the same or similar to those of the disclosed polypeptides or polypeptides. The term "variant" with reference to polypeptides and polynucleotides encompasses all forms of polypeptides and polynucleotides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequence of the present invention. Identity is found over a comparison window of at least 20 nucleotide positions, preferably at least 50 nucleotide positions, more preferably at least 100 nucleotide positions, and most preferably over the entire length of a polynucleotide of the invention.

Polynucleotide sequence identity can be determined in the following manner. The subject polynucleotide sequence is compared to a candidate polynucleotide sequence using BLASTN (from the BLAST suite of programs, version 2.2.5[November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI (ftp<dot>ncbi<dot>nih<dot>gov/blast/). In one embodiment the default parameters of bl2seq are utilized. In a further except the default parameters of bl2seq are utilized, except that filtering of low complexity parts should be turned off.

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp.276-277) which can be obtained from www<dot>hgmp<dot>mrc<dot>ac<dot>uk/Software/EMBOSS/. The European Bioinformatics Institute server also provides the facility to perform EMBOSS-needle global alignments between two sequences on line at www<dot>ebi<dot>ac<dot>uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

A preferred method for calculating polynucleotide % sequence identity is based on aligning sequences to be compared using Clustal X (Jeanmougin et al., 1998, Trends Biochem. Sci. 23, 403-5.)

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ftp<dot>ncbi<dot>nih<dot>gov/blast/).

Alternatively, variant polynucleotides of the present invention hybridize to the specified polynucleotide sequences, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing). Tm for polynucleotide molecules greater than about 100 bases can be calculated by the formula Tm=81. 5+0. 41% (G+C-log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides of the present invention also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from NCBI (ftp<dot>ncbi<dot>nih<dot>gov/blast/) via the tblastx algorithm as previously described.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from NCBI (ftp<dot>ncbi<dot>nih<dot>gov/blast/). In one embodiment the default parameters of bl2seq are utilized. In a further except the default parameters of bl2seq are utilized, except that filtering of low complexity parts should be turned off.

Polypeptide sequence identity may also be calculated over the entire length of the overlap between a candidate and subject polynucleotide sequences using global sequence alignment programs. EMBOSS-needle (available www<dot>ebi<dot>ac<dot>uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

A preferred method for calculating polypeptide % sequence identity is based on aligning sequences to be compared using Clustal X (Jeanmougin et al., 1998, Trends Biochem. Sci. 23, 403-5.)

A variant polypeptide includes a polypeptide wherein the amino acid sequence differs from a polypeptide herein by one or more conservative amino acid substitutions, deletions, additions or insertions which do not affect the biological activity of the peptide. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagines, glutamine; serine, threonine; lysine, arginine; and phenylalanine, tyrosine.

Non-conservative substitutions will entail exchanging a member of one of these classes for a member of another class.

Analysis of evolved biological sequences has shown that not all sequence changes are equally likely, reflecting at least in part the differences in conservative versus non-conservative substitutions at a biological level. For example, certain amino acid substitutions may occur frequently, whereas others are very rare. Evolutionary changes or substitutions in amino acid residues can be modelled by a scoring matrix also referred to as a substitution matrix. Such matrices are used in bioinformatics analysis to identify relationships between sequences, one example being the BLOSUM62 matrix shown below (Table 1).

TABLE 1

The BLOSUM62 matrix containing all possible substitution scores [Henikoff and Henikoff, 1992].

| | A | R | N | D | C | Q | E | G | H | I | L | K | M | F | P | S | T | W | T | V |
|---|---|---|---|---|---|---|---|---|---|---|---|---|---|---|---|---|---|---|---|---|
| A | 4 | −1 | −2 | −2 | 0 | −1 | −1 | 0 | −2 | −1 | −1 | −1 | −1 | −2 | −1 | 1 | 0 | −3 | −2 | 0 |
| R | −1 | 5 | 0 | −2 | −3 | 1 | 0 | −2 | 0 | −3 | −2 | 2 | −1 | −3 | −2 | −1 | −1 | −3 | −2 | −3 |
| N | −2 | 0 | 6 | 1 | −3 | 0 | 0 | 0 | 1 | −3 | −3 | 0 | −2 | −3 | −2 | 1 | 0 | −4 | −2 | −3 |
| D | −2 | −2 | 1 | 6 | −3 | 0 | 2 | −1 | −1 | −3 | −4 | −1 | −3 | −3 | −1 | 0 | −1 | −4 | −3 | −3 |
| C | 0 | −3 | −3 | −3 | 9 | −3 | −4 | −3 | −3 | −1 | −1 | −3 | −1 | −2 | −3 | −1 | −1 | −2 | −2 | −1 |
| Q | −1 | 1 | 0 | 0 | −3 | 5 | 2 | −2 | 0 | −3 | −2 | 1 | 0 | −3 | −1 | 0 | −1 | −2 | −1 | −3 |
| E | −1 | 0 | 0 | 2 | −4 | 3 | 5 | −2 | 0 | −3 | −3 | 1 | −2 | −3 | −1 | 0 | −1 | −3 | −2 | −2 |
| G | 0 | −2 | 0 | −1 | −3 | −2 | −2 | 6 | −2 | −4 | −4 | −2 | −3 | −3 | −2 | 0 | −2 | −2 | −3 | −3 |
| H | −2 | 0 | 1 | −1 | −3 | 0 | 0 | −2 | −3 | −3 | −3 | −1 | −2 | −1 | −2 | −1 | −2 | −2 | 2 | −3 |
| I | −1 | −3 | −3 | −3 | −1 | −3 | −3 | −4 | −3 | 4 | 2 | −3 | 1 | 0 | −3 | −2 | −1 | −3 | −1 | 3 |
| L | −1 | −2 | −3 | −4 | −1 | −2 | −3 | −4 | −3 | 2 | −4 | −2 | 2 | 0 | −3 | −2 | −1 | −2 | −1 | 1 |
| K | −1 | 2 | 0 | −1 | −3 | 1 | 1 | −2 | −1 | −3 | −2 | 5 | −1 | −3 | −1 | 0 | −1 | −3 | −2 | −2 |
| M | −1 | −1 | −2 | −3 | −1 | 0 | −2 | −3 | −2 | 1 | 2 | −1 | 5 | 0 | −2 | −1 | −1 | −1 | −1 | 1 |
| F | −2 | −3 | −3 | −3 | −2 | −3 | −3 | −3 | −1 | 0 | 0 | −3 | 0 | 6 | −4 | −2 | −2 | 1 | 3 | −1 |
| P | −1 | −2 | −2 | −1 | −3 | −1 | −1 | −2 | −2 | −3 | −3 | −1 | −2 | −4 | 7 | −1 | −1 | −4 | −3 | −2 |
| S | 1 | −1 | 1 | 0 | −1 | 0 | 0 | 0 | −1 | −2 | −2 | 0 | −1 | −2 | −1 | 4 | 1 | −3 | −2 | −2 |
| T | 0 | −1 | 0 | −1 | −1 | −1 | −1 | −3 | −2 | −1 | −1 | −1 | −1 | −2 | −1 | 1 | 5 | −2 | −2 | 0 |
| W | −3 | −3 | −4 | −4 | −2 | −2 | −3 | −2 | −2 | −2 | −2 | −3 | −1 | 1 | −4 | −3 | −2 | 11 | 2 | −3 |
| Y | −2 | −2 | −2 | −3 | −2 | −1 | −2 | −3 | 2 | −1 | −1 | −2 | −1 | 3 | −3 | −2 | −2 | 2 | 7 | −1 |
| V | 0 | −3 | −3 | −3 | −1 | −2 | −2 | −3 | −3 | 3 | 1 | −2 | 1 | −1 | −2 | −2 | 0 | −3 | −1 | 4 |

The BLOSUM62 matrix shown is used to generate a score for each aligned amino acid pair found at the intersection of the corresponding column and row. For example, the substitution score from a glutamic acid residue (E) to an aspartic acid residue (D) is 2. The diagonal show scores for amino acids which have not changed. Most substitutions changes have a negative score. The matrix contains only whole numbers.

Determination of an appropriate scoring matrix to produce the best alignment for a given set of sequences is believed to be within the skill of in the art. The BLOSUM62 matrix in table 1 is also used as the default matrix in BLAST searches, although not limited thereto.

Other variants include peptides with modifications which influence peptide stability. Such analogs may contain, for example, one or more non-peptide bonds (which replace the peptide bonds) in the peptide sequence. Also included are analogs that include residues other than naturally occurring L-amino acids, e.g. D-amino acids or non-naturally occurring synthetic amino acids, e.g. beta or gamma amino acids and cyclic analogs Constructs, Vectors and Components thereof The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as *E. coli.*

The term "expression construct" refers to a genetic construct that includes the necessary elements that permit transcribing the insert polynucleotide molecule, and, optionally, translating the transcript into a polypeptide. An expression construct typically comprises in a 5' to 3' direction:

a) a promoter functional in the host cell into which the construct will be transformed,
b) the polynucleotide to be expressed, and
c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to non-transcribed cis-regulatory elements upstream of the coding region that regulate gene transcription. Promoters comprise cis-initiator elements which specify the transcription initiation site and conserved boxes such as the TATA box, and motifs that are bound by transcription factors.

A promoter may be homologous with respect to the polynucleotide to be expressed. This means that the promoter and polynucleotide are found operably linked in nature.

Alternatively the promoter may be heterologous with respect to the polynucleotide to be expressed. This means that the promoter and the polynucleotide are not found operably linked in nature.

A "transgene" is a polynucleotide that is introduced into an organism by transformation. The transgene may be derived from the same species or from a different species as the species of the organism into which the transgene is introduced. The transgene may also be synthetic and not found in nature in any species.

A "transgenic plant" refers to a plant which contains new genetic material as a result of genetic manipulation or transformation. The new genetic material may be derived from a plant of the same species as the resulting transgenic plant or from a different species, or may be synthetic.

Preferably the "transgenic plant" is different from any plant found in nature due the presence of the transgene.

An "inverted repeat" is a sequence that is repeated, where the second half of the repeat is in the complementary strand, e.g.,

```
                                        (SEQ ID NO: 142)
(5')GATCTA TAGATC(3')
                                        (SEQ ID NO: 143)
(3')CTAGAT ATCTAG(5').
```

Read-through transcription will produce a transcript that undergoes complementary base-pairing to form a hairpin structure provided that there is a 3-5 bp spacer between the repeated regions. The spacer can be any polynucleotide sequence but is typically at least 3 base pairs in length.

Host Cells

Host cells may be derived from, for example, bacterial, fungal, insect, mammalian or plant organisms.

Methods for Isolating or Producing Polynucleotides

The polynucleotide molecules of the invention can be isolated by using a variety of techniques known to those of ordinary skill in the art. By way of example, such polypeptides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides of the invention include use of all, or portions of, the polypeptides having the sequence set forth herein as hybridization probes. The technique of hybridizing labelled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5. 0×SSC, 0. 5% sodium dodecyl sulfate, 1×Denhardt's solution; washing (three washes of twenty minutes each at 55° C.) in 1. 0×SSC, 1% (w/v) sodium dodecyl sulfate, and optionally one wash (for twenty minutes) in 0. 5×SSC, 1% (w/v) sodium dodecyl sulfate, at 60° C. An optional further wash (for twenty minutes) can be conducted under conditions of 0. 1×SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence. Such methods include PCR-based methods, 5'RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, *Nucleic Acids Res* 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species.

Variants (including orthologues) may be identified by the methods described.

Methods for Identifying Variants

Physical Methods

Variant polypeptides may be identified using PCR-based methods (Mullis et al., Eds. 1994 The Polymerase Chain Reaction, Birkhauser). Typically, the polynucleotide sequence of a primer, useful to amplify variants of polynucleotide molecules of the invention by PCR, may be based on a sequence encoding a conserved region of the corresponding amino acid sequence.

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Polypeptide variants may also be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

Computer Based Methods

The variant sequences of the invention, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ftp<dot>ncbi<dot>nih<dot>gov/blast/) or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J.D., Higgins, D.G. and Gibson, T.J. (1994) CLUSTALW: improving the sensitivity of progressive multiple sequence alignment through sequence weighting, positions-specific gap penalties and weight matrix choice. Nucleic Acids Research, 22:4673-4680, www-igbmc<dot>u-strasbq<dot>fr/Biolnfo/ClustalW/Top<dot>html) or T-COFFEE (Cedric Notredame, Desmond G. Higgins, Jaap Heringa, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www<dot>expasy<dot>org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Isolating Polypeptides

The polypeptides of the invention, or used in the methods of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention, or used in the methods of the invention, may also be purified from natural sources using a variety of techniques that are well known in the art (e.g. Deutscher, 1990, Ed, Methods in Enzymology, Vol. 182, *Guide to Protein Purification*).

Alternatively the polypeptides and variant polypeptides of the invention, or used in the methods of the invention, may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Polynucleotides, Constructs or Vectors The invention provides a host cell which comprises a genetic construct or vector of the invention.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide of the invention, or used in the methods of the invention. Plants comprising such cells also form an aspect of the invention.

Methods for transforming plant cells, plants and portions thereof with polypeptides are described in Draper et al., 1988, Plant Genetic Transformation and Gene Expression. A Laboratory Manual. Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of plant transformation strategies are available (e.g. Birch, 1997, Ann Rev Plant Phys Plant Mol Biol, 48, 297, Hellens R P, et al (2000) Plant Mol Biol 42: 819-32, Hellens R et al Plant Meth 1: 13). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Genetic constructs for expression of genes in transgenic plants typically include promoters for driving the expression of one or more cloned polynucleotide, terminators and selectable marker sequences to detect presence of the genetic construct in the transformed plant.

The promoters suitable for use in genetic constructs may be functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues, respond to internal developmental signals or external abiotic or biotic stresses are described in the scientific literature. Exemplary promoters are described, e.g., in WO 02/00894, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenberg. Eds) Springer Verlag. Berline, pp. 325-336.

Gene Silencing

Transformation strategies may be designed to reduce expression of a polynucleotide/polypeptide in a plant cell, tissue, organ or at a particular developmental stage which/when it is normally expressed. Such strategies are known as gene silencing strategies.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide of the invention may include an antisense copy of a polynucleotide of the invention. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

| | |
|---|---|
| 5'GATCTA 3' (coding strand) | 3'CTAGAT 5' (antisense strand) |
| 3'CUAGAU 5' mRNA | 5'GAUCUCG 3' antisense RNA |

Genetic constructs designed for gene silencing may also include an inverted repeat. An 'inverted repeat' is a sequence that is repeated where the second half of the repeat is in the complementary strand, e.g.,

```
                                    (SEQ ID NO: 144)
5'-GATCTA . . . TAGATC-3'

                                    (SEQ ID NO: 145)
3'-CTAGAT . . . ATCTAG-5'.
```

The transcript formed may undergo complementary base pairing to form a hairpin structure. Usually a spacer of at least 3-5 bp between the repeated region is required to allow hairpin formation. Constructs including such invented repeat sequences may be used in RNA interference (RNAi) and therefore can be referred to as RNAi constructs.

Another silencing approach involves the use of a small antisense RNA targeted to the transcript equivalent to an miRNA (Llave et al., 2002, Science 297, 2053). Use of such small antisense RNA corresponding to polynucleotide of the invention is expressly contemplated.

The term genetic construct as used herein also includes small antisense RNAs and other such polypeptides effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve overexpression of the whole or a partial coding sequence but may also involve expression of non-coding region of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al., 1998, Planta 204: 499-505). The use of such sense suppression strategies to silence the expression of a polynucleotide of the invention is also contemplated.

The polynucleotide inserts in genetic constructs designed for gene silencing may correspond to coding sequence and/or non-coding sequence, such as promoter and/or intron and/or 5' or 3' UTR sequence, of the corresponding gene.

Other gene silencing strategies include dominant negative approaches and the use of ribozyme constructs (McIntyre, 1996, Transgenic Res, 5, 257).

Pre-transcriptional silencing may be brought about through mutation of the gene itself or its regulatory elements. Such mutations may include point mutations, frameshifts, insertions, deletions and substitutions.

Transformation Protocols

The following are representative publications disclosing genetic transformation protocols that can be used to genetically transform the following plant species: Rice (Alam et al., 1999, Plant Cell Rep. 18, 572); apple (Yao et al., 1995, Plant Cell Reports 14, 407-412); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9, : 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073 and 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792,935); soybean (U.S. Pat. Nos. 5,416, 011; 5,569,834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); *brassica* (U.S. Pat. Nos. 5,188,958; 5,463, 174 and 5,750,871); cereals (U.S. Pat. No. 6,074,877); pear (Matsuda et al., 2005, Plant Cell Rep. 24(1):45-51); *Prunus* (Ramesh et al., 2006 Plant Cell Rep. 25(8):821-8; Song and Sink 2005 Plant Cell Rep. 2006; 25(2):117-23; Gonzalez Padilla et al., 2003 Plant Cell Rep. 22(1):38-45); strawberry (Oosumi et al., 2006 Planta. 223(6):1219-30; Folta et al., 2006 Planta April 14; PMID: 16614818), rose (Li et al., 2003), *Rubus* (Graham et al., 1995 Methods Mol Biol. 1995; 44:129-33), tomato (Dan et al., 2006, Plant Cell Reports V25:432-441), apple (Yao et al., 1995, Plant Cell Rep. 14, 407-412) and *Actinidia eriantha* (Wang et al., 2006, Plant Cell Rep. 25, 5: 425-31), silver birch (Keinonen-Mettala et al., 1998, Plant Cell Rep. 17: 356-361.) and aspen (Nilsson O, et al., 1992, Transgenic Research. 1: 209-220). Transformation of other species is also contemplated by the invention. Suitable methods and protocols are available in the scientific literature.

Several further methods known in the art may be employed to alter expression of activity of a nucleotide and/or polypeptide of the invention. Such methods include but are not limited to Tilling (Till et al., 2003, Methods Mol Biol, 2%, 205), so called "Deletagene" technology (Li et al., 2001, Plant Journal 27(3), 235) and the use of artificial transcription factors such as synthetic zinc finger transcription factors. (e.g. Jouvenot et al., 2003, Gene Therapy 10, 513). Additionally antibodies or fragments thereof, targeted to a particular polypeptide may also be expressed in plants to modulate the activity of that polypeptide (Jobling et al., 2003, Nat. Biotechnol., 21(1), 35). Transposon tagging approaches may also be applied. Additionally peptides interacting with a polypeptide of the invention may be identified through technologies such as phase-display (Dyax Corporation). Such interacting peptides may be expressed in or applied to a plant to affect activity of a polypeptide of the invention. Use of each of the above approaches in alteration of expression of a nucleotide and/or polypeptide of the invention is specifically contemplated.

The terms "to alter expression of" and "altered expression" of a polynucleotide or polypeptide of the invention, or used in the methods of the invention, are intended to encompass the situation where genomic DNA corresponding to a polynucleotide of the invention is modified thus leading to altered expression of a polynucleotide or polypeptide of the invention. Modification of the genomic DNA may be through genetic transformation or other methods known in the art for inducing mutations. The "altered expression" can be related to an increase or decrease in the amount of messenger RNA and/or polypeptide produced and may also result in altered activity of a polypeptide due to alterations in the sequence of a polynucleotide and polypeptide produced.

Methods of Selecting Plants

Methods are also provided for selecting plants with increased root biomass. Such methods involve testing of plants for altered for the expression of at least one PEAPOD polynucleotide or polypeptide, including those as defined or disclosed herein. Such methods may be applied at a young age or early developmental stage when the increased root biomass characteristics may not necessarily be easily measurable.

The expression of a polynucleotide, such as a messenger RNA, is often used as an indicator of expression of a corresponding polypeptide. Exemplary methods for measuring the expression of a polynucleotide include but are not limited to Northern analysis, RT-PCR and dot-blot analysis (Sambrook et al., Molecular Cloning: A Laboratory Manual, 2nd Ed. Cold Spring Harbor Press, 1987). Polynucleotides or portions of the polynucleotides of the invention are thus useful as probes or primers, as herein defined, in methods for the identification of plants with increased root biomass. The polynucleotides of the invention, or disclosed herein, may be used as probes in hybridization experiments, or as primers in PCR based experiments, designed to identify such plants.

Alternatively antibodies may be raised against PEAPOD polypeptides as described or disclosed herein. Methods for raising and using antibodies are standard in the art (see for example: Antibodies, A Laboratory Manual, Harlow A Lane, Eds, Cold Spring Harbour Laboratory, 1998). Such antibodies may be used in methods to detect altered expression of such polypeptides. Such methods may include ELISA (Kemeny, 1991, A Practical Guide to ELISA, NY Pergamon Press) and Western analysis (Towbin & Gordon, 1994, J Immunol Methods, 72, 313).

These approaches for analysis of polynucleotide or polypeptide expression and the selection of plants with increased root biomass are useful in conventional breeding programs designed to produce varieties with such altered characteristics.

Plants

The term "plant" is intended to include a whole plant, any part of a plant, propagules and progeny of a plant.

The term 'propagule' means any part of a plant that may be used in reproduction or propagation, either sexual or asexual, including seeds and cuttings.

The plants of the invention may be grown and either self-ed or crossed with a different plant strain and the resulting hybrids, with the desired phenotypic characteristics, may be identified. Two or more generations may be grown to ensure that the subject phenotypic characteristics are stably maintained and inherited. Plants resulting from such standard breeding approaches also form an aspect of the present invention.

Control of Plant Growth and Development by Gibberellins (GA), Brassinosteroids (BR) and other Plant Hormones Gibberellins (GA) and Brassinosteroids (BR) are two classes of plant hormones; between them they are involved in many aspects of plant morphogenesis and growth; including: seed germination, cell elongation, vascular development, see size, leaf erectness, flowering, leaf and fruit senescence (Mathew et al 2009, NZJAR 52, 213-225; Hou et al 2010, Developmental Cell 19, 884-894; Jiang and Lin 2013, Plant Signaling and Behaviour 8:10, e25928).

Given their roles in plant development the ability to manipulate either the levels of GA and BR or their downstream targets is highly desirable in terms of improving both yield and quality in many plant species. Indeed there are some commercial examples where exogenous applications of either hormone are used to improve agronomic value.

GA can be applied to ryegrass pasture to stimulate out-of-season growth as well as promote flowering (Mathew et al 2009, NZJAR 52, 213-225), it can also be used to counteract the adverse effects of cooler temperatures on sugarcane (a tropical C4 grass). GAs are also used to enlarge fruit size of seedless grapes and cherries, to promote fruit set in apple and pear and to delay rind-aging in particular citrus crops (Sun 2011, Current Biology 21, R338-R345). Similarly, BR preparations are recommended for improving crop yield and quality of tomato, potato, cucumber, pepper and barley, rice, maize, wheat, cotton, and tobacco (Prusakova et al 1999, Agrarian Russia, 41-44; Khripach et al 2000, Annals of Botany 86, 441-447; Anjum et al 2011, J. Agronomy Crop Sci. 197, 177-185; Vardhini 2012, J. Phytology 4, 1-3). However, the low adoption of commercially applied brassinosteroids may reflect the cost and the fact that plants do not efficiently absorb steroids when they are applied exogenously. In addition, the need to strictly control timing and concentration of exogenous supplied GA and BR limits their applications.

For the most part the GA and BR biosynthesis and catabolic pathways in angiosperms have been characterized and include negative regulators and downstream transcription factor targets. Upon binding GA or BR to their respective receptor a complex signal pathway ensues and in both cases a central point of regulation involves the ubiquitin—proteasome pathway altering the level of the negative regulator DELLA (in the case of GA) and the transcriptional regulator BZR1 (in the case of BR).

The removal of DELLA proteins results in the removal of growth repression and promotion of GA-responsive growth and development. Conversely the detection of BR leads to the accumulation of unphosphorylated BZR1 protein in the nucleus. Dephosphorylation of BZR1 prevents its degradation by the proteasome and instead allows the binding of BZR1 with other DNA binding transcription factors and interacts with transcriptional cofactors. This leads to the regulation of thousands of genes involved in growth and other cellular processes, including the inhibition of expression of BR biosynthetic genes (He et al 2005, Science 307, 1634-1638; Guo et al 2013, Current Opinion Plant Biol. 16, 545-553).

There are a number of endogenous signals and environmental cues that influence the GA-GID1-DELLA regulatory module in which DELLA integrates different signalling activities by direct protein-protein interaction with multiple key regulatory proteins from other pathways. As such DELLA proteins are master growth repressors that control plant growth and development by integrating internal signals from other hormone pathways (auxin, abscisic acid, jasmonic acid and ethylene), and external biotic (pathogen) and abiotic (light conditions, cold and salt stresses) cues (Sun 2011, Current Biology 21, R338-R345). Drought is one of the most important environmental constraints limiting plant growth and agricultural productivity. Unsurprisingly, there is a positive correlation between improved drought tolerance with a more extensive root system including deeper roots and more lateral roots both of which enable soil exploration and below-ground resources acquisition (Yu et al 2008, Plant Cell 20, 1134-1151; Werner et al 2010, Plant Cell 22, 3905-3920). Thus it follows that a common agricultural target is the optimization of root system architecture in order to help overcome yield limitations in crop plants caused by water or nutrient shortages. However, of all the abiotic stresses that curtail crop productivity, drought is the most devastating one and the most recalcitrant to breeder's efforts. Classic breeding approaches are difficult because the trait is governed by many genes and is difficult to score (Werner et al 2010, Plant Cell 22, 3905-3920). While marker-assisted selection (MAS), quantitative trait loci (QTL) and other genomic approaches are being widely used to assist breeding efforts to produce drought-resilient cultivars (Tuberosa and Salvi, 2006, Trends in Plant Science, 11:405-412) the system is limited to the variation present in the screening population.

Interestingly, rice has only one DELLA protein (SLR1), Maize has two (d8 and d9)(Lawit et al 2010, Plant Cell Physiol 51, 1854-1868) while *Arabidopsis* has five (GA1, RGA, RGL1, RGL2 and RGL3) (Achard and Genschik 2009, J. Exp. Bot. 60, 1085-1092). Furthermore, in a recent phylogenetic analysis Chen et al 2013 found five out of the six grass species they analysed had only a single DELLA while 14 out of the 18 dicot species had two or more DELLA proteins. In contrast, there are 6 members of the BZR family in rice, 10 in maize (www<dot>Grassius<dot>org) and 6 in *Arabidopsis* (Wang et al 2002, Developmental Cell 2, 505-513).

The growth and development of plants relies on numerous connections between signalling pathways that provides the high developmental plasticity demanded by their sessile life habit (Gallego-Bartolome et al 2012, PNAS 109, 13446-13451). Thus rather than each hormone-signalling pathway existing as an insulated module current evidence indicates that there is a high degree of interaction between different pathways and that a given hormone frequently modulates the output triggered by the rest. By example, it has recently been shown that the cross talk between the GA and BR signalling pathways involves direct interaction between DELLAs and BZR1/BES1 whereby DELLA proteins not only affect the protein stability but also inhibit the transcriptional activity of BZR1 (Li and He 2013, Plant Signaling and Behaviour 8:7, e24686 and references therein). Thus the promotion of cell elongation by GA is partly through the removal of the DELLA-mediated inhibition of BZR1.

It has recently been demonstrated that plant growth and development can be modified through direct manipulation of the master growth regulators DELLA (Lawit, Kundu, Rao and Tomes, 2007, ISOLATED POLYNUCLEOTIDE MOLECULES CORRESPONDING TO MUTANT AND WILD-TYPE ALLELES OF THE MAIZE D9 GENE AND METHODS OF USE, WO 2007124312 A2) and BZR1 (Chory and Wang, 2005, GENES INVOLVED IN BRASSINOSTEROID HORMONE ACTION IN PLANTS, U.S. Pat. No. 6,921,848 B2).

Steroid hormones play an essential role in the coordination of a wide range of developmental and physiological processes in both plants and animals (Thummel and Chory 2002, Genes Dev. 16, 3113-3129). In plants the steroid hormone brassinosteroid (BR) has extensive effects on growth, development and responses to both biotic and abiotic stresses (Zhu et al 2013, Development 140, 1615-1620; Clouse 2011, Plant Cell 23, 1219-1230). In contrast to animal steroid hormone signalling, which functions through nuclear receptors, in plants BRs bind to the extracellular domain of the cell surface receptor kinase BRASSINOSTEROID INSENSITIVE 1 (BRI1) and activate an intracellular signal transduction cascade that regulates gene expression (Clouse 2011, Plant Cell 23, 1219-1230; Kinoshita et al 2005, Nature 433, 167-171). There are multiple steps involving activation and inactivation of intermediates leading to the phosphorylation of two transcription factors, BRASSINAZOLE RESISTANT 1 (BZR1) and BZR2 (also known as BES1). Thus the signal transduction BZR transcription factors are the target components converting signalling into BR responsive gene expression.

There is an emerging pattern in plant hormone signalling where the target transcription factors activated by hormones are also negatively regulated by specific repressor complexes. For example, in the jasmonic acid (JA), auxin, abscisic acid (ABA) and strigolactone (SL) signalling pathways the target transcription factors are negatively regulated by repressor complexes utilising TOPLESS (TPL) as a common co-repressor recruited by a hormone pathway specific repressor (Pauwels et al 2010, Nature 464, 788-791). In the JA transduction pathway the JASMONATE ZIM DOMAIN (JAZ) family of transcriptional repressors both interact with the target JA-responsive transcriptional activator MYC2 and recruit TPL, either directly or via the adaptor protein NOVEL INTERACTOR OF JAZ (NINJA) (Pauwels et al 2010 Nature 464, 788-791).

Accordingly, the ability to regulate the GA and BR pathways to influence many different agricultural traits of interest is of considerable value to commercial agriculture.

The Applicant's Invention

As discussed above, the present invention relates to a method for increasing root biomass in plants by ectopic expression of PEAPOD.

Without wishing to be bound by theory, the applicants have shown that PEAPOD (PPD) appears to be involved in the modulation of both the GA and BR pathways either through directly or indirect interaction with the master growth regulators DELLA and BZR.

Analysis of the primary amino add structure of PPD proteins indicates the presence of a highly conserved novel plant specific domain present only these proteins. There are homologues of PPD in a wide range of eudicot, conifers and some monocot plants (palms, banana, orchids, duckweed) but not Poaceae (grasses).

The PPD genes of *Arabidopsis* encode proteins that are members of the plant-specific TIFY family, named after the core TIF[F/Y]XG (SEQ ID NO: 146) motif found within a domain known as ZIM (Vanholme et al 2007 Trends Plant Sci. 12, 239-244). The two *Arabidopsis* PPD proteins, PPD1 and PPD2, are included in the same class II TIFY group as twelve well characterised JAZ proteins that act as repressors of jasmonate responses. However, the PPD proteins and the one other non-JAZ protein in the group do not appear to be involved in responses to jasmonate hormone signalling (Pauwels et al 2010 Nature 464, 788-791).

Again, without wishing to be bound by theory, the applicants propose that the increases in root biomass, according to the invention, are mediated by a new mechanism for regulating both the GA and BR pathways using the PPD gene. Examples 3 and 4 below support this proposal, This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

The present invention will be better understood with reference to the accompanying drawings in which are described as follows:

FIG. 1 shows the 46 amino acid residues comprising the PEAPOD region from a range of plant species, identical residues are shown by an asterisk.

FIG. 2 shows the internal 27 amino acid residues within the PEAPOD region from a range of plant species, identical residues are shown by an asterisk.

FIG. 3 shows the 6 amino acid residues of the TIFY domain on PEAPOD proteins from a range of plant species, identical residues are shown by an asterisk.

EXAMPLES

Figure 4:
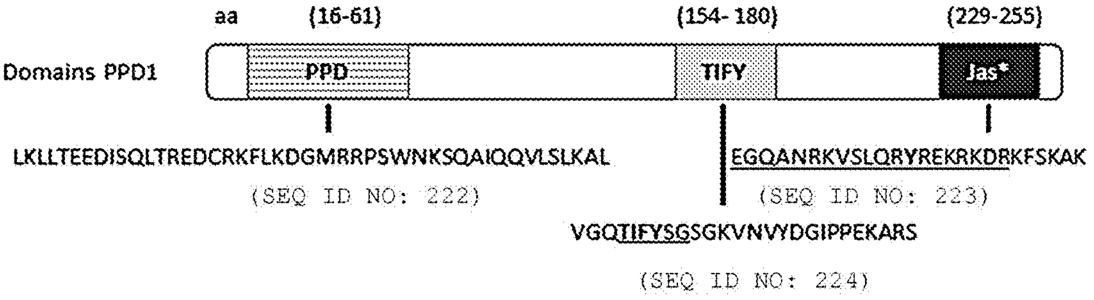
FIG. 4 shows a schematic representation of the PPD protein and the approximate location of conserved PPD, TIFY and Jas* regions

The invention will now be illustrated with reference to the following non-limiting example.

Example 1

Characterisation of PEAPOD Genes Multiple Plant Species

To identify PPD gene orthologues in other plant species the conserved PPD region (46 amino acids) from the *Arabidopsis* PPD1 gene (SEQ ID NO: 27) was used for searches of public plant gene sequence databases using the search programmes TBLASTN and BLASTP (Altschul et al 1990). PEAPOD sequences were identified from a diverse range of plant species including the mosses, conifers, all orders of dicotyledonous examined and some of the monocotyledonous orders, including: palms, bananas, orchids and duckweed. PEAPOD sequences are not found in the grasses. Representative PEAPOD protein and nucleic acid sequences are shown in SEQ ID NO: 1-26 and SEQ ID NO:83-107 respectively.

The 46 amino acid PEAPOD region from *Arabidopsis thaliana* PPD1 is shown in SEQ ID NO:27. This region from polypeptides SEQ ID NO: 1-26 was aligned by vector NTI (VNTI) as shown in FIG. 1.

SEQ ID NO:28 shows the consensus for this 46 amino acid PPD region. SEQ ID NO:29 shows the same consensus region but shows which amino acids can be present at each of the variable positions.

A 27 amino acid subsequence from within the 46 amino acid PEAPOD region from *Arabidopsis thaliana* PPD1 is shown in SEQ ID NO:30.

Alignment of this 27 amino acid subsequence for reach of the same sequences as in FIG. 1, is shown in FIG. 2.

SEQ ID NO:30 shows the consensus for this 27 amino acid PPD region. SEQ ID NO:32 shows the same consensus region but shows which amino acids can be present at each of the variable positions.

In each of the PPD peptide sequences of SEQ ID NO: 1-26 there is also a conserved TIFY motif which is located after the 46 amino acid PPD region. The number of amino acid residues separating the C-terminus of the PPD region and the N-terminus of the TIFY motif depends on the source of the PPD; for example the number varies between 46 to 140 amino acids for SEQ ID NO:1-26.

SEQ ID NO: 33 shows the *Arabidopsis* PPD1 sequence over the TIFY motif. The alignment of the TIFY motif (as described by Vanholme et al 2007 Trends Plant Sci. 12, 239-244) from SEQ ID NO:1-26 is shown in FIG. 3.

SEQ ID NO:34 shows the consensus for this 6 amino acid TIFY motif. SEQ ID NO:35 shows the same consensus region but shows which amino acids can be present at each of the variable positions.

Completely conserved residues in the PPD and TIFY domains are highlighted with asterisks in FIGS. 1-3.

The applicants assert that these regions and motifs described above are found in all PEAPOD proteins identified and are diagnostic for such PEAPOD proteins

Example 2

Demonstrating PEAPOD Functionality of PEAPOD Sequences from Multiple Plant Species The functionality of any PEAPOD sequence can be confirmed by complementation of the *Arabidopsis* Δppd mutant leaf phenotype. Complementation of the *Arabidopsis* Δppd mutant leaf phenotype was first used to identify the *Arabidopsis* PPD gene (White 2006). This was seen by a restoration of the wild type flattened leaf phenotype and normal rosette shape as opposed to the domed leaf and the twisting of the rosette to a "propeller" phenotype.

PEAPOD sequences, such as those of SEQ IN NO: 1-26 (including: palm, conifer, moss, orchid and other dicot species) or any other PEAPOD sequence to be tested can be transformed into the *Arabidopsis* Δppd mutant by methods well known to those skilled in the art. An example of such a method is described below.

Cloning and Gene Constructs

Generation of CaMV35s:: *Arabidopsis thaliana* PPD1 Construct for over Expression of *Arabidopsis* PPD1 in the *Arabidopsis* Δppd Mutant An expression construct was synthesised to enable the over expression of *Arabidopsis thaliana* PPD1 under the CaMV35s promoter (SEQ ID NO.129) in the *Arabidopsis* Δppd mutant. The PPD ORF was optimised for expression in *Arabidopsis*; this included a modified Joshi sequence (Joshi 1997, Nucleic Acid Research 15, 6643-6653), optimisation of condons, removal of mRNA instability sequences, removal of polyA signal sequences, removal of cryptic splice sites, addition of a BamHI removable C-terminal V5 epitope and His tag tail (encoding SEQ ID NO:37) and addition of a double stop codon. The construct (with and without the tail) was then placed between the CaMV35s promoter and ocs terminator by the GATEWAY® LR reaction, which coded for SEQ ID NO:105 and SEQ ID NO:111 respectively.

Generation of CaMV35s:: *Trifolium repens* PPD Construct for over Expression of *Trifolium repens* PPD1 in the *Arabidopsis* Δppd Mutant An expression construct was synthesised to enable the over expression of *Trifolium repens* PPD under the CaMV35s promoter (SEQ ID NO. 129) in the *Arabidopsis* Δppd mutant. The PPD ORF was optimised for expression in *Arabidopsis*; this included a modified Joshi sequence (Joshi 1997, Nucleic Acid Research 15, 6643-6653), optimisation of condons, removal of mRNA instability sequences, removal of polyA signal sequences, removal of cryptic splice sites, addition of a BamHI removable C-terminal V5 epitope and His tag tail (encoding SEQ ID NO:37) and addition of a double stop codon. The construct (with and without the tail) was then placed between the CaMV35s promoter and ocs terminator by the GATEWAY® LR reaction, which coded for SEQ ID NO:106 and SEQ ID NO:112 respectively.

Generation of CaMV35s:: *Amborella trichopoda* PPD Construct for over Expression of *Amborella trichopoda* PPD in the *Arabidopsis* Δppd Mutant An expression construct was synthesised to enable the over expression of *Amborella trichopoda* PPD under the CaMV35s promoter (SEQ ID NO. 129) in the *Arabidopsis* Δppd mutant. The PPD ORF was optimised for expression in *Arabidopsis*; this included a modified Joshi sequence (Joshi 1997, Nucleic Acid Research 15, 6643-6653), optimisation of condons, removal of mRNA instability sequences, removal of polyA signal sequences, removal of cryptic splice sites, addition of a BamHI removable C-terminal V5 epitope and His tag tail (encoding SEQ ID NO:37) and addition of a double stop codon. The construct (with and without the tail) was then placed between the CaMV35s promoter and ocs terminator by the GATEWAY® LR reaction, which coded for SEQ ID NO:107 and SEQ ID NO:113 respectively.

Generation of CaMV35s:: *Musa acuminate* PPD Construct for over Expression of *Musa acuminate* PPD in the *Arabidopsis* Δppd Mutant An expression construct was synthesised to enable the over expression of *Musa acuminate* PPD under the CaMV35s promoter (SEQ ID NO. 129) in the *Arabidopsis* Δppd mutant. The PPD ORF was optimised for expression in *Arabidopsis*; this included a modified Joshi sequence (Joshi 1997, Nucleic Acid Research 15, 6643-6653), optimisation of condons, removal of mRNA instability sequences, removal of polyA signal sequences, removal of cryptic splice sites, addition of a BamHI removable C-terminal V5 epitope and His tag tail (encoding SEQ ID NO:37) and addition of a double stop codon. The construct (with and without the tail) was then placed between the CaMV35s promoter and ocs terminator by the GATEWAY® LR reaction, which coded for SEQ ID NO:108 and SEQ ID NO:114 respectively.

Generation of CaMV35s:: *Picea sitchensis* PPD1 Construct for over Expression of *Picea sitchensis* PPD in the *Arabidopsis* Δppd Mutant An expression construct was synthesised to enable the over expression of *Picea sitchensis* PPD under the CaMV35s promoter (SEQ ID NO. 129) in the *Arabidopsis* Δppd mutant. The PPD ORF was optimised for expression in *Arabidopsis*; this included a modified Joshi sequence (Joshi 1997, Nucleic Acid Research 15, 6643-6653), optimisation of condons, removal of mRNA instability sequences, removal of polyA signal sequences, removal of cryptic splice sites, addition of a BamHI removable C-terminal V5 epitope and His tag tail (encoding SEQ ID NO:37) and addition of a double stop codon. The construct (with and without the tail) was then placed between the CaMV35s promoter and ocs terminator by the GATEWAY® LR reaction, which coded for SEQ ID NO:109 and SEQ ID NO:115 respectively.

Generation of CaMV35s:: *Selaginella moellendorffii* PPD1 Construct for over Expression of *Selaginella moellendorffii* PPD in the *Arabidopsis* Δppd Mutant An expression construct was synthesised to enable the over expression of *Selaginella moellendorffii* PPD under the CaMV35s promoter (SEQ ID NO. 129) in the *Arabidopsis* Δppd mutant. The PPD ORF was optimised for expression in *Arabidopsis*; this included a modified Joshi sequence (Joshi 1997, Nucleic Acid Research 15, 6643-6653), optimisation of condons, removal of mRNA instability sequences, removal of polyA signal sequences, removal of cryptic splice sites, addition of a BamHI removable C-terminal V5 epitope and His tag tail (encoding SEQ ID NO:37) and addition of a double stop codon. The construct (with and without the tail) was then placed between the CaMV35s promoter and ocs terminator by the GATEWAY® LR reaction, which coded for SEQ ID NO:110 and SEQ ID NO:116 respectively.

Plant Materials and Growth Conditions

*Arabidopsis thaliana* (L.)Heynh ecotype Ler can be used as wild-type (WT). The Δppd loss of function deletion mutant (with PPD1 and PPD2 deleted) is as previously described in White 2006 PNAS 103, 13238-13243.

Plants are grown in a temperature-controlled glasshouse at a continuous 21° C. or in a controlled environment cabinet at 23° C. in 16-h light_8-h dark cycles.

Transformation of *Arabidopsis*

Constructs above can be transformed into *Arabidopsis* by the floral dip infiltration method (Clough and Bent, 1998 Plant J 16, 735-43). The Δppd line is transformed to express the PPD polypeptides by standard techniques. Transgenic plants are confirmed by standard PCR analysis techniques with a combination of transgene-specific and T-DNA primers.

Complementation of the Δppd line to produce a wild-type leaf and rosette phenotype in T1 seedlings (the off-spring of the infiltrated plant) confirms PEAPOD functionality of the introduced gene, which can be shown in photographs.

This approach can be use to confirm the PEAPOD functionality of any gene which the applicant asserts, demonstrates it suitability of use in the present invention.

Figure 13:
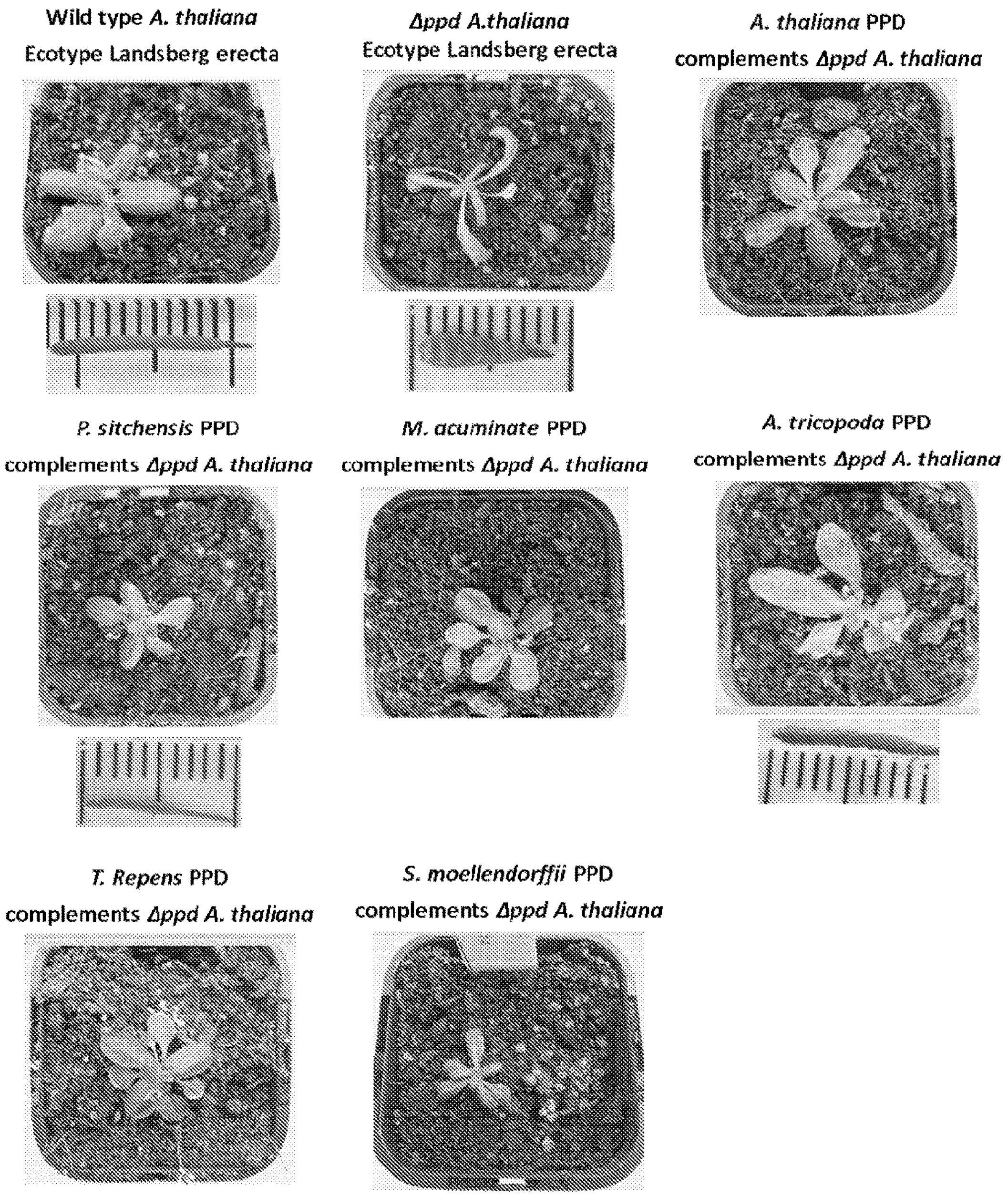
FIG. 13 shows that the PEAPOD proteins from *Arabidopsis thaliana; Picea sitchensis, Amborella trichopoda, Musa acuminate, Trifolium repens* and *Selaginella moellendorffii* are functionally equivalent. An optimized PEAPOD coding sequence from each was used to complement the PEAPOD deletion mutant Δppd *Arabidopsis thaliana* (ecotype *Landsberg erecta*). Seedling images were taken at an equivalent developmental stage.

The PEAPOD proteins from *Arabidopsis thaliana; Picea sitchensis, Amborella trichopoda, Musa acuminate*, and *Selaginella moellendorffii* were shown to be functionally equivalent by the complementation of the PEAPOD deletion mutant Δppd *Arabidopsis thaliana* ecotype *Landsberg erecta* (FIG. 13).

Example 3

PEAPOD may be Involved in Regulating the Brassinosteroid Signalling Pathway

The applicants used yeast two hybrid (Y2H) assays Bimolecular fluorescence (BiFC) to investigate the interactions between PPD, NINJA, TPL and BZR1.

Cloning and Constructs

The constructs for Y2H and BiFC assays were generated as follows. *Arabidopsis* DNA sequences encoding the open reading frames for; At4g14713 (PPD1) and truncation and deletion derivatives of PPD1: PPD1; PPD1Δppd (N-terminal truncation of sequences encoding aa 1-61), PPD1Δtify, (internal deletion of sequences encoding aa 154-186), PPD1Δjas*(C-terminal truncation of sequences encoding aa 229-313) (FIG. 4), At4g28910 (NINJA), At1g15750 (TPL), At1g75080 (BZR1), a synthetic PUAS-35S promoter, and sequences encoding GAL4DBD and c-myc fusion proteins were synthesised and sequence verified by GeneArt. Most sequences were supplied as clones in pENTR221 ready for Gateway cloning into yeast and plant expression vectors. The exception, a promoter sequence for in planta transcription activation assays, incorporating 5' Xho1 and 3' Nco1 restriction enzyme sites, was supplied cloned in pMA-RQ. Plasmids for the transient LUC reporter assay: A synthetic promoter with 5×UAS GAL4 DNA binding sites upstream of a −105 bp CaMV35S promoter was cloned into the XhoI-NcoI sites within a dual luciferase construct pNWA62, which contains an intron-containing Firefly Luciferase gene (LUC) and 35Spro::*Renilla* Luciferase (REN) as an internal standard, to construct pAML7. For the over expression of GAL4DBD fusion proteins DNA sequences encoding a GAL4 DNA-binding domain (GAL4DBD aa 1-147) and N-terminal GAL4DBD fusions (using a linker encoding GGGGS) with 2× the VP16 activator domain (GAL4DBD-VP16) or PPD1 (GAL4DBD-PPD1), were cloned using Gateway technology into pRSh1 (Winichayakul et al 2008) to construct vectors pRSh1-GAL4DBD, pRSh1-GAL4DBD-VP16, and pRSh1-GAL4DBD-PPD1 for expression of the fusion proteins in planta.

Plasmids for Yeast Two-hybrid Analysis

Full length coding sequences of BZR1, NINJA, TPL, and PPD1, together with truncation or deletion derivatives of PPD1 (PPD1Δppd, PPD1Δtify, and PPD1.4jas*), were Gateway sub-cloned into pDEST32 (N-terminal GAL4DBD) or pDEST22 (N-terminal GAL4AD), to construct pDEST32-PPD1, pDEST32-PPD1Δppd, pDEST32-PPD1Δtify, pDEST32-PPD1.4jas*, pDEST32-TPL, as bait vectors and pDEST22-PPD1, pDEST22-BZR1, and pDEST22-NINJA as prey vectors. When expressed these constructs produced proteins listed in SEQ ID NO: 56-67, and 70-72; including: DNA binding domain (DBD), activation domain (AD), PPD1 fused to DBD (PPD1-DBD), PPD1 fused to AD (PPD1-AD), PPD1 with no TIFY domain fused to AD (PPD1-tify-AD), PPD1 with no jas domain fused to AD (PPD1-jas*-AD), TOPLESS (TPL), TPL fused to DBD (TPL-DBD), NINJA, NINJA fused to AD (NINJA-AD), BZR1 fused to AD (BZR1-AD), PPD1 minus the ppd domain fused to DBD (PPD1-Δppd-DBD), PPD1 minus the TIFY domain fused to DBD (PPD1-tify-DBD), PPD1 minus the jas domain fused to DBD (PPD1-jas*-DBD).

Plasmids for Bimolecular Fluorescence Complementation

The binary BiFC-Gateway YFP vectors pDEST-VYNE (R)$^{GW}$ (Venus aa 1-173) and pDEST-VYCE(R)$^{GW}$ (Venus aa 156-239) with N-terminal fusions, were used to construct the following vectors; pDESTnYFP-BZR1, pDESTnYFP-NINJA, pDESTnYFP-PPD1, pDESTcYFP-BZR1, pDEST-cYFP-PPD1, pDESTcYFP-PPD1Δppd, pDESTcYFP-PPD1Δtify and pDESTcYFP-PPD1Δjas*. For transient in planta expression of proteins interacting with PPD1 or BZR, NINJA and TPL were Gateway® sub-cloned into pRSh1, to construct pRSh1-NINJA and pRSh1-TPL. Plasmids for co-immunoprecipitation: A synthesised DNA construct encoding PPD1 with a 3×c-myc C-terminal fusion was sub-cloned into pRSh1 to produce pRSh1-PPD1-3×c-myc, while the NINJA cDNA sequence was sub-cloned into pB7FWG2,0 (Karimi et al 2002, Trends Plant Sci. 7, 193-195) to construct pB7FWG2-NINJA-GFP. When expressed these constructs produced proteins listed in SEQ ID NO: 63, 65, 73-82: including TOPLESS (TPL), NINJA, Bimolecular Fluorescence (BiFC) nYFP, BiFC cYFP, BiFC nYFP-NINJA, BiFC nYFP-BZR1, BiFC cYFP-PPD1, BiFC cYFP-NINJA, BiFC cYFP-BZR1, BiFC cYFP-PPD1-ppd, BiFC cYFP-PPD1-tify, BiFC cYFP-PPD1-jas*.

The ProQuest two-hybrid system (Invitrogen) was used to analyse interactions between PPD1, NINJA, TPL, and BZR1. Combinations of bait and prey constructs were used to co-transform yeast strain MaV203 (Invitrogen), with selection on synthetic dropout (SD) SD/-Leu/-Trp agar plates. Transformed strains were tested for interactions using 10 μl droplets of 1 in 10 and 1 in 100 dilutions on SD/-Leu/-Trp/-His plates with different concentrations of 3-aminotriazol (3-AT) (Sigma).

Transient BiFC experiments were performed using combinations of pDESTnYFP and pDESTcYFP plasmids, with or without plasmids for the expression of NINJA (pRSh1-NINJA) or TPL (pRSh1-TPL) and *Agrobacterium*-infiltration of *Nicotiana benthamiana* leaves. For infiltration *Agrobacterium tumefaciens* GV3101 strains containing the binary vectors were re-suspended from plates and prepared for transformation as described for the LUC assay. All YFP and expression strains were mixed in ratios of 1:1 (vol/vol) with the addition of strain P19 at 1/10th volume. Five leaf discs were sampled from each infiltrated leaf after 40 h. Two hours prior to sampling for microscopic fluorescence observations leaves were infiltrated with a 1 μg/ml DAPI solution to stain nuclei. YFP fluorescence and DAPI staining was detected using an Olympus Fluoview FV10i confocal laser scanning microscope. Each experiment was repeated twice.

Figure 5:
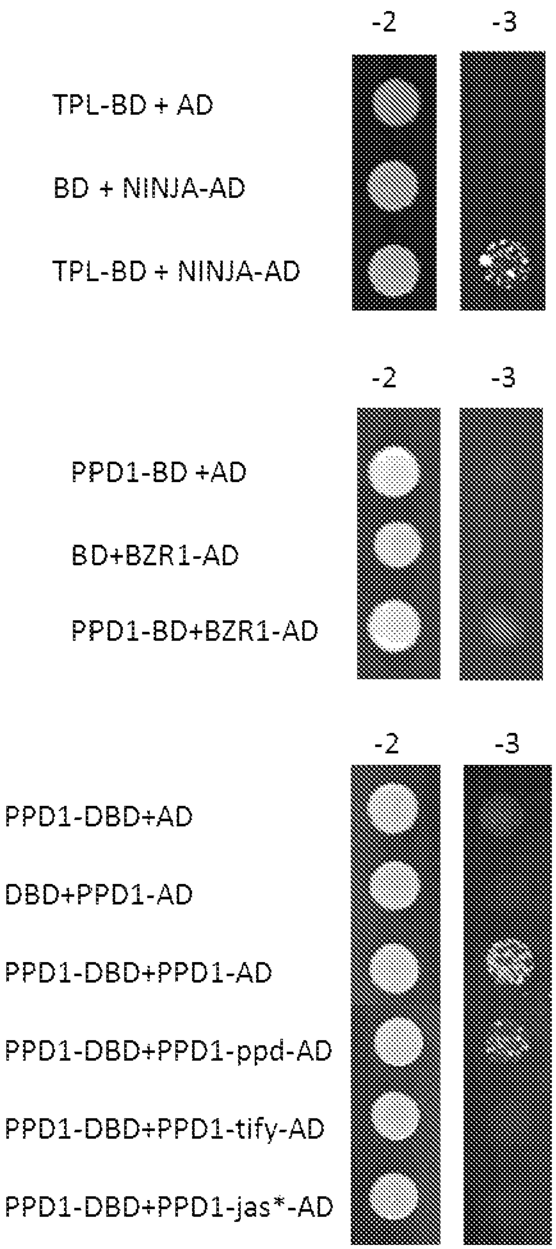
FIG. 5 shows the dimerization of PPD and the interaction between TPL and NINJA in Y2H assays.
Figure 6:
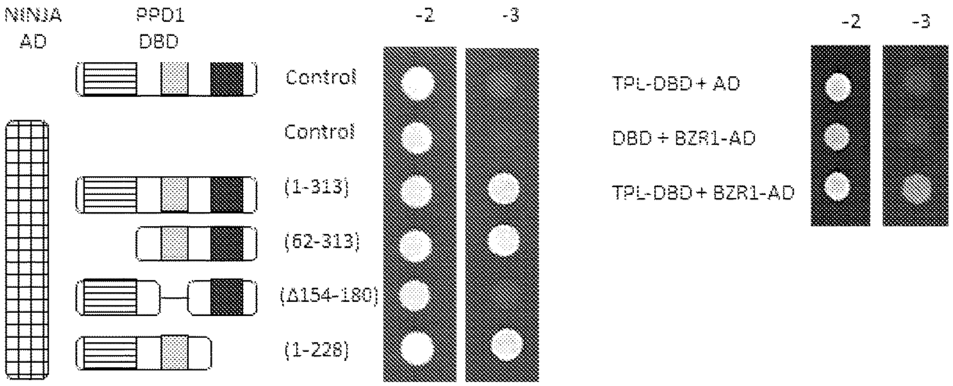
FIG. 6 shows the interaction between PPD and NINJA and the interaction between TPL and BZR1 in Y2H assays.
Figure 7:
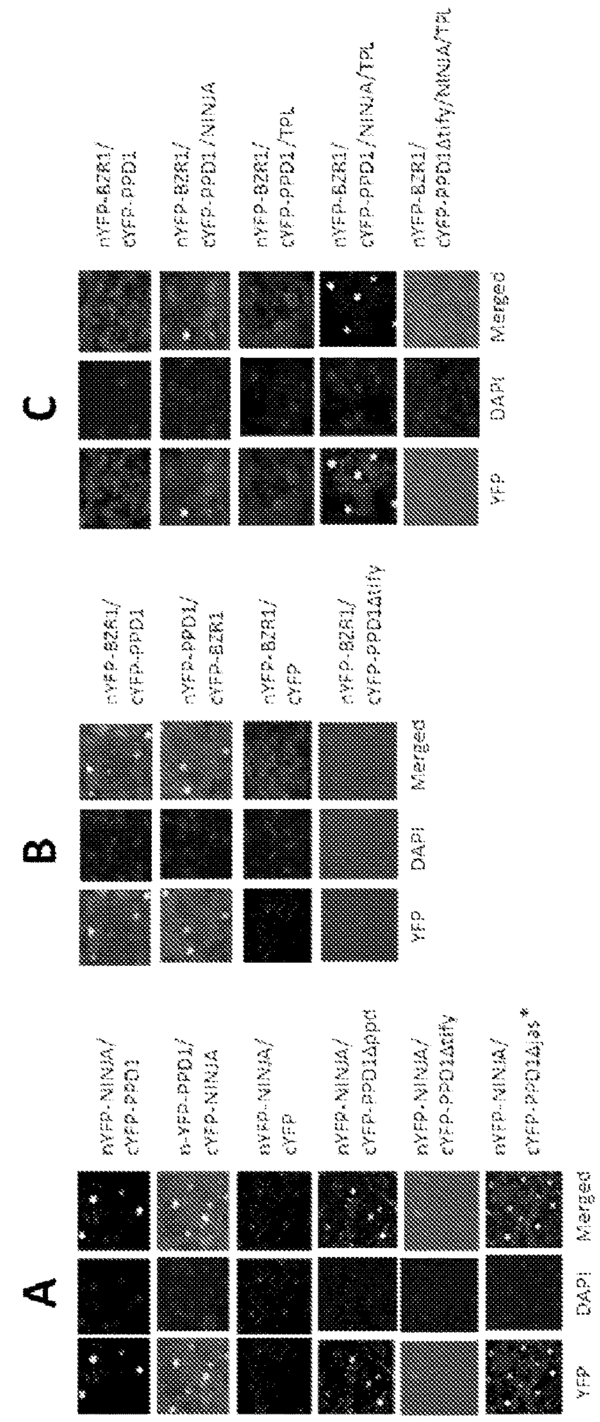
FIG. 7 shows the interaction between PPD, NINJA, TPL and BZR1 in young (A and B) and old (C) leaves using BiFC assays.

Y2H screening using PPD1 as a bait protein identified NINJA as a direct interactor with PPD1. Results from BiFC assays suggested PPD1 interacted with NINJA in plants, and that the TIFY motif was also essential for this interaction (FIG. 7). It is possible that NINJA functions as a bridge between TPL and PPD1. Using Y2H no direct interaction between PPD1 and BZR1 was observed (FIG. 5). However, recent tandem affinity purification (TAP) experiments have shown that TPL may interact with BZR1 (Wang et al 2013, Mol. Cell. Proteomics 12, 3653-3665), and here Y2H results confirmed that a direct interaction occurs (FIG. 6).

To determine the molecular function of the PPD proteins the interactions of PPD1, NINJA, TPL, and BZR1 were studied in planta. Bimolecular fluorescence (BiFC) was used to show that in the pavement cells of immature *Nicotiana benthamiana* leaves PPD1 appears to interact with BZR1 in the nucleus (FIG. 7A,B). The NINJA-binding TIFY motif in PPD1 was essential for this interaction. Moreover, no interaction was observed when nYFP-PPD1 and cYFP-BZR1 were co-expressed in fully expanded leaves (FIG. 7C). Interestingly, interaction between PPD1 and BZR1 was restored upon co-expression of NINJA but not TPL alone, suggesting the lack of interaction in the mature leaf was due to a limitation of endogenous NINJA. As for immature leaves, interaction between PPD1 and BZR1, even in the presence of NINJA and TPL co-expression, was not observed when the PPD1 NINJA-binding TIFY motif was deleted (FIG. 7C). These results suggest that PPD1, NINJA, TPL and BZR1 exist as a complex in plants and that NINJA is required to recruit PPD1 to interact via TPL with BZR1.

Figure 8:
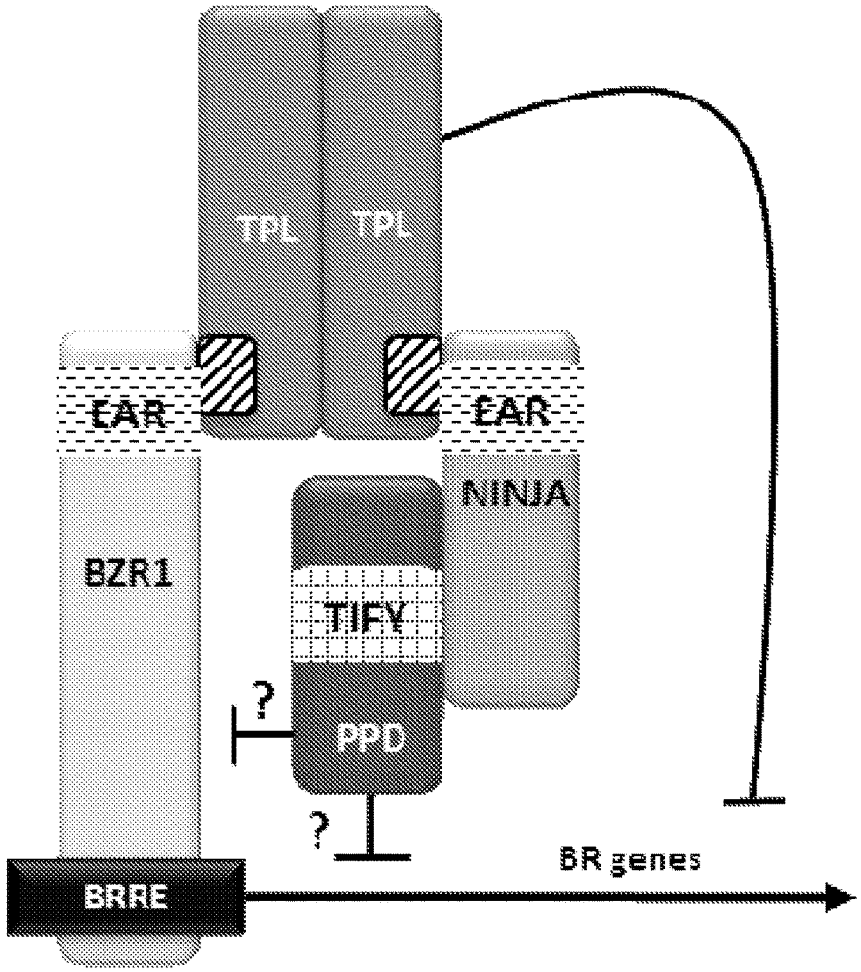
FIG. 8 shows a schematic representation of the PPD-NINJA-TPL-BZR1 complex.

PPD1 does not appear to directly interact with the target BZR1 transcription factor. Instead the results of PPD1 protein interaction experiments suggest a model in which the PPD proteins recruit TPL transcriptional co-repressors, using NINJA as an adaptor, and this PPD-NINJA-TPL complex interacts with the EAR motif of the BZR transcription factors (FIG. 8). Thus in this model the PEAPOD1 (PPD1) protein of *Arabidopsis thaliana* would act as a repressor of the BR signalling pathway and in combination with NINJA and TPL, negatively regulates BZR1.

Example 4

PEAPOD may be Involved in Regulating the Gibberellin Signalling Pathway

Giberellic acid (GA) treatment is known to reduce levels of the DELLA proteins (including RGA1) which are GA repressors; to determine the relationship between PPD, DELLA and the GA signalling pathway the applicants performed a yeast two-hybrid (Y2H) analysis between PPD and DELLA (RGA1) and applied gibberellic acid (GA) hormone and GA biosynthesis inhibitor (paclobutrazol, PAC) to wild type, Δppd mutant, and the Δppd mutant PPD over expressor (PPD-OX).

The ProQuest two-hybrid system (Invitrogen) was used to analyse interactions between PPD1, and RGA1. Full length coding sequences of PPD1, together with truncation or deletion derivatives of PPD1 (PPD1Δppd, PPD1Δtify, and PPD1Δjas*) (FIG. 4), were Gateway sub-cloned into pDEST32 (N-terminal GAL4DBD) or pDEST22 (N-terminal GAL4AD). When translated these generated the following peptide sequences od SEQ ID NO: 58, 68, 69, 70, 71, 72, which are PPD1-DBD, RGA1, RGA1-AD, PPD1-ppd-DBD, PPD1-tify-DBD, PP1-jas*-DBD respectively.

Figure 9:
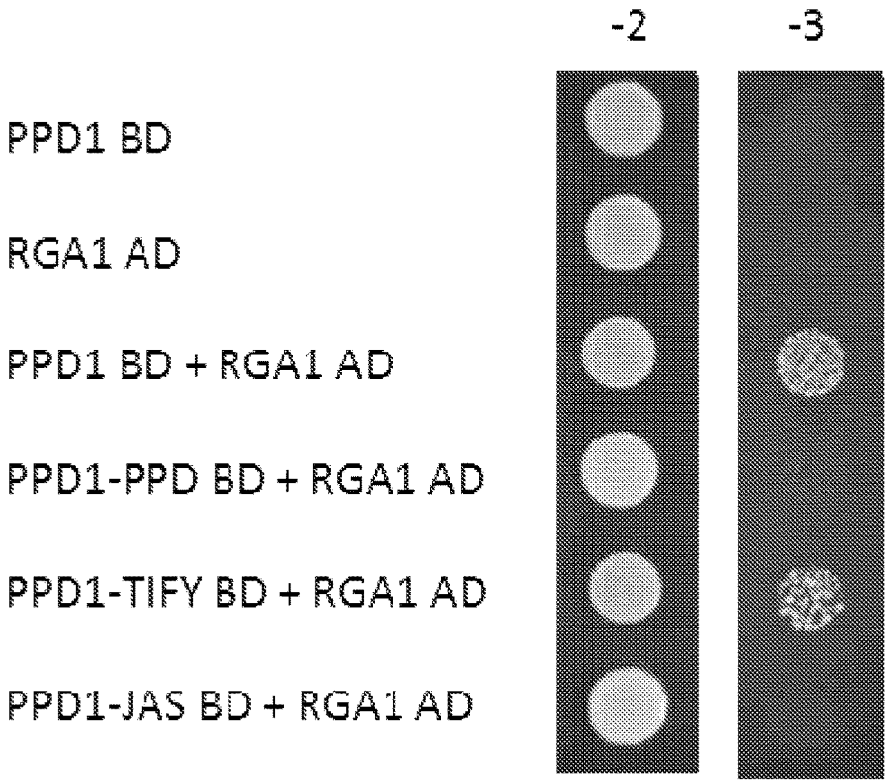
FIG. 9 shows the interaction between PPD and BZR1 in Y2H assays.

Combinations of bait and prey constructs were used to co-transform yeast strain MaV203 (Invitrogen), with selection on synthetic dropout (SD) SD/-Leu/-Trp agar plates. Transformed strains were tested for interactions using 10 μl droplets of 1 in 10 and 1 in 100 dilutions on SD/-Leu/-Trp/-His plates with different concentrations of 3-aminotriazol (3-AT) (Sigma). The PPD1-RGA1 interaction was tested with PPD1-DBD used as bait. Transformed yeast was spotted as a ten-fold dilution on control medium (−2) or selective medium (−3) with 15 mM 3AT. Controls were empty vectors, DBD, GAL4 DNA binding domain, AD, GAL4 activation domain (FIG. 4). The Y2H results suggests that PPD can directly bind to DELLA (FIG. 9).

Figure 10:
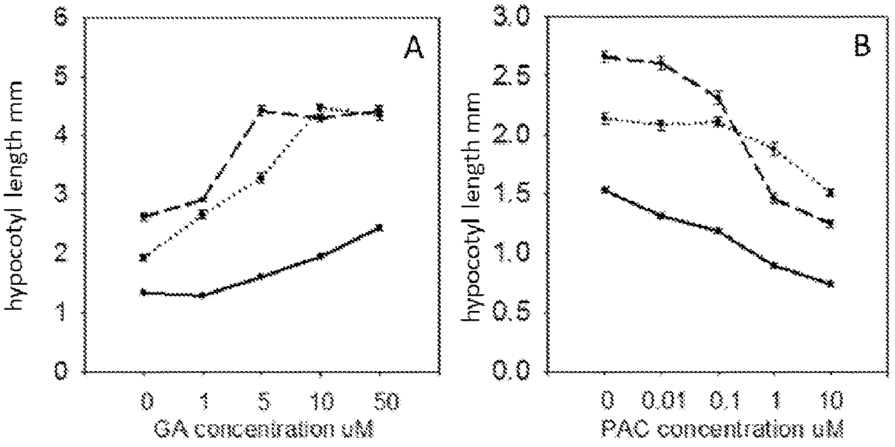
FIG. 10 shows the response of Wild Type, Δppd mutant, and PEAPOD overexpressor (PPD-OX) hypocotyl length to exogenous GA and PAC applications.

For exogenous applications of GA or PAC seeds were surface sterilised with 70% ethanol, 0.01% Triton X-100 for 10 min, followed by 100% ethanol for 5 min, air dried on sterile filter paper, and transferred to media plates containing half-strength MS salts, 1% sucrose and 0.8% agar. Plates were incubated for 5 days at 4° C. in the dark then transferred to 24° C. with a 14 h light/10 h dark daily cycle. Light was provided by fluorescent tubes (Philips TLD 58W/865) at an intensity of 100 μM $m^{-2}$ $s^{-1}$. Wild-type (Col-0) Δppd mutant and transgenic PPD-OX seedlings were grown for five days on medium with different concentrations of GA (FIG. 10A) or PAC (FIG. 10B). GA (ACROS organics), and PAC (Sigma-Aldrich) were dissolved in ethanol and acetone respectively, filter sterilised and incorporated into media plates. Ethanol or acetone (0.5%) was used for mock treatments. Seedlings were grown at 24° C. under a 14 h light/10 h dark daily cycle for 5 days before hypocotyl lengths were analysed (n=35). Each treatment was repeated twice; error bars=standard error of the mean.

A reduction of DELLA leads to an increase in transcription of DELLA target genes promoting cell expansion and can be quantified by measuring hypocotyl elongation of seedlings growing on media containing varying levels of GA. The lowest concentration of GA (1 μM) did not promote elongation of the wild type (WT) hypocotyl whereas both the loss-of-function PPD mutant (Δppd) and the transgenic PPD over expressing (PPD-OX) seedlings showed increased hypocotyl elongation (FIG. 10A). At higher GA concentrations (5-50 μM) elongation of the WT hypocotyl occurred in a dose dependent manner. In comparison the Δppd and PPD-OX seedlings showed hypersensitive elongation up to 5 and 10 μM GA respectively where they both reached approximately the same length (FIG. 10A).

GA biosynthesis is inhibited by applications of exogenous paclobutrazol (PAC); this results in an increase in the DELLA repressor proteins and corresponding reduction in cell expansion. Wild type seedlings demonstrated a dose dependent decrease of hypocotyl elongation from 0 to 10 μM PAC (FIG. 10B). Once again the Δppd seedlings demonstrated a hyper sensitive response which was seen as a larger reduction in hypocotyl elongation over the same range of PAC applications. The PPD-OX seedlings however, were relatively insensitive until the PAC concentration was increased beyond 0.1 μM, after which they too showed a decrease in hypocotyl length (FIG. 10B).

The hypersensitive response to GA by the Δppd seedlings potentially reflects the combination of increased targeting of DELLA for degradation in the absence of transcription factor repression by PPD. Similarly, the addition of PAC in the Δppd background possibly leads to a greater reduction in hypocotyl elongation compared to WT because it is done in the absence of one of DELLAs natural antagonists—PPD, suggesting PPD and GA compete for binding to DELLA.

It can be predicted that the over expression of PPD would result in a higher level of antagonism of DELLA, as such the hypocotyl elongation of these plants ought to be hypersensitive to GA; indeed this is what we observed in the PPD-OX seedlings. In the reverse situation when the GA level was reduced (by the application of PAC) the PPD-OX seedlings were unresponsive until the PAC concentration was greater than 0.1 μM. This likely reflects the point at which there was a sufficient reduction in endogenous GA levels to see the influence of DELLA protein not antagonised by the over expressed PPD.

Example 5

Increasing Root Biomass by Increasing Expression of PEAPOD in Plants

Constructs

Described below are several constructs for expressing PEAPOD sequences from various species, under the control of various promoters, for expression in dicotyledonous and monocotyledonous plants.

Generation of pTobRB7 Δ1.3::PPD Dicot Construct for (Root-preferred) over-expression of *Arabidopsis* PPD in Dicotyledonous Plants Construs were synthesised containing the coding sequence of PPD1 for expression in roots of dicots, the nucleic acid sequences are shown in SEQ ID NO:40 and 126. The PPD ORF was originally from the *Arabidopsis* thaliana PPD1 cDNA (Accession No. NM_202819) and was modified to include a modified Joshi sequence (Joshi 1997, Nucleic Acid Research 15, 6643-6653), removal of cryptic splice sites, in the case of SEQ ID NO: 40 the inclusion of the third intron from *Arabidopsis thaliana* DGAT1 (SEQ ID NO:39), addition of a BamHI removable C-terminal V5 epitope and His tag tail (encoding SEQ ID NO:37) and addition of a double stop codon. The position of the intron was optimised for splice site prediction, performed by NetGene2 (www<dot>cbs<dot>dtu<dot>dk/services/NetGene2/).

The construct of SEQ ID NO: 40 (with and without the tail) was then placed between the TobRB7 Δ1.3 promoter (Yamamoto et al 1991, Plant Cell, 3:371-382) and NOS terminator by the GATEWAY® LR reaction, to create SEQ ID NO:42 and SEQ ID NO:44 which coded for SEQ ID NO:36 and SEQ ID NO:38 respectively. A similar subcloning step was performed on the construct shown in SEQ ID NO: 126 (with and without the C-terminal tail), which coded for SEQ ID NO: 108 and SEQ ID NO: 114 respectively.

Generation of pTobRB7 Δ0.6::PPD Dicot Construct for (Root-preferred) over-expression of *Arabidopsis* PPD in Dicotyledonous Plants Constructs were synthesised containing the coding sequence of PPD1 for expression in roots of dicots, the nucleic acid sequences are shown in SEQ ID NO:40 and 126. The PPD ORF was originally from the *Arabidopsis thaliana* PPD1 cDNA (Accession No. NM_202819) and was modified to include a modified Joshi sequence (Joshi 1997, Nucleic Acid Research 15, 6643-6653), removal of cryptic splice sites, in the case of SEQ ID NO: 40 the inclusion of the third intron from *Arabidopsis thaliana* DGAT1 (SEQ ID NO:39), addition of a BamHI removable C-terminal V5 epitope and His tag tail (encoding SEQ ID NO:37) and addition of a double stop codon. The position of the intron was optimised for splice site prediction, performed by NetGene2 (www<dot>cbs<dot>dtu<dot>dk/services/NetGene2/).

The construct (with and without the tail) was then placed between the TobRB7 Δ0.6 promoter (Yamamoto et al 1991, Plant Cell, 3:371-382) and NOS terminator by the GATEWAY® LR reaction, to create SEQ ID NO:43 and SEQ ID NO:45 which coded for SEQ ID NO:36 and SEQ ID NO:38 respectively. A similar subcloning step was performed on the construct shown in SEQ ID NO: 126 (with and without the C-terminal tail), which coded for SEQ ID NO: 108 and SEQ ID NO: 114 respectively.

Generation of pAtWRKY6::PPD Dicot Construct for (Root-preferred) over-expression of *Arabidopsis* PPD in Dicotyledonous Plants Constructs were synthesised containing the coding sequence of PPD1 for expression in roots of dicots, the nucleic acid sequence is shown in SEQ ID NO:41 and 126. The PPD ORF was originally from the *Arabidopsis thaliana* PPD1 cDNA (Accession No. NM_202819) and was modified to include a modified Joshi sequence (Joshi 1997, Nucleic Acid Research 15, 6643-6653), removal of cryptic splice sites, in the case of SEQ ID NO: 41 the inclusion of the third intron from *Arabidopsis thaliana* DGAT1 (SEQ ID NO:39), addition of a BamHI removable C-terminal V5 epitope and His tag tail (encoding SEQ ID NO:37) and addition of a double stop codon. The position of the intron was optimised for splice site prediction, performed by NetGene2 (www<dot>cbs<dot>dtu<dot>dk/services/NetGene2/).

The construct (with and without the tail) was then placed between the tobacco AtWRKY6 promoter (Robatzek and Somssich 2001, The Plant Journal, 28: 123-133) and NOS terminator by the GATEWAY® LR reaction, to create SEQ ID NO:44 and SEQ ID NO:47 which coded for SEQ ID NO:36 and SEQ ID NO:38 respectively. A similar subcloning step was performed on the construct shown in SEQ ID NO: 126 (with and without the C-terminal tail), which coded for SEQ ID NO: 108 and SEQ ID NO: 114 respectively.

Generation of pTobRB7 Δ1.3::PPD Monocot Construct for (Root-preferred) over-expression of *Arabidopsis* PPD in Monocotyledonous Plants Construct were synthesised containing the coding sequence of PPD1 for expression in roots of monocots, the nucleic acid sequences are shown in SEQ ID NO:49 and SEQ ID NO: 120. The PPD ORF was optimised for expression in monocotyledonous plants; this included a modified Joshi sequence (Joshi 1997, Nucleic Acid Research 15, 6643-6653), optimisation of codons, removal of mRNA instability sequences, removal of polyA signal sequences, removal of cryptic splice sites, in the case of SEQ ID NO: 49 the inclusion of the third intron from Lolium perenne DGAT1 (SEQ ID NO:48), addition of a BamHI removable C-terminal V5 epitope and His tag tail (encoding SEQ ID NO:37) and addition of a double stop codon. The position of the intron was optimised for splice site prediction, performed by deepc2 (www<dot>cbs<dot>dtu<dot>dk/services/NetGene2/).

The construct (with and without the tail) was then placed between the pTobRB7 Δ1.3 promoter (Yamamoto et al 1991, Plant Cell, 3:371-382) and NOS terminator by the GATEWAY® LR reaction, to create SEQ ID NO:50 and SEQ ID NO:53 which coded for SEQ ID NO:36 and SEQ ID NO:38 respectively. A similar subcloning step was performed on the construct shown in SEQ ID NO: 120 (with and without the C-terminal tail), which coded for SEQ ID NO: 108 and SEQ ID NO: 114 respectively.

Generation of pTobRB7 Δ0.6::PPD Monocot Construct for (Root-preferred) over-expression of *Arabidopsis* PPD in Dicotyledonous Plants Constructs were synthesised containing the coding sequence of PPD1 for expression in roots of monocots, the nucleic acid sequences are shown in SEQ ID NO:49 and SEQ ID NO: 120. The PPD ORF was optimised for expression in monocotyledonous plants; this included a modified Joshi sequence (Joshi 1997, Nucleic Acid Research 15, 6643-6653), optimisation of condons, removal of mRNA instability sequences, removal of polyA signal sequences, removal of cryptic splice sites, in the case of SEQ ID NO: 49 the inclusion of the third intron from Lolium perenne DGAT1 (SEQ ID NO: 48), addition of a BamHI removable C-terminal V5 epitope and His tag tail (encoding SEQ ID NO:37) and addition of a double stop codon. The position of the intron was optimised for splice site prediction, performed by deepc2 (www<dot>cbs<dot>dtu<dot>dk/services/NetGene2/).

The construct (with and without the tail) was then placed between the pTobRB7 Δ0.6 promoter (Yamamoto et al 1991, Plant Cell, 3:371-382) and NOS terminator by the GATEWAY® LR reaction, to create SEQ ID NO:51 and SEQ ID NO:54 which coded for SEQ ID NO:36 and SEQ ID NO:38 respectively. A similar subcloning step was performed on the construct shown in SEQ ID NO: 120 (with and without the C-terminal tail), which coded for SEQ ID NO: 108 and SEQ ID NO: 114 respectively.

Generation of pAtWRKY6::PPD Monocot Construct for (Root-preferred) over-expression of *Arabidopsis* PPD in Monocotyledonous Plants Constructs were synthesised containing the coding sequence of PPD1 for expression in roots of monocots, the nucleic acid sequences are shown in SEQ ID NO:49 and SEQ ID NO: 120. The PPD ORF was optimised for expression in monocotyledonous plants; this included a modified Joshi sequence (Joshi 1997, Nucleic Acid Research 15, 6643-6653), optimisation of condons, removal of mRNA instability sequences, removal of polyA signal sequences, removal of cryptic splice sites, in the case of SEQ ID NO: 49 the inclusion of the third intron from Lolium perenne DGAT1 (SEQ ID NO:48), addition of a BamHI removable C-terminal V5 epitope and His tag tail (encoding SEQ ID NO:37) and addition of a double stop codon. The position of the intron was optimised for splice site prediction, performed by deepc2 (www<dot>cbs<dot>dtu<dot>dk/services/NetGene2/).

The construct (with and without the tail) was then placed between the pAtWRKY6 promoter (Robatzek and Somssich 2001 The Plant Journal, 28: 123-133) and NOS terminator by the GATEWAY® LR reaction, to create SEQ ID NO:52 and SEQ ID NO:55 which coded for SEQ ID NO:36 and SEQ ID NO:38 respectively. A similar subcloning step was performed on the construct shown in SEQ ID NO: 120 (with and without the C-terminal tail), which coded for SEQ ID NO: 108 and SEQ ID NO: 114 respectively.

Generation of Expression Constructs Containing PPD from other Plant Species

To demonstrate that PPD from species other than *Arabidopsis* can be used we synthesized constructs that when placed under a suitable promoter would express PPD from *Arabidopsis thaliana* (PPD control), the legume *Trifolium repens*, the primitive angiosperm *Amborella trichopoda,* the monocotoledonous *Musa acuminate*, the conifers *Picea abies* and *Picea sitchensis* and the lycophyte *Selaginella moellendorffii.* These were optimized for expression in either rice (including a monocotoledonous intron) or *Arabidopsis* (no intron). These were engineered to contain a removable tail which considered of two BamHI sites (coding for glycine-serine) on either side of a nucleic acid sequence encoding a V5-His tag. The peptide sequences (with and without the C-terminal V5-His tag tail) are shown in sequences 108-119. The corresponding nucleic acid sequences optimized for expression in rice are shown in sequences 120-125, and optimized for expression in *Arabidopsis* are shown in sequences 126-131.

The *Arabidopsis* optimised versions were placed downstream of appropriate promoters in binary vectors by the GATEWAY LR reaction and transformed into Δppd *Arabidopsis thaliana* by the floral dip method.

The rice optimized versions were placed downstream of appropriate promoters by the GATEWAY LR reaction and transformed into ryegrass biolystically.

Plant Transformation

Transformation of *Arabidopsis*

*Arabidopsis* is transformed as described in Example 2.

Transformation of *Alfalfa*

Alalfa plants over-expressing the Peapod construct were generated by *Agrobacterium*-mediated transformation using a method adapted from Samac et al. 2000 (Methods in Molecular Biology 343: 301-311).

Plant Tissue

Highly regenerable genotypes of Regen-SY (Bingham 1991 Crop Sci. 31, 1098) were identified with an ability to develop whole plants from somatic embryos under in vitro conditions. A single genotype was selected for use in plant transformation experiments using this protocol.

*Agrobacterium* Strains and Vectors

The binary vectors pRSh1::PPD-OP and pRSh1::PPD-OP-V5 were used for all transformation experiments. The vector pRSh1 is a derivative of pART27 (Gleave 1992 Plant Mol Biol 20: 1203-1207) and contains the bar selection gene expressed from the CaMV 35S promoter and the grass optimised Peapod gene also under the expression of the CaMV 35S promoter. The plasmid was transferred into *A. tumefaciens* strain GV310 and transformants were selected on YM plates containing 200 mgl-1 spectinomycin. Successful mobilisation of the plasmid into *Agrobacterium* was confirmed by restriction mapping following preparation of plasmid DNA from the bacterial culture.

A culture of the binary plasmids was added to 25 mL of Mannitol Glutamate Luria (MGL) broth containing 100 mg/L Spectinomycin. Bacterial cultures were grown overnight (16 hours) on a rotary shaker (200 rpm) at 28° C. Cultures were harvested by centrifugation (3000×g), the supernatant removed and the cells re-suspended in a 5 mL solution of 10 mM $MgSO_4$ in preparation for plant transformation.

Plant Transformation

The second and third fully expanded leaves from a tissue culture responsive genotype of Regen-SY were harvested and rinsed for 30 seconds in a 50% Ethanol solution followed by a wash in sterile distilled water before surface sterilisation in a sodium hypochlorite solution (3% available chlorine). Sterile leaves are then cut into leaf disks and then floated on a solution of SH1.5D callus induction medium. For transformation of the leaf disks, approximately 3 mL *Agrobacterium* broth to 12 mL SH1.5D and incubated for 15 minutes with occasional stirring to thoroughly coat the leaves with *Agrobacterium*. The bacterial solution is then removed and the leaf pieces blotted briefly on sterile filter paper before placing adaxial side up on SH1.5D gelled with 0.8% Phytoagar. Plates were then incubated for 5 days in the dark at 25° C.

After inoculation, leaf pieces were removed from plates and rinsed 3-4 times in sterile SH1.5D liquid medium blotted dry on sterile filter paper and placed on SH1.5D plates supplemented with 5 mg/L Ammonium glufosinate and 100 mg/L Cefotaxime and Timentin for selection and incubated for 15 days in the dark at 25° C. Callus developing on leaf pieces were then passaged to fresh SH1.5D selection medium for a further 15 days.

Transformed callus was then transferred to BL0 medium supplemented with Ammonium glufosinate, Cefotaxime and Timentin for formation of somatic embryos. Once embryos developed, they were dissected and transferred to a half strength MSN medium with selection for germination. Whole rooted plants were transferred and established in the glasshouse.

PCR Analysis

PCR analysis was performed to confirm stable integration of the T-DNA into the genome for plants recovered from transformation experiments. Genomic DNA was extracted from approximately 50 mg of in vitro grown leaves using the Genomic DNA Mini Kit (Geneaid).

Primer pairs specific to the ocs3' polyadenylation signal (ocs3'-1f, 5'-GATATGCGAGACGCCTATGA-3' [SEQ ID NO: 132]; ocs3'-1r, 5'-GAGTTCCCTTCAGTGAACGT-3' [SEQ ID NO: 133]) were used to produce an amplification product of 439 bp. Control reactions comprising plasmid DNA template, non-transformed plant DNA or water only were also included. The protocol for PCR reactions consisted of: an initial denaturation of 94° C. for 5 minutes, 30 cycles of 95° C. 30 s, 55° C. 15 s, 72° C. 1 min, and an extension of 72° C. for 10 min. Amplification products were resolved on 1.0% agarose gels by gel electrophoresis in TAE buffer and visualized with a Bio-Rad Gel Doc imaging system.

General Composition of Media used for Alfalfa Transformation

| A. MGL | |
|---|---|
| Mannitol | 5.0 g/L |
| L glutamic acid | 1.0 g/L |
| KH2PO4 | 250 mg/L |
| MgSO4 | 100 mg/L |
| NaCl | 100 mg/L |
| Biotin | 100 mg/L |
| Bactotryptone | 5.0 g/L |
| Yeast extract | 2.5 g/L |
| pH 7.0 | (NaOH) |

| B. SH1.5D<br>SH macro and micro salts (Duchefa)<br>SH vitamins (Duchefa) | |
|---|---|
| K2SO4 | 4.34 g/L |
| Proline | 288 g/L |
| Thioproline | 53 mg/L |
| Sucrose | 30 g/L |
| pH 5.8 | (KOH) |
| Phytoagar | 8.0 g/L |
| Kinetin | 0.2 mg/L (add after autoclaving) |
| 2,4D | 1.5 mg/L (add after autoclaving) |

| C. BL0 (Blaydes Media)<br>Blaydes modified basal medium (PhytoTechnology Laboratories) | |
|---|---|
| L myo-inositol | 100 mg/ |
| yeast extract | 2.0 g/L |
| pH 5.8 | (KOH) |
| Phyta gel | 2.5 g/L |

| D. Half MSN medium<br>MS macro and micro salts, half strength (Duchefa)<br>Nitch & Nitch vitamins (Duchefa) | |
|---|---|
| Sucrose | 15 g/L |
| pH 5.8 | (KOH) |
| Phytoagar | 8.0 g/L |

Transformation of Ryegrass

Ryegrass plants over-expressing the Peapod construct were generated by microprojectile bombardment using a method adapted from Altpeter et al. 2000 (Molecular Breeding 6: 519-528).

Calli for transformation were induced from immature inflorescences up to 7 mm. Floral tillers were harvested, surface sterilised in a sodium hypochlorite solution (4% available chlorine), dissected, then cultured in the dark at 25° C. for four to six weeks prior to transformation on a basal medium of Murashige and Skoog (MS) macro, micronutrients and vitamins (1962 Physiol Plant. 15: 473-497) supplemented with 30 g/L maltose, 5 mg/L 2,4-D, pH adjusted to 5.8 and solidified with 6 g/L agarose.

Plasmids were prepared using the Invitrogen Pure Link Hi Pure Plasmid Maxiprep Kit with the concentration adjusted to 1 μg/μL. The plasmid pAcH1, which contains an expression cassette comprising a chimeric hygromycin phosphotransferase (HPH) gene (Bilang et al. 1991 Gene 100: 247-250) expressed from the rice actin promoter with the first intron and terminated from the nos 3' polyadenylation signal, was used for selection. Plasmids containing PPD expression cassettes were mixed in a 1:1 molar ratio with pAcH1.

Plasmid DNA's were coated onto M17 tungsten particles (1.4 μM diameter mean distribution) using the method of Sanford et al. 1993 (Meth. Enzymol. 217: 483-509.) and transformed into target tissues using a DuPont PDS-1000/He Biolistic Particle Delivery System. Up to 6 hours before transformation the callus was sub-cultured onto the callus initiation media containing 64 g/L mannitol. Following transformation (approximately 16 hours) transformed calli were then transferred to a mannitol-free MS basal medium supplemented with 2 mg/L 2,4-D. After 2 days calli were transferred to the same medium containing 200 mg/L hygromycin and cultured in the dark for 4 weeks for the selection of transgenic events. Regeneration of whole plants from somatic embryos occurred under lights on a MS basal medium supplemented with 0.2 mg/L Kinetin, 30 g/L, sucrose, and 50 mg/L hygromycin, adjusted to pH 5.8 and solidified with 8 g/L phytoagar. Transformed plants were transferred to a contained greenhouse environment for analysis.

PCR Analysis of Transformants

PCR analysis was performed to confirm stable integration of the HPH and PPD transgenes into the genome for plants recovered from transformation experiments. Genomic DNA was extracted from approximately 50 mg of in vitro grown leaves using the Genomic DNA Mini Kit (Geneaid). Primer pairs specific to the HPH gene (hpt-1, 5'-GCTGGGGCGTCGGTTTCCACTATCCG-3' [SEQ ID NO: 134]; hpt-2, 5'-CGCATAACAGCGGTCATTGACTG-GAGC-3' [SEQ ID NO: 135];) and nos3' polyadenylation signal (nos3'-1f, 5'-CTGTTGCCGGTCTTGCGATG-3' [SEQ ID NO: 136]; nos3'-1r, 5'-GTCACATAGATGACAC-CGCG-3' [SEQ ID NO: 137];) were used to produce amplification products of 375 bp and 202 bp respectively. Control reactions comprising plasmid DNA template, non-transformed plant DNA or water only were also included. The protocol for PCR reactions consisted of: an initial denaturation of 94° C. for 5 minutes, 30 cycles of 95° C. 30 s, 55° C. 15 s, 72° C. 1 min, and an extension of 72° C. for 10 min. Amplification products were resolved on 1.0% agarose gels by gel electrophoresis in TAE buffer and visualized with a Bio-Rad Gel Doc imaging system.

Southern Blot Analysis of Grass Transformants

Southern blot hybridization was used to estimate the number of transgene copies per line. Genomic DNA was extracted from leaf material of greenhouse grown plants for Southern blot hybridization using the method of Doyle J and Doyle J 1990 (Focus, 12:13-15). DNA (20 µg) was digested and separated on a 0.8% agarose gel and transferred onto a nylon membrane (Roche) using capillary transfer with 0.4N NaOH. Genomic DNAs were digested with XbaI or HindIII when probing for the HPH and PPD transgenes respectively. Probes were prepared using the DIG PCR synthesis kit. Primer pairs specific to the HPH gene (rgh1, 5'-CTCGT-GCTTTCAGCTTCGATGTAG-3' [SEQ ID NO: 138]; rgh5, 5'-GCTGGGGCGTCGGTTTCCACTATCGG-3' [SEQ ID NO: 139]) and PPD (GrPPD1F, 5'-CACAGGATGGAT-TCTCCAAGG-3' [SEQ ID NO: 140]; GrPPD1R, 5'-TAAGGTCCACGGAGAGGTTC-3' [SEQ ID NO: 141]) were used to produce amplification products of 906 bp and 586 bp for probes respectively. Prehybridization (1 hour) and hybridization (12 hours) were performed at 45° C. using standard buffers (Roche). Detection was achieved using a non-radioactive method according to the manufacturer's protocol with CDP-Star as the chemiluminescent substrate. Light signals were detected using a Bio-Rad ChemiDoc MP System and software.

Generation of Polyclonal Antibodies Against PPD1 Protein and Immunoblotting

Custom made anti-PPD1 affinity-purified rabbit polyclonal antibodies were produced by GenScript using a full length *Arabidopsis thaliana* PPD1 protein. At a 1:5000 dilution the antibodies were capable of detecting less than 10 ng of purified PPD protein by immunoblot. Plant tissue was frozen in liquid nitrogen and ground to a fine powder. The frozen tissue powder was added to extraction buffer containing 50 mM Tris pH 7.5, 150 mM NaCl, 1 mM EDTA, 10% (vol/vol) glycerol, 5 mM DTT, 1% (vol/vol) complete protease inhibitor cocktail (Sigma), and 1% (vol/vol) Triton X-100 at a ratio of 1.0/1.5 (wt/vol), homogenised until thawed and then centrifuged for 12 min at 16,300 g and 4° C. Total soluble protein in the supernatant was quantified by Bradford assay (Coomassie Plus, Thermo Scientific), adjusted to give equivalent total protein concentrations per sample (typically between 10-40 µg), denatured in 1×Nu-PAGE LDS sample buffer (Invitrogen) and run in a 4-12% Bis-Tris SDS/PAGE gel (Novex). Following blotting to PVDF membrane using an iBlot apparatus (Invitrogen) protein detection was with a 1:5,000 dilution of the 1° anti-PPD1 polyclonal antibodies, followed by a 1:5,000 dilution of 2° anti-rabbit goat HRP antibodies (Sigma), application of Western Bright ECL reagent (Advansta), and image capture using a ChemiDoc™ instrument (BioRad).

Root Biomass Analysis of Transformants

Figure 11:
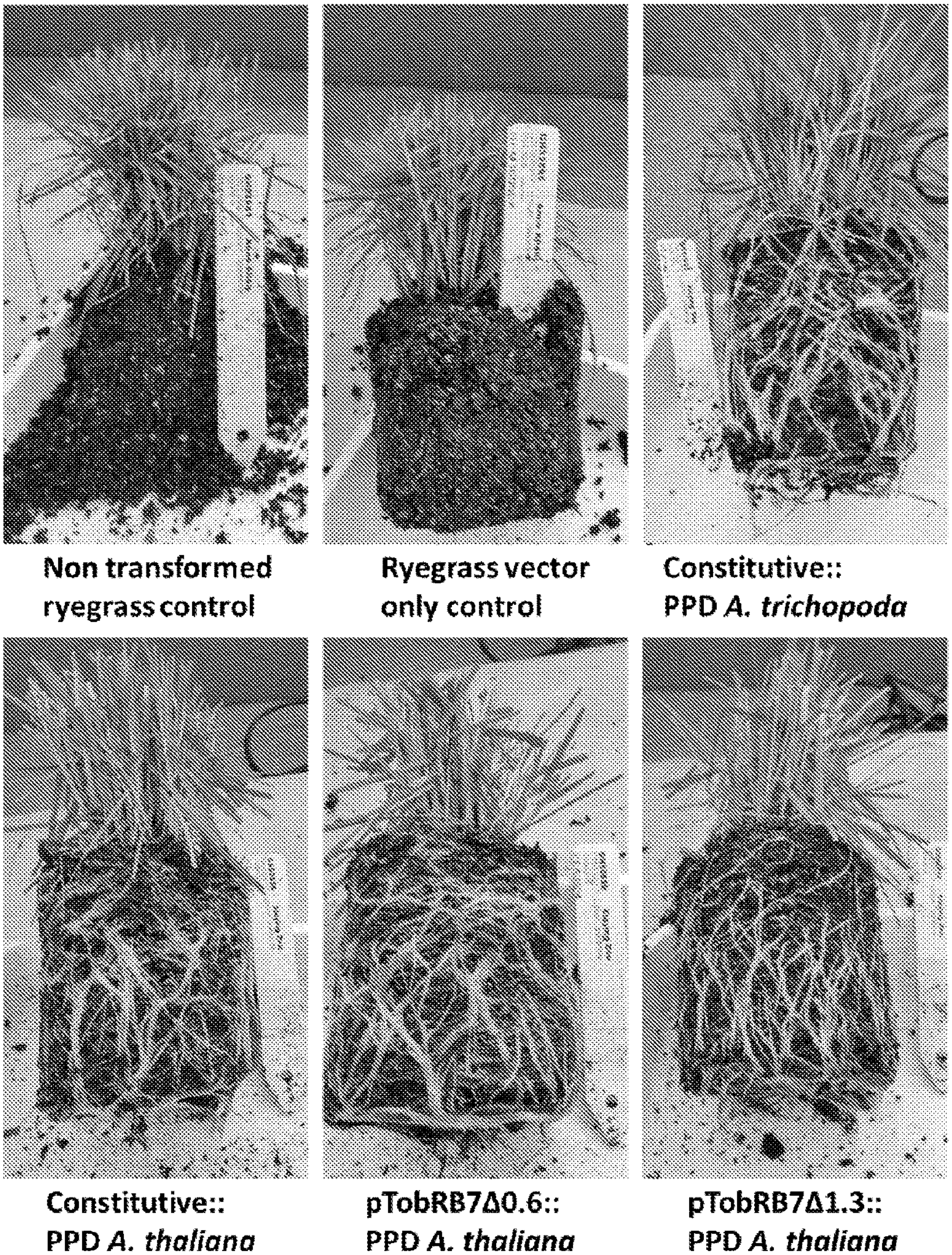
FIG. 11 shows the increase in root growth of ryegrass plants over expressing PPD (PPD-OX) from *Arabidopsis thaliana* or PEAPOD from *Abroella trichopoda* compared to the wild type and vector control.

An equal number (typically 4-10) of tillers were taken from WT and ryegrass plants transformed with *Arabidopsis* PPD under a constitutive promoter. Tillers were planted into plastic grow bags containing potting mix and pruned to be of equal height. Plants were grown for approximately 6 weeks in the glasshouse; the increase in root biomass/growth/length/branching of ryegrass plants transformed with *Arabidopsis* PPD under a constitutive promoter compared to WT plants could be seen by observing the root growth beyond the grow bag (FIG. 11). The increase in root biomass was quantified by washing the roots under running water then removing the attached above ground portion (leaves and stems) and drying the roots at 65° C. for 48 hr then weighing the dry weights (Table 2).

TABLE 2

| | wt ryegrass | Vector control | Constit promoter:: Arabidopsis PPD line 1 | Constit promoter:: Arabidopsis PPD line 2 | Constit promoter:: Arabidopsis PPD line 3 | Constit promoter:: Arabidopsis PPD line 4 |
|---|---|---|---|---|---|---|
| Av root weight (g) (n = 12) | 0.0733 | 0.0387 | 0.4506 | 0.5657 | 0.3077 | 0.3503 |
| SE | 0.0138 | 0.0125 | 0.0428 | 0.0625 | 0.0426 | 0.0638 |

Figure 12:
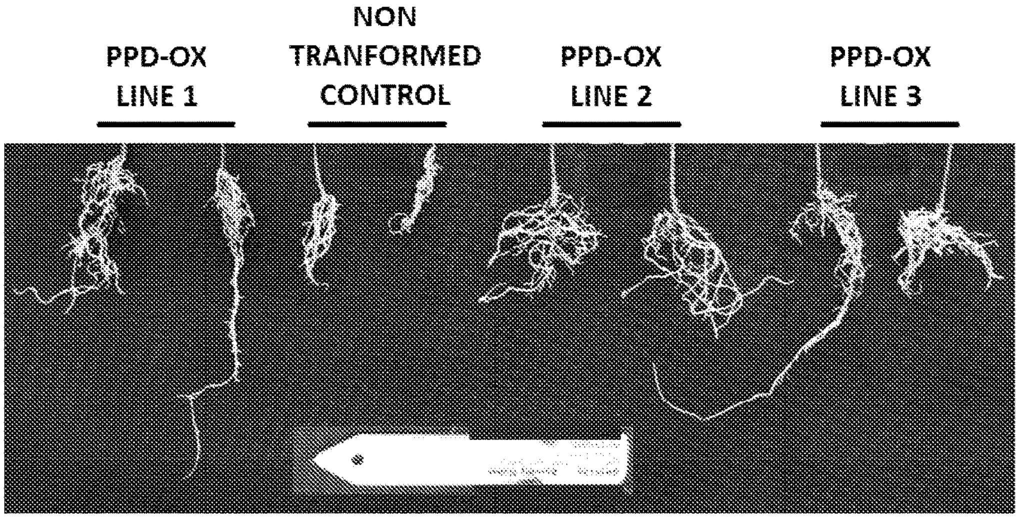
FIG. 12 shows the increase in root length of alfalfa plants over expressing PPD (PPD-OX) compared to the control plants.

An equal number (typically 4-10) of tillers were taken from WT and ryegrass plants transformed with *Arabidopsis* PPD under one of three root promoters. Tillers were planted into plastic grow bags containing potting mix and pruned to be of equal height. Plants were grown for approximately 6 weeks in the glasshouse; the increase in root biomass/growth/length/branching of ryegrass plants transformed with *Arabidopsis* PPD under a constitutive promoter compared to WT plants could be seen by observing the root growth beyond the grow bag (FIG. 12). The increase in root biomass was quantified by washing the roots under running water then removing the attached above ground portion (leaves and stems) and drying the roots at 65° C. for 48 hr then weighing the dry weights (Table 3 and Table 4)

TABLE 3

| | Wt ryegrass | Vector control | pTobRB7Δ0.6:: *Arabidopsis* PPD line 1 | pTobRB7Δ0.6:: *Arabidopsis* PPD line 2 | pTobRB7Δ0.6:: *Arabidopsis* PPD line 3 |
|---|---|---|---|---|---|
| Av root weight (g) (n = 12) | 0.0733 | 0.0387 | 0.2338 | 0.3686 | 0.3704 |
| SE | 0.0138 | 0.0125 | 0.0357 | 0.0356 | 0.0611 |

TABLE 4

| | wt ryegrass | Vector control | pTobRB7Δ1.3:: *Arabidopsis* PPD line 1 | pTobRB7Δ1.3:: *Arabidopsis* PPD line 2 | pTobRB7Δ1.3:: *Arabidopsis* PPD line 3 | pTobRB7Δ1.3:: *Arabidopsis* PPD line 4 |
|---|---|---|---|---|---|---|
| Av root weight (g) (n = 12) | 0.0733 | 0.0387 | 0.3227 | 0.2338 | 0.2720 | 0.4014 |
| SE | 0.0138 | 0.0125 | 0.0556 | 0.0191 | 0.0581 | 0.0445 |

Cuttings of approximately equal size were taken from WT and alfalfa (variety USD5) plants transformed with *Arabidopsis* PPD under a constitutive promoter. Cuttings were planted into plastic grow bags containing potting mix. Plants were grown for approximately 6 weeks in a growth cabinet with x hours day length; the increase in root biomass/growth/length/branching of alfalfa plants transformed with *Arabidopsis* PPD under a constitutive promoter compared to WT plants could be seen by observing the root growth beyond the grow bag. The increase in root biomass was quantified by washing the roots under running water (these were photographed, FIG. 12) then the attached above ground portion (leaves and stems) was removed and the roots dried at 65° C. for 48 hr then weighed Table 5.

TABLE 5

| Plant line | Combined dry root weights from 10 cuttings (mg) |
|---|---|
| Untransformed control | 43 |
| Transformant line 1 | 110 |
| Transformant line 2 | 54 |
| Transformant line 3 | 160 |
| Transformant line 4 | 59 |
| Transformant line 5 | 53 |
| Transformant line 6 | 85 |
| Transformant line 7 | 148 |

An equal number (typically 4-10) of tillers were taken from WT and ryegrass plants transformed with *T. repens* PPD under a constitutive promoter. Tillers were planted into plastic grow bags containing potting mix and pruned to be of equal height. Plants were grown for approximately 6 weeks in the glasshouse; the increase in root biomass/growth/length/branching of ryegrass plants transformed with *T. repens* PPD under a constitutive promoter compared to WT plants could be seen by observing the root growth beyond the grow bag. The increase in root biomass can be quantified by washing the roots under running water then removing the attached above ground portion (leaves and stems) and drying the roots at 65° C. for 48 hr then weighing the dry weights.

An equal number (typically 4-10) of tillers were taken from WT and ryegrass plants transformed with *T. repens* PPD under one of three root promoters. Tillers were planted into plastic grow bags containing potting mix and pruned to be of equal height. Plants were grown for approximately 6 weeks in the glasshouse; the increase in root biomass/growth/length/branching of ryegrass plants transformed with *T. repens* PPD under a constitutive promoter compared to WT plants could be seen by observing the root growth beyond the grow bag. The increase in root biomass can be quantified by washing the roots under running water then removing the attached above ground portion (leaves and stems) and drying the roots at 65° C. for 48 hr then weighing the dry weights.

An equal number (typically 4-10) of tillers were taken from WT and ryegrass plants transformed with *A. trichopoda* PPD under a constitutive promoter. Tillers were planted into plastic grow bags containing potting mix and pruned to be of equal height. Plants were grown for approximately 6 weeks in the glasshouse; the increase in root biomass/growth/length/branching of ryegrass plants transformed with *A. trichopoda* PPD under a constitutive promoter compared to WT plants could be seen by observing the root growth beyond the grow bag (FIG. 11). The increase in root biomass can be quantified by washing the roots under running water then removing the attached above ground portion (leaves and stems) and drying the roots at 65° C. for 48 hr then weighing the dry weights.

An equal number (typically 4-10) of tillers were taken from WT and ryegrass plants transformed with *A. trichopoda* PPD under one of three root promoters. Tillers were planted into plastic grow bags containing potting mix and pruned to be of equal height. Plants were grown for approximately 6 weeks in the glasshouse; the increase in root biomass/growth/length/branching of ryegrass plants transformed with *A. trichopoda* PPD under a constitutive promoter compared to WT plants could be seen by observing the root growth beyond the grow bag. The increase in root biomass can be quantified by washing the roots under running water then removing the attached above ground portion (leaves and stems) and drying the roots at 65° C. for 48 hr then weighing the dry weights.

An equal number (typically 4-10) of tillers were taken from WT and ryegrass plants transformed with *M. acuminate* PPD under a constitutive promoter. Tillers were planted into plastic grow bags containing potting mix and pruned to be of equal height. Plants were grown for approximately 6 weeks in the glasshouse; the increase in root biomass/growth/length/branching of ryegrass plants transformed with *M. acuminate* PPD under a constitutive promoter compared to WT plants could be seen by observing the root growth beyond the grow bag. The increase in root biomass can be quantified by washing the roots under running water then removing the attached above ground portion (leaves and stems) and drying the roots at 65° C. for 48 hr then weighing the dry weights.

An equal number (typically 4-10) of tillers were taken from WT and ryegrass plants transformed with *M. acuminate* PPD under one of three root promoters. Tillers were planted into plastic grow bags containing potting mix and pruned to be of equal height. Plants were grown for approximately 6 weeks in the glasshouse; the increase in root biomass/growth/length/branching of ryegrass plants transformed with *M. acuminate* PPD under a constitutive promoter compared to WT plants could be seen by observing the root growth beyond the grow bag. The increase in root biomass can be quantified by washing the roots under running water then removing the attached above ground portion (leaves and stems) and drying the roots at 65° C. for 48 hr then weighing the dry weights.

An equal number (typically 4-10) of tillers were taken from WT and ryegrass plants transformed with *P. sitchensis* PPD under a constitutive promoter. Tillers were planted into plastic grow bags containing potting mix and pruned to be of equal height. Plants were grown for approximately 6 weeks in the glasshouse; the increase in root biomass/growth/length/branching of ryegrass plants transformed with *P. sitchensis* PPD under a constitutive promoter compared to WT plants could be seen by observing the root growth beyond the grow bag. The increase in root biomass can be quantified by washing the roots under running water then removing the attached above ground portion (leaves and stems) and drying the roots at 65° C. for 48 hr then weighing the dry weights.

An equal number (typically 4-10) of tillers were taken from WT and ryegrass plants transformed with *P. sitchensis* PPD under one of three root promoters. Tillers were planted into plastic grow bags containing potting mix and pruned to be of equal height. Plants were grown for approximately 6 weeks in the glasshouse; the increase in root biomass/growth/length/branching of ryegrass plants transformed with *P. sitchensis* PPD under a constitutive promoter compared to WT plants could be seen by observing the root growth beyond the grow bag. The increase in root biomass can be quantified by washing the roots under running water then removing the attached above ground portion (leaves and stems) and drying the roots at 65° C. for 48 hr then weighing the dry weights.

An equal number (typically 4-10) of tillers were taken from WT and ryegrass plants transformed with *S. moellendorffii* PPD under a constitutive promoter. Tillers were planted into plastic grow bags containing potting mix and pruned to be of equal height. Plants were grown for approximately 6 weeks in the glasshouse; the increase in root biomass/growth/length/branching of ryegrass plants transformed with *S. moellendorffii* PPD under a constitutive promoter compared to WT plants could be seen by observing the root growth beyond the grow bag. The increase in root biomass can be quantified by washing the roots under running water then removing the attached above ground portion (leaves and stems) and drying the roots at 65° C. for 48 hr then weighing the dry weights.

An equal number (typically 4-10) of tillers were taken from WT and ryegrass plants transformed with *S. moellendorffii* PPD under one of three root promoters. Tillers were planted into plastic grow bags containing potting mix and pruned to be of equal height. Plants were grown for approximately 6 weeks in the glasshouse; the increase in root biomass/growth/length/branching of ryegrass plants transformed with *S. moellendorffii* PPD under a constitutive promoter compared to WT plants could be seen by observing the root growth beyond the grow bag. The increase in root biomass can be quantified by washing the roots under running water then removing the attached above ground portion (leaves and stems) and drying the roots at 65° C. for 48 hr then weighing the dry weights.

Seeds from WT and Δppd *Arabidopsis* plants transformed with *T. repens* PPD under a constitutive promoter were scarified and sown into potting mix. Plants were grown for approximately 6 weeks in a growth cabinet with x hours day length; the increase in root biomass/growth/length/branching of *Arabidopsis* plants transformed with *T. repens* PPD under a constitutive promoter compared to WT plants could be seen by observing the root growth beyond the pot. The increase in root biomass was quantified by washing the roots under running water then the attached above ground portion (leaves and stems) was removed and the roots dried at 65° C. for 48 hr then weighed.

Seeds from WT and Δppd *Arabidopsis* plants transformed with *M. acuminate* PPD under a constitutive promoter were scarified and sown into potting mix. Plants were grown for approximately 6 weeks in a growth cabinet with x hours day length; the increase in root biomass/growth/length/branching of *Arabidopsis* plants transformed with *M. acuminate* PPD under a constitutive promoter compared to WT plants could be seen by observing the root growth beyond the pot. The increase in root biomass was quantified by washing the roots under running water then the attached above ground portion (leaves and stems) was removed and the roots dried at 65° C. for 48 hr then weighed.

Seeds from WT and Δppd *Arabidopsis* plants transformed with *A. trichopoda* PPD under a constitutive promoter were scarified and sown into potting mix. Plants were grown for approximately 6 weeks in a growth cabinet with x hours day length; the increase in root biomass/growth/length/branching of *Arabidopsis* plants transformed with *A. trichopoda* PPD under a constitutive promoter compared to WT plants could be seen by observing the root growth beyond the pot. The increase in root biomass was quantified by washing the roots under running water then the attached above ground portion (leaves and stems) was removed and the roots dried at 65° C. for 48 hr then weighed.

Seeds from WT and Δppd *Arabidopsis* plants transformed with *P. abies* PPD under a constitutive promoter were scarified and sown into potting mix. Plants were grown for approximately 6 weeks in a growth cabinet with x hours day length; the increase in root biomass/growth/length/branching of *Arabidopsis* plants transformed with *P. abies* PPD under a constitutive promoter compared to WT plants could be seen by observing the root growth beyond the pot. The increase in root biomass was quantified by washing the roots under running water then the attached above ground portion (leaves and stems) was removed and the roots dried at 65° C. for 48 hr then weighed.

Seeds from WT and Δppd *Arabidopsis* plants transformed with *S. moellendorffii* PPD under a constitutive promoter were scarified and sown into potting mix. Plants were grown for approximately 6 weeks in a growth cabinet with x hours day length; the increase in root biomass/growth/length/ branching of *Arabidopsis* plants transformed with *S. moellendorffii* PPD under a constitutive promoter compared to WT plants could be seen by observing the root growth beyond the pot. The increase in root biomass was quantified by washing the roots under running water then the attached above ground portion (leaves and stems) was removed and the roots dried at 65° C. for 48 hr then weighed.

Drought Tolerance Analysis of Transformants

An equal number (typically 4-10) of tillers were taken from WT and ryegrass plants transformed with *Arabidopsis* PPD under a constitutive promoter. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of tillers were taken from WT and ryegrass plants transformed with *T. repens* PPD under a constitutive promoter. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of tillers were taken from WT and ryegrass plants transformed with *M. acuminate* PPD under a constitutive promoter. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of tillers were taken from WT and ryegrass plants transformed with *A. trichopoda* PPD under a constitutive promoter. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of tillers were taken from WT and ryegrass plants transformed with *P. sitchensis* PPD under a constitutive promoter. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of tillers were taken from WT and ryegrass plants transformed with *S. moellendorffii* PPD under a constitutive promoter. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of tillers were taken from WT and ryegrass plants transformed with *Arabidopsis* PPD under one of three root promoters. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of tillers were taken from WT and ryegrass plants transformed with *T. repens* PPD under one of three root promoters. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of tillers were taken from WT and ryegrass plants transformed with *M. acuminate* PPD under one of three root promoters. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of tillers were taken from WT and ryegrass plants transformed with *A. trichopoda* PPD under one of three root promoters. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of tillers were taken from WT and ryegrass plants transformed with *P. sitchensis* PPD under one of three root promoters. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of tillers were taken from WT and ryegrass plants transformed with *S. moellendorffii* PPD under one of three root promoters. Tillers were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of WT and Δppd *Arabidopsis* seedlings transformed with *Arabidopsis* PPD under a constitutive promoter were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of WT and Δppd *Arabidopsis* seedlings transformed with *T. repens* PPD under a constitutive promoter were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of WT and Δppd *Arabidopsis* seedlings transformed with *M. acuminate* PPD under a constitutive promoter were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of WT and Δppd *Arabidopsis* seedlings transformed with *A. trichopoda* PPD under a constitutive promoter were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of WT and Δppd *Arabidopsis* seedlings transformed with *P. abies* PPD under a constitutive promoter were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

An equal number (typically 4-10) of WT and Δppd *Arabidopsis* seedlings transformed with *S. moellendorffii* PPD under a constitutive promoter were planted in large pots containing potting mix and soil. Plants were allowed to establish in the glasshouse before half the plants of each type were subjected to water stress (typically 12% gravimetric water content, just above permanent wilting point) while the other half were kept watered (typically 22% gravimetric water content, approximately field capacity). The increased tolerance to drought stress of the PPD over expressing plants can be quantified by comparing root and shoot biomass with WT plants.

REFERENCES

Achard, P. Genschik P. (2009). Releasing the brakes of plant growth: how Gas shutdown DELLA proteins. J. Exp. Bot., 60:1985-1092.

Altschul, S. F., Gish, W., Miller, W., Myers, E. W., Lipman, D. J. (1990). Basic local alignment search tool. J. Mol. Biol. 215:403-410.

Anjum, S A., Wang, L C., Farooq, M., Hussain, M., Zou, C M. (2011) Brassinolide application improves the drought tolerance in maize through modulation of enzymatic antioxidants and leaf gas exchange. J. Agronomy and Crop Sci. 197:177-185.

Chory and Wang, 2005, Genes involved in brassinosteroid hormone action in plants, U.S. Pat. No. 6,921,848 B2

Clough S. J. and Bent A. F. (1998) Floral dip: a simplified method for *Agrobacterium*-mediated transformation of *Arabidopsis thaliana. Plant J.* 16: 735-743.

Clouse, S. D. Brassinosteroid signal transduction: from receptor kinase activation to transcriptional networks regulating plant development. Plant Cell 23, 1219-1230 (2011).

Clouse, S. D. & Sasse, J. M. BRASSINOSTEROIDS: Essential regulators of plant growth and development. Annu. Rev. Plant Physiol. Plant Mol. Biol. 16, 427-451 (1998).

Gallego-Bartolome, J., Minguet, E G., Grau-Enguix, F., Abbas, M., Locascio, A., Thomas, S G., Alabadi, D., Blazquez, M A. (2012). Molecular mechanism for the interaction between gibberellin and brassionosteroid signalling pathways in *Arabidopsis*. PNAS, 109:13446-13451.

Garcia, M. E., Lynch, T., Peeters, J., Snowden, C. & Finkelstein, R. A small plant-specific protein family of ABI five binding proteins (AFPs) regulates stress response in germinating *Arabidopsis* seeds and seedlings. Plant Mol. Biol. 67, 643-658 (2008).

Guo, H., Li, L., Aluru, M., Sluru, S., Yin, Y. (2013). Mechanisms and networkes for brassinosteroid regulated gene expression. Current Opinion in Plant Biology 16:545-553.

He, J-X., Gendron, J M., Sun, Y., Gampaia, S L., Gendron, N., Sun, C Q., Wang, Z-Y. (2005). BZR1 is a transcriptional repressor with dual roles in brassinosteroid homeostasis and growth responses. Science 307:1634-1638.

Hothorn, M., Belkhadir, Y., Dreux, M., Dabi, T., Noel, J. P., Wilson, I. A. & Chory, J. Structural basis of steroid hormone perception by the receptor kinase BRI1. Nature 474, 467-471 (2011).

Hou, X., Lee L Y C, Xia, K., Yan, Y., Yu H. (2010). DELLAs modulate jasmonate signalling via competitive binding to JAZs. Devel. Cell 19:884-894.

Jiang, W-B., Lin, W-H. (2013). Brassinosteroid functions in *Arabidopsis* seed development. Plant Signaling & Behavior 8:10, e25928; October 2013.

Jiang, L., Liu, X., Xiong, G., Liu, H., Chen, F., Wang, L., Meng, X., Liu, G., Yu, H., Yuan, Y., Yi, W., Zhao, L., Ma, H., He, Y., Wu, Z., Melcher, K., Qian, Q., Xu, H. E., Wang, Y. & Li, J. DWARF 53 acts as a repressor of strigolactone signalling in rice. Nature 504, 401-405 (2013).

Karimi, M., Inzé, D. & Depicker, A. Gateway vectors for *Agrobacterium*-mediated plant transformation. Trends Plant Sci. 7, 193-195 (2002).

Khripach, V., Zhabinskii, V., Groot, A D. (2000). Twenty years of brassinosteroids: Steroidal plant hormones warrant better crops for the XXI century. Ann. Bot., 86:441-447.

Kinoshita, T., Caño-Delgado, A., Seto, H., Hiranuma, S., Fujioka, S., Yoshida, S. & Chory, J. Binding of brassinosteroids to the extracellular domain of plant receptor kinase BRI1. Nature 433, 167-171 (2005).

Lawit, Kundu, Rao and Tomes, 2007, Isolated polynucleotide molecules corresponding to mutant and wild-type alleles of the maize D9 gene and methods of use, WO 2007124312 A2

Li, Q-F., He, J-X. (2013). Mechanisms of signalling crosstalk between brassinosteroids and gibberellins. Plant Signaling & Behavior 8:7,e24686; July 2013; © 2013 Landes Bioscience.

Mathew, C., Hofmann, W A., Osborne, M A. (2009). Pasture response to gibberellins: A review and recommendations. N Z. J. Agric. Res., 52:213-225.

Pauwels, L., Barbero, G. F., Geerink, J., Tilleman, S., Grunewald, W., Perez, A. C., Chico, J. M., Bossche, R. V., Sewell, J., Gil, E., Garcia-Casado, G., Witters, E., Inzé, D., Long, J. A., Jaeger, G. D., Solano, R. & Goossens, A. NINJA connects the co-repressor TOPLESS to jasmonate signalling. Nature 464, 788-791 (2010).

Pérez, A. C., Durand, A. N., Bossche, R. V., De Clercq, R., Persiau, G., Van Wees, S. C. M., Pieterse, C. M. J., Gevaert, K., De Jaeger, G., Goossens, A. & Pauwels, L. The non-JAZ TIFY protein TIFY8 from *Arabidopsis thaliana* is a transcriptional repressor. PLos ONE 9, e84891 (2014).

Prusakova, L D., Ezhov, M N., Salnikov, A I. (1999). The use of emistim, epibrassinolide and uniconazole to overcome quality difference of buckwheat grains. Agrarian Russia: 41-44.

Robatzek and Somssich (2001). The Plant Journal, 28: 123-133

She, J., Han, Z., Kim, T. W., Wang, J., Cheng, W., Chang, J., Shi, S., Wang, J., Yang, M., Wang, Z-Y. & Chai, J. Structural insight into brassinosteroid perception by BRI1. Nature 474, 472-476 (2011).

Sun, T-P. (2011). The molecular mechanism and evolution of the GA-GID1-DELLA signalling module in plants. Review. Current Biology, 21:R338-R345.

Szemenyei, H., Hannon, M. & Long, J. A. TOPLESS mediates auxin-dependent transcriptional repression during *Arabidopsis* embryogenesis. Science 319, 1384-1386 (2008).

Thummel, C. S. & Chory, J. Steroid signalling in plants and insects-common themes, different pathways. Genes Dev. 16, 3113-3129 (2002).

Vanhaeren, H., Gonzalez, N, Coppens, F, De Milde, L, Van Daele, T, Vermeesch, M, Eloy, N B, Storme, V, Inez, D. (2014). Combining growth-promoting genes leads topositive epistasis in *Arabidopsis thaliana*. eLife 2014; 3:e02252. DOI: 10.7554/eLife.02252

Vanholme, B., Grunewald, W., Bateman, A., Kohchi, T., Gheysen, G. (2007). The tify family previously known as ZIM. Trends in Plant Science, 12:239-244.

Vardhini, B V. (2012). Application of brassinolide mitigates saline stress of certain metabolites of sorghum grown in Karaikal. J. Phytology, 4:1-3.

Wang, Z-Y., Nakano T., Gendron, J., He, J., Chen, M., Vafeados, D., Yang, Y., Fujioka, S., Yoshida, S., Asami, T., Chory, J. (2002). Nuclear-localised BZR1 mediates brassinosteroid-induced growth and feedback suppression of brassinosteroid biosynthesis. Developmental Cell 2:505-513.

Wang, C-M., Shang, J-X., Chen, Q-X., Oses-Prieto, J. A., Bai, M-Y, Yang, Y., Yuan, M., Zhang, Y-L., Mu, C-C., Deng, Z., Wei C-Q., Burlingame, A. L., Wang, Z-Y. & Sun, Y. Identification of BZR1-interacting proteins as potential components of the brassinosteroid signalling pathway in *Arabidopsis* through tandem affinity purification. Mol. Cell. Proteomics 12, 3653-3665 (2013).

Winichayakul, S., Pernthaner, A., Scott, R., Vlaming, R. & Roberts, N. (2008) Head-to-tail fusions of camelid antibodies can be expressed in planta and bind in rumen fluid. Biotech. & Appl. Biochem. 53, 111-122.

White, D. (2006) PEAPOD regulates lamina size and curvature in *Arabidopsis*. PNAS, 103:13238-13243.

White, D. (2007). Novel plant genes and uses thereof, WO 2007105967A8.

Yamamoto et al (1991). Characterization of cis-acting sequences regulating root-specific gene expression in tobacco. Plant Cell, 3:371-382.

Zhu, J-Y., Sae-Seaw, J. & Wang, Z-Y. Brassinosteroid signalling. Development 140, 1615-1620 (2013).

SUMMARY OF SEQUENCES

| SEQ ID NO: | Sequence type | Species/Source | Reference |
|---|---|---|---|
| 1 | polypeptide | *Arabidopsis thaliana* | PEAPOD 1 protein |
| 2 | polypeptide | *Arabidopsis thaliana* | PEAPOD 2 protein |
| 3 | polypeptide | *Populus euphratica* | PEAPOD protein |
| 4 | polypeptide | *Picea abies* | PEAPOD protein |
| 5 | Polypeptide | *Picea sitchensis* | PEAPOD protein |
| 6 | polypeptide | *Gossypium raimondii* | PEAPOD protein |

-continued

SUMMARY OF SEQUENCES

| SEQ ID NO: | Sequence type | Species/Source | Reference |
|---|---|---|---|
| 7 | polypeptide | *Aquilegia coerulea* | PEAPOD protein 1 |
| 8 | polypeptide | *Aquilegia coerulea* | PEAPOD protein 2 |
| 9 | polypeptide | *Medicago truncatula* | PEAPOD protein |
| 10 | polypeptide | *Solanum lycopersicum* | PEAPOD protein |
| 11 | polypeptide | *Trifolium repens* | PEAPOD protein |
| 12 | polypeptide | *Amborella A. Trichopoda* | PEAPOD protein |
| 13 | polypeptide | *Selaginella moellendorffii* | PEAPOD protein 1 |
| 14 | polypeptide | *Selaginella moellendorffii* | PEAPOD protein 2 |
| 15 | polypeptide | *Nicotiana tabacum* | PEAPOD protein |
| 16 | polypeptide | *Solanum tuberosum* | PEAPOD protein |
| 17 | polypeptide | *Glycine max* | PEAPOD protein |
| 18 | polypeptide | *Citrus clementine* | PEAPOD protein |
| 19 | polypeptide | *Ricinus communus* | PEAPOD protein |
| 20 | polypeptide | *Vitis vinifera* | PEAPOD protein |
| 21 | polypeptide | *Morus notabilis* | PEAPOD protein |
| 22 | polypeptide | *Phoenix dactylifera* | PEAPOD protein |
| 23 | polypeptide | *Theobroma cacao* | PEAPOD protein |
| 24 | polypeptide | *Spirodela polyrhiza* | PEAPOD protein |
| 25 | polypeptide | *Musa species* | PEAPOD protein |
| 26 | polypeptide | *Phalaenopsis aphrodite* | PEAPOD protein |
| 27 | polypeptide | artificial | internal 46 amino acid *Arabidopsis* PPD1 region |
| 28 | polypeptide | artificial | internal 46 amino acid consensus motif 1, identical residues |
| 29 | polypeptide | artificial | internal 46 amino acid consensus motif 2, variable residues |
| 30 | polypeptide | artificial | internal 27 amino acid *Arabidopsis* PPD1 region |
| 31 | polypeptide | artificial | internal 27 amino acid consensus motif 1, identical residues |
| 32 | polypeptide | artificial | internal 27 amino acid consensus motif 2, variable residues |
| 33 | polypeptide | artificial | 6 amino acid TIFY motif from *Arabidopsis* PPD1 |
| 34 | polypeptide | artificial | 6 amino acid TIFY consensus motif 1, identical residues |
| 35 | polypeptide | artificial | 6 amino acid TIFY consensus motif 1, variable residues |
| 36 | polypeptide | artificial | PPD1 V5-HIS tail peptide sequence expressed in roots |
| 37 | polypeptide | artificial | Linker and V5-His tail peptide sequence |
| 38 | polypeptide | artificial | PPD1 (no tail) peptide sequence expressed in roots |
| 39 | polynucleotide | | *Arabidopsis thaliana* DGAT1 intron 3 nucleic acid sequence |
| 40 | polynucleotide | artificial | GenScript synthesised optimised *Arabidopsis* PPD1 coding region (with intron) nucleic acid sequence for expression in dicot roots under the tobacco TobRB7 Δ1.3 root promoter; the tobacco TobRB7 Δ0.6 root promoter |
| 41 | polynucleotide | artificial | GenScript synthesised optimised *Arabidopsis* PPD1 coding region (with intron) nucleic acid sequence for expression in |

-continued

| SUMMARY OF SEQUENCES | | | |
|---|---|---|---|
| SEQ ID NO: | Sequence type | Species/Source | Reference |
| | | | dicot roots under *Arabidopsis* AtWRKY6 root promoter |
| 42 | polynucleotide | artificial | TobRB7 Δ1.3 promoter::attB1:: optimised *Arabidopsis* PPD-V5-His(INTRON)::attB2::nos terminator expression cassette nucleic acid sequence |
| 43 | polynucleotide | artificial | TobRB7 Δ0.6 promoter::attB1:: optimised *Arabidopsis* PPD-V5-His(INTRON)::attB2::nos terminator expression cassette nucleic acid sequence |
| 44 | polynucleotide | artificial | AtWRKY6 promoter::attB1:: optimised *Arabidopsis* PPD-V5-His(INTRON)::attB2::nos terminator expression cassette nucleic acid sequence |
| 45 | polynucleotide | artificial | TobRB7 Δ1.3 promoter::attB1:: optimised *Arabidopsis* PPD (INTRON)::attB2::nos terminator expression cassette |
| 46 | polynucleotide | artificial | TobRB7 Δ0.6 promoter::attB1:: optimised *Arabidopsis* PPD (INTRON)::attB2::nos terminator expression cassette |
| 47 | polynucleotide | artificial | AtWRKY6 promoter::attB1:: optimised *Arabidopsis* PPD (INTRON)::attB2::nos terminator expression cassette. |
| 48 | polynucleotide | | *Lolium perenne* DGAT1 intron 3 nucleic acid sequence |
| 49 | polynucleotide | artificial | GENEART synthesised rice optimised PPD1 coding region (with intron) nucleic acid sequence for expression in grass roots using the tobacco TobRB7 Δ1.3 root promoter; the tobacco TobRB7 Δ0.6 root promoter; and the *Arabidopsis* AtWRKY6 root promoter. |
| 50 | polynucleotide | artificial | TobRB7 Δ1.3 promoter::attB1::rice optimised PPD-V5-His(INTRON)::attB2::nos terminator expression cassette nucleic acid sequence |
| 51 | polynucleotide | artificial | TobRB7 Δ0.6 promoter::attB1::rice optimised PPD-V5-His(INTRON)::attB2::nos terminator expression cassette nucleic acid sequence |

-continued

SUMMARY OF SEQUENCES

| SEQ ID NO: | Sequence type | Species/Source | Reference |
|---|---|---|---|
| 52 | polynucleotide | artificial | AtWRKY6 promoter::attB1::rice optimised PPD-V5-His(INTRON)::attB2::nos terminator expression cassette nucleic acid sequence |
| 53 | polynucleotide | artificial | TobRB7 Δ1.3 promoter::attB1::rice optimised PPD (INTRON)::attB2::nos terminator expression cassette |
| 54 | polynucleotide | artificial | TobRB7 Δ0.6 promoter::attB1::rice optimised PPD (INTRON)::attB2::nos terminator expression cassette |
| 55 | polynucleotide | artificial | AtWRKY6 promoter::attB1::rice optimised PPD (INTRON)::attB2::nos terminator expression cassette |
| 56 | polypeptide | artificial | Yeast two Hybrid (Y2H) DNA binding domain (DBD) peptide sequence |
| 57 | polypeptide | artificial | Y2H activation domain (AD) peptide sequence |
| 58 | polypeptide | artificial | Y2H PPD1-DBD peptide sequence |
| 59 | polypeptide | artificial | Y2H PPD1-AD peptide sequence |
| 60 | polypeptide | artificial | Y2H PPD1-ppd-AD peptide sequence |
| 61 | polypeptide | artificial | Y2H PPD1-tify-AD peptide sequence |
| 62 | polypeptide | artificial | Y2H PPD1-jas*-AD peptide sequence |
| 63 | polypeptide | artificial | TPL peptide sequence |
| 64 | polypeptide | artificial | Y2H TPL-DBD peptide sequence |
| 65 | polypeptide | artificial | NINJA peptide sequence |
| 66 | polypeptide | artificial | Y2H NINJA-AD peptide sequence |
| 67 | polypeptide | artificial | Y2H BZR1-AD peptide sequence |
| 68 | polypeptide | artificial | Y2H RGA1 peptide sequence |
| 69 | polypeptide | artificial | Y2H RGA1-AD peptide sequence |
| 70 | polypeptide | artificial | Y2H PPD1-ppd-DBD peptide sequence |
| 71 | polypeptide | artificial | Y2H PPD1-tify-DBD peptide sequence |
| 72 | polypeptide | artificial | Y2H PPD1-jas*-DBD peptide sequence |
| 73 | polypeptide | artificial | Bimolecular Fluorescence (BiFC) nYFP peptide sequence |
| 74 | polypeptide | artificial | BiFC cYFP peptide sequence |
| 75 | polypeptide | artificial | BiFC nYFP-NINJA peptide sequence |
| 76 | polypeptide | artificial | BiFC nYFP-BZR1 peptide sequence |
| 77 | polypeptide | artificial | BiFC cYFP-PPD1 peptide sequence |
| 78 | polypeptide | artificial | BiFC cYFP-NINJA peptide sequence |
| 79 | polypeptide | artificial | BiFC cYFP-BZR1 peptide sequence |

-continued

SUMMARY OF SEQUENCES

| SEQ ID NO: | Sequence type | Species/Source | Reference |
|---|---|---|---|
| 80 | polypeptide | artificial | BiFC cYFP-PPD1-ppd peptide sequence |
| 81 | polypeptide | artificial | BiFC cYFP-PPD1-tify peptide sequence |
| 82 | polypeptide | artificial | BiFC cYFP-PPD1-jas* peptide sequence |
| 83 | polynucleotide | *Arabidopsis thaliana* | *Arabidopsis thaliana* PPD1 coding sequence |
| 84 | Polynucleotide | *Arabidopsis thaliana* | *Arabidopsis thaliana* PPD2 coding sequence |
| 85 | Polynucleotide | *Populus euphratica* | *Populus trichocarpa*, PPD coding sequence |
| 86 | Polynucleotide | *Picea abies* | *Picea abies*, PPD genomic sequence |
| 87 | Polynucleotide | *Gossypium raimondii* | *Gossypium raimondii*, PPD coding sequence |
| 88 | Polynucleotide | *Aquilegia coerulea* | *Aquilegia coerulea*, PPD coding sequence 1 |
| 89 | Polynucleotide | *Aquilegia coerulea* | *Aquilegia coerulea*, PPD coding sequence 2 |
| 90 | Polynucleotide | Medicago truncatula | Medicago truncatula, PPD coding sequence |
| 91 | Polynucleotide | *Solanum lycopersicum* | *Solanum lycopersicum*, PPD coding sequence |
| 92 | Polynucleotide | *Trifolium repens* | *Trifolium repens*, PPD coding sequence |
| 93 | Polynucleotide | *Amborella trichopoda* | *Amborella trichopod*, PPD coding sequence |
| 94 | Polynucleotide | *Selaginella moellendorffii* | *Selaginella moellendorffii*, PPD coding sequence 1 |
| 95 | Polynucleotide | *Selaginella moellendorffii* | *Selaginella moellendorffii*, PPD coding sequence 2 |
| 96 | Polynucleotide | *Nicotiana tabacum* | *Nicotiana tabacum*, PPD coding sequence |
| 97 | Polynucleotide | *Solanum tuberosum* | *Solanum tuberosum*, PPD coding sequence |
| 98 | Polynucleotide | *Glycine max* | *Glycine max*, PPD coding sequence |
| 99 | Polynucleotide | *Citrus clementine* | *Citrus clementine*, PPD coding sequence |
| 100 | Polynucleotide | *Ricinus communus* | *Ricinus communus*, PPD coding sequence |
| 101 | Polynucleotide | *Vitis vinifera* | *Vitis vinifera*, PPD coding sequence |
| 102 | Polynucleotide | *Morus notabilis* | *Morus notabilis*, PPD coding sequence |
| 103 | Polynucleotide | *Phoenix dactylifera* | *Phoenix dactylifera*, PPD coding sequence |
| 104 | Polynucleotide | *Theobroma cacao* | *Theobroma cacao*, PPD coding sequence |
| 105 | Polynucleotide | *Spirodela polyrhiza* | *Spirodela polyrhiza*, PPD genomic sequence |
| 106 | Polynucleotide | *Musa* species | *Musa* species, PPD coding sequence |
| 107 | Polynucleotide | *Phalaenopsis aphrodite* | *Phalaenopsis aphrodite*, PPD coding sequence |
| 108 | Polypeptide | artificial | *Arabidopsis thaliana* PPD1 + V5-His tag |
| 109 | Polypeptide | artificial | *Trifolium repens* PPD + V5-His tag |
| 110 | Polypeptide | artificial | *Amborella trichopoda* PPD + V5-His tag |
| 111 | Polypeptide | artificial | *Musa acuminate* PPD + V5-His tag |
| 112 | Polypeptide | artificial | *Picea sitchensis* PPD + V5-His tag |
| 113 | Polypeptide | artificial | *Selaginella moellendorffii* PPD + V5-His tag |
| 114 | Polypeptide | artificial | *Arabidopsis thaliana* PPD - no tag |
| 115 | Polypeptide | artificial | *Trifolium repens* PPD - no tag |
| 116 | Polypeptide | artificial | *Amborella trichopoda* PPD - no tag |

-continued

| SUMMARY OF SEQUENCES | | | |
|---|---|---|---|
| SEQ ID NO: | Sequence type | Species/Source | Reference |
| 117 | Polypeptide | artificial | *Musa acuminate* PPD -no tag |
| 118 | Polypeptide | artificial | *Picea abies* PPD - no tag |
| 119 | Polypeptide | artificial | *Selaginella moellendorffii* PPD - no tag |
| 120 | Polynucleotide | artificial | *Arabidopsis thaliana* PPD - monocot optimised nucleic acid sequence |
| 121 | Polynucleotide | artificial | *Trifolium repens* PPD - monocot optimised nucleic acid sequence |
| 122 | Polynucleotide | artificial | *Amborella trichopoda* PPD - monocot optimised nucleic acid sequence |
| 123 | Polynucleotide | artificial | *Musa acuminate* PPD - monocot optimised nucleic acid sequence |
| 124 | Polynucleotide | artificial | *Picea sitchensis* PPD - monocot optimised nucleic acid sequence |
| 125 | Polynucleotide | artificial | *Selaginella moellendorffii* PPD - monocot optimised nucleic acid sequence |
| 126 | Polynucleotide | artificial | *Arabidopsis thaliana* PPD - dicot optimised nucleic acid sequence |
| 127 | Polynucleotide | artificial | *Trifolium repens* PPD - dicot optimised nucleic acid sequence |
| 128 | Polynucleotide | artificial | *Amborella trichopoda* PPD - dicot optimised nucleic acid sequence |
| 129 | Polynucleotide | artificial | *Musa acuminate* PPD - dicot optimised nucleic acid sequence |
| 130 | Polynucleotide | artificial | *Picea abies* PPD - dicot optimised nucleic acid sequence |
| 131 | Polynucleotide | artificial | *Selaginella moellendorffii* PPD - dicot optimised nucleic acid sequence |
| 132 | Polynucleotide | artificial | Primer, ocs3'-1f |
| 133 | Polynucleotide | artificial | Primer, ocs3'-1r |
| 134 | Polynucleotide | artificial | Primer, hpt-1 |
| 135 | Polynucleotide | artificial | Primer, hpt-2 |
| 136 | Polynucleotide | artificial | Primer, nos3'-1f |
| 137 | Polynucleotide | artificial | Primer, nos3'-1r |
| 138 | Polynucleotide | artificial | Primer, rgh1 |
| 139 | Polynucleotide | artificial | Primer, rgh5 |
| 140 | Polynucleotide | artificial | Primer, GrPPD1F |
| 141 | Polynucleotide | artificial | Primer, GrPPD1R |

The invention claimed is:

1. A method for at least one of:

a) increasing root biomass in a plant, and b) producing a plant increased root biomass, the method comprising the step of increasing the expression of at least one PEAPOD protein, or fragment thereof, in the plant.

2. The method of claim 1 in which the increased expression is a consequence of the plant, or its ancestor plant or plant cell, being transformed with a polynucleotide encoding the PEAPOD protein, or fragment thereof.

3. The method of claim 1 in which the plant is transgenic for at least one polynucleotide encoding and expressing the PEAPOD protein, or fragment thereof.

4. The method of claim 1 in which the plant is transformed with at least one polynucleotide encoding a PEAPOD protein, or fragment thereof.

5. The method of claim 1 comprising the step of transforming the plant, or transforming a plant cell which is regenerated into the plant, with a polynucleotide encoding the PEAPOD protein.

6. The method of claim 1 which includes the additional step of testing or assessing the plant for increased root biomass.

7. The method of claim 1 in which the PEAPOD protein, or fragment thereof, is a polypeptide comprising the sequence of at least one of SEQ ID NO: 28, 29, 31, 32, 34 and 35.

8. The method of claim 1 in which the PEAPOD protein is a polypeptide comprising a sequence with at least 70% identity to any one of SEQ ID NO: 1 to 26.

9. The method of claim 1 in which expression is increased by introducing a polynucleotide encoding a PEAPOD protein, or fragment thereof, into the plant cell or plant.

10. The method of claim 9 in which the polynucleotide comprises a sequence with at least 70% identity to the coding sequence of any one of SEQ ID NO: 83-107 or a fragment thereof.

11. The method of claim 9 in which the polynucleotide comprises a sequence with at least 70% identity to the sequence of any one of SEQ ID NO: 83-107 or a fragment thereof.

12. The method of claim 9 in which the polynucleotide, or fragment thereof, is introduced into the plant as part of an expression construct.

13. The method of claim 12 in which the expression construct comprises a promoter operatively linked to the polynucleotide or fragment thereof.

14. The method of claim 13 in which the promoter is capable of driving, or drives, expression of the operatively linked polynucleotide or fragment thereof, constitutively in all tissues of the plant.

15. The method of claim 13 in which the promoter is a tissue-preferred promoter.

16. The method of claim 13 in which the promoter is capable of driving, or drives, expression of the operatively linked polynucleotide, or fragment thereof, in the below ground tissues of the plant.

17. The method of claim 13 in which the promoter is a below ground tissues-preferred promoter.

18. The method of claim 13 in which the promoter is a light-repressed promoter.

19. The method of claim 13 in which the promoter is capable of driving, or drives, expression of the operatively linked polynucleotide, or fragment thereof, in the roots of the plant.

20. The method of claim 13 in which the promoter is a root-preferred promoter.

21. The method of claim 13 in which the promoter is a root-specific promoter.

22. A plant that has increased root biomass as a result of having increased expression a PEAPOD protein, or fragment thereof, wherein expression is from a polynucleotide encoding the PEAPOD protein or fragment thereof, wherein the polynucleotide is operatively linked to a promoter that is at least one of:

a) a tissue-preferred promoter, b) a below ground tissues-preferred promoter, c) a below ground tissue-specific promoter, d) a light-repressed promoter, e) a root-preferred promoter, and f) a root-specific promoter, and wherein the increased root biomass is relative to that of a control plant.

23. The plant of claim 22 wherein expression of the PEAPOD protein, or fragment thereof, is increased as a consequence of the plant, or its ancestor plant or plant cell, having been transformed with the polynucleotide encoding the PEAPOD protein, or fragment thereof.

24. The plant of claim 22 that is transgenic for a polynucleotide expressing the PEAPOD protein, or fragment thereof.

25. A cell, part, propagule or progeny of the plant of claim 22 that is transgenic for the polynucleotide.

26. A cell, part, propagule or progeny of the plant of claim 22 that is transgenic for the polynucleotide operatively linked to the promoter.

* * * * *